(12) United States Patent
Bahceci et al.

(10) Patent No.: US 8,796,294 B2
(45) Date of Patent: Aug. 5, 2014

(54) INHIBITORS OF THE HEDGEHOG PATHWAY

(75) Inventors: Suleyman Bahceci, San Mateo, CA (US); William Bajjalieh, San Francisco, CA (US); Jeff Chen, San Francisco, CA (US); Sergey Epshteyn, Fremont, CA (US); Timothy Patrick Forsyth, Hayward, CA (US); Tai Phat Huynh, New York, NY (US); Byung Gyu Kim, San Mateo, CA (US); James W. Leahy, San Leandro, CA (US); Matthew Sangyup Lee, San Francisco, CA (US); Gary L. Lewis, San Francisco, CA (US); Morrison B. Mac, San Francisco, CA (US); Grace Mann, San Mateo, CA (US); Charles K. Marlowe, Emerald Hills, CA (US); Brian Hugh Ridgway, Belmont, CA (US); Joan C. Sangalang, Mountain View, CA (US); Xian Shi, San Bruno, CA (US); Craig Stacy Takeuchi, Burlingame, CA (US); Yong Wang, Foster City, CA (US)

(73) Assignee: Exelixis Patent Company LLC, South San Francisco, CA (US)

( * ) Notice: Subject to any disclaimer, the term of this patent is extended or adjusted under 35 U.S.C. 154(b) by 92 days.

(21) Appl. No.: 13/487,559

(22) Filed: Jun. 4, 2012

(65) Prior Publication Data
US 2012/0238570 A1 Sep. 20, 2012

Related U.S. Application Data

(62) Division of application No. 12/049,225, filed on Mar. 14, 2008, now Pat. No. 8,222,263.

(60) Provisional application No. 60/918,160, filed on Mar. 14, 2007, provisional application No. 60/962,617, filed on Jul. 30, 2007.

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ............... 514/266.2; 514/266.1; 544/278; 544/279; 544/280; 544/281; 544/283; 544/284

(58) Field of Classification Search
USPC ............ 514/266.1, 266.2; 544/283, 284, 278, 544/279, 280, 281
See application file for complete search history.

(56) References Cited

U.S. PATENT DOCUMENTS

| | | | |
|---|---|---|---|
| 5,817,674 A | 10/1998 | Clemence et al. | |
| 6,004,979 A | 12/1999 | Clemence et al. | |
| 6,750,214 B2 | 6/2004 | Collis et al. | |
| 6,838,559 B2 | 1/2005 | Vaccaro et al. | |
| 7,022,849 B2 | 4/2006 | Pitts et al. | |
| 7,087,614 B2 | 8/2006 | Guo et al. | |
| 7,105,667 B2 | 9/2006 | Pitts et al. | |
| 7,235,551 B2 * | 6/2007 | Adams et al. | 514/234.2 |
| 8,222,263 B2 | 7/2012 | Bahceci et al. | |
| 2005/0009817 A1 | 1/2005 | Savoy et al. | |
| 2005/0267115 A1 | 12/2005 | Stenkamp et al. | |
| 2006/0116516 A1 | 6/2006 | Pitts et al. | |
| 2006/0235028 A1 | 10/2006 | Li et al. | |
| 2007/0225271 A1 * | 9/2007 | Binggeli et al. | 514/210.21 |
| 2007/0232661 A1 | 10/2007 | Beachy et al. | |
| 2007/0281949 A1 * | 12/2007 | Bacon et al. | 514/258.1 |
| 2009/0318424 A1 * | 12/2009 | Corsi et al. | 514/217.06 |
| 2010/0144755 A1 * | 6/2010 | Corsi et al. | 514/255.05 |

FOREIGN PATENT DOCUMENTS

| | | |
|---|---|---|
| AU | 658163 B2 | 4/1995 |
| EP | 1 903 045 A1 | 3/2008 |
| WO | 02/060874 A8 | 2/2003 |
| WO | 02/102315 A3 | 11/2003 |
| WO | 2004/099159 A1 | 11/2004 |
| WO | 2004/087698 A3 | 12/2004 |
| WO | 2004/087699 A3 | 12/2004 |
| WO | 2005/028467 A1 | 3/2005 |
| WO | 2005/033288 A3 | 10/2005 |
| WO | 2006/028958 A2 | 3/2006 |
| WO | 2006/078283 A2 | 7/2006 |
| WO | 2006/052936 A3 | 10/2006 |
| WO | 2006/128172 A3 | 4/2008 |
| WO | 2006/128129 A3 | 10/2008 |

OTHER PUBLICATIONS

McMahon et al (2001).*
Pinedo et al (2001).*
Chemcats Database, Chemical Abstracts, Registry No. 312525-36-3, entered on Jan. 2, 2001, 1 page.
Plnedo et al., "Translational Research: The Role of VEGF in Tumor Angiogenesis," (Accepted for publication Feb. 22, 2000), AlphaMed Press 1083-7159.

(Continued)

*Primary Examiner* — Paul V. Ward
(74) *Attorney, Agent, or Firm* — Fox Rothschild LLP; Gerard P. Norton; Robert N. Henrie, II

(57) ABSTRACT

The present invention is directed to a compound of Formula I

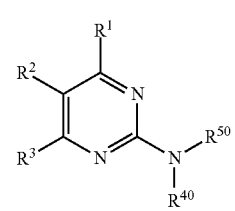

or a single isomer thereof; where the compound is optionally as a pharmaceutically acceptable salt, hydrate, solvate or combination thereof, in addition to methods of preparing a Compound of Formula I, and methods of using a Compound of Formula I to treat cancer.

14 Claims, No Drawings

(56) References Cited

OTHER PUBLICATIONS

McMahon, Gerald, "VEGF Receptor Signaling in Tumor Angiogenesis," (Accepted for Publication Feb. 14, 2000) AlphaMed Press 1083-7159.
Vippagunta et al., "Crystalline Solids", Adv. Drug Del. Rev., 48 (2001) 3-26.
Chemcats Database, Chemical Abstracts, Registry No. 871808-21-8, entered on Jan. 12, 2006, 1 page.
Chemcats Database, Chemical Abstracts, Registry No. 438481-70-0, entered on Jul. 12, 2002, 1 page.
Chemcats Database, Chemical Abstracts, Registry No. 438481-64-2, entered on Jul. 12, 2002, 1 page.
Chemcats Database, Chemical Abstracts, Registry No. 401824-55-3, entered on Mar. 19, 2002, 1 page.
Chemcats Database, Chemical Abstracts, Registry No. 394225-37-7, entered on Feb. 21, 2002, 1 page.
Chemcats Database, Chemical Abstracts, Registry No. 394225-35-5, entered on Feb. 21, 2002, 1 page.
Chemcats Database, Chemical Abstracts, Registry No. 392327-82-1, entered on Feb. 14, 2002, 1 page.
Chemcats Database, Chemical Abstracts, Registry No. 392327-80-9, entered on Feb. 14, 2002, 1 page.
Chemcats Database, Chemical Abstracts, Registry No. 392289-80-4, entered on Feb. 14, 2002, 1 page.
Chemcats Database, Chemical Abstracts, Registry No. 392289-79-1, entered on Feb. 14, 2002, 2 pages.
Chemcats Database, Chemical Abstracts, Registry No. 392289-54-2, entered on Feb. 14, 2002, 1 page.
Chemcats Database, Chemical Abstracts, Registry No. 392289-53-1, entered on Feb. 14, 2002, 1 page.
Chemcats Database, Chemical Abstracts, Registry No. 392289-52-0, entered on Feb. 14, 2002, 2 pages.
Chemcats Database, Chemical Abstracts, Registry No. 392289-51-9, entered on Feb. 14, 2002, 1 page.
Chemcats Database, Chemical Abstracts, Registry No. 392289-50-8, entered on Feb. 14, 2002, 1 page.
Chemcats Database, Chemical Abstracts, Registry No. 392289-49-5, entered on Feb. 14, 2002, 1 page.
Chemcats Database, Chemical Abstracts, Registry No. 329989-48-4, entered on Feb. 14, 2002, 1 page.
Chemcats Database, Chemical Abstracts, Registry No. 392289-47-3, entered on Feb. 14, 2002, 1 page.
Chemcats Database, Chemical Abstracts, Registry No. 392289-46-2, entered on Feb. 14, 2002, 1 page.
Chemcats Database, Chemical Abstracts, Registry No. 392289-45-1, entered on Feb. 14, 2002, 1 page.
Chemcats Database, Chemical Abstracts, Registry No. 375830-31-2, entered on Dec. 17, 2001, 1 page.
Chemcats Database, Chemical Abstracts, Registry No. 375828-33-4, entered on Dec. 17, 2001, 2 pages.
Chemcats Database, Chemical Abstracts, Registry No. 375359-49-2, entered on Dec. 14, 2001, 1 page.
Chemcats Database, Chemical Abstracts, Registry No. 375351-42-1, entered on Dec. 14, 2001, 1 page.
Chemcats Database, Chemical Abstracts, Registry No. 375349-70-5, entered on Dec. 14, 2001, 1 page.
Chemcats Database, Chemical Abstracts, Registry No. 361474-70-6, entered on Oct. 11, 2001, 1 page.
Chemcats Database, Chemical Abstracts, Registry No. 361472-42-6, entered on Oct. 11, 2001, 1 page.
Chemcats Database, Chemical Abstracts, Registry No. 361471-76-3, entered on Oct. 11, 2001, 1 page.
Chemcats Database, Chemical Abstracts, Registry No. 361471-74-1, entered on Oct. 11, 2001, 1 page.
Chemcats Database, Chemical Abstracts, Registry No. 361468-04-4, entered on Oct. 11, 2001, 1 page.
Chemcats Database, Chemical Abstracts, Registry No. 361175-16-8, entered on Oct. 9, 2001, 1 page.
Chemcats Database, Chemical Abstracts, Registry No. 361166-22-5, entered on Oct. 9, 2001, 1 page.
Chemcats Database, Chemical Abstracts, Registry No. 361166-21-4, entered on Oct. 9, 2001, 2 pages.
Chemcats Database, Chemical Abstracts, Registry No. 361166-20-3, entered on Oct. 9, 2001, 1 page.
Chemcats Database, Chemical Abstracts, Registry No. 361160-50-1, entered on Oct. 9, 2001, 1 page.
Chemcats Database, Chemical Abstracts, Registry No. 337483-27-9, entered on May 23, 2001, 2 pages.
Chemcats Database, Chemical Abstracts, Registry No. 337483-23-5, entered on May 23, 2001, 1 page.
Chemcats Database, Chemical Abstracts, Registry No. 332118-07-07, entered on Apr. 24, 2001, 1 page.
Chemcats Database, Chemical Abstracts, Registry No. 332118-06-6, entered on Apr. 24, 2001, 2 pages.
Chemcats Database, Chemical Abstracts, Registry No. 330189-38-3, entered on Apr. 5, 2001, 1 page.
Chemcats Database, Chemical Abstracts, Registry No. 313399-16-5, entered on Jan. 10, 2001, 1 page.
Chemcats Database, Chemical Abstracts, Registry No. 313399-07-4, entered on Jan. 10, 2001, 2 pages.
Chemcats Database, Chemical Abstracts, Registry No. 313399-05-2, entered on Jan. 10, 2001, 1 page.
Chemcats Database, Chemical Abstracts, Registry No. 313399-04-1, entered on Jan. 10, 2001, 1 page.
Chemcats Database, Chemical Abstracts, Registry No. 313398-23-1, entered on Jan. 10, 2001, 1 page.
Chemcats Database, Chemical Abstracts, Registry No. 313398-22-0, entered on Jan. 10, 2001, 1 page.
Chemcats Database, Chemical Abstracts, Registry No. 313398-21-9, entered on Jan. 10, 2001, 1 page.
Chemcats Database, Chemical Abstracts, Registry No. 313398-13-9, entered on Jan. 10, 2001, 2 pages.
Chemcats Database, Chemical Abstracts, Registry No. 312589-034, entered on Jan. 3, 2001, 1 page.

* cited by examiner

INHIBITORS OF THE HEDGEHOG PATHWAY

CROSS-REFERENCE TO RELATED APPLICATION

This application is a Divisional of U.S. patent application Ser. No. 12/049,225 filed Mar. 14, 2008, which claims priority to U.S. Provisional Application Nos. 60/918,160 filed Mar. 14, 2007 and 60/962,617 filed Jul. 30, 2007. The disclosures of all applications are incorporated herein by reference.

FIELD OF THE INVENTION

This invention relates to methods of treating cancer with a compound that modulates the Hedgehog pathway and the resultant modulation of cellular activities (such as proliferation, differentiation, programmed cell death, migration, chemoinvasion and metabolism) alone or in combination with anticancer agents.

BACKGROUND OF THE INVENTION

Hedgehog (Hh) proteins are understood as a family of secreted signal proteins which are responsible for the formation of numerous structures in embryogenesis (J. C. Smith, Cell 76 (1994) 193 196, N. Perrimon, Cell 80 (1995) 517 520, C. Chiang et al., Nature 83 (1996) 407, M. J. Bitgood et al., Curr. Biol. 6 (1996) 296, A. Vortkamp et al., Science 273 (1996) 613, C. J. Lai et al., Development 121 (1995) 2349). During its biosynthesis a 20 kD N-terminal domain and a 25 kD C-terminal domain are obtained after cleavage of the signal sequence and autocatalytic cleavage. In the naturally occurring protein the N-terminal domain is modified with cholesterol at its C-terminus after cleavage of the C-terminal domain (J. A. Porter et al., Science 274 (1996) 255 259). In higher life-forms the Hh family is composed of at least three members namely sonic, indian and desert Hh (sHh, IHh, DHh; M. Fletz et al., Development (Suppl.) (1994) 43 51). Differences in the activity of hedgehog proteins that were produced recombinantly were observed after production in prokaryotes and eukaryotes (M. Hynes et al., Neuron 15 (1995) 35 44 and T. Nakamura et al., Biochem. Biophys. Res. Comm. 237 (1997) 485 469).

Improvements in the specificity of agents used to treat various disease states such as cancer, metabolic, and inflammatory diseases is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Aberrant hedgehog (Hh) pathway signaling has been implicated in human malignancies ranging from semi-malignant tumors of the skin to highly aggressive cancers of the brain, lung, pancreas, breast, prostate and lymphoid lineages (Rubin, L. L. and de Sauvage, F. J. *Nat Rev Drug Discov,* 2006, 5, 1026-1033). Dysregulation of this pathway contributes to uncontrolled proliferation, invasion, metastasis, evasion of apoptosis and resistance to chemotherapy treatments through regulation of the GLI family of transcription factors (GLI1-3), which reside at the distal end of the pathway (Kasper, M., et. al. *Eur J Cancer,* 2006, 42, 437-445). The initial evidence that aberrant Hh signaling plays a critical role in cancer initiation and/or progression came from the observations that important regulatory pathway components are mutated in a number of cancers. These include loss-of-function mutations in the 12-transmembrane Hh receptor, patched1 (PTCH1) and activating mutations in the 7-transmembrane "GPCR-like" protein smoothened (SMO) observed in basal cell carcinomas, medulloblastomas and rhabdomyosaracomas. (See Johnson et. al. *Science,* 272: 1668-1671, 1996; Hahn, et. al. Cell, 85: 841-851, 1996; Unden, et. al. Cancer Res, 56: 4562-4565, 1996; and Chidambaram, et. al. Cancer Res, 56: 4599-4601, 1996).

Where a Sporadic loss-of-function mutation in PTCH1 is observed, these cancers are implicated: basal cell carcinomas (Wolter, M., et. al. *Cancer Res,* 1997, 57, 2581-2585; Reifenberger, J., et. al. *Cancer Res,* 1998, 58, 1798-1803; Lam, C. W., et. al. *Oncogene,* 1999, 18, 833-836; Couve-Privat, S., et. al. *Cancer Res,* 2002, 62, 7186-7189; Xie, J., et. al. *Nature,* 1998, 391, 90-92), medulloblastomas (Wolter, M., et. al. *Cancer Res,* 1997, 57, 2581-2585; Raffel, C., et. al. *Cancer Res,* 1997, 57, 842-845; Pietsch, T., et. al. *Cancer Res,* 1997, 57, 2085-2088; Vorechovsky, I., et. al. *Oncogene,* 1997, 15, 361-366; Couve-Privat, S., et. al. *Cancer Res,* 2002, 62, 7186-7189; Xie, J., et. al. *Nature,* 1998, 391, 90-92), breast carcinomas (Xie, J., et. al. *Cancer Res,* 1997, 57, 2369-2372), meningiomas (id.), and rhabdomyosarcoma (Calzada-Wack, J., et. al. *Hum Mutat,* 2002, 20, 233-234).

In addition, the activity of the Hh pathway has been shown to be critical for the growth and metastasis of a number of tumors that do not contain mutations within any of the defined pathway components including those of the pancreas (Berman, D. et. al. *Nature,* 425: 846-851, 2003; Thayer, S. P., et. al. *Nature* 2003, 425, 851-856; Pasca di Magliano, M., *Genes Dev,* 20: 3161-3173, 2006; and Gao, J., et. al. *Gene Ther,* 13: 1587-1594, 2006), prostate (Karhadkar, S. S., et. al. *Nature,* 431: 707-712, 2004; Sanchez, P., et. al. *Proc Natl Acad Sci USA,* 101: 12561-12566, 2004; Sheng, T., et. al. *Mol Cancer,* 3: 29, 2004; and Fan, L., et. al. *Endocrinology,* 145: 3961-3970, 2004), digestive tract (Berman, D. et. al. *Nature,* 425: 846-851, 2003; Thayer, S. P., et. al. *Nature* 2003, 425, 851-856; Fukaya, M., et. al. *Gastroenterology,* 131: 14-29, 2006; Ohta, M., et. al. *Cancer Res,* 65: 10822-10829, 2005), and small cell lung cancers (Watkins, D. N., et. al. *Nature,* 422: 313-317, 2003), and non-small cell lung cancers (Yuan, Z., et. al. Oncogene, 26: 1046-1055, 2007).

The Hh pathway components are implicated in esophageal cancer (Ma, X., et. al. Int J Cancer, 118: 139-148, 2006; Berman, D. et. al. *Nature,* 425: 846-851, 2003) and are highly expressed in the vast majority (87%, n=43) of chemotherapy-resistant esophageal cancer specimens (Sims-Mourtada, J. et. al. Clin Cancer Res, 12: 6565-6572, 2006). Other cancers where the Hh pathway are involved include biliary tract cancers (Berman, D. et. al. *Nature,* 425: 846-851, 2003), melanoma (Stecca, B., et. al. Proc Natl Acad Sci USA, 104: 5895-5900, 2007), and stomach cancer (Berman, D. et. al. *Nature,* 425: 846-851, 2003; Ma, X., et. al. Carcinogenesis, 26: 1698-1705, 2005). Tumors that contain highly proliferative "tumor stem cells" and which represent areas of therapy include glial cell cancers (Clement, V., et. al. *Curr Biol,* 17: 165-172, 2007), prostate cancers (Li, C., Heidt, et. al. *Cancer Res,* 67: 1030-1037, 2007), breast cancers (Liu, S., et. al. *Cancer Res,* 66: 6063-6071, 2006), multiple myelomas (Peacock, C. D., et. al. *PNAS,* 104: 4048-4053, 2007), and colon cancers (Ricci-Vitiani, L., et. al. *Nature,* 445: 111-115, 2007).

Finally, the Hh pathway is an essential regulator of "cancer stem cells (CSC)", which are discrete tumor cell populations that display highly enhanced survival, self-renewal, and tumorigenicity properties (Beachy, P. A., et. al. Nature, 432: 324-331, 2004). Activation of the Hh pathway has been shown to be critical for CSCs of the breast (Liu, S., et. al. Cancer Res, 66: 6063-6071, 2006), central nervous system (Clement, V., Curr Biol, 17: 165-172, 2007) as well as in hematological malignancies (Peacock, C. D., PNAS, 104: 4048-4053, 2007). These cells, in some experimental contexts, have shown to confer resistance to currently used chemotherapy (Bao, S., et. al. Nature, 444: 756-760, 2006; Dean, M., et. al. Nat Rev Cancer, 5: 275-284, 2005). Therefore, a Hh pathway inhibitor may have broad clinical utility treating of a wide range of chemotherapy-resistant malignancies.

In view of the important role of the Hedgehog pathway in biological processes and disease states, modulators of this pathway are desirable.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The compositions of the invention are used to treat diseases associated with abnormal and or unregulated cellular activities. Disease states which can be treated by the methods and compositions provided herein include cancer. The invention is directed to compounds of Formula I and methods of treating these diseases by administering a Compound of Formula I, alone or in combination with other anti-cancer agents.

One aspect of the Invention is directed to a Compound of Formula I:

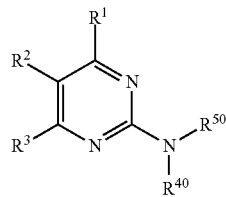

or a single isomer thereof; where the compound is optionally as a pharmaceutically acceptable salt, hydrate, solvate or combination thereof, wherein $R^1$ is alkyl, cycloalkyl, phenyl, heteroaryl, or heterocycloalkyl where the cycloalkyl, phenyl, heteroaryl, and heterocycloalkyl are optionally substituted with 1, 2, or 3 $R^6$;

$R^2$ and $R^3$ together with the pyrimidinyl to which they are attached form a quinazolinyl optionally substituted at the 5-, 6-, 7-positions with one or two groups independently selected from alkyl, alkoxy, halo, hydroxy, heterocycloalkylalkyloxy, heterocycloalkyl, and heterocycloalkyl substituted with alkyl; or $R^2$ and $R^3$ together with the pyrimidinyl to which they are attached form a pyrido[3,2-d]pyrimidinyl, pyrido[4,3-d]pyrimidinyl, pyrido[3,4-d]pyrimidinyl, or pyrido[2,3-d]pyrimidinyl, each of which is optionally substituted at a carbon atom at the 5-, 6-, 7-, and 8-positions with one or two groups independently selected from alkyl, alkoxy, halo, hydroxy, heterocycloalkylalkyloxy, heterocycloalkyl, and heterocycloalkyl substituted with alkyl; or $R^2$ and $R^3$ together with the pyrimidinyl to which they are attached form a 6,7-dihydro-5H-cyclopenta[d]pyrimidinyl, 5,6,7,8-tetrahydroquinazolinyl, or 6,7,8,9-tetrahydro-5H-cyclohepta[d]pyrimidinyl; or $R^2$ and $R^3$ together with the pyrimidinyl to which they are attached form a 5,6,7,8-tetrahydropyrido[3,2-d]pyrimidinyl, 5,6,7,8-tetrahydropyrido[4,3-d]pyrimidinyl, 5,6,7,8-tetrahydropyrido[3,4-d]pyrimidinyl, or 5,6,7,8-tetrahydropyrido[2,3-d]pyrimidinyl, each of which is optionally substituted at the 5-, 6-, 7-, and 8-positions with one or two groups independently selected from alkyl, alkoxycarbonyl, benzyloxycarbonyl, and optionally substituted phenylalkyl;

each $R^6$, when $R^6$ is present, is independently selected from alkyl, alkoxy, amino, alkylamino, dialkylamino, halo, haloalkyl, haloalkoxy, halophenyl, aminocarbonyl, alkylaminocarbonyl, dialkylaminocarbonyl, hydroxyalkyl, alkoxycarbonyl, aminoalkyl, alkylaminoalkyl, dialkylaminoalkyl, aminoalkylamino, alkylaminoalkylamino, dialkylaminoalkylamino, alkyloxyalkylamino, heterocycloalkyl, and heterocycloalkylalkyl where the heterocycloalkyl, either alone or as part of heterocycloalkylalkyl, is optionally substituted with alkyl or alkoxycarbonyl;

$R^{40}$ is hydrogen or alkyl;

$R^{50}$ is selected from

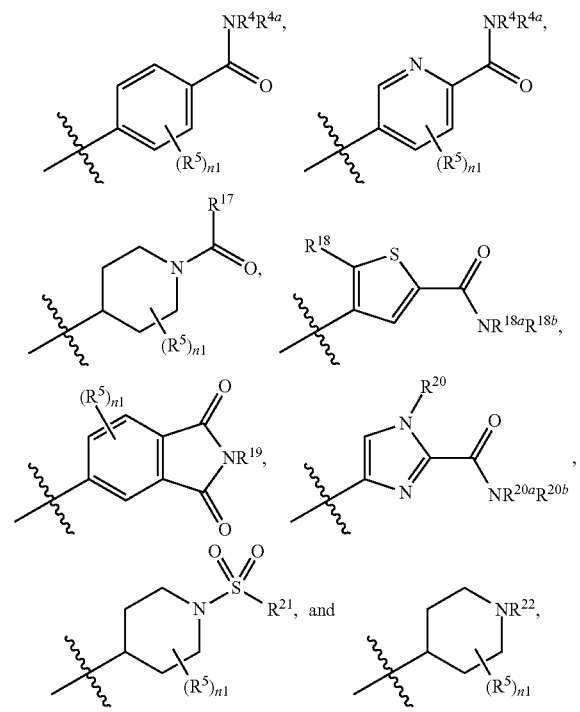

n1 is 0, 1, or 2;

each $R^5$, when $R^5$ is present, is independently alkyl, hydroxy, alkoxy, amino, alkylamino, dialkylamino, halo, nitro, heterocycloalkyl, heterocycloalkylamino, or heterocycloalkylalkyloxy; where each heterocycloalkyl, either alone or as part of another group in $R^5$, is independently optionally substituted with alkyl or alkoxycarbonyl;

$R^{4a}$ is hydrogen or alkyl;

$R^4$ is heteroaryl substituted with one $R^8$ and additionally substituted with 1 or 2 $R^{8a}$; $R^4$ is phenyl substituted with one $R^{29}$ and additionally substituted with 1 or 2 $R^{9a}$; $R^4$ is cycloalkyl optionally substituted with one or two groups independently selected from alkyl, hydroxy, alkoxy, amino, alkylamino, and dialkylamino; or $R^4$ is heterocycloalkyl optionally substituted with alkyl or alkoxycarbonyl;

R$^{17}$ is cycloalkyl, heterocycloalkyl (optionally substituted with one or two groups selected from alkyl and alkoxycarbonyl), phenylalkylamino, phenylalkyl, or phenyl; and where each phenyl, either alone or as part of a group in R$^{17}$, is substituted with 1, 2, or 3 R$^{9a}$;

R$^{18}$ is hydrogen, halo, or alkyl;

R$^{18a}$ is hydrogen or alkyl;

R$^{18b}$ is heteroaryl substituted with 1, 2, or 3 R$^{8a}$ or R$^{18b}$ is phenyl substituted with 1, 2, or 3 R$^{9a}$;

R$^{19}$ is phenyl substituted with 1, 2, or 3 R$^{9a}$ or R$^{19}$ is heteroaryl substituted with 1, 2, or 3 R$^{8a}$;

R$^{20}$ is hydrogen, alkyl, alkylcarbonyl, alkylsulfonyl, or alkoxycarbonyl;

R$^{20a}$ is hydrogen or alkyl;

R$^{20b}$ is heteroaryl substituted with 1, 2, or 3 R$^{8a}$ or R$^{20b}$ is phenyl substituted with 1, 2, or 3 R$^{9a}$;

R$^{21}$ is phenyl substituted with 1, 2, or 3 R$^{9a}$; or R$^{21}$ is heteroaryl substituted with 1, 2, or 3 R$^{8a}$; or R$^{21}$ is heterocycloalkyl optionally substituted with alkyl or alkoxycarbonyl;

R$^{22}$ is phenyl substituted with 1, 2, or 3 R$^{9a}$ or R$^{22}$ is heteroaryl substituted with 1, 2, or 3 R$^{8a}$;

each R$^8$ is independently alkyl, cycloalkyl, phenylalkyloxyalkyl, or R$^{9b}$;

each R$^{8a}$ is independently hydrogen, halo, or R$^8$;

each R$^{9a}$ is independently hydrogen, R$^{9b}$, or R$^{9c}$;

R$^{29}$ is R$^{9b}$ or R$^{9c}$; provided that R$^{29}$ is R$^{9b}$ when R$^1$ is heterocycloalkyl, when R$^1$ is unsubstituted phenyl, and when R$^1$ is phenyl substituted with 1, 2, or 3 R$^6$ independently selected from alkyl, halo, alkoxy, hydroxyalkyl, aminoalkyl, and alkoxycarbonyl;

each R$^{9b}$, when R$^{9b}$ is present, is independently cyano, alkyl substituted with one or two R$^{11}$; amino; alkylamino; dialkylamino; optionally substituted heterocycloalkyl; optionally substituted heterocycloalkylalkyloxy; aminoalkyloxy; alkylaminoalkyloxy; dialkylaminoalkyloxy; optionally substituted heteroaryl; cyano; —C(O)R$^{14}$; —CR$^{14a}$(=NR$^{14b}$); —C(=NR$^{24}$)R$^{24a}$; —S(O)$_2$NR$^{13}$R$^{13a}$; —NR$^{23}$C(O)R$^{23a}$ or —C(O)NR$^{12}$R$^{12a}$;

each R$^{9c}$, when R$^{9c}$ is present, is independently alkyl, haloalkyl, hydroxyalkyl, halo, hydroxy, alkoxy, cyano, nitro, or phenylcarbonyl;

each R$^{11}$ is independently selected from hydroxy, —NR$^{15}$R$^{15a}$ optionally substituted heteroaryl, optionally substituted heterocycloalkyl, and optionally substituted cycloalkyl;

R$^{12}$ is hydrogen or alkyl; and R$^{12a}$ is hydrogen, hydroxy, alkoxy, alkyl, aminoalkyl, alkylaminoalkyl, dialkylaminoalkyl, hydroxyalkyl, optionally substituted heterocycloalkyl, optionally substituted heterocycloalkylalkyl, or optionally substituted heteroaryl; or R$^{12}$ and R$^{12a}$ together with the nitrogen to which they are attached form a heterocycloalkyl optionally substituted with 1, 2, or 3 groups independently selected from alkyl, hydroxyalkyl, haloalkyl, alkylcarbonyl, alkoxycarbonyl, optionally substituted cycloalkyl, optionally substituted cycloalkylalkyl, optionally substituted heteroaryl, optionally substituted heteroarylalkyl, optionally substituted phenyl, and optionally substituted phenylalkyl;

R$^{13}$ is hydrogen or alkyl;

R$^{13a}$ is alkyl, aminoalkyl, alkylaminoalkyl, or dialkylaminoalkyl;

each R$^{14}$ is independently hydrogen, alkyl, hydroxy, alkoxy, optionally substituted heteroarylalkyl, or optionally substituted heterocycloalkylalkyl;

each R$^{14a}$ is hydrogen or alkyl; and R$^{14b}$ is alkoxy, amino, alkylamino, dialkylamino, or optionally substituted heterocycloalkyl;

R$^{15}$ is hydrogen, alkyl, alkoxyalkyl, hydroxyalkyl, or haloalkyl;

R$^{15a}$ is hydrogen, alkyl, alkoxyalkyl, haloalkyl, hydroxyalkyl, carboxyalkyl, aminocarbonylalkyl, alkylaminocarbonylalkyl, dialkylaminocarbonylalkyl, optionally substituted cycloalkyl, or optionally substituted phenylalkyl;

R$^{23}$ is hydrogen or alkyl;

R$^{23a}$ is hydrogen, alkyl, aminoalkyl, alkylaminoalkyl, dialkylaminoalkyl, or optionally substituted heterocycloalkylalkyl; and R$^{24}$ is hydrogen or alkyl, hydroxy, or alkoxy; R$^{24a}$ is hydroxy, alkoxy, amino, alkylamino, or dialkylamino.

A second aspect of the invention is directed to a method of preparing compounds of Formula I which method comprises
(a) reacting an intermediate of formula 5, or a salt thereof:

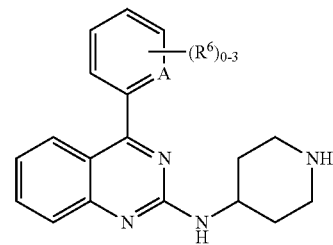

5 where A is CH or N and R$^6$ is as defined in the Summary of the Invention for a Compound of Formula I; with an intermediate of formula R$^{17}$C(O)OH, R$^{21}$S(O)$_2$Cl, or R$^{22c}$Cl where R$^{17}$, R$^{21}$, and R$^{22}$ are as defined in the Summary of the Invention for a Compound of Formula I to yield a Compound of the Invention of Formula 6:

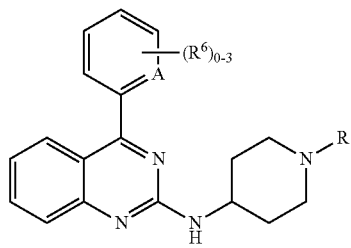

6 where R is —C(O)R$^{17}$; —S(O)$_2$R$^{21}$; or —R$^{22}$; and optionally separating individual isomers; and optionally modifying any of the R$^6$, R$^{17}$, R$^{21}$, and R$^{22}$ groups; and optionally forming a pharmaceutically acceptable salt, hydrate, solvate or combination thereof; or (b) reacting an intermediate of formula 8:

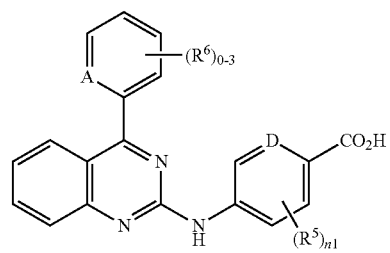

8 where A and D are independently CH or N and R$^6$ is as defined in the Summary of the Invention for a Compound of Formula I; with an intermediate of formula 9:

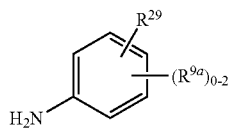

where $R^{9a}$ and $R^{29}$ are as defined in the Summary of the Invention for a Compound of Formula I to yield a Compound of the Invention of Formula XI:

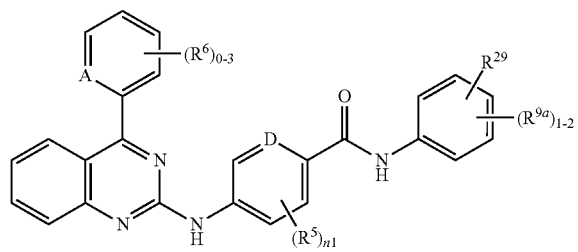

and optionally separating individual isomers; and optionally modifying any of the $R^6$, $R^{29}$, and $R^{9a}$ groups; and optionally forming a pharmaceutically acceptable salt, hydrate, solvate or combination thereof; or (c) reacting an intermediate of formula 8a:

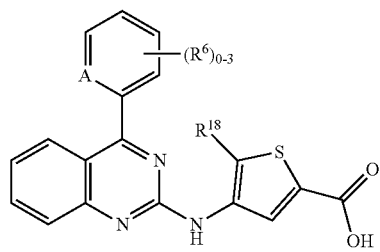

where A is CH or N, $R^6$ and $R^{18}$ as defined in the Summary of the Invention for a Compound of Formula I; with an intermediate of formula $NHR^{18a}R^{18b}$ yield a Compound of the Invention of formula 8d:

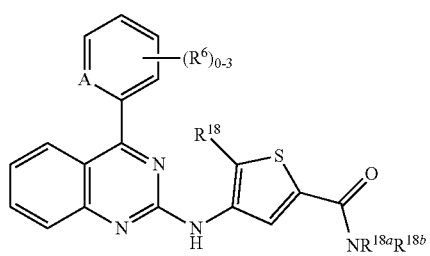

where $R^{18a}$ and $R^{18b}$ are as defined in the Summary of the Invention for a Compound of Formula I and optionally separating individual isomers; and optionally modifying any of the $R^6$, $R^{18}$, and $R^{18b}$ groups; and optionally forming a pharmaceutically acceptable salt, hydrate, solvate or combination thereof; or (d) reacting an intermediate of formula 8b:

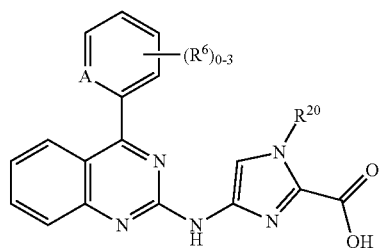

where A is CH or N, $R^6$ and $R^{20}$ as defined in the Summary of the Invention for a Compound of Formula I; with an intermediate of formula $NHR^{20a}R^{20b}$ to yield a Compound of formula 8e

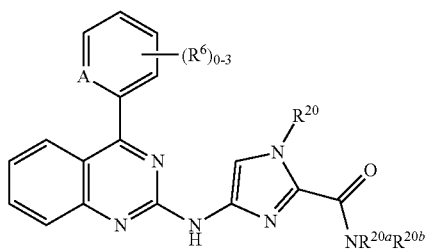

where $R^{20a}$ and $R^{20b}$ are as defined in the Summary of the Invention for a Compound of Formula I; and optionally separating individual isomers; and optionally modifying any of the $R^6$ and $R^{20b}$ groups; and optionally forming a pharmaceutically acceptable salt, hydrate, solvate or combination thereof; or (e) reacting an intermediate of formula 11:

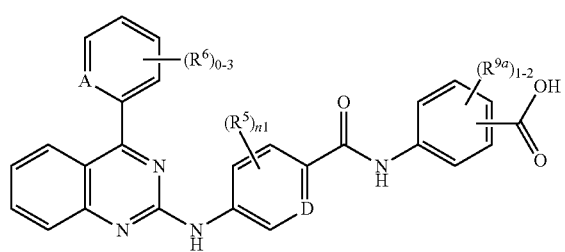

where A and D are independently CH or N, and $R^{9a}$ and $R^6$ are as defined in the Summary of the Invention for a Compound of Formula I; with an intermediate of formula $NHR^{12}R^{12a}$ to yield a Compound of the Invention according to formula 8f

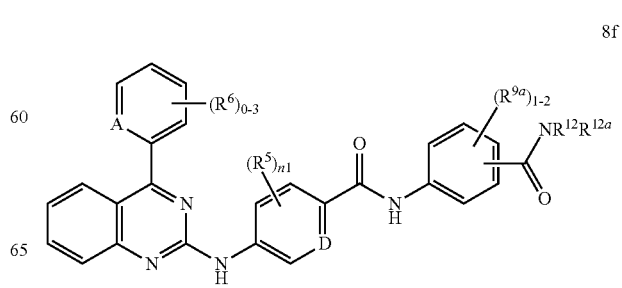

where $R^{12}$ and $R^{12b}$ are as defined in the Summary of the Invention for a Compound of Formula I; and optionally separating individual isomers; and optionally modifying any of the $R^6$, $R^{9a}$, and $R^{12b}$ groups; and optionally forming a pharmaceutically acceptable salt, hydrate, solvate or combination thereof; or (f) reacting an intermediate of formula 13:

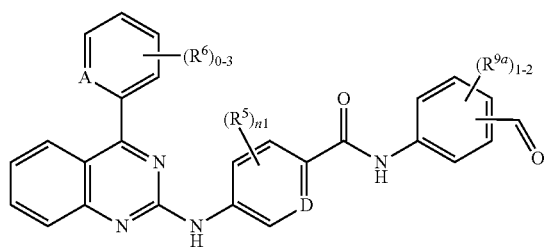

13 where A and D are independently CH or N, and $R^{9a}$ and $R^6$ are as defined in the Summary of the Invention for a Compound of Formula I; with an intermediate of formula $NHR^{15}R^{15a}$ to yield a Compound of the Invention of Formula XII:

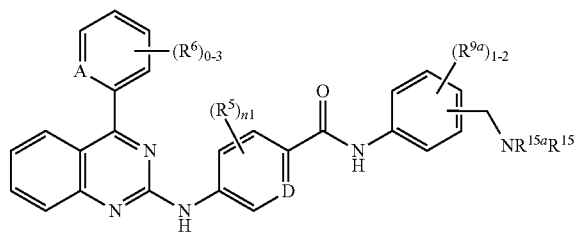

XII where $R^{15}$ and $R^{15a}$ are as defined in the Summary of the Invention for a Compound of Formula I; and optionally separating individual isomers; and optionally modifying any of the $R^6$, $R^{9a}$, and $R^{15}$ groups; and optionally forming a pharmaceutically acceptable salt, hydrate, solvate or combination thereof; or (g) reacting an intermediate of formula 15a:

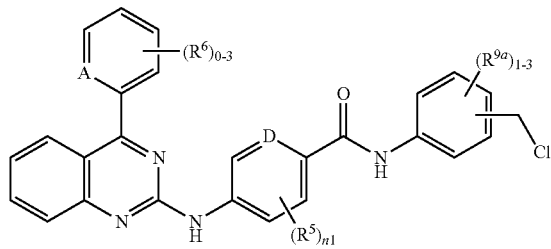

15a where A and D are independently CH or N, and $R^{9a}$ and $R^6$ are as defined in the Summary of the Invention for a Compound of Formula I; with an intermediate of formula $NH_2R^{15}$ to yield a Compound of the Invention of Formula XIII:

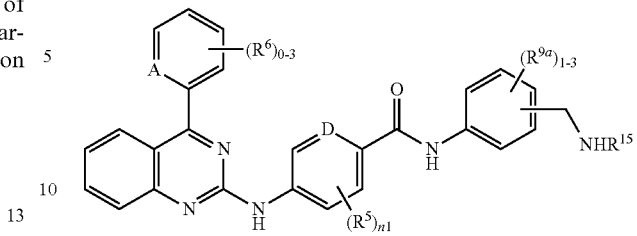

XIII where $R^{15}$ is as defined in the Summary of the Invention for a Compound of Formula I; and optionally separating individual isomers; and optionally modifying any of the $R^6$, $R^{9a}$, and $R^{15}$ groups; and optionally forming a pharmaceutically acceptable salt, hydrate, solvate or combination thereof; or (h) reacting an intermediate of formula 23:

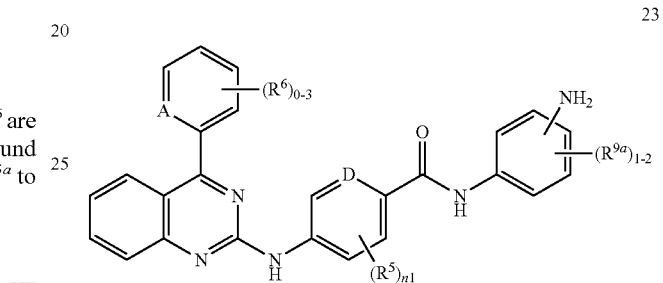

23 where A and D are independently CH or N, and $R^{9a}$ and $R^6$ are as defined in the Summary of the Invention for a Compound of Formula I; with an intermediate of formula $R^{23a}C(O)OH$ or $R^{23a}C(O)Cl$ where $R^{23a}$ is as defined in the Summary of the Invention for a Compound of Formula I to yield a Compound of the Invention of Formula XIV

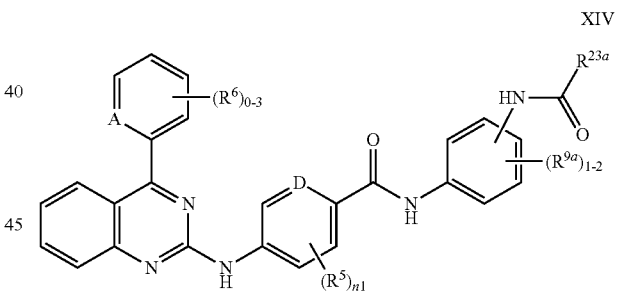

XIV and optionally separating individual isomers; and optionally modifying any of the $R^6$, $R^{9a}$, and $R^{23a}$ groups; and optionally forming a pharmaceutically acceptable salt, hydrate, solvate or combination thereof; or (i) reacting an intermediate of formula 26:

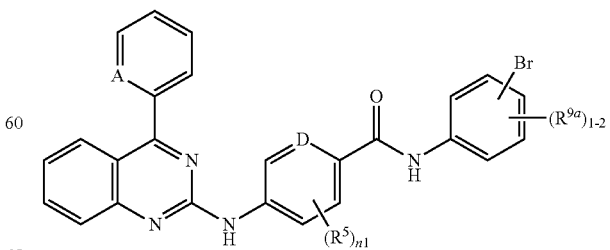

26 where A and D are independently CH or N, and $R^{9a}$ and $R^6$ are as defined in the Summary of the Invention for a Compound of Formula I; with an intermediate of formula R"B(OH)$_2$ where R" is optionally substituted heteroaryl to yield a Compound of the Invention of Formula XV:

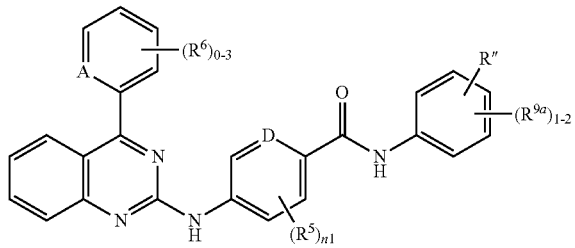

XV and optionally separating individual isomers; and optionally modifying any of the R$^6$, R$^{9a}$, and R" groups; and optionally forming a pharmaceutically acceptable salt, hydrate, solvate or combination thereof; or (j) reacting an intermediate of formula 28

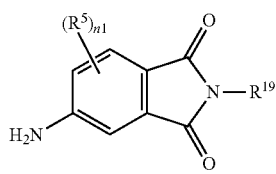

28 where R$^{19}$ is as defined in the Summary of the Invention for a Compound of Formula I; with an intermediate of formula 17

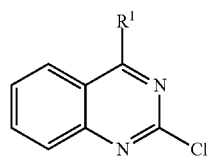

17 where R$^1$ is phenyl or heteroaryl, each of which is optionally substituted with 1, 2, or 3 R$^6$ where R$^6$ is as defined in the Summary of the Invention for a Compound of Formula I to yield a Compound of the Invention of Formula VII

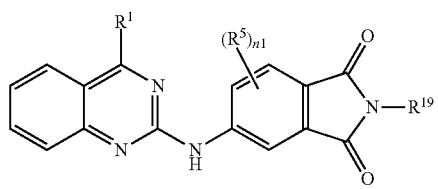

VII and optionally separating individual isomers; and optionally modifying any of the R$^6$, R$^1$, and R$^{19}$ groups; and optionally forming a pharmaceutically acceptable salt, hydrate, solvate or combination thereof; or (k) reacting an intermediate of formula 31

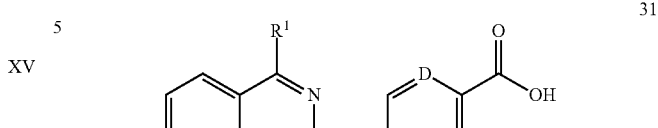

31 where R$^1$ is cycloalkyl, and D is CH or N; with an intermediate of formula 9 as defined above to yield a Compound of the Invention of Formula XVI

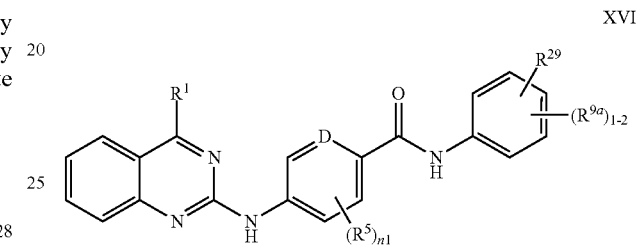

XVI where R$^{29}$ and R$^{9a}$ are as defined in the Summary of the Invention for a Compound of Formula I; and optionally separating individual isomers; and optionally modifying any of the R$^6$, R$^1$, R$^{9a}$, and R$^{29}$ groups; and optionally forming a pharmaceutically acceptable salt, hydrate, solvate or combination thereof; or (l) reacting an intermediate of formula 33

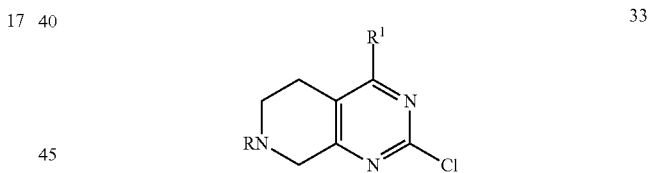

33 where R$^1$ is phenyl or heteroaryl each of which is optionally substituted with 1, 2, or 3 R$^6$ and R is alkyl, alkoxycarbonyl, benzyloxycarbonyl, and optionally substituted phenylalkyl with an intermediate of formula 34

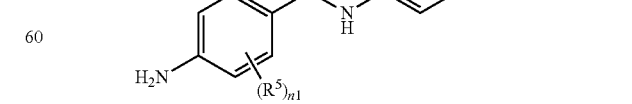

34 where R$^{29}$ and R$^{9a}$ are as defined in the Summary of the Invention for a Compound of Formula I to yield a Compound of the Invention of Formula XVIIa XVIIa

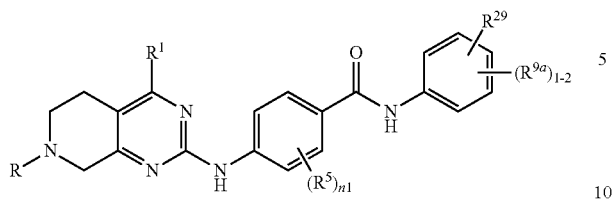

and optionally separating individual isomers; and optionally modifying any of the R, $R^6$, $R^1$, $R^{9a}$, and $R^{29}$ groups; and optionally forming a pharmaceutically acceptable salt, hydrate, solvate or combination thereof.

A third aspect of the invention is directed to a method of treating a disease mediated by a protein in the Hedgehog pathway, the method comprising administering to a patient having the disease a therapeutically effective amount of a compound of Formula I or a single isomer thereof; where the compound is optionally as a pharmaceutically acceptable salt, hydrate, solvate or combination thereof, and, optionally, a pharmaceutically acceptable carrier, excipient, or diluent.

A fourth aspect of the invention is directed to a method of treating a disease mediated by a protein in the Hedgehog pathway, the method comprising administering to a patient having the disease a therapeutically effective amount of a compound of Formula I or a single isomer thereof; where the compound is optionally as a pharmaceutically acceptable salt, hydrate, solvate or combination thereof and, optionally, a pharmaceutically acceptable carrier, excipient, or diluent in combination with an anticancer agent.

A fifth aspect of the Invention is directed to a Compound of Formula XX:

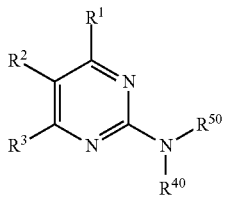

XX or a single isomer thereof; where the compound is optionally as a pharmaceutically acceptable salt, hydrate, solvate or combination thereof, wherein
$R^1$ is alkyl, cycloalkyl, phenyl, heteroaryl, or heterocycloalkyl where the cycloalkyl, phenyl, heteroaryl, and heterocycloalkyl are independently optionally substituted with 1, 2, or 3 $R^6$;
$R^2$ and $R^3$ together with the carbons to which they are attached form phenyl; wherein the phenyl is optionally substituted with one or two groups independently selected from alkyl, alkoxy, halo, hydroxy, heterocycloalkylalkyloxy, and heterocycloalkyl which is optionally substituted with alkyl;
each $R^6$, when $R^6$ is present, is independently selected from alkyl, alkoxy, amino, alkylamino, dialkylamino, aminoalkyl, alkylaminoalkyl, dialkylaminoalkyl, aminoalkylamino, alkylaminoalkylamino, dialkylaminoalkylamino, alkyloxyalkylamino, halo, haloalkyl, haloalkoxy, halophenyl, aminocarbonyl, alkylaminocarbonyl, dialkylaminocarbonyl, alkoxycarbonyl, and heterocycloalkylalkyl where the heterocycloalkyl is optionally substituted with alkyl or alkoxycarbonyl;

$R^{40}$ is hydrogen or alkyl;
$R^{50}$ is selected from

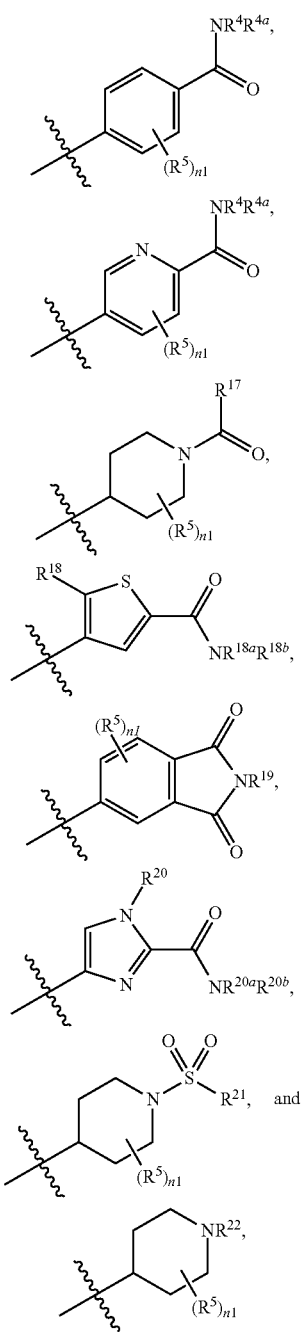

$R^4$ is heteroaryl optionally substituted with 1, 2, or 3 $R^8$; phenyl substituted with $R^9$ and optionally additionally substituted with 1 or 2 $R^{9a}$; cycloalkyl or heterocycloalkyl, where the cycloalkyl is optionally substituted with alkyl, hydroxy, alkoxy, amino, alkylamino, or dialkylamino and where the heterocycloalkyl is optionally substituted with alkyl or alkoxycarbonyl;
$R^{4a}$ is hydrogen or alkyl;
n1 is 0, 1, or 2;
each $R^5$, when $R^5$ is present, is alkyl, hydroxy, alkoxy, amino, alkylamino, dialkylamino, halo, nitro, heterocycloalkyl, heterocycloalkylamino, or heterocycloalkylalkyloxy; where each heterocycloalkyl, either alone or as part of another group in $R^5$, is independently optionally substituted with alkyl or alkoxycarbonyl;

$R^{17}$ is phenylalkylamino, cycloalkyl, heterocycloalkyl optionally substituted with alkyl or alkoxycarbonyl, phenylalkyl, or phenyl; and wherein each phenyl, either alone or as part of a group in $R^{17}$, is optionally substituted with 1, 2, or 3 $R^9$;

$R^{18}$ is hydrogen, halo, or alkyl;

$R^{18a}$ is hydrogen or alkyl;

$R^{18b}$ is heteroaryl optionally substituted with 1, 2, or 3 $R^8$ or $R^{18b}$ is phenyl optionally substituted with 1, 2, or 3 $R^9$;

$R^{19}$ is phenyl optionally substituted with 1, 2, or 3 $R^9$ or $R^{19}$ is heteroaryl optionally substituted with 1, 2, or 3 $R^8$;

$R^{20}$ is hydrogen, alkyl, alkylcarbonyl, alkylsulfonyl, or alkoxycarbonyl;

$R^{20a}$ is hydrogen or alkyl;

$R^{20b}$ is phenyl optionally substituted with 1, 2, or 3 $R^9$;

$R^{21}$ is phenyl optionally substituted with 1, 2, or 3 $R^9$, or $R^{21}$ is heteroaryl optionally substituted with 1 to 3 $R^8$, or $R^{21}$ is heterocycloalkyl optionally substituted with alkyl or alkoxycarbonyl;

$R^{22}$ is phenyl optionally substituted with 1, 2, or 3 $R^9$ or heteroaryl optionally substituted with 1, 2, or 3 $R^8$;

each $R^8$, when $R^8$ is present, is independently selected from alkyl, cycloalkyl, hydroxyalkyl, and phenylalkyloxyalkyl;

each $R^9$, when $R^9$ is present, is independently halo; alkoxy; alkyl optionally substituted with one or two $R^{11}$; optionally substituted phenylcarbonyl; hydroxy; hydroxyalkyl, amino; alkylamino; dialkylamino; optionally substituted heterocycloalkyl; optionally substituted heterocycloalkylalkyloxy; aminoalkyloxy; alkylaminoalkyloxy; dialkylaminoalkyloxy; optionally substituted heteroaryl; nitro; cyano; —C(O)$R^{14}$; —C(N$R^{14a}$)$R^{14b}$; —S(O)$_2$N$R^{13}R^{13a}$; —N$R^{16}$C(O)$R^{16a}$; or —C(O)N$R^{12}R^{12a}$, wherein each $R^{11}$, when $R^{11}$ is present, is independently selected from hydroxy, —N$R^{15}R^{15a}$ optionally substituted heteroaryl, optionally substituted heterocycloalkyl, and optionally substituted cycloalkyl;

$R^{15}$ is hydrogen, alkyl, alkoxyalkyl, hydroxyalkyl, or haloalkyl;

$R^{15a}$ is hydrogen, alkyl, alkoxyalkyl, haloalkyl, hydroxyalkyl, carboxyalkyl, aminocarbonyl, alkylaminocarbonyl, dialkylaminocarbonyl, optionally substituted cycloalkyl, or optionally substituted phenylalkyl;

$R^{12}$ is hydrogen or alkyl; and $R^{12a}$ is hydrogen, hydroxy, alkoxy, alkyl, aminoalkyl, alkylaminoalkyl, dialkylaminoalkyl, hydroxyalkyl, optionally substituted heterocycloalkyl, optionally substituted heterocycloalkylalkyl, or optionally substituted heteroaryl; or $R^{12}$ and $R^{12a}$ together with the nitrogen to which they are attached form a heterocycloalkyl optionally substituted with 1, 2, or 3 groups independently selected from alkyl, hydroxyalkyl, haloalkyl, alkylcarbonyl, alkoxycarbonyl, optionally substituted cycloalkylalkyl, optionally substituted heteroaryl, optionally substituted heteroarylalkyl, and optionally substituted phenylalkyl;

$R^{13}$ is hydrogen or alkyl;

$R^{13a}$ is alkyl, aminoalkyl, alkylaminoalkyl, or dialkylaminoalkyl;

each $R^{14}$ is independently hydrogen, alkyl, hydroxy, alkoxy, amino, alkylamino, dialkylamino, optionally substituted heteroarylalkyl, or optionally substituted heterocycloalkylalkyl;

each $R^{14a}$ is hydrogen, alkyl, hydroxy, alkoxy, or optionally substituted heterocycloalkyl; $R^{14b}$ is alkoxy, amino, alkylamino, dialkylamino, or optionally substituted heterocycloalkyl;

$R^{16}$ is hydrogen or alkyl;

$R^{16a}$ is hydrogen, alkyl, aminoalkyl, alkylaminoalkyl, dialkylaminoalkyl or optionally substituted heterocycloalkylalkyl; and $R^{9a}$ is $R^9$.

A sixth aspect of the Invention is directed to a Compound of Formula XXI:

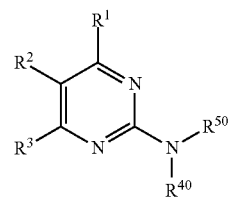

XXI or a single isomer thereof; where the compound is optionally as a pharmaceutically acceptable salt, hydrate, solvate or combination thereof, wherein:

$R^1$ is alkyl, cycloalkyl, phenyl, heteroaryl, or heterocycloalkyl where the cycloalkyl, phenyl, heteroaryl, and heterocycloalkyl are independently optionally substituted with 1, 2, or 3 $R^6$;

$R^2$ and $R^3$ together with the carbons to which they are attached form a benzo group optionally substituted with one or two groups independently selected from alkyl, alkoxy, halo, hydroxy, heterocycloalkylalkyloxy, heterocycloalkyl, and heterocycloalkyl substituted with alkyl; or $R^2$ and $R^3$ together with the carbons to which they are attached form a pyrido group optionally substituted with one or two groups independently selected from alkyl, alkoxy, halo, hydroxy, heterocycloalkylalkyloxy, heterocycloalkyl, and heterocycloalkyl substituted with alkyl; or $R^2$ and $R^3$ together with the carbons to which they are attached form a piperidino group optionally substituted with one or two groups independently selected from alkyl, alkoxycarbonyl, benzyloxycarbonyl, or phenylalkyl each $R^6$, when $R^6$ is present, is independently selected from alkyl, alkoxy, amino, alkylamino, dialkylamino, halo, haloalkyl, haloalkoxy, halophenyl, aminocarbonyl, alkylaminocarbonyl, dialkylaminocarbonyl, hydroxyalkyl, alkoxycarbonyl, aminoalkyl, alkylaminoalkyl, dialkylaminoalkyl, aminoalkylamino, alkylaminoalkylamino, dialkylaminoalkylamino, alkyloxyalkylamino, heterocycloalkyl, and heterocycloalkylalkyl where the heterocycloalkyl, either alone or as part of heterocycloalkylalkyl, is optionally substituted with alkyl or alkoxycarbonyl;

$R^{40}$ is hydrogen or alkyl;

$R^{50}$ is selected from

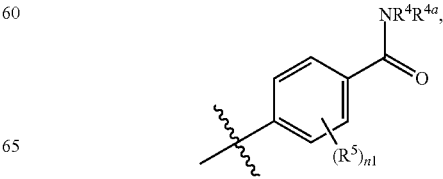

-continued

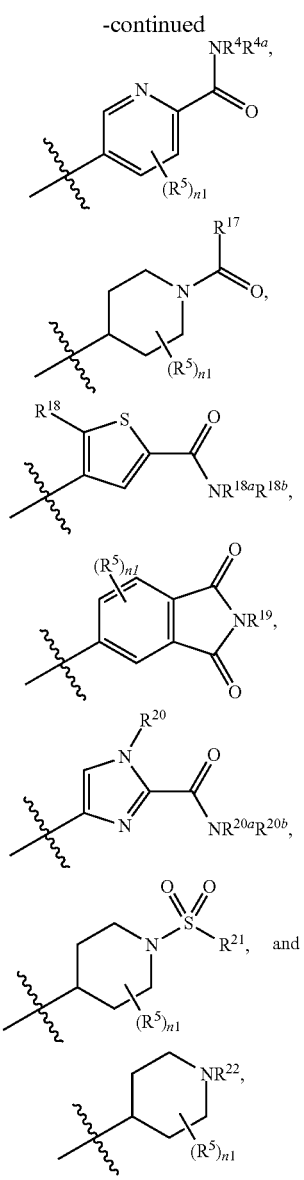

n1 is 0, 1, or 2;

each $R^5$, when $R^5$ is present, is alkyl, hydroxy, alkoxy, amino, alkylamino, dialkylamino, halo, nitro, heterocycloalkyl, heterocycloalkylamino, or heterocycloalkylalkyloxy; where each heterocycloalkyl, either alone or as part of another group in $R^5$, is independently optionally substituted with alkyl or alkoxycarbonyl;

$R^{4a}$ is hydrogen or alkyl;

$R^4$ is heteroaryl substituted with one $R^8$ and additionally substituted with 1 or 2 $R^{8a}$; $R^4$ is phenyl substituted with one $R^{29}$ and additionally substituted with 1 or 2 $R^{9a}$; $R^4$ is cycloalkyl optionally substituted with alkyl, hydroxy, alkoxy, amino, alkylamino, or dialkylamino; or $R^4$ is heterocycloalkyl optionally substituted with alkyl or alkoxycarbonyl;

$R^{17}$ is cycloalkyl, heterocycloalkyl (optionally substituted with alkyl or alkoxycarbonyl), phenylalkylamino, phenylalkyl, or phenyl; and wherein each phenyl, either alone or as part of a group in $R^{17}$, is substituted with 1, 2, or 3 $R^{9a}$;

$R^{18}$ is hydrogen, halo, or alkyl;

$R^{18a}$ is hydrogen or alkyl;

$R^{18b}$ is heteroaryl substituted with 1, 2, or 3 $R^{8a}$ or $R^{18b}$ is phenyl substituted with 1, 2, or 3 $R^{9a}$;

$R^{19}$ is phenyl substituted with 1, 2, or 3 $R^{9a}$ or $R^{19}$ is heteroaryl substituted with 1, 2, or 3 $R^{8a}$;

$R^{20}$ is hydrogen, alkyl, alkylcarbonyl, alkylsulfonyl, or alkoxycarbonyl;

$R^{20a}$ is hydrogen or alkyl;

$R^{20b}$ is phenyl substituted with 1, 2, or 3 $R^{9a}$;

$R^{21}$ is phenyl substituted with 1, 2, or 3 $R^{9a}$, or $R^{21}$ is heteroaryl substituted with 1, 2, or 3 $R^{8a}$, or $R^{21}$ is heterocycloalkyl optionally substituted with alkyl or alkoxycarbonyl;

$R^{22}$ is phenyl substituted with 1, 2, or 3 $R^{9a}$ or $R^{22}$ is heteroaryl substituted with 1, 2, or 3 $R^{8a}$;

each $R^8$ is independently alkyl, cycloalkyl, phenylalkyloxyalkyl, or $R^{9b}$;

each $R^{8a}$ is independently hydrogen, halo, or $R^8$;

each $R^{9a}$ is independently hydrogen, $R^{9b}$ or $R^{9c}$;

$R^{29}$ is $R^{9b}$ or $R^{9c}$ provided that when $R^1$ is unsubstituted phenyl or when $R^1$ is phenyl substituted with 1, 2, or 3 $R^6$ independently selected from alkyl, halo, alkoxy, hydroxyalkyl, aminoalkyl, and alkoxycarbonyl; then $R^{29}$ is $R^{9b}$;

each $R^{9b}$, when $R^{9b}$ is present, is independently alkyl substituted with one or two $R^{11}$; amino; alkylamino; dialkylamino; optionally substituted heterocycloalkyl; optionally substituted heterocycloalkylalkyloxy; aminoalkyloxy; alkylaminoalkyloxy; dialkylaminoalkyloxy; optionally substituted heteroaryl; cyano; —C(O)$R^{14}$; —C$R^{14a}$(=N$R^{14b}$)—C(=N$R^{24}$)$R^{24a}$; —S(O)$_2$N$R^{13}R^{13a}$; —N$R^{23}$C(O)$R^{23a}$; or —C(O)N$R^{12}R^{12a}$;

each $R^{9c}$, when $R^{9c}$ is present, is independently halo, hydroxy, alkoxy, nitro, alkyl, haloalkyl, phenylcarbonyl, or —N$R^{16}$C(O)$R^{16a}$;

each $R^{11}$ is independently selected from hydroxy, N$R^{15}R^{15a}$ optionally substituted heteroaryl, optionally substituted heterocycloalkyl, and optionally substituted cycloalkyl;

$R^{12}$ is hydrogen or alkyl; and $R^{12a}$ is hydrogen, hydroxy, alkoxy, alkyl, aminoalkyl, alkylaminoalkyl, dialkylaminoalkyl, hydroxyalkyl, optionally substituted heterocycloalkyl, optionally substituted heterocycloalkylalkyl, or optionally substituted heteroaryl; or $R^{12}$ and $R^{12a}$ together with the nitrogen to which they are attached form a heterocycloalkyl optionally substituted with 1, 2, or 3 groups independently selected from alkyl, hydroxyalkyl, haloalkyl, alkylcarbonyl, alkoxycarbonyl, optionally substituted cycloalkylalkyl, optionally substituted heteroaryl, optionally substituted heteroarylalkyl, and optionally substituted phenylalkyl;

$R^{13}$ is hydrogen or alkyl;

$R^{13a}$ is alkyl, aminoalkyl, alkylaminoalkyl, or dialkylaminoalkyl;

each $R^{14}$ is independently hydrogen, alkyl, hydroxy, alkoxy, optionally substituted heteroarylalkyl, or optionally substituted heterocycloalkylalkyl;

each $R^{14a}$ is hydrogen or alkyl; and $R^{14b}$ is alkoxy, amino, alkylamino, dialkylamino, or optionally substituted heterocycloalkyl;

$R^{15}$ is hydrogen, alkyl, alkoxyalkyl, hydroxyalkyl, or haloalkyl;

$R^{15a}$ is hydrogen, alkyl, alkoxyalkyl, haloalkyl, hydroxyalkyl, carboxyalkyl, aminocarbonylalkyl, alkylaminocarbonylalkyl, dialkylaminocarbonylalkyl, optionally substituted cycloalkyl, or optionally substituted phenylalkyl;

$R^{16}$ is hydrogen or alkyl;

$R^{16a}$ is hydrogen, alkyl, aminoalkyl, alkylaminoalkyl, dialkylaminoalkyl or optionally substituted heterocycloalkylalkyl;

$R^{23}$ is hydrogen or alkyl; and $R^{23a}$ is aminoalkyl, alkylaminoalkyl, dialkylaminoalkyl, or optionally substituted heterocycloalkylalkyl; and $R^{24}$ is hydrogen or alkyl, hydroxy, or alkoxy; $R^{24a}$ is hydroxy, alkoxy, amino, alkylamino, or dialkylamino.

DETAILED DESCRIPTION OF THE INVENTION

The following paragraphs present a number of embodiments of compounds of the invention. In each instance the embodiment includes both the recited compounds, as well as single isomers thereof, as well as pharmaceutically acceptable salts, hydrates, solvates or combinations thereof.

In one embodiment, the invention provides a compound of Formula I wherein $R^{40}$ is hydrogen and all other groups are as defined in the Summary of the Invention for a Compound of Formula I.

In another embodiment, the invention provides a compound of Formula I, where $R^2$ and $R^3$ together with the pyrimidinyl to which they are attached form a quinazolinyl optionally substituted at the 5-, 6-, 7-, and 8-positions with one or two groups independently selected from alkyl, alkoxy, halo, hydroxy, heterocycloalkylalkyloxy, heterocycloalkyl, and heterocycloalkyl substituted with alkyl; and all other groups are as defined in the Summary of the Invention for a Compound of Formula I. In another embodiment, the invention provides a Compound of Formula I where $R^2$ and $R^3$ together with the pyrimidinyl to which they are attached form a quinazolinyl that is not substituted at the 5-, 6-, 7-, or 8-positions or is substituted at the 5-, 6-, 7-, or 8-position with one group selected from methyl, chloro, methoxy, 4-methylpiperaziny-1-yl, and 3-(morpholin-4-yl)-propyloxy; and all other groups are as defined in the Summary of the Invention for a Compound of Formula I. In another embodiment, the invention provides a Compound of Formula I where $R^2$ and $R^3$ together with the pyrimidinyl to which they are attached form a quinazolinyl that is not substituted at the 5-, 6-, 7-, or 8-position or is substituted at the 5-, 6-, 7-, or 8-position with one chloro; and all other groups are as defined in the Summary of the Invention for a Compound of Formula I. In another embodiment, the invention provides a Compound of Formula I where $R^2$ and $R^3$ together with the pyrimidinyl to which they are attached form a quinazolinyl that is not substituted at the 5-, 6-, 7-, or 8-position and all other groups are as defined in the Summary of the Invention for a Compound of Formula I.

In another embodiment, the invention provides a Compound of Formula I where $R^2$ and $R^3$ together with the pyrimidinyl to which they are attached form a pyrido[3,2-d]pyrimidinyl, pyrido[4,3-d]pyrimidinyl, pyrido[3,4-d]pyrimidinyl, or pyrido[2,3-d]pyrimidinyl, each of which is optionally substituted at a carbon atom at the 5-, 6-, 7-, and 8-positions with one or two groups independently selected from alkyl, alkoxy, halo, hydroxy, heterocycloalkylalkyloxy, heterocycloalkyl, and heterocycloalkyl substituted with alkyl; and all other groups are as defined in the Summary of the Invention for a Compound of Formula I. In another embodiment, the invention provides a Compound of Formula I where $R^2$ and $R^3$ together with the pyrimidinyl to which they are attached form a pyrido[2,3-d]pyrimidinyl that is not substituted at the 5-, 6-, 7-, or 8-position; and all other groups are as defined in the Summary of the Invention for a Compound of Formula I.

In another embodiment, the invention provides a Compound of Formula I where $R^2$ and $R^3$ together with the pyrimidinyl to which they are attached form a 6,7-dihydro-5H-cyclopenta[d]pyrimidinyl, 5,6,7,8-tetrahydroquinazolinyl, or 6,7,8,9-tetrahydro-5H-cyclohepta[d]pyrimidinyl; and all other groups are as defined in the Summary of the Invention for a Compound of Formula I. In another embodiment, the invention provides a Compound of Formula I where $R^2$ and $R^3$ together with the pyrimidinyl to which they are attached form a 6,7-dihydro-5H-cyclopenta[d]pyrimidinyl; and all other groups are as defined in the Summary of the Invention for a Compound of Formula I In another embodiment, the invention provides a Compound of Formula I where $R^2$ and $R^3$ together with the pyrimidinyl to which they are attached form a 5,6,7,8-tetrahydropyrido[3,2-d]pyrimidinyl, 5,6,7,8-tetrahydropyrido[4,3-d]pyrimidinyl, 5,6,7,8-tetrahydropyrido[3,4-d]pyrimidinyl, or 5,6,7,8-tetrahydropyrido[2,3-d]pyrimidinyl, each of which is optionally substituted at the 5-, 6-, 7-, and 8-positions with one or two groups independently selected from alkyl, alkoxycarbonyl, benzyloxycarbonyl, and optionally substituted phenylalkyl; and all other groups are as defined in the Summary of the Invention for a Compound of Formula I. In another embodiment, the invention provides a Compound of Formula I where $R^2$ and $R^3$ together with the pyrimidinyl to which they are attached form a 5,6,7,8-tetrahydropyrido[3,4-d]pyrimidinyl optionally substituted at the 7-position with optionally substituted phenylalkyl; and all other groups are as defined in the Summary of the Invention for a Compound of Formula I. In another embodiment, the invention provides a Compound of Formula I where $R^2$ and $R^3$ together with the pyrimidinyl to which they are attached form a 5,6,7,8-tetrahydropyrido[3,4-d]pyrimidinyl optionally substituted at the 7-position with benzyl; and all other groups are as defined in the Summary of the Invention for a Compound of Formula I. In another embodiment, the invention provides a Compound of Formula I where $R^2$ and $R^3$ together with the pyrimidinyl to which they are attached form a 5,6,7,8-tetrahydropyrido[4,3-d]pyrimidinyl optionally substituted at the 7-position with optionally substituted phenylalkyl; and all other groups are as defined in the Summary of the Invention for a Compound of Formula I. In another embodiment, the invention provides a Compound of Formula I where $R^2$ and $R^3$ together with the pyrimidinyl to which they are attached form a 5,6,7,8-tetrahydropyrido[4,3-d]pyrimidinyl optionally substituted at the 7-position with benzyl; and all other groups are as defined in the Summary of the Invention for a Compound of Formula I.

In another embodiment, the invention provides a Compound of Formula I where $R^1$ is alkyl, cycloalkyl, phenyl, heteroaryl, or heterocycloalkyl where the cycloalkyl, phenyl, heteroaryl, and heterocycloalkyl are optionally substituted with 1, 2, or 3 $R^6$ and all other groups are as defined in the Summary of the Invention for a Compound of Formula I. In another embodiment, the invention provides a compound of Formula I, wherein $R^1$ is alkyl, cycloalkyl, phenyl, or heteroaryl where the cycloalkyl, phenyl, and heteroaryl are optionally substituted with 1, 2, or 3 $R^6$ and all other groups are as defined in the Summary of the Invention for a Compound of Formula I.

In another embodiment, the invention provides a Compound of Formula I, wherein $R^1$ is alkyl and all other groups are as defined in the Summary of the Invention for a Compound of Formula I. In another embodiment, the invention provides a Compound of Formula I where $R^1$ is methyl, ethyl, or isopropyl and all other groups are as defined in the Summary of the Invention for a Compound of Formula I.

In another embodiment, the invention provides a compound of Formula I, wherein $R^1$ is heteroaryl optionally substituted with 1, 2, or 3 $R^6$ where $R^6$ and all other groups are as defined in the Summary of the Invention for a Compound of Formula I. In another embodiment, the invention provides a Compound of Formula I where $R^1$ is pyrrolyl (optionally substituted with alkyl), thienyl, pyridinyl, pyrazolyl (optionally substituted with alkyl), furanyl, oxazolyl (optionally substituted with one or two alkyl), or indolyl (optioanlly substituted with alkyl) and all other groups are as defined in the Summary of the Invention for a Compound of Formula I. In another embodiment, the invention provides a Compound of Formula I where $R^1$ is N-methyl-pyrrol-2-yl, thien-2-yl, pyridin-2-yl, pyrazol-4-yl, N-methyl-pyrazol-4-yl, furan-3-yl, 3,5-dimethyl-1,2-oxazol-4-yl, or indol-5-yl and all other groups are as defined in the Summary of the Invention for a Compound of Formula I.

In another embodiment, the invention provides a compound of Formula I, wherein $R^1$ is heterocycloalkyl optionally substituted with 1, 2, or 3 $R^6$ where $R^6$ and all other groups are as defined in the Summary of the Invention for a Compound of Formula I. In another embodiment, the invention provides a Compound of Formula I where $R^1$ is piperidinyl optionally substituted with alkyl or $R^1$ is morpholinyl and all other groups are as defined in the Summary of the Invention for a Compound of Formula I. In another embodiment, the invention provides a Compound of Formula I where $R^1$ is N-methyl-piperidin-4-yl, or morpholin-4-yl and all other groups are as defined in the Summary of the Invention for a Compound of Formula I.

In another embodiment, the invention provides a compound of Formula I, wherein $R^1$ is cycloalkyl optionally substituted with 1, 2, or 3 $R^6$ where $R^6$ and all other groups are as defined in the Summary of the Invention for a Compound of Formula I. In another embodiment, the invention provides a Compound of Formula I where $R^1$ is cyclopropyl or cyclohexyl and all other groups are as defined in the Summary of the Invention for a Compound of Formula I. In another embodiment, the invention provides a Compound of Formula I where $R^1$ is cyclopropyl and all other groups are as defined in the Summary of the Invention for a Compound of Formula I.

In another embodiment, the invention provides the compound of Formula I, wherein $R^1$ is phenyl optionally substituted with 1, 2, or 3 $R^6$ where $R^6$ and all other groups are as defined in the Summary of the Invention for a Compound of Formula I.

In another embodiment, the invention provides a Compound of Formula I where $R^1$ is unsubstituted phenyl or phenyl substituted with one, two, or three $R^6$ where each $R^6$ is independently halo or alkoxy; and all other groups are as defined in the Summary of the Invention for a Compound of Formula I. In another embodiment, the invention provides a Compound of Formula I where $R^1$ is unsubstituted phenyl or phenyl substituted with one or two $R^6$ selected from fluoro, chloro, bromo, and methoxy and all other groups are as defined in the Summary of the Invention for a Compound of Formula I. In another embodiment, the invention provides a Compound of Formula I where $R^1$ is phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 2,6-difluorophenyl, 2,4-difluorophenyl, 3,5-diflorophenyl, 2,3-dichlorophenyl, 2,4-dichlorophenyl, 3,4-dichlorophenyl, 2,5-dichlorophenyl, 3,5-dichlorophenyl, 2-methoxy-phenyl, 3-methoxy-phenyl, or 4-methoxy-phenyl and all other groups are as defined in the Summary of the Invention for a Compound of Formula I. In another embodiment, the invention provides a Compound of Formula I where $R^1$ is unsubstituted phenyl and all other groups are as defined in the Summary of the Invention for a Compound of Formula I.

In another embodiment, the invention provides a Compound of Formula I where $R^1$ is phenyl substituted with one, two, or three $R^6$ where each $R^6$ is independently haloalkoxy, alkylaminoalkyl, or dialkylaminoalkyl; and all other groups are as defined in the Summary of the Invention for a Compound of Formula I. In another embodiment, the invention provides a Compound of Formula I where $R^1$ is phenyl substituted with one or two $R^6$ selected from trifluoromethoxy and N,N-dimethylaminomethyl and all other groups are as defined in the Summary of the Invention for a Compound of Formula I. In another embodiment, the invention provides a Compound of Formula I where $R^1$ is 4-trifluoromethoxyphenyl, 3-(N,N-dimethylaminomethyl)-phenyl, or 4-(N,N-dimethylaminomethyl)-phenyl and all other groups are as defined in the Summary of the Invention for a Compound of Formula I.

In another embodiment, the invention provides a Compound of Formula I where $R^1$ is phenyl substituted with one or two $R^6$ where each $R^6$ is independently amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, or dialkylaminoalkylamino; and all other groups are as defined in the Summary of the Invention for a Compound of Formula I. In another embodiment, the invention provides a Compound of Formula I where $R^1$ is phenyl substituted with one or two $R^6$ selected from amino, methylamino, dimethylamino, isopropylamino, isobutylamino, aminocarbonyl, methylaminocarbonyl, dimethylaminocarbonyl, morpholin-4-methyl, 4-methyl-piperazin-1-ylmethyl, or 3-(N,N-dimethylamino)-propylamino and all other groups are as defined in the Summary of the Invention for a Compound of Formula I. In another embodiment, the invention provides a Compound of Formula I where $R^1$ is 4-methylamino-phenyl, 4-isopropylaminophenyl, 4-isobutylamino-phenyl, 4-dimethylamino-phenyl, 3-dimethylaminocarbonyl)-phenyl, 4-(aminocarbonyl)-phenyl, 3-(morpholin-4-methyl)-phenyl, 4-(morpholin-4-methyl)-phenyl, 3-(4-methyl-piperazin-1-ylmethyl)-phenyl, or 4-(4-methylpiperazin-1-ylmethyl)-phenyl and all other groups are as defined in the Summary of the Invention for a Compound of Formula I.

In another embodiment, the invention provides a compound of Formula I, wherein n1 is 0 or 1; and all other groups are as defined in the Summary of the Invention for a Compound of Formula I. In another embodiment, the invention provides a Compound of Formula I where n1 is 0 and all other groups are as defined in the Summary of the Invention for a Compound of Formula I.

In another embodiment, the invention provides a compound of Formula I, wherein each $R^5$, when $R^5$ is present, is independently alkyl, alkoxy, amino, halo, heterocycloalkyl, heterocycloalkylamino, or heterocycloalkylalkyloxy; where each heterocycloalkyl, either alone or as part of another group in $R^5$, is independently optionally substituted with alkyl or alkoxycarbonyl; and all other groups are as defined in the Summary of the Invention for a Compound of Formula I. In another embodiment, the invention provides a Compound of Formula I where n1 is 1 and $R^5$ is alkyl, methoxy, amino, halo, morpholinylethyloxy, pyrrolidinylethyloxy, N-methylpiperazinyl, or N-methylpiperidinylamino and all other groups are as defined in the Summary of the Invention for a Compound of Formula I. In another embodiment, the invention provides a Compound of Formula I where n1 is 1 and $R^5$ is halo, alkyl, or amino and all other groups are as defined in the Summary of the Invention for a Compound of Formula I. In another embodiment, the invention provides a Compound of Formula I where n1 is 1 and $R^5$ is bromo, chloro, fluoro, methyl, or amino and all other groups are as defined in the Summary of the Invention for a Compound of Formula I.

In another embodiment, the invention provides a compound of Formula I, where $R^{50}$ is

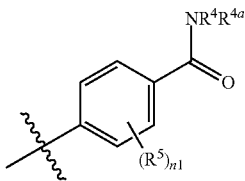

where $R^4$, $R^{4a}$, $R^5$, n1, and all other groups are as defined in the Summary of the Invention for a Compound of Formula I.

In another embodiment, the invention provides a compound of Formula I where $R^{50}$ is

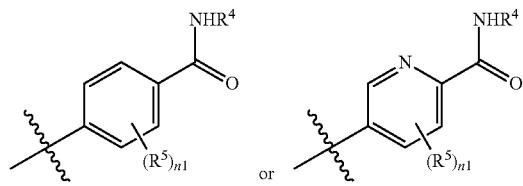

and $R^4$, $R^5$, and n1 are as defined in the Summary of the Invention for a Compound of Formula I.

In another embodiment, the invention provides a compound of Formula Ia,

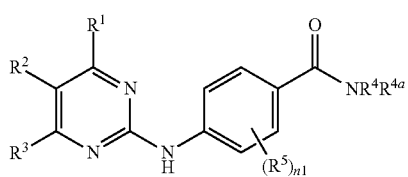

where $R^1$, $R^2$, $R^3$, $R^4$, $R^{4a}$, $R^5$, and n1 are as defined in the Summary of the Invention for a Compound of Formula I.

In another embodiment, the invention provides a compound of Formula Ia where $R^4$ is cycloalkyl optionally substituted with one or two groups independently selected from alkyl, hydroxy, alkoxy, amino, alkylamino, and dialkylamino; n1 is 0 or 1; and $R^1$, $R^2$, $R^3$, $R^5$, $R^{4a}$, and all other groups are as defined in the Summary of the Invention for a Compound of Formula I. In another embodiment, the invention provides a Compound of Formula Ia where n1 is 0 or 1; $R^5$, when $R^5$ is present, is halo or alkyl; $R^{4a}$ is hydrogen; $R^4$ is cyclopropyl; and $R^1$, $R^2$, $R^3$, and all other groups are as defined in the Summary of the Invention for a Compound of Formula I.

In another embodiment, the invention provides a compound of Formula Ia where $R^4$ is cycloalkyl; n1 is 0; $R^{4a}$ is hydrogen; $R^2$ and $R^3$ together with the pyrimidinyl to which they are attached form a quinazolinyl optionally substituted at the 5-, 6-, 7-, or 8-position with one group selected from halo and alkyl; and $R^1$, $R^5$, and all other groups are as defined in the Summary of the Invention for a Compound of Formula I.

In another embodiment, the invention provides a compound of Formula Ia where $R^4$ is cycloalkyl; n1 is 0; $R^{4a}$ is hydrogen; $R^2$ and $R^3$ together with the pyrimidinyl to which they are attached form a quinazolinyl that is not substituted at the 5-, 6-, 7-, or 8-position; and $R^1$, $R^5$, and all other groups are as defined in the Summary of the Invention for a Compound of Formula I.

In another embodiment, the invention provides a compound of Formula Ia, where $R^4$ is heterocycloalkyl optionally substituted with alkyl or alkoxycarbonyl; $R^1$, $R^2$, $R^3$, $R^5$, $R^{4a}$, n1, and all other groups are as defined in the Summary of the Invention for a Compound of Formula I. In another embodiment, the invention provides a Compound of Formula Ia where n1 is 0 or 1; $R^5$, when $R^5$ is present, is halo or alkyl; $R^{4a}$ is hydrogen; $R^4$ is pyrrolidinyl optionally substituted with alkyl; and $R^1$, $R^2$, $R^3$, and all other groups are as defined in the Summary of the Invention for a Compound of Formula I. In another embodiment, the invention provides a Compound of Formula Ia where n1 is 0; $R^{4a}$ is hydrogen; $R^4$ is 4-methyl-pyrrolidinyl; $R^1$, $R^2$, $R^3$, and all other groups are as defined in the Summary of the Invention for a Compound of Formula I.

In another embodiment, the invention provides a compound of Formula Ia, where $R^4$ is heterocycloalkyl optionally substituted with alkyl or alkoxycarbonyl; n1 is 0; $R^{4a}$ is hydrogen; $R^2$ and $R^3$ together with the pyrimidinyl to which they are attached form a quinazolinyl optionally substituted at the 5-, 6-, 7-, or 8-position with one group selected from halo and alkyl; and $R^1$ and all other groups are as defined in the Summary of the Invention for a Compound of Formula I.

In another embodiment, the invention provides a compound of Formula Ia, where $R^4$ is heterocycloalkyl optionally substituted with alkyl or alkoxycarbonyl; n1 is 0; $R^{4a}$ is hydrogen; $R^2$ and $R^3$ together with the pyrimidinyl to which they are attached form a quinazolinyl that is not substituted at the 5-, 6-, 7-, or 8-position; and $R^1$ and all other groups are as defined in the Summary of the Invention for a Compound of Formula I.

In another embodiment, the invention provides a compound of Formula Ia, where $R^4$ is heteroaryl substituted with one $R^8$ and additionally substituted with 1 or 2 $R^{8a}$, or $R^4$ is phenyl substituted with $R^{29}$ and additionally substituted with 1 or 2 $R^{9a}$; and $R^1$, $R^2$, $R^3$, $R^5$, $R^{4a}$, n1, and all other groups are as defined in the Summary of the Invention for a Compound of Formula I.

In another embodiment, the invention provides a compound of Formula Ia, where $R^4$ is heteroaryl substituted with one $R^8$ and additionally substituted with 1 or 2 $R^{8a}$; and $R^1$, $R^2$, $R^3$, $R^5$, $R^{4a}$, n1, and all other groups are as defined in the Summary of the Invention for a Compound of Formula I.

In another embodiment, the invention provides a compound of Formula Ia, where where $R^4$ is heteroaryl substituted with one $R^8$ and additionally substituted with one or two $R^{8a}$; n1 is 0 or 1; and $R^1$, $R^2$, $R^3$, $R^5$, $R^{4a}$, and all other groups are as defined in the Summary of the Invention for a Compound of Formula I. In another embodiment, $R^{4a}$ is hydrogen; n1 is 0; and $R^4$ is heteroaryl substituted with one $R^8$ and additionally substituted with one or two $R^{8a}$; $R^8$ is independently selected from alkyl, cycloalkyl, phenylalkyloxyalkyl, and $R^{9b}$ where the $R^{9b}$ is as defined in the Summary of the invention for a Compound of Formula I; each $R^{8a}$ is independently hydrogen or alkyl; and $R^1$, $R^2$, $R^3$, and all other groups are as defined in the Summary of the Invention for a Compound of Formula I. In another embodiment, $R^{4a}$ is hydrogen; n1 is 0; and $R^4$ is heteroaryl substituted with one $R^8$ and additionally substituted with one or two $R^{8a}$; $R^8$ is independently selected from alkyl, cycloalkyl, phenylalkyloxyalkyl, and hydroxyalkyl; $R^{8a}$ is hydrogen or methyl; and $R^1$, $R^2$, $R^3$, and all other groups are as defined in the Summary of the Invention for a Compound of Formula I. In another embodiment, R⁴ᵃ is hydrogen; n1 is 0; R⁴ is 1,2,3,4-tetrahydroisoquinolinyl substituted with one R⁸ and additionally substituted with one or two R⁸ᵃ; R⁸ is alkyl, hydroxyalkyl, or phenylalkyloxyalkyl; R⁸ᵃ is hydrogen or methyl; and R¹, R², R³, and all other groups are as defined in the Summary of the Invention for a Compound of Formula I. In another embodiment, R⁴ᵃ is hydrogen; n1 is 0; R⁴ is thiadiazolyl optionally substituted with one R⁸ where R⁸ is cycloalkyl; and R¹, R², R³, and all other groups are as defined in the Summary of the Invention for a Compound of Formula I. In another embodiment, R⁴ᵃ is hydrogen; n1 is 0; R⁴ is 2,3,4,5-tetrahydrobenzo[f][1,4]oxazepinyl optionally substituted with one R⁸ where R⁸ is alkyl; and R¹, R², R³, and all other groups are as defined in the Summary of the Invention for a Compound of Formula I. In another embodiment, R⁴ᵃ is hydrogen; n1 is 0; R⁴ is pyrazolyl optionally substituted with one R⁸ where R⁸ is alkyl or cycloalkyl; and R¹, R², R³, and all other groups are as defined in the Summary of the Invention for a Compound of Formula I. In another embodiment, R⁴ᵃ is hydrogen; n1 is 0; R⁴ is 1,2,3,4-tetrahydroisoquinolin-5-yl, 1,2,3,4-tetrahydroisoquinolin-7-yl, 2-methyl-1,2,3,4-tetrahydroisoquinolin-5-yl, 2-(2-hydroxy-ethyl)-1,2,3,4-tetrahydroisoquinolin-5-yl, 2-(2-(phenylmethyloxy)ethyl)-1,2,3,4-tetrahydroisoquinolin-5-yl, 2-methyl-1,2,3,4-tetrahydroisoquinolin-7-yl, 2,3,3-trimethyl-1,2,3,4-tetrahydroisoquinolin-7-yl, 2-cyclopropyl-1,3,4-thiadiazol-5-yl, 4-methyl-2,3,4,5-tetrahydrobenzo[f][1,4]oxazepinyl, or 3-cyclopropyl-pyrazol-5-yl; and R¹, R², R³, and all other groups are as defined in the Summary of the Invention for a Compound of Formula I.

In another embodiment, the invention provides a compound of Formula Ia, where R⁴ is heteroaryl substituted with one R⁸ and additionally substituted with one or two R⁸ᵃ; R² and R³ together with the pyrimidinyl to which they are attached form a quinazolinyl optionally substituted at the 5-, 6-, 7-, or 8-position with one group selected from halo and alkyl; and R¹, R⁴ᵃ, n1, and R⁵ and all other groups are as defined in the Summary of the Invention for a Compound of Formula I.

In another embodiment, the invention provides a compound of Formula Ia, where R⁴ is heteroaryl substituted with one R⁸ and additionally substituted with one or two R⁸ᵃ; R² and R³ together with the pyrimidinyl to which they are attached form a quinazolinyl that is not substituted at the 5-, 6-, 7-, or 8-position; and R¹, R⁴ᵃ, n1, and R⁵ and all other groups are as defined in the Summary of the Invention for a Compound of Formula I.

In another embodiment, the invention provides a compound of Formula Ia where R² and R³ together with the pyrimidinyl to which they are attached form a quinazolinyl that is not substituted at the 5-, 6-, 7-, or 8-position; R⁴ᵃ is hydrogen; n1 is 0; R⁴ is heteroaryl substituted with one R⁸ and additionally substituted with one or two R⁸ᵃ; R⁸ is selected from alkyl, cycloalkyl, phenylalkyloxyalkyl, and R⁹ᵇ where the R⁹ᵇ is as defined in the Summary of the invention for a Compound of Formula I; each R⁸ᵃ is independently hydrogen or alkyl; and R¹ and all other groups are as defined in the Summary of the Invention for a Compound of Formula I. In another embodiment, R² and R³ together with the pyrimidinyl to which they are attached form a quinazolinyl that is not substituted at the 5-, 6-, 7-, or 8-position; R⁴ᵃ is hydrogen; n1 is 0; R⁴ is heteroaryl substituted with one R⁸ and additionally substituted with one or two R⁸ᵃ; R⁸ is selected from alkyl, cycloalkyl, phenylalkyloxyalkyl, and hydroxyalkyl; each R⁸ᵃ is independently hydrogen or alkyl; and R¹ and all other groups are as defined in the Summary of the Invention for a Compound of Formula I.

In another embodiment, the invention provides a compound of Formula Ib

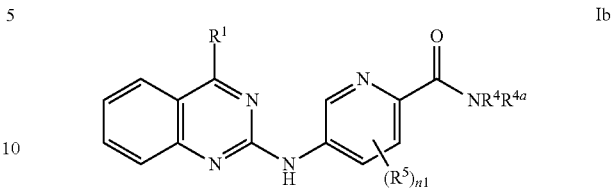

where R¹, R⁴, R⁴ᵃ, R⁵, and n1 are as defined in the Summary of the Invention for a Compound of Formula I.

In another embodiment, the invention provides a Compound of Formula Ib where R⁴ is heteroaryl substituted with one R⁸ and additionally substituted with 1 or 2 R⁸ᵃ or R⁴ is phenyl substituted with R²⁹ and additionally substituted with 1 or 2 R⁹ᵃ; n1 is 0 or 1; R¹, R⁵, R⁴ᵃ, R⁸, R⁸ᵃ, R²⁹, R⁹ᵃ, and all other groups are as defined in the Summary of the Invention for a Compound of Formula Ib. In another embodiment, the compound is of Formula Ib where R⁴ is phenyl substituted with R²⁹ and additionally substituted with 1 or 2 R⁹ᵃ; n1 is 0 or 1; and R⁵, when R⁵ is present, is halo or alkyl; R⁴ᵃ is hydrogen; and R¹, R²⁹, R⁹ᵃ, and all other groups are as defined in the Summary of the Invention for a Compound of Formula Ib.

In another embodiment, the invention provides the compound of Formula Id

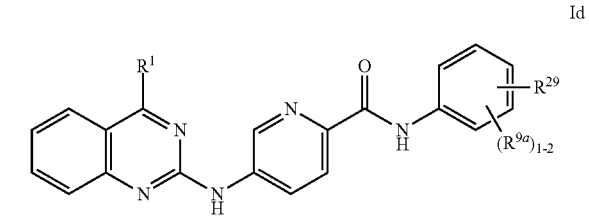

where R¹, R²⁹, and R⁹ᵃ are as defined in the Summary of the Invention for a Compound of Formula I.

In another embodiment, the invention provides a Compound of Formula Id where R¹ is unsubstituted phenyl or is phenyl substituted with one or two R⁶ selected from alkyl, halo, alkoxy, hydroxyalkyl, aminoalkyl, and alkoxycarbonyl; and R²⁹ and R⁹ᵃ, and all other groups are as defined in the Summary of the Invention for a Compound of Formula I. In another embodiment, the invention provides a Compound of Formula Id where R¹ is unsubstituted phenyl or is phenyl substituted with one or two R⁶ selected from alkyl, halo, alkoxy, hydroxyalkyl, aminoalkyl, and alkoxycarbonyl; each R⁹ᵃ is independently hydrogen or R⁹ᶜ; and R²⁹ is R⁹ᵇ; and R⁹ᶜ, R⁹ᵇ, and all other groups are as defined in the Summary of the Invention for a Compound of Formula Id. In another embodiment, the invention provides a Compound of Formula Id where R¹ is unsubstituted phenyl or is phenyl substituted with one or two R⁶ selected from alkyl, halo, alkoxy, hydroxyalkyl, aminoalkyl, and alkoxycarbonyl; one R⁹ᵃ is hydrogen and the other R⁹ᵃ is alkyl and R²⁹ is R⁹ᵇ; and R⁹ᵇ and all other groups are as defined in the Summary of the Invention for a Compound of Formula I. In another embodiment, the invention provides a Compound of Formula Id where R¹ is unsubstituted phenyl or is phenyl substituted with one or two R⁶ selected from alkyl, halo, alkoxy, hydroxyalkyl, aminoalkyl, and alkoxycarbonyl; one $R^{9a}$ is hydrogen and the other $R^{9a}$ is methyl and $R^{29}$ is $R^{9b}$; and $R^{9b}$ and all other groups are as defined in the Summary of the Invention for a Compound of Formula I.

In another embodiment, the invention provides a Compound of Formula Id where $R^1$ is unsubstituted phenyl or is phenyl substituted with one or two $R^6$ selected from alkyl, halo, alkoxy, hydroxyalkyl, aminoalkyl, and alkoxycarbonyl; $R^{29}$ is $R^{9b}$ and $R^{9b}$ is optionally substituted heterocycloalkyl, optionally substituted heterocycloalkylalkyloxy, aminoalkyloxy, alkylaminoalkyloxy, dialkylaminoalkyloxy, optionally substituted heteroaryl, —C(O)$R^{14}$, —N$R^{23}$C(O)$R^{23a}$, —C(O)N$R^{12}R^{12a}$, or alkyl substituted with one or two $R^{11}$; and $R^{9a}$, $R^{14}$, $R^{23}$, $R^{23a}$, $R^{12}$, $R^{12a}$, and all other groups are as defined for a Compound of Formula I.

In another embodiment, the invention provides a Compound of Formula Id where $R^1$ is unsubstituted phenyl or is phenyl substituted with one or two $R^6$ selected from alkyl, halo, alkoxy, hydroxyalkyl, aminoalkyl, and alkoxycarbonyl; $R^{29}$ is $R^{9b}$ and $R^{9b}$ is —N$R^{23}$C(O)$R^{23a}$, dialkylaminoalkyloxy, or alkyl substituted with one or two $R^{11}$; and each $R^{9a}$ is independently hydrogen or alkyl; and $R^{23}$, $R^{23a}$, $R^{11}$, and all other groups are as defined in the Summary of the Invention for a Compound of Formula I. In another embodiment, the invention provides a Compound of Formula Id where $R^1$ is unsubstituted phenyl; $R^{29}$ is $R^{9b}$ and $R^{9b}$ is —N$R^{23}$C(O)$R^{23a}$, dialkylaminoalkyloxy, or alkyl substituted with one or two $R^{11}$; each $R^{9a}$ is independently hydrogen or alkyl; and $R^{23}$, $R^{23a}$, $R^{11}$, and all other groups are as defined in the Summary of the Invention for a Compound of Formula I. In another embodiment, the invention provides a Compound of Formula Id where $R^1$ is unsubstituted phenyl; $R^{29}$ is $R^{9b}$ and $R^{9b}$ is alkyl substituted with one or two $R^{11}$; each $R^{9a}$ is independently hydrogen or alkyl; and $R^{11}$ and all other groups are as defined in the Summary of the Invention for a Compound of Formula I.

In another embodiment, the invention provides a Compound of Formula Id where $R^1$ is unsubstituted phenyl; one $R^{9a}$ is hydrogen and the other $R^{9a}$ is methyl; $R^{29}$ is $R^{9b}$ and $R^{9b}$ is —N$R^{23}$C(O)$R^{23a}$, dialkylaminoalkyloxy, or alkyl substituted with one $R^{11}$ where $R^{11}$ is optionally substituted heterocycloalkyl or $R^{11}$ is —N$R^{15}R^{15a}$ and $R^{23}$ is hydrogen or alkyl and $R^{23a}$ is dialkylaminoalkyl; and $R^{15}$, $R^{15a}$, and all other groups are as defined in the Summary of the Invention for a Compound of Formula I. In another embodiment, the invention provides a Compound of Formula Id where $R^1$ is unsubstituted phenyl; one $R^{9a}$ is hydrogen and the other $R^{9a}$ is methyl; $R^{29}$ is $R^{9b}$ and $R^{9b}$ is —NHC(O)$R^{23a}$ (where $R^{23a}$ is dialkylaminoalkyl), dialkylaminoalkyloxy, or alkyl substituted with one $R^{11}$ where $R^{11}$ is optionally substituted heterocycloalkyl or —N$R^{15}R^{15a}$ where $R^{15}$ is hydrogen, alkyl, alkoxyalkyl, hydroxyalkyl, or haloalkyl and $R^{15a}$ is hydrogen, alkyl, alkoxyalkyl, haloalkyl, or hydroxyalkyl; and all other groups are as defined in the Summary of the Invention for a Compound of Formula I. In another embodiment, the invention provides a Compound of Formula Id where $R^1$ is unsubstituted phenyl; one $R^{9a}$ is hydrogen and the other $R^{9a}$ is methyl; $R^{29}$ is $R^{9b}$ and $R^{9b}$ is alkyl substituted with one $R^{11}$ where $R^{11}$ is optionally substituted heterocycloalkyl or —N$R^{15}R^{15a}$; and $R^{15}$, $R^{15a}$, and all other groups are as defined in the Summary of the Invention for a Compound of Formula I. In another embodiment, the invention provides a Compound of Formula Id where $R^1$ is unsubstituted phenyl; one $R^{9a}$ is hydrogen and the other $R^{9a}$ is methyl; $R^{29}$ is $R^{9b}$ and $R^{9b}$ is alkyl substituted with one $R^{11}$ where $R^{11}$ is —N$R^{15}R^{15a}$ and $R^{15}$ is hydrogen or alkyl and $R^{15a}$ is hydrogen or alkyl; in another example, $R^{15}$ is alkyl and $R^{15a}$ is hydrogen or alkyl; and all other groups are as defined in the Summary of the Invention for a Compound of Formula I.

In another embodiment, the invention provides a Compound of Formula Id where $R^1$ is alkyl or $R^1$ is phenyl substituted with 1 or 2 $R^6$ where each $R^6$ is independently amino, alkylamino, dialkylamino, haloalkyl, haloalkoxy, halophenyl, aminocarbonyl, alkylaminocarbonyl, dialkylaminocarbonyl, alkylaminoalkyl, dialkylaminoalkyl, aminoalkylamino, alkylaminoalkylamino, dialkylaminoalkylamino, alkyloxyalkylamino, heterocycloalkyl, or heterocycloalkylalkyl where the heterocycloalkyl, either alone or as part of heterocycloalkylalkyl, is optionally substituted with alkyl or alkoxycarbonyl; and $R^{29}$, $R^{9a}$ and all other groups are as defined in the Summary of the Invention for a Compound of Formula I.

In another embodiment, the invention provides a Compound of Formula Id where $R^1$ is alkyl or $R^1$ is phenyl substituted with 1 or 2 $R^6$ where each $R^6$ is independently amino, alkylamino, dialkylamino, haloalkyl, haloalkoxy, halophenyl, aminocarbonyl, alkylaminocarbonyl, dialkylaminocarbonyl, dialkylaminoalkyl, aminoalkylamino, alkylaminoalkylamino, dialkylaminoalkylamino, alkyloxyalkylamino, heterocycloalkyl, or heterocycloalkylalkyl; and $R^{29}$, $R^{9a}$ and all other groups are as defined in the Summary of the Invention for a Compound of Formula I.

In another embodiment, the invention provides a Compound of Formula Id where $R^1$ is alkyl or $R^1$ is phenyl substituted with one $R^6$ selected from haloalkoxy, alkylamino, dialkylamino, aminocarbonyl, alkylaminocarbonyl, dialkylaminocarbonyl, heterocycloalkylalkyl optionally substituted on the ring with alkyl, dialkylaminoalkyl, dialkylaminoalkylamino, and alkyloxyalkylamino; each $R^{9a}$ is independently hydrogen or $R^{9c}$; and $R^{29}$ is $R^{9b}$ or $R^{9c}$; and $R^{9b}$, $R^{9c}$, and all other groups are as defined in the Summary of the Invention for a Compound of Formula I. In another embodiment, the invention provides a Compound of Formula Id where $R^1$ is alkyl or $R^1$ is phenyl substituted with one $R^6$ selected from haloalkoxy, alkylamino, dialkylamino, aminocarbonyl, alkylaminocarbonyl, dialkylaminocarbonyl, heterocycloalkylalkyl (optionally substituted on the ring with alkyl), dialkylaminoalkyl, dialkylaminoalkylamino, and alkyloxyalkylamino; one $R^{9a}$ is hydrogen and the other $R^{9a}$ is alkyl; and $R^{29}$ is $R^{9b}$ or $R^{9c}$; and $R^{9b}$, $R^{9c}$, and all other groups are as defined in the Summary of the Invention for a Compound of Formula I. In another embodiment, the invention provides a Compound of Formula Id where $R^1$ is alkyl or $R^1$ is phenyl substituted with one $R^6$ selected from haloalkoxy, alkylamino, dialkylamino, aminocarbonyl, alkylaminocarbonyl, dialkylaminocarbonyl, heterocycloalkylalkyl (optionally substituted on the ring with alkyl), dialkylaminoalkyl, dialkylaminoalkylamino, and alkyloxyalkylamino; one $R^{9a}$ is hydrogen and the other $R^{9a}$ is methyl; $R^{29}$ is $R^{9c}$ where $R^{9c}$ is alkyl; and all other groups are as defined in the Summary of the Invention for a Compound of Formula I. In another embodiment, the invention provides a Compound of Formula Id where $R^1$ is alkyl or $R^1$ is phenyl substituted with one $R^6$ selected from haloalkoxy, alkylamino, dialkylamino, aminocarbonyl, alkylaminocarbonyl, dialkylaminocarbonyl, heterocycloalkylalkyl optionally substituted on the ring with alkyl, dialkylaminoalkyl, dialkylaminoalkylamino, and alkyloxyalkylamino; one $R^{9a}$ is hydrogen and the other $R^{9a}$ is methyl; $R^{29}$ is methyl; and all other groups are as defined in the Summary of the Invention for a Compound of Formula I.

In another embodiment, the invention provides a Compound of Formula I where $R^8$ is alkyl, cycloalkyl, phenylalkyloxyalkyl, or $R^{9b}$; and $R^{9b}$ and all other groups are as defined in the Summary of the Invention for a Compound of Formula I. In another embodiment, the invention provides a Compound of Formula I where $R^8$ is alkyl, cycloalkyl, phenylalkyloxyalkyl, or $R^{9b}$ where $R^{9b}$ is alkyl substituted with one or two $R^{11}$ and $R^{11}$ is hydroxy; and all other groups are as defined in the Summary of the Invention for a Compound of Formula I. In another embodiment, the invention provides a Compound of Formula I where $R^8$ is alkyl, cycloalkyl, hydroxyalkyl, or phenylalkyloxyalkyl; and all other groups are as defined in the Summary of the Invention for a Compound of Formula I. In another embodiment, the invention provides a Compound of Formula I where $R^8$ is methyl, cyclopropyl, hydroxyethyl, 2-(phenylmethyloxy)-ethyl; and all other groups are as defined in the Summary of the Invention for a Compound of Formula I. In another embodiment, the invention provides a Compound of Formula I where $R^8$ is methyl; and all other groups are as defined in the Summary of the Invention for a Compound of Formula I.

In another embodiment, the invention provides a Compound of Formula I where each $R^{8a}$ is independently hydrogen or alkyl; and all other groups are as defined in the Summary of the Invention for a Compound of Formula I. In another embodiment, each $R^{8a}$ is independently hydrogen or methyl; and all other groups are as defined in the Summary of the Invention for a Compound of Formula I.

In another embodiment, the invention provides a Compound of Formula I where $R^4$ is heteroaryl substituted with one $R^8$ and additionally substituted with 1 or 2 $R^{8a}$; and $R^8$, $R^{8a}$, and all other groups are as defined in the Summary of the Invention for a Compound of Formula I. In another embodiment, the invention provides a Compound of Formula I where $R^8$ is alkyl or cycloalkyl and each $R^{8a}$ is independently hydrogen or alkyl; and all other groups are as defined in the Summary of the Invention for a Compound of Formula I.

In another embodiment, the invention is directed to a Compound of Formula I where $R^4$ is phenyl substituted with one $R^{29}$ and additionally substituted with 1 or 2 $R^{9a}$ where each $R^{9a}$ is independently hydrogen or alkyl and all other groups are as defined in the Summary of the Invention for a Compound of Formula I.

In another embodiment, the invention is directed to a Compound of Formula I where $R^4$ is phenyl substituted with one $R^{29}$ and additionally substituted with one $R^{9a}$ where the $R^{9a}$ is $R^{9b}$; and $R^{29}$, $R^{9b}$, and all other groups are as defined in the Summary of the Invention for a Compound of Formula I. In another embodiment, the invention is directed to a Compound of Formula I where $R^4$ is phenyl substituted with one $R^{29}$ and additionally substituted with one $R^{9a}$; $R^{9a}$ is $R^{9b}$ and the $R^{9b}$ is alkyl substituted with one or two $R^{11}$ where $R^{11}$ is hydroxy; and $R^{29}$ and all other groups are as defined in the Summary of the Invention for a Compound of Formula I.

In another embodiment, the invention is directed to a Compound of Formula I where $R^4$ is phenyl substituted with one $R^{29}$ and additionally substituted with one $R^{9a}$; the $R^{9a}$ is $R^{9c}$; and $R^{29}$, $R^{9c}$ and all other groups are as defined in the Summary of the Invention for a Compound of Formula I. In another embodiment, the invention is directed to a Compound of Formula I where $R^4$ is phenyl substituted with one $R^{29}$ and additionally substituted with one $R^{9a}$; the $R^{9a}$ is $R^{9c}$ and $R^{9c}$ is halo, alkyl, or nitro; and $R^{29}$ and all other groups are as defined in the Summary of the Invention for a Compound of Formula I.

In another embodiment, $R^1$ is alkyl, cycloalkyl, or heteroaryl where the cycloalkyl and heteroaryl are independently optionally substituted with 1, 2, or 3 $R^6$; $R^4$ is phenyl substituted with one $R^{29}$ and additionally substituted with 1 or 2 $R^{9a}$; $R^{29}$ is $R^{9c}$; each $R^{9a}$ is independently hydrogen or $R^{9c}$; and $R^6$, $R^{9c}$, and all other groups are as defined in the Summary of the Invention for a compound of Formula I.

In another embodiment, the invention is directed to a Compound of Formula Ic

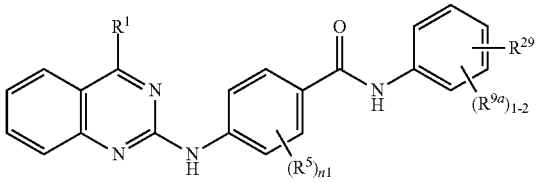

Ic where $R^1$, n1, $R^5$, $R^{29}$, and $R^{9a}$ are as defined in the Summary of the Invention for a Compound of Formula I.

In another embodiment, the invention is directed to a Compound of Formula Ic where $R^1$ is alkyl; n1 is 0 or 1; $R^5$, when $R^5$ is present; is halo, amino, or alkyl; each $R^{9a}$ is independently hydrogen or $R^{9c}$; and $R^{29}$, $R^{9c}$ and all other groups are as defined in the Summary of the Invention for a Compound of Formula I. In another embodiment, $R^1$ is alkyl; n1 is 0 or 1; $R^5$, when $R^5$ is present, is chloro, fluoro, amino, or methyl; each $R^{9a}$ is independently hydrogen or $R^{9c}$; and $R^{29}$, $R^9$ and all other groups are as defined in the Summary of the Invention for a Compound of Formula I. In another embodiment, $R^1$ is alkyl; n1 is 0 or 1; $R^5$, when $R^5$ is present, is chloro, fluoro, amino, or methyl; each $R^{9a}$ is independently hydrogen or $R^{9c}$; and $R^{29}$, and $R^{9c}$ are as defined in the Summary of the Invention for a Compound of Formula I.

In another embodiment, the invention is directed to a Compound of Formula Ic where $R^1$ is alkyl; n1 is 0; $R^{29}$ is $R^{9b}$ where $R^{9b}$ is —$NR^{23}C(O)R^{23a}$, dialkylaminoalkyloxy, or alkyl substituted with one or two $R^{11}$; each $R^{9a}$ is independently hydrogen or alkyl; and $R^{11}$, $R^{23}$, $R^{23a}$, and all other groups are as defined in the Summary of the Invention for a Compound of Formula I. In another embodiment, the invention is directed to a Compound of Formula Ic where $R^1$ is alkyl; n1 is 0; $R^{29}$ is $R^{9b}$ where $R^{9b}$ is —$NR^{23}C(O)R^{23a}$, dialkylaminoalkyloxy, or alkyl substituted with one or two $R^{11}$; each $R^{9a}$ is independently hydrogen or alkyl; each $R^{11}$ is independently selected from —$NR^{15}R^{15a}$ and optionally substituted heterocycloalkyl; $R^{23}$ is hydrogen or alkyl; $R^{23a}$ is dialkylaminoalkyl; and $R^{15}$, $R^{15a}$, and all other groups are as defined in the Summary of the Invention for a Compound of Formula I.

In another embodiment, the invention is directed to a Compound of Formula Ic where $R^1$ is methyl, ethyl, or isopropyl; n1 is 0; $R^{29}$ is $R^{9b}$ where $R^{9b}$ is —$NR^{23}C(O)R^{23a}$, dialkylaminoalkyloxy, or alkyl substituted with one or two $R^{11}$; each $R^{9a}$ is independently hydrogen or alkyl; and $R^{11}$, $R^{23}$, $R^{23a}$, and all other groups are as defined in the Summary of the Invention for a Compound of Formula I. In another embodiment, the invention is directed to a Compound of Formula Ic where $R^1$ is methyl, ethyl, or isopropyl; n1 is 0; $R^{29}$ is $R^{9b}$ where $R^{9b}$ is —$NR^{23}C(O)R^{23a}$, dialkylaminoalkyloxy, or alkyl substituted with one or two $R^{11}$; each $R^{9a}$ is independently hydrogen or alkyl; each $R^{11}$ is independently morpholinyl or —$NR^{15}R^{15a}$ where $R^{15}$ is hydrogen or alkyl and $R^{15a}$ is hydrogen, alkyl, or optionally substituted phenylalkyl; $R^{23}$ is hydrogen; $R^{23a}$ is dialkylaminoalkyl; and all other groups are as defined in the Summary of the Invention for a Compound of Formula I. In another embodiment, the invention is directed to a Compound of Formula Ic where $R^1$ is methyl, ethyl, or isopropyl; n1 is 0; $R^{29}$ is $R^{9b}$ where $R^{9b}$ is alkyl substituted with one or two $R^{11}$; each $R^{9a}$ is independently hydrogen or alkyl; and each $R^{11}$ is independently morpholinyl or —NR$^{15}$R$^{15a}$ where R$^{15}$ is hydrogen or methyl and R$^{15a}$ is hydrogen, methyl, or phenylmethyl; and all other groups are as defined in the Summary of the Invention for a Compound of Formula I.

In another embodiment, the invention is directed to a Compound of Formula Ic where R$^1$ is alkyl; n1 is 0; R$^{29}$ is R$^{9c}$ where R$^{9c}$ is alkyl; each R$^{9a}$ is independently hydrogen or R$^9$ where R$^{9c}$ is alkyl; and all other groups are as defined in the Summary of the Invention for a Compound of Formula I. In another embodiment, the invention is directed to a Compound of Formula Ic where R$^1$ is alkyl; n1 is 0; R$^{29}$ is methyl; one R$^{9a}$ is methyl and the other R$^{9a}$ is hydrogen; and all other groups are as defined in the Summary of the Invention for a Compound of Formula I.

In another embodiment, the invention is directed to a Compound of Formula Ic where R$^1$ is methyl, ethyl, or isopropyl; n1 is 0; R$^{29}$ is R$^{9c}$ where R$^{9c}$ is alkyl; and each R$^{9a}$ is independently hydrogen or R$^{9c}$ where R$^{9c}$ is alkyl; and all other groups are as defined in the Summary of the Invention for a Compound of Formula I. In another embodiment, the invention is directed to a Compound of Formula Ic where R$^1$ is methyl, ethyl, or isopropyl; n1 is 0; R$^{29}$ is methyl; one R$^{9a}$ is hydrogen and the other R$^{9a}$ is methyl; and all other groups are as defined in the Summary of the Invention for a Compound of Formula I.

In another embodiment, the invention is directed to a Compound of Formula Ic where R$^1$ is heteroaryl optionally substituted with one or two R$^6$; n1 is 0 or 1; R$^5$, when R$^5$ is present; is halo, amino, or alkyl; each R$^{9a}$ is independently hydrogen or R$^{9c}$; and R$^6$, R$^{29}$, R$^{9c}$, and all other groups are as defined in the Summary of the Invention for a Compound of Formula I. In another embodiment, the invention is directed to a Compound of Formula Ic where R$^1$ is heteroaryl optionally substituted with one or two R$^6$; n1 is 0 or 1 and R$^5$, when R$^5$ is present, is chloro, fluoro, amino, or methyl; each R$^{9a}$ is independently hydrogen or R$^{9c}$; and R$^6$, R$^{29}$, R$^{9c}$ and all other groups are as defined in the Summary of the Invention for a Compound of Formula I. In another embodiment, R$^1$ is heteroaryl optionally substituted with one or two R$^6$; n1 is 0; each R$^{9a}$ is independently hydrogen or R$^{9c}$; and R$^6$, R$^{29}$, R$^{9c}$ and all other groups are as defined in the Summary of the Invention for a Compound of Formula I.

In another embodiment, the invention is directed to a Compound of Formula Ic where R$^1$ is heteroaryl optionally substituted with one or two R$^6$; n1 is 0; R$^{29}$ is R$^{9b}$ where R$^{9b}$ is —NR$^{23}$C(O)R$^{23a}$, dialkylaminoalkyloxy, or alkyl substituted with one or two R$^{11}$; each R$^{9a}$ is independently hydrogen or alkyl; and R$^6$, R$^{11}$, R$^{23}$, R$^{23a}$, and all other groups are as defined in the Summary of the Invention for a Compound of Formula I. In another embodiment, the invention is directed to a Compound of Formula Ic where R$^1$ is heteroaryl optionally substituted with one or two R$^6$; n1 is 0; R$^{29}$ is R$^{9b}$ where R$^{9b}$ is —NR$^{23}$C(O)R$^{23a}$, dialkylaminoalkyloxy, or alkyl substituted with one or two R$^{11}$; each R$^{11}$ is independently selected from —NR$^{15}$R$^{15a}$ and optionally substituted heterocycloalkyl; R$^{23}$ is hydrogen or alkyl; R$^{23a}$ is dialkylaminoalkyl; each R$^{9a}$ is independently hydrogen or alkyl; and R$^6$, R$^{15}$, R$^{15a}$ and all other groups are as defined in the Summary of the Invention for a Compound of Formula I.

In another embodiment, the invention is directed to a Compound of Formula Ic where R$^1$ is pyrrolyl, thienyl, pyridinyl, pyrazolyl, furanyl, or oxazolyl, each of which is optionally substituted with one or two R$^6$ where R$^6$ is alkyl; n1 is 0; R$^{29}$ is R$^{9b}$ where R$^{9b}$ is —NR$^{23}$C(O)R$^{23a}$, dialkylaminoalkyloxy, or alkyl substituted with one or two R$^{11}$; each R$^{9a}$ is independently hydrogen or alkyl; and R$^{11}$ and all other groups are as defined in the Summary of the Invention for a Compound of Formula I. In another embodiment, the invention is directed to a Compound of Formula Ic where R$^1$ is pyrrolyl, thienyl, pyridinyl, pyrazolyl, furanyl, or oxazolyl, each of which is optionally substituted with one or two R$^6$ where R$^6$ is alkyl; n1 is 0; R$^{29}$ is R$^{9b}$ where R$^{9b}$ is —NR$^{23}$C(O)R$^{23a}$, dialkylaminoalkyloxy, or alkyl substituted with one or two R$^{11}$; each R$^{9a}$ is independently hydrogen or alkyl; each R$^{11}$ is —NR$^{15}$R$^{15a}$ where R$^{15}$ is hydrogen or alkyl and R$^{15a}$ is hydrogen or alkyl; R$^{23}$ is hydrogen or alkyl; R$^{23a}$ is dialkylaminoalkyl; and all other groups are as defined in the Summary of the Invention for a Compound of Formula I. In another embodiment, the invention is directed to a Compound of Formula Ic where R$^1$ is pyrrolyl, thienyl, pyridinyl, pyrazolyl, furanyl, or oxazolyl, each of which is optionally substituted with one or two R$^6$ where R$^6$ is alkyl; n1 is 0; R$^{29}$ is R$^{9b}$ where R$^{9b}$ is —NHC(O)R$^{23a}$, dialkylaminoalkyloxy, or alkyl substituted with one or two R$^{11}$; each R$^{9a}$ is independently hydrogen or alkyl; each R$^{11}$ is —NR$^{15}$R$^{15a}$ where R$^{15}$ is hydrogen or methyl and R$^{15a}$ is hydrogen or methyl; R$^{23a}$ is dialkylaminoalkyl; and all other groups are as defined in the Summary of the Invention for a Compound of Formula I.

In another embodiment, the invention is directed to a Compound of Formula Ic where R$^1$ is heteroaryl optionally substituted with one or two R$^6$; n1 is 0; R$^{29}$ is R$^{9c}$ where R$^9$ is alkyl; each R$^{9a}$ is independently hydrogen or R$^{9c}$ where R$^9$ is alkyl; R$^6$ and all other groups are as defined in the Summary of the Invention for a Compound of Formula I. In another embodiment, the invention is directed to a Compound of Formula Ic where R$^1$ is heteroaryl optionally substituted with one or two R$^6$; n1 is 0; R$^{29}$ is methyl; one R$^{9a}$ is methyl and the other R$^{9a}$ is hydrogen; and all other groups are as defined in the Summary of the Invention for a Compound of Formula I.

In another embodiment, the invention is directed to a Compound of Formula Ic where R$^1$ is pyrrolyl, thienyl, pyridinyl, pyrazolyl, furanyl, or oxazolyl, each of which is optionally substituted with one or two R$^6$ where R$^6$ is alkyl; n1 is 0; R$^{29}$ is R$^{9c}$ where R$^{9c}$ is alkyl; and each R$^{9a}$ is independently hydrogen or R$^{9c}$ where R$^{9c}$ is alkyl; and all other groups are as defined in the Summary of the Invention for a Compound of Formula I. In another embodiment the invention is directed to a Compound of Formula Ic where R$^1$ is pyrrolyl, thienyl, pyridinyl, pyrazolyl, furanyl, or oxazolyl, each of which is optionally substituted with one or two R$^6$ where R$^6$ is alkyl; n1 is 0; R$^{29}$ is methyl; one R$^{9a}$ is hydrogen and the other R$^{9a}$ is methyl; and all other groups are as defined in the Summary of the Invention for a Compound of Formula I.

In another embodiment, the invention is directed to a Compound of Formula Ic where R$^1$ is cycloalkyl; n1 is 0 or 1; R$^5$, when R$^5$ is present, is halo, amino, or alkyl; each R$^{9a}$ is independently hydrogen or R$^{9c}$; and R$^{29}$, R$^{9c}$, and all other groups are as defined in the Summary of the Invention for a Compound of Formula I. In another embodiment, the invention is directed to a Compound of Formula Ic where R$^1$ is cycloalkyl; n1 is 0 or 1; R$^5$, when R$^5$ is present, is chloro, fluoro, amino, or methyl; each R$^{9a}$ is independently hydrogen or R$^{9c}$; and R$^{29}$, R$^{9c}$, and all other groups are as defined in the Summary of the Invention for a Compound of Formula I. In another embodiment, the invention is directed to a Compound of Formula Ic where R$^1$ is cycloalkyl; n1 is 0; each R$^{9a}$ is independently hydrogen or R$^{9c}$; and R$^{29}$, R$^{9c}$, and all other groups are as defined in the Summary of the Invention for a Compound of Formula I.

In another embodiment, the invention is directed to a Compound of Formula Ic where R$^1$ is cycloalkyl; n1 is 0; R$^{29}$ is R$^{9b}$ where R$^{9b}$ is —NR$^{23}$C(O)R$^{23a}$, dialkylaminoalkyloxy, or alkyl substituted with one or two R$^{11}$; each R$^{9a}$ is independently hydrogen or alkyl; and R$^{11}$, R$^{23}$, R$^{23a}$, and all other groups are as defined in the Summary of the Invention for a Compound of Formula I. In another embodiment, the invention is directed to a Compound of Formula Ic where R$^1$ is cycloalkyl; n1 is 0; R$^{29}$ is R$^{9b}$ where R$^{9b}$ is —NR$^{23}$C(O)R$^{23a}$, dialkylaminoalkyloxy, or alkyl substituted with one or two R$^{11}$; each R$^{9a}$ is independently hydrogen or alkyl; and each $R^{11}$ is independently selected from —$NR^{15}R^{15a}$ and optionally substituted heterocycloalkyl; $R^{23}$ is hydrogen or alkyl; $R^{23a}$ is dialkylaminoalkyl; and $R^{15}$, $R^{15a}$, and all other groups are as defined in the Summary of the Invention for a Compound of Formula I.

In another embodiment, the invention is directed to a Compound of Formula Ic where $R^1$ is cyclopropyl or cyclohexyl; n1 is 0; $R^{29}$ is $R^{9b}$ where $R^{9b}$ is —$NR^{23}C(O)R^{23a}$, dialkylaminoalkyloxy, or alkyl substituted with one or two $R^{11}$; each $R^{9a}$ is independently hydrogen or alkyl; and $R^{11}$, $R^{23}$, $R^{23a}$, and all other groups are as defined in the Summary of the Invention for a Compound of Formula I. In another embodiment, the invention is directed to a Compound of Formula Ic where $R^1$ is cyclopropyl or cyclohexyl; n1 is 0; $R^{29}$ is $R^{9b}$ where $R^{9b}$ is —$NR^{23}C(O)R^{23a}$, dialkylaminoalkyloxy, or alkyl substituted with one or two $R^{11}$; each $R^{9a}$ is independently hydrogen or alkyl; each $R^{11}$ is optionally substituted heterocycloalkyl or —$NR^{15}R^{15a}$ where $R^{15}$ is hydrogen or alkyl and $R^{15a}$ is hydrogen or alkyl; $R^{23}$ is hydrogen or alkyl; $R^{23a}$ is dialkylaminoalkyl; and all other groups are as defined in the Summary of the Invention for a Compound of Formula I. In another embodiment, the invention is directed to a Compound of Formula Ic where $R^1$ is cyclopropyl or cyclohexyl; n1 is 0; $R^{29}$ is $R^{9b}$ where $R^{9b}$ is morpholinyl, or $R^{9b}$ is alkyl substituted with one $R^{11}$ where $R^{11}$ is —$NR^{15}R^{15a}$ and where $R^{15}$ is hydrogen or methyl and $R^{15a}$ is hydrogen or methyl; and all other groups are as defined in the Summary of the Invention for a Compound of Formula I.

In another embodiment, the invention is directed to a Compound of Formula Ic where $R^1$ is cycloalkyl; n1 is 0; $R^{29}$ is $R^{9c}$ where $R^9$ is alkyl; each $R^{9a}$ is independently hydrogen or $R^9$ where $R^{9c}$ is alkyl; and all other groups are as defined in the Summary of the Invention for a Compound of Formula I. In another embodiment, the invention is directed to a Compound of Formula Ic where $R^1$ is cycloalkyl; n1 is 0; $R^{29}$ is methyl; one $R^{9a}$ is methyl and the other $R^{9a}$ is hydrogen; and all other groups are as defined in the Summary of the Invention for a Compound of Formula I.

In another embodiment, the invention is directed to a Compound of Formula Ic where $R^1$ is cyclopropyl or cyclohexyl; n1 is 0; $R^{29}$ is $R^{9c}$ where $R^9$ is alkyl; and each $R^{9a}$ is independently hydrogen or $R^{9c}$ where $R^9$ is alkyl; and all other groups are as defined in the Summary of the Invention for a Compound of Formula I. In another embodiment the invention is directed to a Compound of Formula Ic where $R^1$ is cyclopropyl or cyclohexyl; n1 is 0; $R^{29}$ is methyl; one $R^{9a}$ is hydrogen and the other $R^{9a}$ is methyl; and all other groups are as defined in the Summary of the Invention for a Compound of Formula I.

In another embodiment, the invention is directed to a Compound of Formula Ie

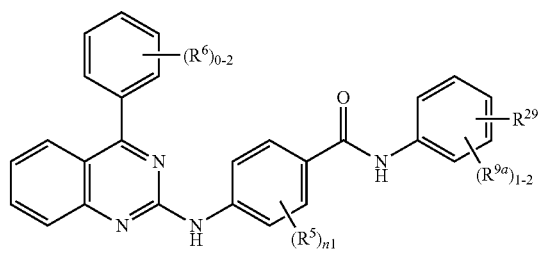

Ie where $R^6$, when $R^6$ is present, is independently amino, alkylamino, dialkylamino, aminocarbonyl, alkylaminocarbonyl, dialkylaminocarbonyl, heterocycloalkylalkyl (optionally substituted with alkyl or alkoxycarbonyl), aminoalkylamino, alkylaminoalkylamino, or dialkylaminoalkylamino; $R^{29}$ is $R^{9c}$ where $R^{9c}$ is alkyl; $R^{9a}$ is hydrogen or $R^{9c}$ where $R^{9c}$ is alkyl; and n1, $R^5$, and all other groups are as defined in the Summary of the Invention for a Compound of Formula I.

In another embodiment, the invention is directed to a Compound of Formula If where one $R^{9a}$ is hydrogen, and $R^{29}$ and the other $R^{9a}$ are independently $R^{9c}$:

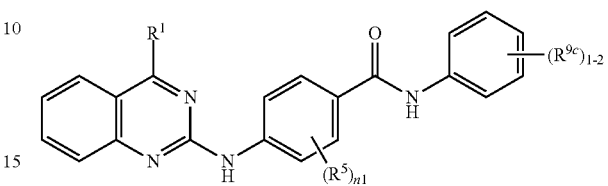

If where $R^1$, n1, $R^5$, $R^9$, and all other groups are as defined in the Summary of the Invention for a Compound of Formula I.

In another embodiment, the invention is directed to a Compound of Formula If where $R^1$ is alkyl, heteroaryl, or heterocycloalkyl, where the heteroaryl and heterocycloalkyl are optionally substituted with one or two $R^6$; n1 is 0 or 1; $R^5$, when $R^5$ is present is halo, alkyl, or amino; one $R^{9c}$ is hydrogen, halo, or alkyl and the other $R^{9c}$ is amino, halo, alkyl, nitro, or cyano; and $R^6$ and all other groups are as defined in the Summary of the Invention for a Compound of Formula I. In another embodiment, the invention is directed to a Compound of Formula If where $R^1$ is alkyl or heteroaryl; n1 is 0; one $R^{9c}$ is hydrogen or methyl, and the other $R^{9c}$ is fluoro, chloro, bromo, methyl, ethyl, amino, nitro, or cyano; and all other groups are as defined in the Summary of the Invention for a Compound of Formula I. In another embodiment, the invention is directed to a Compound of Formula If where $R^1$ is alkyl or heteroaryl; n1 is 0; each $R^{9c}$ is methyl; and all other groups are as defined in the Summary of the Invention for a Compound of Formula I.

In another embodiment, the invention is directed to a Compound of Formula If where $R^1$ is phenyl substituted with one or two $R^6$ where $R^6$ is selected from alkylaminoalkyl, dialkylaminoalkyl, amino, alkylamino, dialkylamino, haloalkyl, haloalkoxy, halophenyl, aminocarbonyl, alkylaminocarbonyl, dialkylaminocarbonyl, dialkylaminoalkyl, aminoalkylamino, alkylaminoalkylamino, dialkylaminoalkylamino, alkyloxyalkylamino, heterocycloalkyl, or heterocycloalkylalkyl; n1 is 0 or 1; $R^5$, when $R^5$ is present is halo, alkyl, or amino; one $R^9$ is hydrogen, halo, or alkyl and the other $R^9$ is amino, halo, alkyl, nitro, or cyano; and all other groups are as defined in the Summary of the Invention for a Compound of Formula I.

In another embodiment, the invention is directed to a Compound of Formula If where $R^1$ is phenyl substituted with one or two $R^6$ where $R^6$ is selected from amino, alkylamino, dialkylamino, haloalkyl, haloalkoxy, halophenyl, aminocarbonyl, alkylaminocarbonyl, dialkylaminocarbonyl, dialkylaminoalkyl, aminoalkylamino, alkylaminoalkylamino, dialkylaminoalkylamino, alkyloxyalkylamino, heterocycloalkyl, and heterocycloalkylalkyl; n1 is 0; one $R^9$ is hydrogen or methyl, and the other $R^9$ is fluoro, chloro, bromo, methyl, ethyl, amino, nitro, or cyano; and all other groups are as defined in the Summary of the Invention for a Compound of Formula I.

In another embodiment, the invention is directed to a Compound of Formula If where $R^1$ is phenyl substituted with one or two $R^6$ where $R^6$ is selected from trifluoromethoxy, dimethylamino, dimethylaminocarbonyl, morpholinylmethyl, dimethylaminomethyl, methylamino, isobutylamino, isopropylamino, and 3-(ethyloxy)-propylamino; n1 is 0; and each $R^{9c}$ is methyl. In another embodiment, the invention is directed to a Compound of Formula If where $R^1$ is phenyl substituted with one or two $R^6$ where $R^6$ is selected from dimethylamino, dimethylaminocarbonyl, morpholinylmethyl, dimethylaminomethyl, methylamino, isobutylamino, isopropylamino, and 3-(ethyloxy)-propylamino; n1 is 0; and each $R^9$ is methyl.

In another embodiment, the invention is directed to a Compound of Formula Ie or Ig

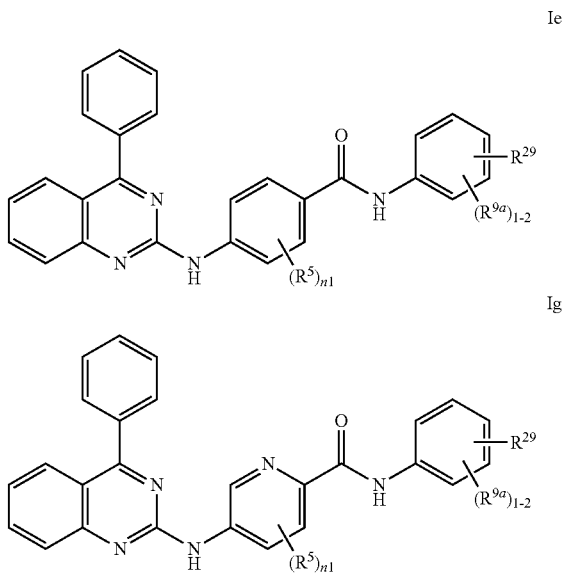

where n1 is 0 or 1; each $R^5$, when $R^5$ is present is independently halo or alkyl; and all other groups are as defined in the Summary of the Invention for a Compound of Formula I.

In another embodiment, the invention is directed to a Compound of Formula Ig where n1 is 0; each $R^{9a}$ is independently hydrogen or alkyl; and $R^{29}$ is $R^{9b}$ where $R^{9b}$ and all other groups are as defined in the Summary of the Invention for a Compound of Formula I. In another embodiment, the invention is directed to a Compound of Formula Ig where n1 is 0; each $R^{9a}$ is independently hydrogen or alkyl; $R^{29}$ is $R^{9b}$; $R^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, or —NR$^{23}$C(O)R$^{23a}$, or alkyl substituted with one $R^{11}$; and $R^{12}$, $R^{12a}$, $R^{13}$, $R^{13a}$, $R^{14}$, $R^{23}$, $R^{23a}$, $R^{11}$, and all other groups are as defined in the Summary of the Invention for a Compound of Formula I.

In another embodiment, the invention is directed to a Compound of Formula Ie where n1 is 0; each $R^{9a}$ is independently hydrogen or alkyl; and $R^{29}$ is $R^{9b}$ where $R^{9b}$ and all other groups are as defined in the Summary of the Invention for a Compound of Formula I. In another embodiment, the invention is directed to a Compound of Formula Ie where n1 is 0; each $R^{9a}$ is independently hydrogen or alkyl; $R^{29}$ is $R^{9b}$; $R^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, or —NR$^{23}$C(O)R$^{23a}$, or alkyl substituted with one $R^{11}$; and $R^{12}$, $R^{12a}$, $R^{13}$, $R^{13a}$, $R^{14}$, $R^{23}$, $R^{23a}$, $R^{11}$, all other groups are as defined in the Summary of the Invention for a Compound of Formula I.

In another embodiment, the invention is directed to a Compound of Formula Ie where n1 is 0; each $R^{9a}$ is independently hydrogen or alkyl; $R^{29}$ is $R^{9b}$ where $R^{9b}$ is alkyl substituted with one or two $R^{11}$; and $R^{11}$ and all other groups are as defined in the Summary of the Inventions for a Compound of Formula I. In another embodiment, the invention is directed to a Compound of Formula Ie where n1 is 0; each $R^{9a}$ is independently hydrogen or alkyl; $R^{29}$ is $R^{9b}$ where $R^{9b}$ is alkyl substituted with one or two $R^{11}$; each $R^{11}$ is independently hydroxy, —NR$^{15}$R$^{15a}$ (where $R^{15}$ is hydrogen, alkyl, haloalkyl, alkoxyalkyl, or hydroxyalkyl and $R^{15a}$ is hydrogen, alkyl, haloalkyl, carboxyalkyl, aminocarbonylalkyl, hydroxyalkyl, alkoxyalkyl, cycloalkyl, or phenylmethyl), optionally substituted heterocycloalkyl, or optionally substituted heteroaryl; and all other groups are as defined in the Summary of the Inventions for a Compound of Formula I. In another embodiment, the invention is directed to a Compound of Formula Ie where n1 is 0; each $R^{9a}$ is independently hydrogen or alkyl; $R^{29}$ is $R^{9b}$ where $R^{9b}$ is methyl or ethyl substituted with one $R^{11}$ where $R^{11}$ is hydroxy, amino, alkylamino, dialkylamino, haloalkylamino, di-(haloalkyl)-amino, hydroxyalkylamino, di-(hydroxyalkyl)-amino, carboxyalkylamino, aminocarbonylalkylamino, N-alkyl-N-hydroxyalkylamino, N-alkyl-N-haloalkylamino, alkoxyalkylamino, di-(alkoxyalkyl)-amino, heterocycloalkyl, heterocycloalkyl substituted with alkyl, heterocycloalkyl substituted with alkylcarbonyl, heterocycloalkyl substituted with cycloalkylcarbonyl, heterocycloalkyl substituted with phenylcarbonyl, heterocycloalkyl substituted with alkoxyalkylcarbonyl, N-cycloalkylamino, N-alkyl-N-cycloalkylamino, N-phenylmethylamino, N-alkyl-N-phenylmethylamino, N-(1-phenylethyl)-amino, 1,2,3,4-tetrahydroisoquinolin-2-yl, or 1,2,3,4-tetrahydroquinolin-1-yl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is hydroxymethyl, aminomethyl, methylaminomethyl, ethylaminomethyl, n-propylaminomethyl, isopropylaminomethyl, iso-butylaminomethyl, sec-butylaminomethyl, tert-butylaminomethyl, 3-methylbutan-2-aminomethyl, 2,4,4-trimethylpentan-2-aminomethyl, 4-methylpentan-2-aminomethyl, dimethylaminomethyl, 1-(dimethylamino)-ethyl, N,N-diethylaminomethyl, di-isopropylaminomethyl, N-methyl-N-ethylaminomethyl, N-methyl-N-isopropylaminomethyl, N-ethyl-N-isopropylaminomethyl, 1-[N-(3,3,3-trifluoropropyl)-N-ethyl-amino]-ethyl, N-ethyl-N-(2,2,2-trifluoroethyl)-aminomethyl, 1-(bis(3,3,3-trifluoropropyl) amino)-ethyl, N-(2-hydroxyethyl)aminomethyl, N-(2-hydroxy-1,1-dimethyl-ethyl)-aminomethyl, N,N-di-(2-hydroxyethyl)aminomethyl, N-ethyl-N-(2-hydroxyethyl) aminomethyl, N-(2-hydroxy-1-hydroxymethyl-ethyl)-aminomethyl, N-(2-hydroxyethyl)-N-ethyl-aminomethyl, N-(2-methoxy-ethyl)-aminomethyl, N-di-(2-methoxyethyl)-aminomethyl, N-methyl-N-(2-hydroxyethyl)aminomethyl, carboxymethylaminomethyl, aminocarbonylmethylaminomethyl, 3-carboxy-azetidinylmethyl, pyrrolidinylmethyl, morpholinylmethyl, 1-(morpholinyl)-ethyl, piperazinylmethyl, 4-(methylcarbonyl)-piperazinylmethyl, 4-(isobutylcarbonyl)-piperazinylmethyl, 4-(cyclopropylcarbonyl)-piperazinylmethyl, 4-(cyclopentylcarbonyl)-piperazinylmethyl, 4-(phenylcarbonyl)-piperazinylmethyl, 4-(methoxymethylcarbonyl)-piperazinylmethyl, piperidinylmethyl, 2,6-dimethylpiperidinylmethyl, 2,2,6,6-tetramethylpiperidinylmethyl, 4-methyl-piperazinylmethyl, homopiperidinylmethyl, 7-azabicyclo[2.2.1]heptan-7-ylmethyl, N-cyclopropylaminomethyl, N-methyl-N-cyclohexylaminomethyl, N-phenylmethylaminomethyl, N-(1-phenylethyl)-aminomethyl, N-methyl-N-phenylmethylaminomethyl, 1,2,3,4-tetrahydroisoquinolin-2-ylmethyl, or 1,2,3,4-tetrahydroquinolin-1-ylmethyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is hydroxymethyl, aminomethyl, methylaminomethyl, iso-butylaminomethyl, dimethylaminomethyl, diethylaminomethyl, N-methyl-N-ethyl-aminomethyl, N-methyl-N-isopropyl-aminomethyl, diethylaminomethyl, N-cyclopropylaminomethyl, N-methyl-N-phenylmethylaminomethyl, pyrrolidinylmethyl, piperidinylmethyl, or morpholinylmethyl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is optionally substituted heterocycloalkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is morpholinyl, piperazinyl, or 4-methyl-piperazinyl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is dialkylaminoalkyloxy. In another embodiment, $R^{9b}$ is 2-(dimethylamino)-ethyloxy.

In another embodiment, the invention is directed to a Compound of Formula Ie where n1 is 0; each $R^{9a}$ is independently hydrogen or alkyl; and $R^{29}$ is $R^{9b}$ where $R^{9b}$ is heterocycloalkylalkyloxy. In another embodiment, the invention is directed to a Compound of Formula Ie where n1 is 0; each $R^{9a}$ is independently hydrogen or alkyl; and $R^{29}$ is $R^{9b}$ where $R^{9b}$ is 2-(morpholinyl)-ethyloxy or 3-(morpholinyl)-propyloxy.

In another embodiment, the invention is directed to a Compound of Formula Ie where n1 is 0; each $R^{9a}$ is independently hydrogen or alkyl; $R^{29}$ is $R^{9b}$ and $R^{9b}$ is —C(O)NR$^{12}$R$^{12a}$ where $R^{12}$ is hydrogen or alkyl and $R^{12a}$ is hydrogen, hydroxy, alkoxy, alkyl, aminoalkyl, alkylaminoalkyl, dialkylaminoalkyl, hydroxyalkyl, optionally substituted heterocycloalkyl, optionally substituted heterocycloalkylalkyl, or optionally substituted heteroaryl. In another embodiment, the invention is directed to a Compound of Formula Ie where n1 is 0; each $R^{9a}$ is independently hydrogen or alkyl; and $R^{29}$ is $R^{9b}$ and $R^{9b}$ is —C(O)NR$^{12}$R$^{12a}$ where $R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is aminocarbonyl, dimethylaminocarbonyl, 2-(dimethylamino)-ethylaminocarbonyl, 3-(dimethylamino)-propylaminocarbonyl, 3-(morpholinyl)-propylaminocarbonyl, 8-methyl-8-azabicyclo[3.2.1]octan-3-ylaminocarbonyl, (2-morpholin-4-yl-1,1-dimethyl-ethyl)-aminocarbonyl, 2-hydroxyethylaminocarbonyl, or 1,2,3,4-tetrazol-5-ylaminocarbonyl. In another embodiment, $R^{9b}$ is dimethylaminocarbonyl, 2-(dimethylamino)-ethylaminocarbonyl, 3-(dimethylamino)-propylaminocarbonyl, 2-(morpholinyl)-ethylaminocarbonyl, or 3-(morpholinyl)-propylaminocarbonyl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is —C(O)NR$^{12}$R$^{12a}$ and $R^{12}$ and $R^{12a}$ together with the nitrogen to which they are attached form a heterocycloalkyl optionally substituted with 1, 2, or 3 groups independently selected from alkyl, hydroxyalkyl, haloalkyl, alkylcarbonyl, alkoxycarbonyl, optionally substituted cycloalkylalkyl, optionally substituted heteroaryl, optionally substituted heteroarylalkyl, and optionally substituted phenylalkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is —CO(O)NR$^{12}$R$^{12a}$ and $R^{12}$ and $R^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo). In another embodiment, the invention is directed to a Compound of Formula Ie where n1 is 0; each $R^{9a}$ is independently hydrogen or alkyl; and $R^{29}$ is $R^{9b}$ and $R^{9b}$ is —C(O)NR$^{12}$R$^{12a}$ and $R^{12}$ and $R^{12a}$ together with the nitrogen to which they are attached form piperazinyl, 4-methylpiperazinyl, 4-ethylpiperazinyl, 4-(2-hydroxyethyl)piperazinyl, 4-(cyclopropylmethyl)-piperazinyl, 4-(1-methyl-imidazol-2-ylmethyl)-piperazinyl, 4-(furan-2-ylmethyl)-piperazinyl, 4-(furan-3-yl)-piperazinyl, 4-(phenylmethyl)-piperazinyl, 4-(4-fluoro-phenylmethyl)-piperazinyl, 4-(pyridin-2-ylmethyl)-piperazinyl, 4-(pyridin-3-ylmethyl)-piperazinyl, 4-(pyridin-4-ylmethyl)-piperazinyl, (R)-octahydropyrrolo[1,2-a]pyrazin-2-yl, or (S)-octahydropyrrolo[1,2-a]pyrazin2-yl.

In another embodiment, the invention is directed to a Compound of Formula Ie where n1 is 0; each $R^{9a}$ is independently hydrogen or alkyl; $R^{29}$ is $R^{9b}$ where $R^{9b}$ is —S(O)$_2$NR$^{13}$R$^{13a}$; and $R^{13}$ and $R^{13a}$ are as defined in the Summary of the Invention for a Compound of Formula I. In another embodiment, the invention is directed to a Compound of Formula Ie where n1 is 0; each $R^{9a}$ is independently hydrogen or alkyl; $R^{29}$ is $R^{9b}$ where $R^{9b}$ is —S(O)$_2$NR$^{13}$R$^{13a}$; $R^{13}$ is hydrogen or alkyl; and $R^{13a}$ is hydrogen, alkyl, or dialkylaminoalkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is 2-(dimethylamino)-ethylaminosulfonyl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is —C(O)R$^{14}$ and $R^{14}$ is as defined in the Summary of the Invention for a Compound for Formula I. In another embodiment, the invention is directed to a Compound of Formula Ie where n1 is 0; each $R^{9a}$ is independently hydrogen or alkyl; and $R^{29}$ is $R^{9b}$ where $R^{9b}$ is —C(O)R$^{14}$ and $R^{14}$ is optionally substituted heterocycloalkylalkyl or optionally substituted heteroarylalkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is morpholinylmethylcarbonyl, imidazolylmethyl, or 2-methylimidazolylmethyl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is heteroaryl optionally substituted with alkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is pyrazol-1-yl, pyrazol-2-yl, pyrazol-3-yl, pyrazol-4-yl, pyrazol-5-yl, 1,2,3,4-tetrazol-5-yl, 1,2,4-triazol-5-yl, 1-methyl-1,2,4,5-tetrazol-3-yl, 1-methyl-1,3,4,5-tetrazol-2-yl, imidazol-1-yl, or imidazol-2-yl.

In another embodiment, the invention is directed to a Compound of Formula Ie where n1 is 0; each $R^{9a}$ is independently hydrogen or alkyl; and $R^{29}$ is $R^{9b}$ where $R^{9b}$ is —NR$^{23}$C(O)R$^{23a}$ and $R^{23}$ and $R^{23a}$ are as defined in the Summary of the Invention for a Compound of Formula I. In another embodiment, the invention is directed to a Compound of Formula Ie where n1 is 0; each $R^{9a}$ is independently hydrogen or alkyl; and $R^{29}$ is $R^{9b}$ where $R^{9b}$ is —NR$^{23}$C(O)R$^{23a}$ where $R^{23}$ is hydrogen or alkyl and $R^{23a}$ is aminoalkyl, alkylaminoalkyl, dialkylaminoalkyl, or heterocycloalkylalkyl. In another embodiment, the invention is directed to a Compound of Formula Ie where n1 is 0; each $R^{9a}$ is independently hydrogen or alkyl; and $R^{29}$ is $R^{9b}$ where $R^{9b}$ is 1-amino-1-methyl-ethylcarbonylamino, diethylaminomethylcarbonylamino, dimethylaminomethylcarbonylamino, or morpholin-4-ylmethylcarbonylamino.

In another embodiment, the invention provides the compound of Formula I, wherein one $R^{9a}$ is hydrogen or alkyl; and all other groups are as defined in the Summary of the Invention for a Compound of Formula I.

In another embodiment, the invention is directed to a Compound of Formula I where each $R^{9b}$ is independently alkyl substituted with one $R^{11}$; optionally substituted heterocycloalkyl; dialkylaminoalkyloxy; heterocycloalkylalkyloxy; —C(O)NR$^{12}$R$^{12a}$; —S(O)$_2$NR$^{13}$R$^{13a}$; —C(O)R$^{14}$; optionally substituted heteroaryl; or —NR$^{23}$C(O)R$^{23a}$; and all other groups are as defined in the Summary of the Invention for a Compound of Formula I.

In another embodiment, the invention is directed to a Compound of Formula I where $R^{9b}$ is alkyl substituted with one or two $R^{11}$; and $R^{11}$ and all other groups are as defined in the Summary of the Invention for a Compound of Formula I. In another embodiment, the invention is directed to a Compound of Formula I where $R^{9b}$ is alkyl substituted with one or two $R^{11}$ and each $R^{11}$ is independently hydroxy, —NR$^{15}$R$^{15a}$ (where $R^{15}$ is hydrogen, alkyl, haloalkyl, alkoxyalkyl, or hydroxyalkyl and $R^{15a}$ is hydrogen, alkyl, haloalkyl, carboxyalkyl, aminocarbonylalkyl, hydroxyalkyl, alkoxyalkyl, cycloalkyl, or phenylmethyl), optionally substituted heterocycloalkyl, or optionally substituted heteroaryl; and all other groups are as defined in the Summary of the Invention for a Compound of Formula I. In another embodiment, the invention is directed to a Compound of Formula I where $R^{9b}$ is methyl or ethyl substituted with one $R^{11}$ and $R^{11}$ is hydroxy, amino, alkylamino, dialkylamino, haloalkylamino, di-(haloalkyl)-amino, hydroxyalkylamino, di-(hydroxyalkyl)-amino, carboxyalkylamino, aminocarbonylalkylamino, N-alkyl-N-hydroxyalkylamino, N-alkyl-N-haloalkylamino, alkoxyalkylamino, di-(alkoxyalkyl)-amino, heterocycloalkyl, heterocycloalkyl substituted with alkyl, heterocycloalkyl substituted with alkylcarbonyl, heterocycloalkyl substituted with cycloalkylcarbonyl, heterocycloalkyl substituted with phenylcarbonyl, heterocycloalkyl substituted with alkoxyalkylcarbonyl, N-cycloalkylamino, N-alkyl-N-cycloalkylamino, N-phenylmethylamino, N-alkyl-N-phenylmethylamino, N-(1-phenyl-ethyl)-amino, 1,2,3,4-tetrahydroisoquinolin-2-yl, or 1,2,3,4-tetrahydroquinolin-1-yl; and all other groups are as defined in the Summary of the Invention for a Compound of Formula I.

In another embodiment, the invention is directed to a Compound of Formula I where $R^{9b}$ is hydroxymethyl, aminomethyl, methylaminomethyl, ethylaminomethyl, n-propylaminomethyl, isopropylaminomethyl, iso-butylaminomethyl, sec-butylaminomethyl, tert-butylaminomethyl, 3-methylbutan-2-aminomethyl, 2,4,4-trimethylpentan-2-aminomethyl, 4-methylpentan-2-aminomethyl, dimethylaminomethyl, 1-(dimethylamino)-ethyl, N,N-diethylaminomethyl, di-isopropylaminomethyl, N-methyl-N-ethylaminomethyl, N-methyl-N-isopropylaminomethyl, N-ethyl-N-isopropylaminomethyl, 1-[N-(3,3,3-trifluoropropyl)-N-ethyl-amino]-ethyl, N-ethyl-N-(2,2,2-trifluoroethyl)-aminomethyl, 1-(bis(3,3,3-trifluoropropyl)amino)-ethyl, N-(2-hydroxyethyl)aminomethyl, N-(2-hydroxy-1,1-dimethyl-ethyl)-aminomethyl, N,N-di-(2-hydroxyethyl)aminomethyl, N-ethyl-N-(2-hydroxyethyl)aminomethyl, N-(2-hydroxy-1-hydroxymethyl-ethyl)-aminomethyl, N-(2-hydroxyethyl)-N-ethyl-aminomethyl, N-(2-methoxy-ethyl)-aminomethyl, N-di-(2-methoxy-ethyl)-aminomethyl, N-methyl-N-(2-hydroxyethyl)aminomethyl, carboxymethylaminomethyl, aminocarbonylmethylaminomethyl, 3-carboxy-azetidinylmethyl, pyrrolidinylmethyl, morpholinylmethyl, 1-(morpholinyl)-ethyl, piperazinylmethyl, 4-(methylcarbonyl)-piperazinylmethyl, 4-(isobutylcarbonyl)-piperazinylmethyl, 4-(cyclopropylcarbonyl)-piperazinylmethyl, 4-(cyclopentylcarbonyl)-piperazinylmethyl, 4-(phenylcarbonyl)-piperazinylmethyl, 4-(methoxymethylcarbonyl)-piperazinylmethyl, piperidinylmethyl, 2,6-dimethylpiperidinylmethyl, 2,2,6,6-tetramethylpiperidinylmethyl, 4-methyl-piperazinylmethyl, homopiperidinylmethyl, 7-azabicyclo[2.2.1]heptan-7-ylmethyl, N-cyclopropylaminomethyl, N-methyl-N-cyclohexylaminomethyl, N-phenylmethylaminomethyl, N-(1-phenylethyl)-aminomethyl, N-methyl-N-phenylmethylaminomethyl, 1,2,3,4-tetrahydroisoquinolin-2-ylmethyl, or 1,2,3,4-tetrahydroquinolin-1-ylmethyl; and all other groups are as defined in the Summary of the Invention for a Compound of Formula I. In another embodiment, the invention is directed to a Compound of Formula I where $R^{9b}$ is hydroxymethyl, aminomethyl, methylaminomethyl, iso-butylaminomethyl, dimethylaminomethyl, diethylaminomethyl, N-methyl-N-ethyl-aminomethyl, N-methyl-N-isopropyl-aminomethyl, diethylaminomethyl, N-cyclopropylaminomethyl, N-methyl-N-phenylmethylaminomethyl, pyrrolidinylmethyl, piperidinylmethyl, or morpholinylmethyl; and all other groups are as defined in the Summary of the Invention for a Compound of Formula I.

In another embodiment, the invention is directed to a Compound of Formula I where $R^{9b}$ is optionally substituted heterocycloalkyl; and all other groups are as defined in the Summary of the Invention for a Compound of Formula I. In another embodiment, the invention is directed to a Compound of Formula I where $R^{9b}$ is morpholinyl, piperazinyl, or 4-methyl-piperazinyl; and all other groups are as defined in the Summary of the Invention for a Compound of Formula I.

In another embodiment, the invention is directed to a Compound of Formula I where $R^{9b}$ is dialkylaminoalkyloxy; and all other groups are as defined in the Summary of the Invention for a Compound of Formula I. In another embodiment, the invention is directed to a Compound of Formula I where $R^{9b}$ is 2-(dimethylamino)-ethyloxy; and all other groups are as defined in the Summary of the Invention for a Compound of Formula I.

In another embodiment, the invention is directed to a Compound of Formula I where $R^{9b}$ is heterocycloalkylalkyloxy; and all other groups are as defined in the Summary of the Invention for a Compound of Formula I. In another embodiment, the invention is directed to a Compound of Formula I where $R^{9b}$ is 2-(morpholinyl)-ethyloxy or 3-(morpholinyl)-propyloxy; and all other groups are as defined in the Summary of the Invention for a Compound of Formula I.

In another embodiment, the invention is directed to a Compound of Formula I where $R^{9b}$ is —C(O)NR$^{12}$R$^{12a}$ where $R^{12}$ is hydrogen or alkyl and $R^{12a}$ is hydrogen, hydroxy, alkoxy, alkyl, aminoalkyl, alkylaminoalkyl, dialkylaminoalkyl, hydroxyalkyl, optionally substituted heterocycloalkyl, optionally substituted heterocycloalkylalkyl, or optionally substituted heteroaryl; and all other groups are as defined in the Summary of the Invention for a Compound of Formula I. In another embodiment, the invention is directed to a Compound of Formula I where $R^{9b}$ is —C(O)NR$^{12}$R$^{12a}$ and $R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl; and all other groups are as defined in the Summary of the Invention for a Compound of Formula I. In another embodiment, the invention is directed to a Compound of Formula I where $R^{9b}$ is aminocarbonyl, dimethylaminocarbonyl, 2-(dimethylamino)-ethylaminocarbonyl, 3-(dimethylamino)-propylaminocarbonyl, 3-(morpholinyl)-propylaminocarbonyl, 8-methyl-8-azabicyclo[3.2.1]octan-3-ylaminocarbonyl, (2-morpholin-4-yl-1,1-dimethyl-ethyl)-aminocarbonyl, 2-hydroxyethylaminocarbonyl, or 1,2,3,4-tetrazol-5-ylaminocarbonyl; and all other groups are as defined in the Summary of the Invention for a Compound of Formula I. In another embodiment, $R^{9b}$ is dimethylaminocarbonyl, 2-(dimethylamino)-ethylaminocarbonyl, 3-(dimethylamino)-propylaminocarbonyl, 2-(morpholinyl)-ethylaminocarbonyl, or 3-(morpholinyl)-propylaminocarbonyl; and all other groups are as defined in the Summary of the Invention for a Compound of Formula I.

In another embodiment, the invention is directed to a Compound of Formula I where $R^{9b}$ is —C(O)NR$^{12}$R$^{12a}$ and $R^{12}$ and $R^{12a}$ together with the nitrogen to which they are attached form a heterocycloalkyl optionally substituted with 1, 2, or 3 groups independently selected from alkyl, hydroxyalkyl, haloalkyl, alkylcarbonyl, alkoxycarbonyl, optionally substituted cycloalkylalkyl, optionally substituted heteroaryl, optionally substituted heteroarylalkyl, and optionally substituted phenylalkyl; and all other groups are as defined in the Summary of the Invention for a Compound of Formula I. In another embodiment, the invention is directed to a Compound of Formula I where $R^{9b}$ is —C(O)NR$^{12}$R$^{12a}$ and $R^{12}$ and $R^{12}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo); and all other groups are as defined in the Summary of the Invention for a Compound of Formula I. In another embodiment, the invention is directed to a Compound of Formula I where $R^{9b}$ is —C(O)NR$^{12}$R$^{12a}$ and $R^{12}$ and $R^{12a}$ together with the nitrogen to which they are attached form piperazinyl, 4-methylpiperazinyl, 4-ethylpiperazinyl, 4-(2-hydroxyethyl)piperazinyl, 4-(cyclopropylmethyl)-piperazinyl, 4-(1-methyl-imidazol-2-ylmethyl)-piperazinyl, 4-(furan-2-ylmethyl)-piperazinyl, 4-(furan-3-yl)-piperazinyl, 4-(phenylmethyl)-piperazinyl, 4-(4-fluoro-phenylmethyl)-piperazinyl, 4-(pyridin-2-ylmethyl)-piperazinyl, 4-(pyridin-3-ylmethyl)-piperazinyl, 4-(pyridin-4-ylmethyl)-piperazinyl, (R)-octahydropyrrolo[1,2-a]pyrazin-2-yl, or (S)-octahydropyrrolo[1,2-a]pyrazin-2-yl; and all other groups are as defined in the Summary of the Invention for a Compound of Formula I.

In another embodiment, the invention is directed to a Compound of Formula I where $R^{9b}$ is —S(O)$_2$NR$^{13}$R$^{13a}$; and $R^{13}$, $R^{13a}$, and all other groups are as defined in the Summary of the Invention for a Compound of Formula I. In another embodiment, the invention is directed to a Compound of Formula I where $R^{9b}$ is —S(O)$_2$NR$^{13}$R$^{13a}$ where $R^{13}$ is hydrogen or alkyl and $R^{13a}$ is hydrogen, alkyl, or dialkylaminoalkyl; and all other groups are as defined in the Summary of the Invention for a Compound of Formula I. In another embodiment, the invention is directed to a Compound of Formula I where $R^{9b}$ is 2-(dimethylamino)-ethylaminosulfonyl; and all other groups are as defined in the Summary of the Invention for a Compound of Formula I.

In another embodiment, the invention is directed to a Compound of Formula I where $R^{9b}$ is —C(O)R$^{14}$ and $R^{14}$ and all other groups are as defined in the Summary of the Invention for a Compound for Formula I. In another embodiment, the invention is directed to a Compound of Formula I where $R^{9b}$ is —C(O)R$^{14}$ and $R^{14}$ is optionally substituted heterocycloalkylalkyl or optionally substituted heteroarylalkyl; and all other groups are as defined in the Summary of the Invention for a Compound for Formula I. In another embodiment, the invention is directed to a Compound of Formula I where $R^{9b}$ is morpholinylmethylcarbonyl, imidazolylmethyl, or 2-methylimidazolylmethyl; and all other groups are as defined in the Summary of the Invention for a Compound for Formula I.

In another embodiment, the invention is directed to a Compound of Formula I where $R^{9b}$ is heteroaryl optionally substituted with alkyl; and all other groups are as defined in the Summary of the Invention for a Compound for Formula I. In another embodiment, the invention is directed to a Compound of Formula I where $R^{9b}$ is pyrazol-1-yl, pyrazol-2-yl, pyrazol-3-yl, pyrazol-4-yl, pyrazol-5-yl, 1,2,3,4-tetrazol-5-yl, 1,2,4-triazol-5-yl, 1-methyl-1,2,4,5-tetrazol-3-yl, 1-methyl-1,3,4,5-tetrazol-2-yl, imidazol-1-yl, or imidazol-2-yl; and all other groups are as defined in the Summary of the Invention for a Compound for Formula I.

In another embodiment, the invention is directed to a Compound of Formula I where $R^{9b}$ is —NR$^{23}$C(O)R$^{23a}$ and $R^{23}$, $R^{23a}$, and all other groups are as defined in the Summary of the Invention for a Compound of Formula I. In another embodiment, the invention is directed to a Compound of Formula I where $R^{9b}$ is —NR$^{23}$C(O)R$^{23a}$; $R^{23}$ is hydrogen or alkyl; $R^{23a}$ is aminoalkyl, alkylaminoalkyl, dialkylaminoalkyl, or heterocycloalkylalkyl; and all other groups are as defined in the Summary of the Invention for a Compound of Formula I. In another embodiment, the invention is directed to a Compound of Formula I where $R^{9b}$ is 1-amino-1-methylethylcarbonylamino, diethylaminomethylcarbonylamino, dimethylaminomethylcarbonylamino, or morpholin-4-ylmethylcarbonylamino; and all other groups are as defined in the Summary of the Invention for a Compound of Formula I.

In another embodiment, the invention provides the compound of Formula I wherein $R^4$ is phenyl substituted with one $R^{29}$ and additionally substituted with 1 or 2 $R^{9a}$; each $R^{9a}$ is independently hydrogen or alkyl; $R^{29}$ is $R^{9b}$ where $R^{9b}$ is alkyl substituted with one or two $R^{11}$; and $R^{11}$ and all other groups are as defined in the Summary of the Invention for a Compound of Formula I.

In another embodiment, the invention provides the compound of Formula I wherein $R^4$ is phenyl substituted with one $R^{29}$ and additionally substituted with 1 or 2 $R^{9a}$; each $R^{9a}$ is independently hydrogen or alkyl; $R^{29}$ is $R^{9b}$ where $R^{9b}$ is optionally substituted heterocycloalkyl; and all other groups are as defined in the Summary of the Invention for a Compound of Formula I.

In another embodiment, the invention provides the compound of Formula I wherein $R^4$ is phenyl substituted with one $R^{29}$ and additionally substituted with 1 or 2 $R^{9a}$; each $R^{9a}$ is independently hydrogen or alkyl; $R^{29}$ is $R^{9b}$ where $R^{9b}$ is dialkylaminoalkyloxy; and all other groups are as defined in the Summary of the Invention for a Compound of Formula I.

In another embodiment, the invention provides the compound of Formula I wherein $R^4$ is phenyl substituted with one $R^{29}$ and additionally substituted with 1 or 2 $R^{9a}$; each $R^{9a}$ is independently hydrogen or alkyl; $R^{29}$ is $R^{9b}$ where $R^{9b}$ is heterocycloalkylalkyloxy; and all other groups are as defined in the Summary of the Invention for a Compound of Formula I.

In another embodiment, the invention provides the compound of Formula I wherein $R^4$ is phenyl substituted with one $R^{29}$ and additionally substituted with 1 or 2 $R^{9a}$; each $R^{9a}$ is independently hydrogen or alkyl; $R^{29}$ is $R^{9b}$ where $R^{9b}$ is —C(O)NR$^{12}$R$^{12a}$; and all other groups are as defined in the Summary of the Invention for a Compound of Formula I.

In another embodiment, the invention provides the compound of Formula I wherein R$^4$ is phenyl substituted with one R$^{29}$ and additionally substituted with 1 or 2 R$^{9a}$; each R$^{9a}$ is independently hydrogen or alkyl; R$^{29}$ is R$^{9b}$ where R$^{9b}$ is —S(O)$_2$NR$^{13}$R$^{13a}$; and R$^{13}$, R$^{13a}$, and all other groups are as defined in the Summary of the Invention for a Compound of Formula I.

In another embodiment, the invention provides the compound of Formula I wherein R$^4$ is phenyl substituted with one R$^{29}$ and additionally substituted with 1 or 2 R$^{9a}$; each R$^{9a}$ is independently hydrogen or alkyl; R$^{29}$ is R$^{9b}$ where R$^{9b}$ is —C(O)R$^{14}$; and R$^{14}$ and all other groups are as defined in the Summary of the Invention for a Compound of Formula I.

In another embodiment, the invention provides the compound of Formula I wherein R$^4$ is phenyl substituted with one R$^{29}$ and additionally substituted with 1 or 2 R$^{9a}$; each R$^{9a}$ is independently hydrogen or alkyl; R$^{29}$ is R$^{9b}$ where R$^{9b}$ is optionally substituted heteroaryl; and all other groups are as defined in the Summary of the Invention for a Compound of Formula I.

In another embodiment, the invention provides the compound of Formula I wherein R$^4$ is phenyl substituted with one R$^{29}$ and additionally substituted with 1 or 2 R$^{9a}$; each R$^{9a}$ is independently hydrogen or alkyl; R$^{29}$ is R$^{9b}$ where R$^{9b}$ is —NR$^{23}$C(O)R$^{23a}$; and R$^{23}$, R$^{23a}$, all other groups are as defined in the Summary of the Invention for a Compound of Formula I.

In another embodiment, the invention is directed to a Compound of Formula II

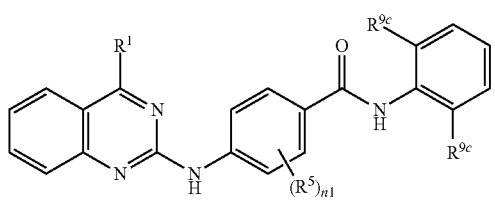

wherein n1 is 0 or 1; R$^5$, when R$^5$ is present, is halo or alkyl; one R$^9$ is alkyl and the other R$^9$ is hydrogen or alkyl; and R$^1$ is alkyl, R$^1$ is heteroaryl, or R$^1$ is phenyl substituted with trifluoromethoxy, methylamino, isopropylamino, isobutylamino, dimethylamino, dimethylaminocarbonyl, aminocarbonyl, morpholinylmethyl, 4-methylpiperazinylmethyl, or dimethylaminomethyl. In another embodiment, the invention is directed to a Compound of Formula II where n1 is 0 or 1; R$^5$, when R$^5$ is present, is halo or alkyl; both R$^{9c}$ are alkyl; and R$^1$ is alkyl, R$^1$ is heteroaryl, or R$^1$ is phenyl substituted with trifluoromethoxy, methylamino, isopropylamino, isobutylamino, dimethylamino, dimethylaminocarbonyl, aminocarbonyl, morpholinylmethyl, 4-methylpiperazinylmethyl, or dimethylaminomethyl.

In another embodiment, the invention is directed to a Compound of Formula III

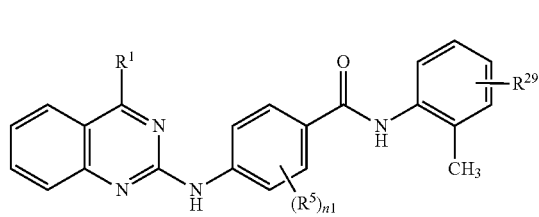

where R$^1$, n1, R$^5$, and R$^{29}$ are as defined in the Summary of the Invention for a Compound of Formula I.

In another embodiment, the invention is directed to a Compound of Formula III where R$^1$ is alkyl or heteroaryl; n1 is 0 or 1; R$^5$, when R$^5$ is present, is halo or alkyl; and R$^{29}$ is R$^{9b}$ or R$^{9c}$; and R$^{9b}$, R$^{9c}$, and all other groups are as defined in the Summary of the Invention for a Compound of Formula I.

In another embodiment, the invention is directed to a Compound of Formula III where R$^1$ is alkyl or heteroaryl; n1 is 0 or 1; R$^5$, when R$^5$ is present, is halo or alkyl; and R$^{29}$ is R$^{9b}$ and R$^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, —NR$^{23}$C(O)R$^{23a}$, or alkyl substituted with one R$^{11}$; where R$^{11}$ is hydroxy, optionally substituted heterocycloalkyl, optionally substituted heteroaryl, or —NR$^{15}$R$^{15a}$ (where R$^{15}$ is hydrogen, alkyl, haloalkyl, alkoxyalkyl, or hydroxyalkyl and R$^{15a}$ is hydrogen, alkyl, haloalkyl, carboxyalkyl, aminocarbonylalkyl, hydroxyalkyl, alkoxyalkyl, cycloalkyl, or phenylmethyl);

R$^{12}$ is hydrogen or alkyl and R$^{12a}$ is hydrogen, alkyl, dialkylaminoalkyl, optionally substituted heterocycloalkyl, optionally substituted heterocycloalkylalkyl, or hydroxyalkyl; or R$^{12}$ and R$^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo);

R$^{13}$ is hydrogen or alkyl and R$^{13a}$ is hydrogen, alkyl, or dialkylaminoalkyl;

R$^{14}$ is optionally substituted heterocycloalkylalkyl or optionally substituted heteroarylalkyl; and R$^{23}$ is hydrogen or alkyl and R$^{23a}$ is aminoalkyl, alkylaminoalkyl, dialkylaminoalkyl, or heterocycloalkylalkyl.

In another embodiment, the invention is directed to a Compound of Formula III where R$^1$ is alkyl or heteroaryl; n1 is 0 or 1; R$^5$, when R$^5$ is present, is halo or alkyl; and R$^{29}$ is R$^{9c}$ and R$^{9c}$ is alkyl, halo, or alkoxy.

In another embodiment, the invention is directed to a Compound of Formula III where R$^1$ is phenyl substituted with one R$^6$ selected from amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, and dialkylaminoalkylamino; n1 is 0 or 1; R$^5$, when R$^5$ is present, is halo or alkyl; and R$^{29}$ is R$^{9b}$ or R$^{9c}$; and R$^{9b}$, R$^{9c}$, and all other groups are as defined in the Summary of the Invention for a Compound of Formula I.

In another embodiment, the invention is directed to a Compound of Formula III where R$^1$ is phenyl substituted with one R$^6$ selected from amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, and dialkylaminoalkylamino; n1 is 0 or 1; R$^5$, when R$^5$ is present, is halo or alkyl; and R$^{29}$ is R$^{9b}$ and R$^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, —NR$^{23}$C(O)R$^{23a}$, or alkyl substituted with one R$^{11}$; where R$^{11}$ is hydroxy, optionally substituted heterocycloalkyl, optionally substituted heteroaryl, —NR$^{15}$R$^{15a}$ (where R$^{15}$ is hydrogen, alkyl, haloalkyl, alkoxyalkyl, or hydroxyalkyl and R$^{15a}$ is hydrogen, alkyl, haloalkyl, carboxyalkyl, aminocarbonylalkyl, hydroxyalkyl, alkoxyalkyl, cycloalkyl, or phenylmethyl);

$R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl; or $R^{12}$ and $R^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo);

$R^{13}$ is hydrogen or alkyl and $R^{13a}$ is hydrogen, alkyl, or dialkylaminoalkyl;

$R^{14}$ is optionally substituted heterocycloalkylalkyl or optionally substituted heteroarylalkyl; and $R^{23}$ is hydrogen or alkyl and $R^{23a}$ is aminoalkyl, alkylaminoalkyl, dialkylaminoalkyl, or heterocycloalkylalkyl.

In another embodiment, the invention is directed to a Compound of Formula III where $R^1$ is phenyl substituted with one $R^6$ selected from amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, and dialkylaminoalkylamino; n1 is 0 or 1; $R^5$, when $R^5$ is present, is halo or alkyl; and $R^{29}$ is $R^{9c}$ and $R^{9c}$ is alkyl, halo, or alkoxy.

In another embodiment, the invention is directed to a Compound of Formula III where $R^1$ is phenyl optionally substituted with 1, 2, or 3 $R^6$ independently selected from alkyl, halo, alkoxy, hydroxyalkyl, aminoalkyl, and alkoxycarbonyl; n1 is 0 or 1; $R^5$, when $R^5$ is present, is halo or alkyl; and $R^{29}$ is $R^{9b}$ where $R^{9b}$ is as defined in the Summary of the Invention for a Compound of Formula I. In another embodiment, the invention is directed to a Compound of Formula III where $R^1$ is phenyl optionally substituted with 1, 2, or 3 $R^6$ independently selected from alkyl, halo, alkoxy, hydroxyalkyl, aminoalkyl, and alkoxycarbonyl; n1 is 0 or 1; $R^5$, when $R^5$ is present, is halo or alkyl; $R^{29}$ is $R^{9b}$; and $R^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, —NR$^{23}$C(O)R$^{23a}$, or alkyl substituted with one $R^{11}$; where $R^{11}$ is hydroxy, optionally substituted heterocycloalkyl, optionally substituted heteroaryl, or —NR$^{15}$R$^{15a}$ (where $R^{15}$ is hydrogen, alkyl, haloalkyl, alkoxyalkyl, or hydroxyalkyl and $R^{15a}$ is hydrogen, alkyl, haloalkyl, carboxyalkyl, aminocarbonylalkyl, hydroxyalkyl, alkoxyalkyl, cycloalkyl, or phenylmethyl);

$R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl; or $R^{12}$ and $R^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo);

$R^{13}$ is hydrogen or alkyl and $R^{13a}$ is hydrogen, alkyl, or dialkylaminoalkyl;

$R^{14}$ is optionally substituted heterocycloalkylalkyl or optionally substituted heteroarylalkyl; and $R^{23}$ is hydrogen or alkyl and $R^{23a}$ is aminoalkyl, alkylaminoalkyl, dialkylaminoalkyl, or heterocycloalkylalkyl.

In another embodiment, the invention is directed to a Compound of Formula IV

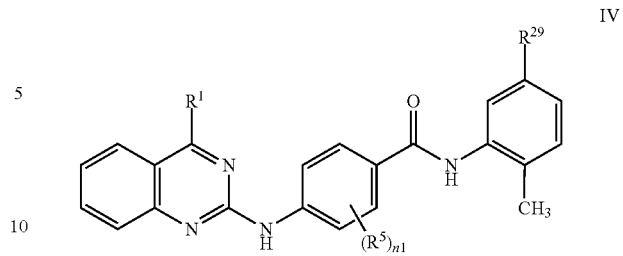

where $R^1$, n1, $R^5$, and $R^{29}$ are as defined in the Summary of the Invention for a Compound of Formula I.

In another embodiment, the invention is directed to a Compound of Formula IV where $R^1$ is alkyl or heteroaryl; n1 is 0 or 1; $R^5$, when $R^5$ is present, is halo or alkyl; and $R^{29}$ is $R^{9b}$ or $R^{9c}$; and $R^{9b}$, $R^{9c}$, and all other groups are as defined in the Summary of the Invention for a Compound of Formula I.

In another embodiment, the invention is directed to a Compound of Formula IV where $R^1$ is alkyl or heteroaryl; n1 is 0 or 1; $R^5$, when $R^5$ is present, is halo or alkyl; and $R^{29}$ is $R^{9b}$ and $R^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, —NR$^{23}$C(O)R$^{23a}$, or alkyl substituted with one $R^{11}$; where $R^{11}$ is hydroxy, optionally substituted heterocycloalkyl, optionally substituted heteroaryl, or —NR$^{15}$R$^{15a}$ (where $R^{15}$ is hydrogen, alkyl, haloalkyl, alkoxyalkyl, or hydroxyalkyl and $R^{15a}$ is hydrogen, alkyl, haloalkyl, carboxyalkyl, aminocarbonylalkyl, hydroxyalkyl, alkoxyalkyl, cycloalkyl, or phenylmethyl);

$R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl; or $R^{12}$ and $R^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo);

$R^{13}$ is hydrogen or alkyl and $R^{13a}$ is hydrogen, alkyl, or dialkylaminoalkyl;

$R^{14}$ is optionally substituted heterocycloalkylalkyl or optionally substituted heteroarylalkyl; and $R^{23}$ is hydrogen or alkyl and $R^{23a}$ is aminoalkyl, alkylaminoalkyl, dialkylaminoalkyl, or heterocycloalkylalkyl.

In another embodiment, the invention is directed to a Compound of Formula IV where $R^1$ is alkyl or heteroaryl; n1 is 0 or 1; $R^5$, when $R^5$ is present, is halo or alkyl; and $R^{29}$ is $R^{9c}$ and $R^{9c}$ is alkyl, halo, or alkoxy.

In another embodiment, the invention is directed to a Compound of Formula IV where $R^1$ is phenyl substituted with one $R^6$ selected from amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, and dialkylaminoalkylamino; n1 is 0 or 1; $R^5$, when $R^5$ is present, is halo or alkyl; and $R^{29}$ is $R^{9b}$ or $R^{9c}$; and $R^{9b}$, $R^{9c}$, and all other groups are as defined in the Summary of the Invention for a Compound of Formula I.

In another embodiment, the invention is directed to a Compound of Formula IV where $R^1$ is phenyl substituted with one $R^6$ selected from amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, and dialkylaminoalkylamino; n1 is 0 or 1; $R^5$, when $R^5$ is present, is halo or alkyl; and $R^{29}$ is $R^{9b}$ and $R^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, —NR$^{23}$C(O)R$^{23a}$, or alkyl substituted with one $R^{11}$; where $R^{11}$ is hydroxy, optionally substituted heterocycloalkyl, optionally substituted heteroaryl, or —NR$^{15}$R$^{15a}$ (where $R^{15}$ is hydrogen, alkyl, haloalkyl, alkoxyalkyl, or hydroxyalkyl and $R^{15a}$ is hydrogen, alkyl, haloalkyl, carboxyalkyl, aminocarbonylalkyl, hydroxyalkyl, alkoxyalkyl, cycloalkyl, or phenylmethyl);

$R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl; or $R^{12}$ and $R^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo);

$R^{13}$ is hydrogen or alkyl and $R^{13a}$ is hydrogen, alkyl, or dialkylaminoalkyl;

$R^{14}$ is optionally substituted heterocycloalkylalkyl or optionally substituted heteroarylalkyl; and $R^{23}$ is hydrogen or alkyl and $R^{23a}$ is aminoalkyl, alkylaminoalkyl, dialkylaminoalkyl, or heterocycloalkylalkyl.

In another embodiment, the invention is directed to a Compound of Formula IV where $R^1$ is phenyl substituted with one $R^6$ seleced from amino, alkylamino, dialkylamino, aminocarbonyl, alkylaminocarbonyl, dialkylaminocarbonyl, heterocycloalkylalkyl optionally substituted with alkyl or alkoxycarbonyl, aminoalkylamino, alkylaminoalkylamino, and dialkylaminoalkylamino; n1 is 0 or 1; $R^5$, when $R^5$ is present, is halo or alkyl; and $R^{29}$ is $R^9$ and $R^{9c}$ is alkyl, halo, or alkoxy.

In another embodiment, the invention is directed to a Compound of Formula IV where $R^1$ is phenyl optionally substituted with 1, 2, or 3 $R^6$ independently selected from alkyl, halo, alkoxy, hydroxyalkyl, aminoalkyl, and alkoxycarbonyl; n1 is 0 or 1; $R^5$, when $R^5$ is present, is halo or alkyl; and $R^{29}$ is $R^{9b}$ where $R^{9b}$ is as defined in the Summary of the Invention for a Compound of Formula I. In another embodiment, the invention is directed to a Compound of Formula IV where $R^1$ is phenyl optionally substituted with 1, 2, or 3 $R^6$ independently selected from alkyl, halo, alkoxy, hydroxyalkyl, aminoalkyl, and alkoxycarbonyl; n1 is 0 or 1; $R^5$, when $R^5$ is present, is halo or alkyl; and $R^{29}$ is $R^{9b}$ where $R^{9b}$ is optionally substituted heterocycloalkyl, dialkylaminoalkyloxy, heterocycloalkylalkyloxy, —C(O)NR$^{12}$R$^{12a}$, —S(O)$_2$NR$^{13}$R$^{13a}$, —C(O)R$^{14}$, optionally substituted heteroaryl, —NR$^{23}$C(O)R$^{23a}$, or alkyl substituted with one $R^{11}$; where $R^{11}$ is hydroxy, optionally substituted heterocycloalkyl, optionally substituted heteroaryl, or —NR$^{15}$R$^{15a}$ (where $R^{15}$ is hydrogen, alkyl, haloalkyl, alkoxyalkyl, or hydroxyalkyl and $R^{15a}$ is hydrogen, alkyl, haloalkyl, carboxyalkyl, aminocarbonylalkyl, hydroxyalkyl, alkoxyalkyl, cycloalkyl, or phenylmethyl);

$R^{12}$ is hydrogen or alkyl and $R^{12a}$ is hydrogen, alkyl, dialkylaminoalkyl, optionally substituted heterocycloalkyl, optionally substituted heterocycloalkylalkyl, or hydroxyalkyl; or $R^{12}$ and $R^{12a}$ together with the nitrogen to which they are attached form a heterocycloalkyl optionally substituted with alkyl, hydroxyalkyl, cycloalkylalkyl, optionally substituted heteroarylalkyl, or phenylalkyl (where the phenyl ring is optionally substituted with halo);

$R^{13}$ is hydrogen or alkyl and $R^{13a}$ is hydrogen, alkyl, or dialkylaminoalkyl;

$R^{14}$ is optionally substituted heterocycloalkylalkyl or optionally substituted heteroarylalkyl; and $R^{23}$ is hydrogen or alkyl and $R^{23a}$ is aminoalkyl, alkylaminoalkyl, dialkylaminoalkyl, or heterocycloalkylalkyl.

In another embodiment, the invention provides a compound of formula V

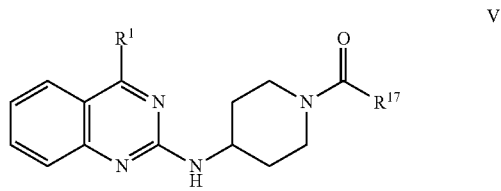

where $R^1$ is alkyl, cycloalkyl, phenyl, or heteroaryl where the cycloalkyl, phenyl, and heteroaryl are optionally substituted with one or two $R^6$ as defined in the Summary of the Invention for a Compound of Formula I; and $R^{17}$ is phenyl, phenylalkyl, phenylalkylamino, heterocycloalkyl (optionally substituted with one or two groups selected from alkyl and alkoxycarbonyl), or cycloalkyl where each phenyl, either alone or as part of a group in $R^{17}$, is substituted with 1, 2, or 3 $R^{9a}$ where $R^{9a}$ is as defined in the Summary of the Invention for a Compound of Formula I.

In another embodiment, the invention provides a compound of formula V where $R^1$ is alkyl, unsubstituted cycloalkyl, unsubstituted phenyl, or unsubstituted heteroaryl; and all other groups are as defined in the Summary of the Invention for a Compound of Formula I.

In another embodiment, the invention provides a compound of Formula V where $R^1$ is unsubstituted phenyl and $R^{17}$ is phenyl, phenylalkyl, phenylalkylamino, heterocycloalkyl (optionally substituted with one alkoxycarbonyl), or cycloalkyl where the phenyl, either alone or as part of a group in $R^{17}$, is substituted with one or two halo. In another embodiment, the invention provides a compound of Formula V where $R^1$ is unsubstituted phenyl and $R^{17}$ is phenyl, 2,6-dichlorophenyl, phenylmethyl, 1-phenylethyl, 2,6-dichloro-phenylmethyl, 3,4-dichlorophenylmethylamino, N-(tert-butoxycarbonyl)-piperidin-3-yl, or cyclohexyl.

In another embodiment, the invention provides a compound of formula V, wherein $R^1$ is phenyl and $R^{17}$ is phenylalkyl where the phenyl is optionally substituted with one or two halo.

In another embodiment, the invention provides a compound of formula VI

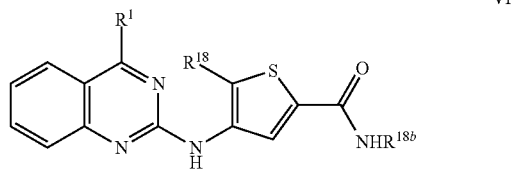

where $R^1$ is alkyl, cycloalkyl, phenyl, or heteroaryl where the cycloalkyl, phenyl, and heteroaryl are optionally substituted with one or two $R^6$ as defined in the Summary of the Invention for a Compound of Formula I; $R^{18}$ is hydrogen, halo, or alkyl; and $R^{18b}$ is phenyl substituted with 1, 2, or 3 $R^{9a}$ where $R^{9a}$ is as defined in the Summary of the Invention for a Compound of Formula I.

In another embodiment, the invention provides a compound of formula VI, wherein $R^1$ is unsubstituted phenyl, $R^{18}$ is hydrogen or chloro; and $R^{18b}$ is phenyl substituted with one or two $R^{9a}$ where each $R^{9a}$ is independently alkyl or $R^{9b}$, and $R^{9b}$ is as defined in the Summary of the Invention for a Compound of Formula I.

In another embodiment, the invention provides a compound of formula VII,

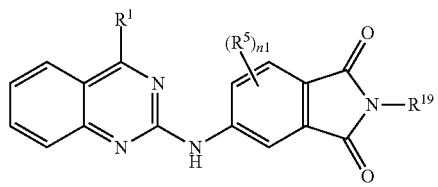

VII wherein $R^1$ is alkyl, cycloalkyl, phenyl, or heteroaryl where the cycloalkyl, phenyl, and heteroaryl are optionally substituted with one or two $R^6$ as defined in the Summary of the Invention for a Compound of Formula I; and $R^{19}$ is phenyl substituted with 1, 2, or 3 $R^{9a}$ where $R^{9a}$ is as defined in the Summary of the Invention for a Compound of Formula I.

In another embodiment, the invention provides a compound of formula VII where $R^1$ is unsubstituted phenyl and $R^{19}$ is phenyl substituted with one or two $R^{9a}$ where each $R^{9a}$ is independently alkyl or $R^{9b}$, where $R^{9b}$ is as defined in the Summary of the Invention for a Compound of Formula I.

In another embodiment, the invention provides a Compound of Formula VIII

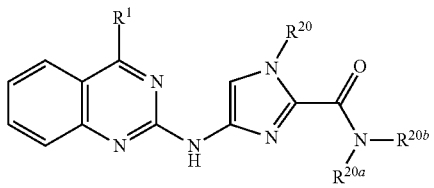

VIII where $R^1$ is alkyl, cycloalkyl, phenyl, or heteroaryl where the cycloalkyl, phenyl, and heteroaryl are optionally substituted with one or two $R^6$ as defined in the Summary of the Invention for a Compound of Formula I; $R^{20}$ is hydrogen, alkyl, alkylcarbonyl, alkylsulfonyl, or alkoxycarbonyl; $R^{20a}$ is hydrogen or alkyl; and $R^{20b}$ is phenyl substituted with 1, 2, or 3 $R^{9a}$ where $R^{9a}$ is as defined in the Summary of the Invention for a Compound of Formula I.

In another embodiment, the invention provides a Compound of Formula VIII where $R^1$ is unsubstituted phenyl; $R^{20}$ is alkyl; $R^{20a}$ is hydrogen; and $R^{20b}$ is phenyl substituted with one or two $R^{9a}$ where each $R^{9a}$ is independently alkyl or $R^{9b}$, where $R^{9b}$ is as defined in the Summary of the Invention for a Compound of Formula I.

In another embodiment, the invention provides a Compound of Formula IX

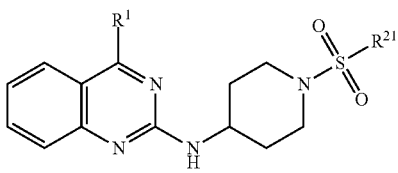

IX where $R^1$ is alkyl, cycloalkyl, phenyl, or heteroaryl where the cycloalkyl, phenyl, and heteroaryl are optionally substituted with one or two $R^6$ as defined in the Summary of the Invention for a Compound of Formula I; and $R^{21}$ is phenyl substituted with 1, 2, or 3 $R^{9a}$ where $R^{9a}$ is as defined in the Summary of the Invention for a Compound of Formula I, or $R^{21}$ is heteroaryl substituted with 1, 2, or 3 $R^{8a}$ where $R^{8a}$ is as defined in the Summary of the Invention for a Compound of Formula I.

In another embodiment, the invention provides a Compound of Formula IX where $R^1$ is unsubstituted phenyl and $R^{21}$ is heteroaryl substituted with one or two $R^{8a}$ where each $R^{8a}$ is alkyl.

In another embodiment, the invention provides a Compound of formula X

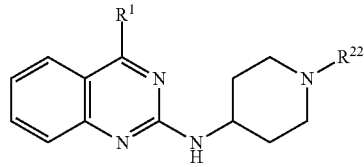

X where $R^1$ is alkyl, cycloalkyl, phenyl, or heteroaryl where the cycloalkyl, phenyl, and heteroaryl are optionally substituted with one or two $R^6$ as defined in the Summary of the Invention for a Compound of Formula I; and $R^{22}$ is phenyl substituted with 1, 2, or 3 $R^{9a}$ or $R^{22}$ is heteroaryl substituted with 1, 2, or 3 $R^{8a}$ where $R^{9a}$ and $R^{8a}$ are as defined in the Summary of the Invention for a Compound of Formula I.

In another embodiment, the invention provides a compound of formula X, wherein $R^1$ is unsubstituted phenyl and $R^{22}$ is heteroaryl.

In another embodiment, the invention provides a method of treating cancer which method comprises administering to a patient a therapeutically effective amount of a Compound of any of the above embodiments or a pharmaceutically acceptable salt, hydrate, solvate or combination thereof, or administering a pharmaceutical composition comprising a therapeutically effective amount of a Compound of any of the above embodiments and a pharmaceutically acceptable carrier, excipient, or diluent in combination with gemcitabine or an alkylating agent, such as temozolomide. In another embodiment, the Compound is selected from a Compound of Formula I, Ia, Ib, Ic, Id, Ie, If, Ig, II, III, IV, V, VI, VII, VIII, IX, and X. In yet another embodiment, the Compound is selected from a Compound of Formula Ia, Ib, Ic, Ie, III, and IV. In yet another embodiment, the Compound is selected from a Compound of Formula Ia, Ib, Ic, Ie, III, and IV and is administered in combination with gemcitabine. In yet another embodiment, the Compound is selected from a Compound of Formula Ia, Ib, Ic, Ie, III, and IV and is administered in combination with temozolomide. In yet another embodiment, the Compound is selected from a Compound in Table 1 and is administered in combination with gemcitabine. In yet another embodiment, the Compound is selected from a Compound in Table 1 and is administered in combination with temozolomide.

Representative Compounds

Representative compounds of Formula I are depicted below. The examples are merely illustrative and do not limit the scope of the invention in any way. Compounds in Table 1 are named according to systematic application of the nomenclature rules agreed upon by the International Union of Pure and Applied Chemistry (IUPAC), International Union of Biochemistry and Molecular Biology (IUBMB), and the Chemical Abstracts Service (CAS) using ACD/Labs software v. 8.08. Structures in Table 1 were generated using ISIS Draw.

TABLE 1

| Cmpd No. | Structure | Name |
| --- | --- | --- |
| 1 | 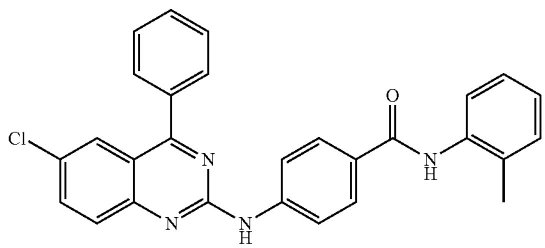 [SMILES: Cc1ccccc1NC(=O)c1ccc(Nc2nc(-c3ccccc3)c3cc(Cl)ccc3n2)cc1] | 4-[(6-chloro-4-phenylquinazolin-2-yl)amino]-N-(2-methylphenyl)benzamide |
| 2 | 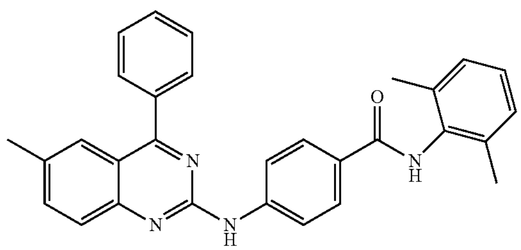 [SMILES: Cc1ccc2nc(Nc3ccc(C(=O)Nc4c(C)cccc4C)cc3)nc(-c3ccccc3)c2c1] | N-(2,6-dimethylphenyl)-4-[(6-methyl-4-phenylquinazolin-2-yl)amino]benzamide |
| 3 | 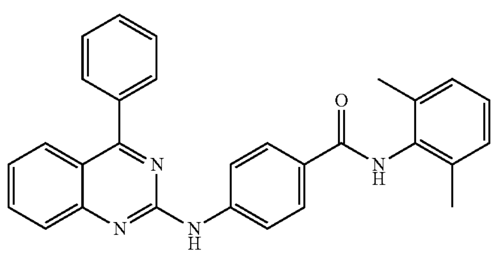 | N-(2,6-dimethylphenyl)-4-[(4-phenylquinazolin-2-yl)amino]benzamide |
| 4 | 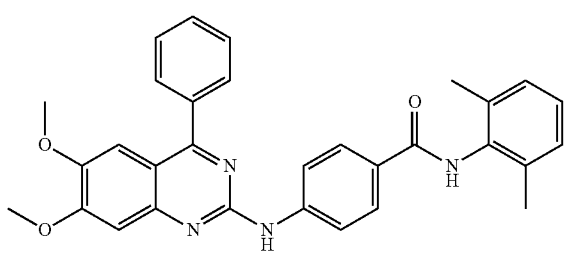 [SMILES: COc1cc2nc(Nc3ccc(C(=O)Nc4c(C)cccc4C)cc3)nc(-c3ccccc3)c2cc1OC] | 4-{[6,7-bis(methyloxy)-4-phenylquinazolin-2-yl]amino}-N-(2,6-dimethylphenyl)benzamide |
| 5 | 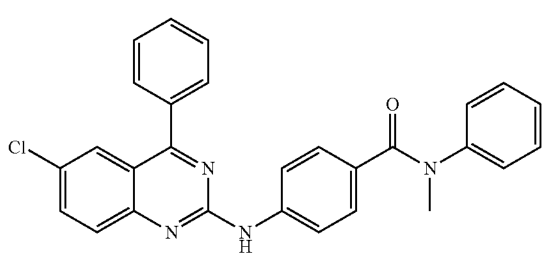 [SMILES: CN(C(=O)c1ccc(Nc2nc(-c3ccccc3)c3cc(Cl)ccc3n2)cc1)c1ccccc1] | 4-[(6-chloro-4-phenylquinazolin-2-yl)amino]-N-methyl-N-phenylbenzamide |

TABLE 1-continued

| Cmpd No. | Structure | Name |
|---|---|---|
| 6 | 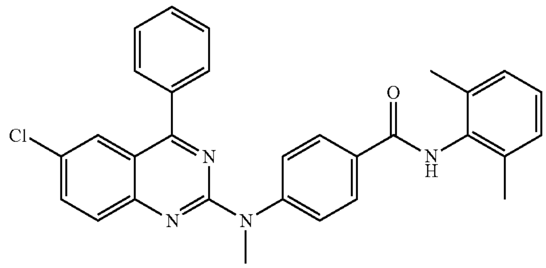 [SMILES: Cc1cccc(C)c1NC(=O)c1ccc(N(C)c2nc(-c3ccccc3)c3cc(Cl)ccc3n2)cc1] | 4-[(6-chloro-4-phenylquinazolin-2-yl)(methyl)amino]-N-(2,6-dimethylphenyl)benzamide |
| 7 | 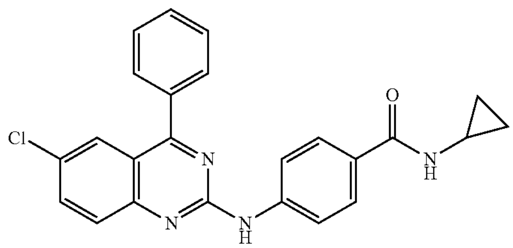 [SMILES: O=C(NC1CC1)c1ccc(Nc2nc(-c3ccccc3)c3cc(Cl)ccc3n2)cc1] | 4-[(6-chloro-4-phenylquinazolin-2-yl)amino]-N-cyclopropylbenzamide |
| 8 | 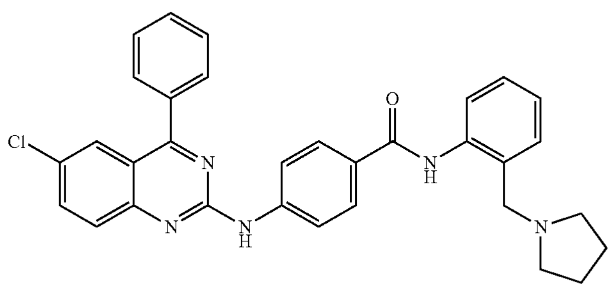 [SMILES: O=C(Nc1ccccc1CN1CCCC1)c1ccc(Nc2nc(-c3ccccc3)c3cc(Cl)ccc3n2)cc1] | 4-[(6-chloro-4-phenylquinazolin-2-yl)amino]-N-[2-(pyrrolidin-1-ylmethyl)phenyl]benzamide |
| 9 | 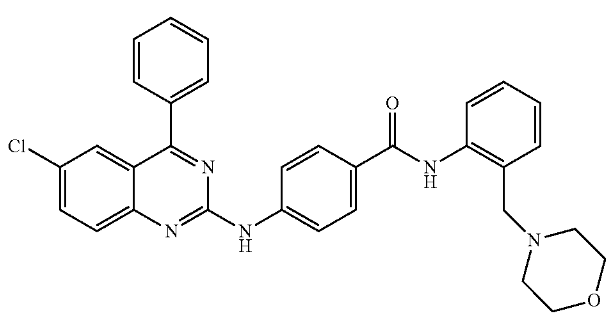 [SMILES: O=C(Nc1ccccc1CN1CCOCC1)c1ccc(Nc2nc(-c3ccccc3)c3cc(Cl)ccc3n2)cc1] | 4-[(6-chloro-4-phenylquinazolin-2-yl)amino]-N-[2-(morpholin-4-ylmethyl)phenyl]benzamide |
| 10 | 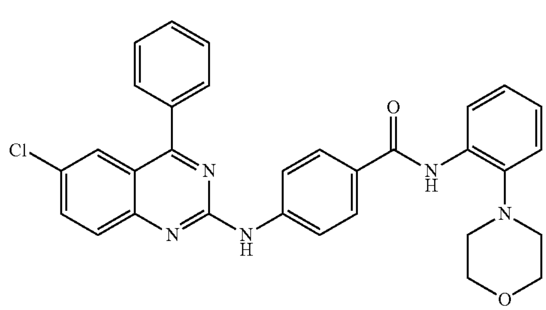 [SMILES: O=C(Nc1ccccc1N1CCOCC1)c1ccc(Nc2nc(-c3ccccc3)c3cc(Cl)ccc3n2)cc1] | 4-[(6-chloro-4-phenylquinazolin-2-yl)amino]-N-(2-morpholin-4-ylphenyl)benzamide |

TABLE 1-continued

| Cmpd No. | Structure | Name |
|---|---|---|
| 11 | 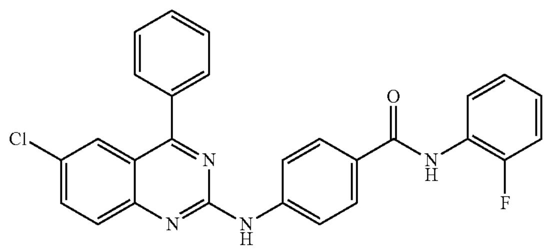 [SMILES: O=C(Nc1ccccc1F)c1ccc(Nc2nc(-c3ccccc3)c3cc(Cl)ccc3n2)cc1] | 4-[(6-chloro-4-phenylquinazolin-2-yl)amino]-N-(2-fluorophenyl)benzamide |
| 12 | 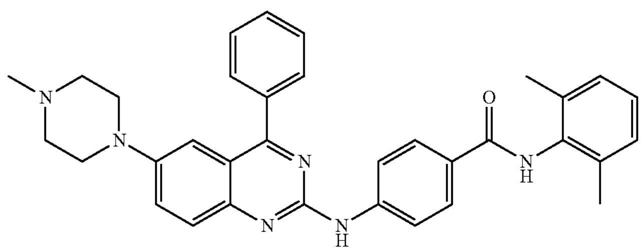 [SMILES: Cc1cccc(C)c1NC(=O)c1ccc(Nc2nc(-c3ccccc3)c3cc(N4CCN(C)CC4)ccc3n2)cc1] | N-(2,6-dimethylphenyl)-4-{[6-(4-methylpiperazin-1-yl)-4-phenylquinazolin-2-yl]amino}benzamide |
| 13 | 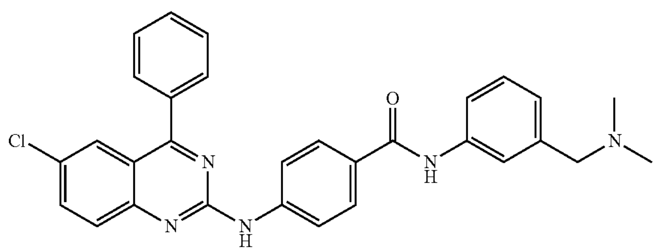 [SMILES: CN(C)Cc1cccc(NC(=O)c2ccc(Nc3nc(-c4ccccc4)c4cc(Cl)ccc4n3)cc2)c1] | 4-[(6-chloro-4-phenylquinazolin-2-yl)amino]-N-{3-[(dimethylamino)methyl]phenyl}benzamide |
| 14 | 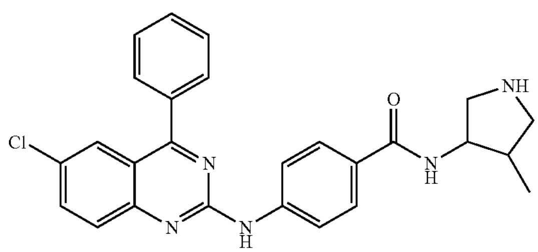 [SMILES: CC1CNCC1NC(=O)c1ccc(Nc2nc(-c3ccccc3)c3cc(Cl)ccc3n2)cc1] | 4-[(6-chloro-4-phenylquinazolin-2-yl)amino]-N-(4-methylpyrrolidin-3-yl)benzamide |
| 15 | 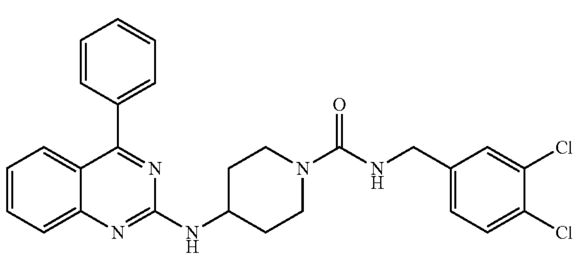 [SMILES: O=C(NCc1ccc(Cl)c(Cl)c1)N1CCC(Nc2nc(-c3ccccc3)c3ccccc3n2)CC1] | N-[(3,4-dichlorophenyl)methyl]-4-[(4-phenylquinazolin-2-yl)amino]piperidine-1-carboxamide |
| 16 | 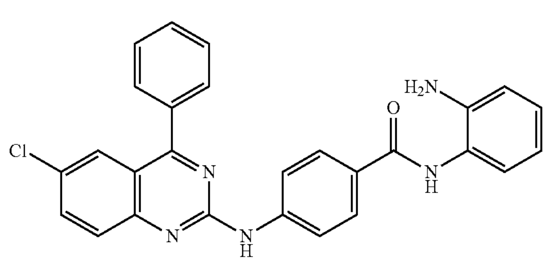 [SMILES: Nc1ccccc1NC(=O)c1ccc(Nc2nc(-c3ccccc3)c3cc(Cl)ccc3n2)cc1] | N-(2-aminophenyl)-4-[(6-chloro-4-phenylquinazolin-2-yl)amino]benzamide |

TABLE 1-continued

| Cmpd No. | Structure | Name |
|---|---|---|
| 17 | 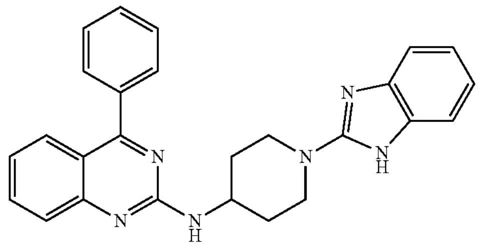 [SMILES: c1ccc(-c2nc(NC3CCN(c4nc5ccccc5[nH]4)CC3)nc3ccccc23)cc1] | N-[1-(1H-benzimidazol-2-yl)piperidin-4-yl]-4-phenylquinazolin-2-amine |
| 18 | 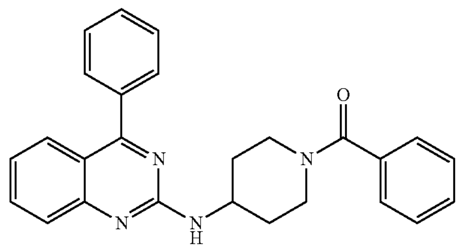 [SMILES: O=C(c1ccccc1)N1CCC(Nc2nc(-c3ccccc3)c3ccccc3n2)CC1] | 4-phenyl-N-[1-(phenylcarbonyl)piperidin-4-yl]quinazolin-2-amine |
| 19 | 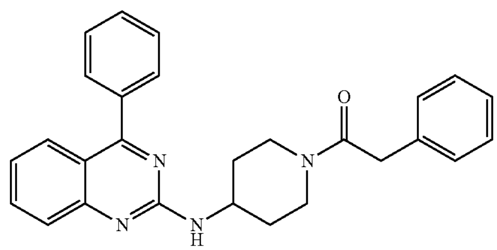 [SMILES: O=C(Cc1ccccc1)N1CCC(Nc2nc(-c3ccccc3)c3ccccc3n2)CC1] | 4-phenyl-N-[1-(phenylacetyl)piperidin-4-yl]quinazolin-2-amine |
| 20 | 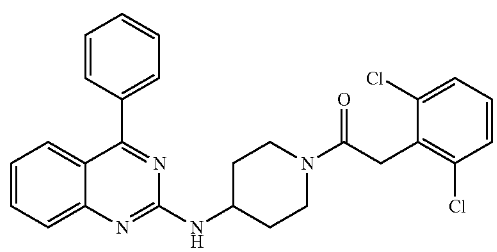 [SMILES: O=C(Cc1c(Cl)cccc1Cl)N1CCC(Nc2nc(-c3ccccc3)c3ccccc3n2)CC1] | N-{1-[(2,6-dichlorophenyl)acetyl]piperidin-4-yl}-4-phenylquinazolin-2-amine |
| 21 | 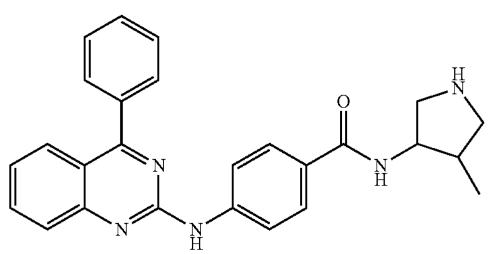 [SMILES: CC1CNCC1NC(=O)c1ccc(Nc2nc(-c3ccccc3)c3ccccc3n2)cc1] | N-(4-methylpyrrolidin-3-yl)-4-[(4-phenylquinazolin-2-yl)amino]benzamide |
| 22 | 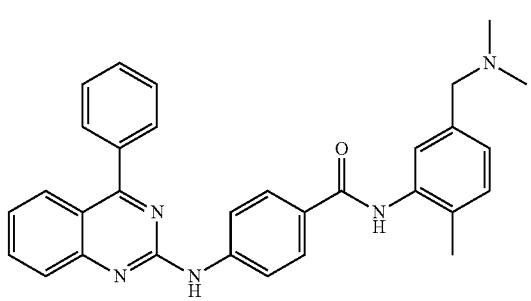 [SMILES: Cc1ccc(CN(C)C)cc1NC(=O)c1ccc(Nc2nc(-c3ccccc3)c3ccccc3n2)cc1] | N-{5-[(dimethylamino)methyl]-2-methylphenyl}-4-[(4-phenylquinazolin-2-yl)amino]benzamide |

TABLE 1-continued

| Cmpd No. | Structure | Name |
|---|---|---|
| 23 | 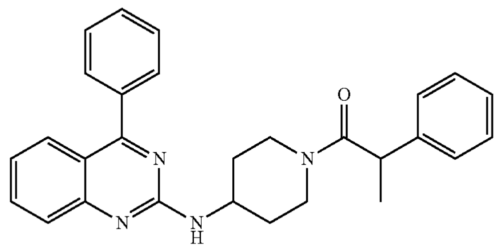 [SMILES: CC(C(=O)N1CCC(Nc2nc(-c3ccccc3)c3ccccc3n2)CC1)c1ccccc1] | 4-phenyl-N-[1-(2-phenylpropanoyl)piperidin-4-yl]quinazolin-2-amine |
| 24 | 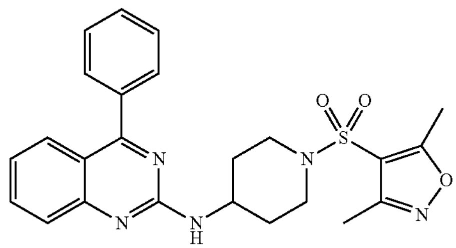 [SMILES: Cc1noc(C)c1S(=O)(=O)N1CCC(Nc2nc(-c3ccccc3)c3ccccc3n2)CC1] | N-{1-[(3,5-dimethylisoxazol-4-yl)sulfonyl]piperidin-4-yl}-4-phenylquinazolin-2-amine |
| 25 | 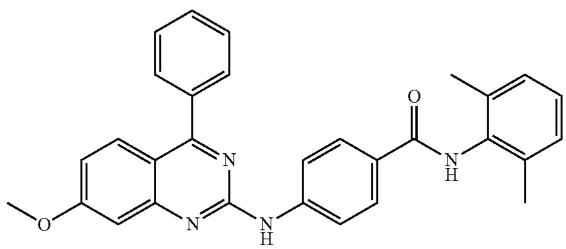 [SMILES: COc1ccc2c(-c3ccccc3)nc(Nc3ccc(C(=O)Nc4c(C)cccc4C)cc3)nc2c1] | N-(2,6-dimethylphenyl)-4-{[7-(methyloxy)-4-phenylquinazolin-2-yl]amino}benzamide |
| 26 | 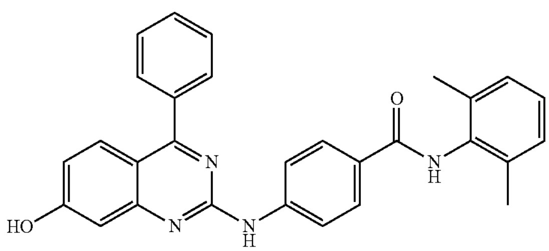 [SMILES: Cc1cccc(C)c1NC(=O)c1ccc(Nc2nc(-c3ccccc3)c3ccc(O)cc3n2)cc1] | N-(2,6-dimethylphenyl)-4-[(7-hydroxy-4-phenylquinazolin-2-yl)amino]benzamide |
| 27 | 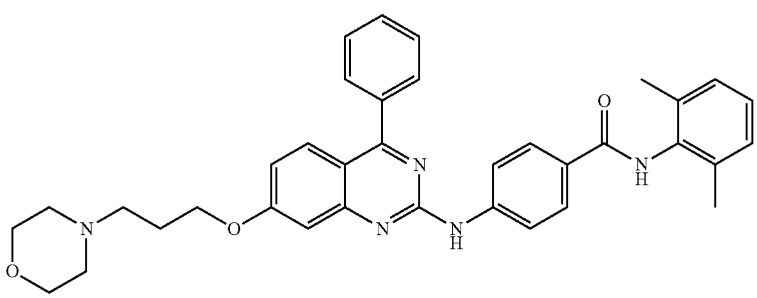 [SMILES: Cc1cccc(C)c1NC(=O)c1ccc(Nc2nc(-c3ccccc3)c3ccc(OCCCN4CCOCC4)cc3n2)cc1] | N-(2,6-dimethylphenyl)-4-({7-[(3-morpholin-4-ylpropyl)oxy]-4-phenylquinazolin-2-yl}amino)benzamide |
| 28 | 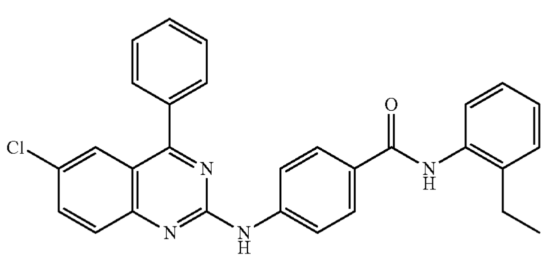 [SMILES: CCc1ccccc1NC(=O)c1ccc(Nc2nc(-c3ccccc3)c3cc(Cl)ccc3n2)cc1] | 4-[(6-chloro-4-phenylquinazolin-2-yl)amino]-N-(2-ethylphenyl)benzamide |

TABLE 1-continued

| Cmpd No. | Structure | Name |
|---|---|---|
| 29 | 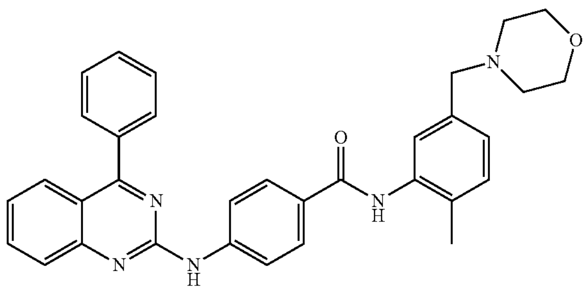 [SMILES: Cc1ccc(CN2CCOCC2)cc1NC(=O)c1ccc(Nc2nc(-c3ccccc3)c3ccccc3n2)cc1] | N-[2-methyl-5-(morpholin-4-ylmethyl)phenyl]-4-[(4-phenylquinazolin-2-yl)amino]benzamide |
| 30 | 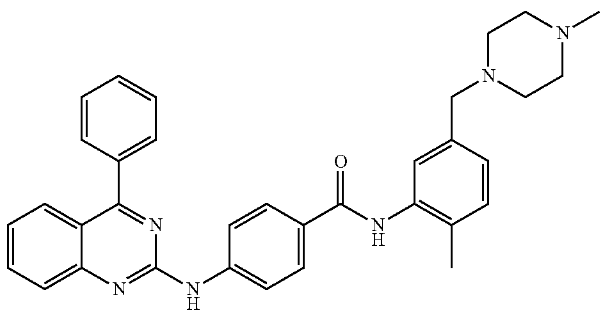 [SMILES: Cc1ccc(CN2CCN(C)CC2)cc1NC(=O)c1ccc(Nc2nc(-c3ccccc3)c3ccccc3n2)cc1] | N-{2-methyl-5-[(4-methylpiperazin-1-yl)methyl]phenyl}-4-[(4-phenylquinazolin-2-yl)amino]benzamide |
| 31 | 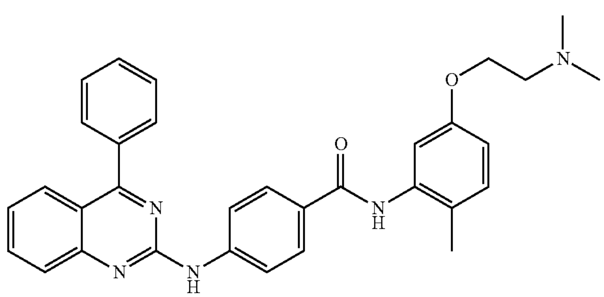 [SMILES: Cc1ccc(OCCN(C)C)cc1NC(=O)c1ccc(Nc2nc(-c3ccccc3)c3ccccc3n2)cc1] | N-(5-{[2-(dimethylamino)ethyl]oxy}-2-methylphenyl)-4-[(4-phenylquinazolin-2-yl)amino]benzamide |
| 32 | 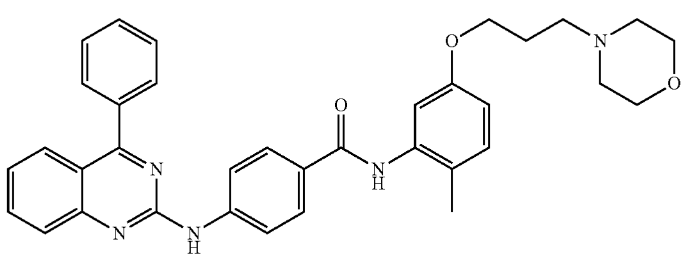 [SMILES: Cc1ccc(OCCCN2CCOCC2)cc1NC(=O)c1ccc(Nc2nc(-c3ccccc3)c3ccccc3n2)cc1] | N-{2-methyl-5-[(3-morpholin-4-ylpropyl)oxy]phenyl}-4-[(4-phenylquinazolin-2-yl)amino]benzamide |
| 33 | 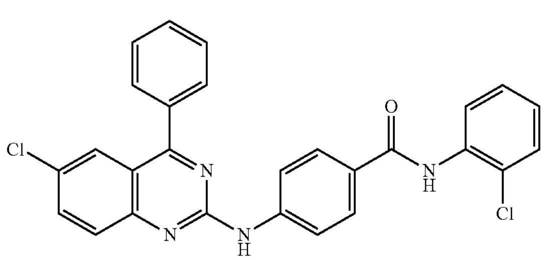 [SMILES: O=C(Nc1ccccc1Cl)c1ccc(Nc2nc(-c3ccccc3)c3cc(Cl)ccc3n2)cc1] | N-(2-chlorophenyl)-4-[(6-chloro-4-phenylquinazolin-2-yl)amino]benzamide |

63 64

TABLE 1-continued

| Cmpd No. | Structure | Name |
|---|---|---|
| 34 | 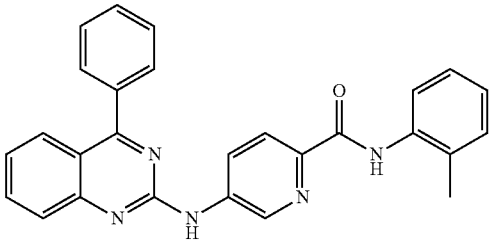 [SMILES: Cc1ccccc1NC(=O)c1ccc(Nc2nc(-c3ccccc3)c3ccccc3n2)cn1] | N-(2-methylphenyl)-5-[(4-phenylquinazolin-2-yl)amino]pyridine-2-carboxamide |
| 35 | 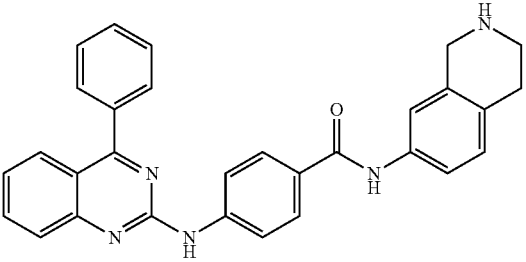 [SMILES: O=C(Nc1ccc2c(c1)CNCC2)c1ccc(Nc2nc(-c3ccccc3)c3ccccc3n2)cc1] | 4-[(4-phenylquinazolin-2-yl)amino]-N-(1,2,3,4-tetrahydroisoquinolin-7-yl)benzamide |
| 36 | 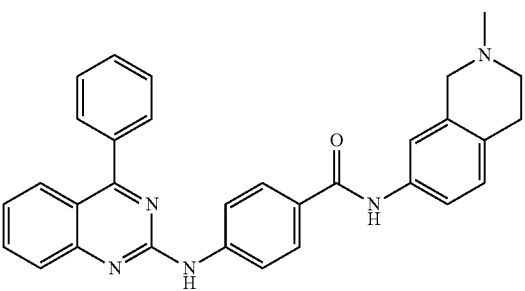 [SMILES: CN1CCc2ccc(NC(=O)c3ccc(Nc4nc(-c5ccccc5)c5ccccc5n4)cc3)cc2C1] | N-(2-methyl-1,2,3,4-tetrahydroisoquinolin-7-yl)-4-[(4-phenylquinazolin-2-yl)amino]benzamide |
| 37 | 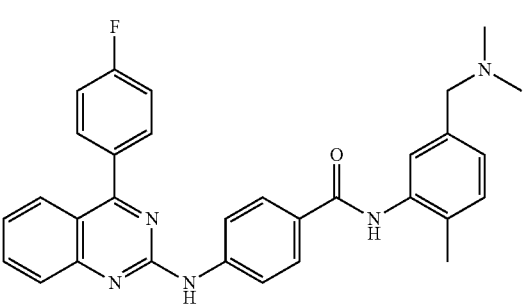 [SMILES: Cc1ccc(CN(C)C)cc1NC(=O)c1ccc(Nc2nc(-c3ccc(F)cc3)c3ccccc3n2)cc1] | N-{5-[(dimethylamino)methyl]-2-methylphenyl}-4-{[4-(4-fluorophenyl)quinazolin-2-yl]amino}benzamide |
| 38 | 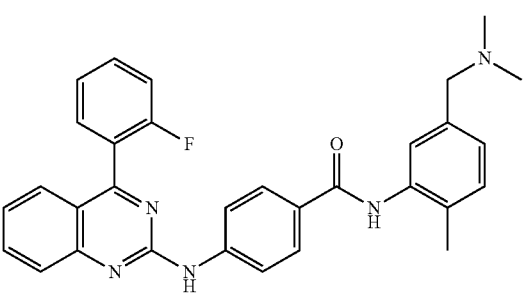 [SMILES: Cc1ccc(CN(C)C)cc1NC(=O)c1ccc(Nc2nc(-c3ccccc3F)c3ccccc3n2)cc1] | N-{5-[(dimethylamino)methyl]-2-methylphenyl}-4-{[4-(2-fluorophenyl)quinazolin-2-yl]amino}benzamide |

TABLE 1-continued

| Cmpd No. | Structure | Name |
|---|---|---|
| 39 | 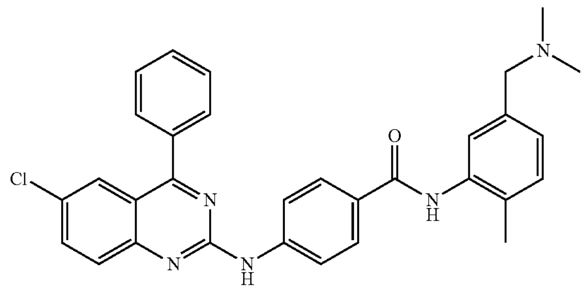 [SMILES: Cc1ccc(CN(C)C)cc1NC(=O)c1ccc(Nc2nc(-c3ccccc3)c3cc(Cl)ccc3n2)cc1] | 4-[(6-chloro-4-phenylquinazolin-2-yl)amino]-N-{5-[(dimethylamino)methyl]-2-methylphenyl}benzamide |
| 40 | 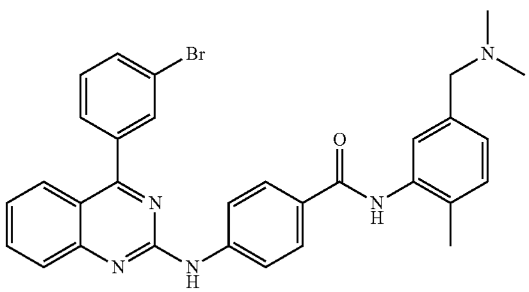 [SMILES: Cc1ccc(CN(C)C)cc1NC(=O)c1ccc(Nc2nc(-c3cccc(Br)c3)c3ccccc3n2)cc1] | 4-{[4-(3-bromophenyl)quinazolin-2-yl]amino}-N-{5-[(dimethylamino)methyl]-2-methylphenyl}benzamide |
| 41 | 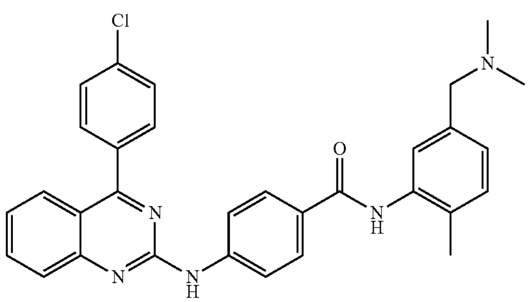 [SMILES: Cc1ccc(CN(C)C)cc1NC(=O)c1ccc(Nc2nc(-c3ccc(Cl)cc3)c3ccccc3n2)cc1] | 4-{[4-(4-chlorophenyl)quinazolin-2-yl]amino}-N-{5-[(dimethylamino)methyl]-2-methylphenyl}benzamide |
| 42 | 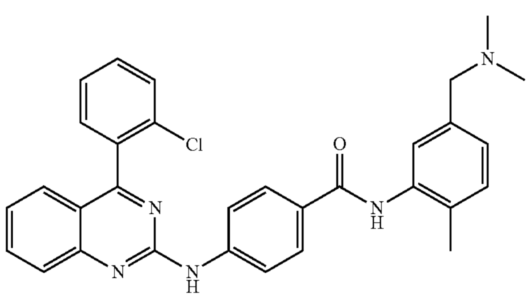 [SMILES: Cc1ccc(CN(C)C)cc1NC(=O)c1ccc(Nc2nc(-c3ccccc3Cl)c3ccccc3n2)cc1] | 4-{[4-(2-chlorophenyl)quinazolin-2-yl]amino}-N-{5-[(dimethylamino)methyl]-2-methylphenyl}benzamide |
| 43 | 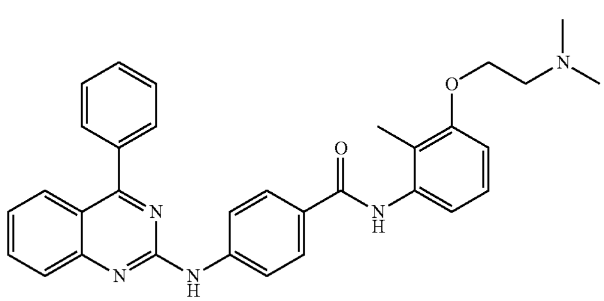 [SMILES: Cc1c(NC(=O)c2ccc(Nc3nc(-c4ccccc4)c4ccccc4n3)cc2)cccc1OCCN(C)C] | N-(3-{[2-(dimethylamino)ethyl]oxy}-2-methylphenyl)-4-[(4-phenylquinazolin-2-yl)amino]benzamide |

TABLE 1-continued

| Cmpd No. | Structure | Name |
|---|---|---|
| 44 | 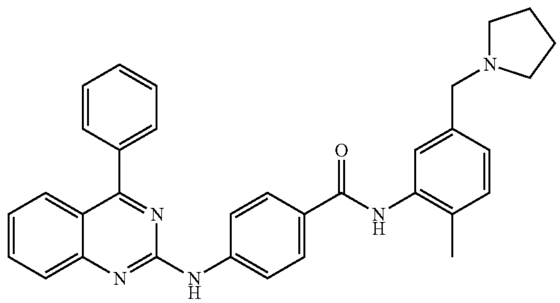 [SMILES: Cc1ccc(CN2CCCC2)cc1NC(=O)c1ccc(Nc2nc(-c3ccccc3)c3ccccc3n2)cc1] | N-[2-methyl-5-(pyrrolidin-1-ylmethyl)phenyl]-4-[(4-phenylquinazolin-2-yl)amino]benzamide |
| 45 | 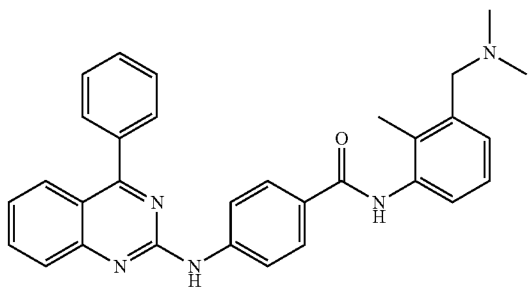 [SMILES: Cc1c(CN(C)C)cccc1NC(=O)c1ccc(Nc2nc(-c3ccccc3)c3ccccc3n2)cc1] | N-{3-[(dimethylamino)methyl]-2-methylphenyl}-4-[(4-phenylquinazolin-2-yl)amino]benzamide |
| 46 | 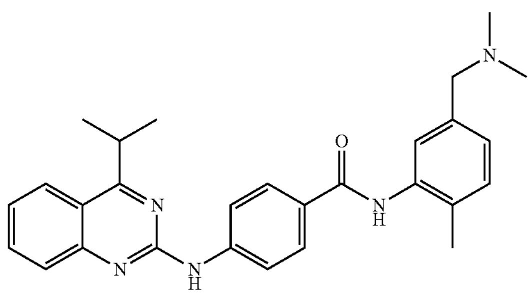 [SMILES: Cc1ccc(CN(C)C)cc1NC(=O)c1ccc(Nc2nc(C(C)C)c3ccccc3n2)cc1] | N-{5-[(dimethylamino)methyl]-2-methylphenyl}-4-{[4-(1-methylethyl)quinazolin-2-yl]amino}benzamide |
| 47 | 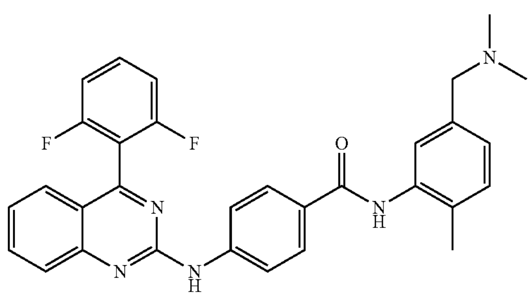 [SMILES: Cc1ccc(CN(C)C)cc1NC(=O)c1ccc(Nc2nc(-c3c(F)cccc3F)c3ccccc3n2)cc1] | 4-{[4-(2,6-difluorophenyl)quinazolin-2-yl]amino}-N-{5-[(dimethylamino)methyl]-2-methylphenyl}benzamide |
| 48 | 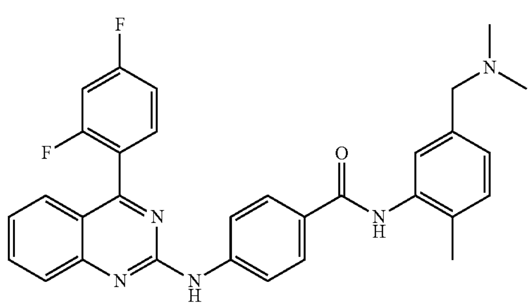 [SMILES: Cc1ccc(CN(C)C)cc1NC(=O)c1ccc(Nc2nc(-c3ccc(F)cc3F)c3ccccc3n2)cc1] | 4-{[4-(2,4-difluorophenyl)quinazolin-2-yl]amino}-N-{5-[(dimethylamino)methyl]-2-methylphenyl}benzamide |

TABLE 1-continued

| Cmpd No. | Structure | Name |
|---|---|---|
| 49 | 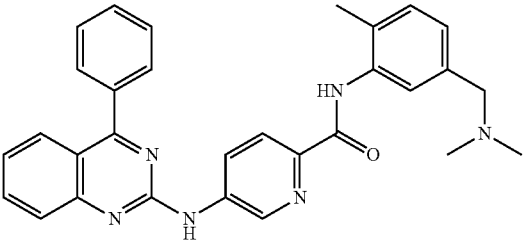 [SMILES: Cc1ccc(CN(C)C)cc1NC(=O)c1ccc(Nc2nc(-c3ccccc3)c3ccccc3n2)cn1] | N-{5-[(dimethylamino)methyl]-2-methylphenyl}-5-[(4-phenylquinazolin-2-yl)amino]pyridine-2-carboxamide |
| 50 | 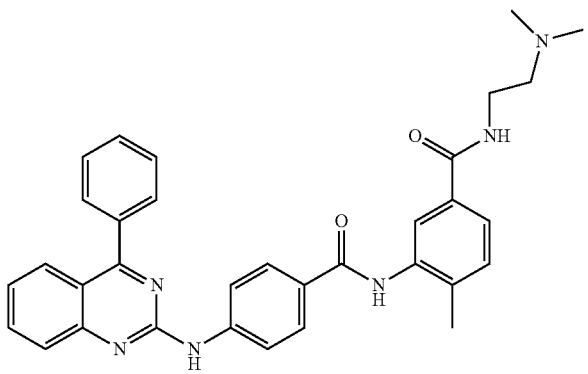 [SMILES: Cc1ccc(C(=O)NCCN(C)C)cc1NC(=O)c1ccc(Nc2nc(-c3ccccc3)c3ccccc3n2)cc1] | N-[2-(dimethylamino)ethyl]-4-methyl-3-[({4-[(4-phenylquinazolin-2-yl)amino]phenyl}carbonyl)amino]benzamide |
| 51 | 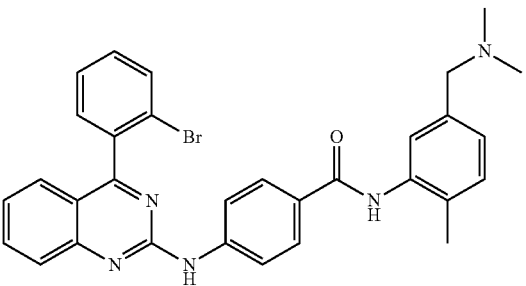 [SMILES: Cc1ccc(CN(C)C)cc1NC(=O)c1ccc(Nc2nc(-c3ccccc3Br)c3ccccc3n2)cc1] | 4-{[4-(2-bromophenyl)quinazolin-2-yl]amino}-N-{5-[(dimethylamino)methyl]-2-methylphenyl}benzamide |
| 52 | 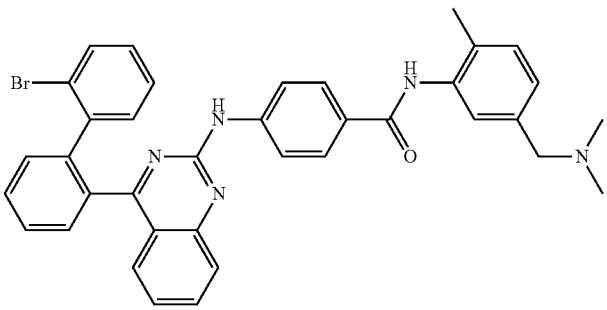 [SMILES: Cc1ccc(CN(C)C)cc1NC(=O)c1ccc(Nc2nc(-c3ccccc3-c3ccccc3Br)c3ccccc3n2)cc1] | 4-{[4-(2'-bromobiphenyl-2-yl)quinazolin-2-yl]amino}-N-{5-[(dimethylamino)methyl]-2-methylphenyl}benzamide |
| 53 | 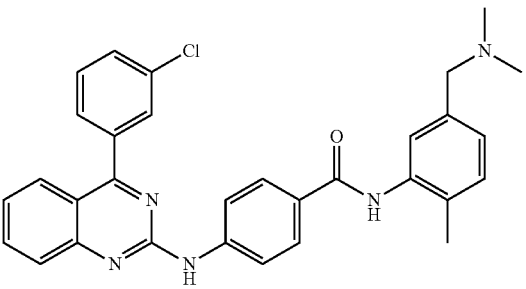 [SMILES: Cc1ccc(CN(C)C)cc1NC(=O)c1ccc(Nc2nc(-c3cccc(Cl)c3)c3ccccc3n2)cc1] | 4-{[4-(3-chlorophenyl)quinazolin-2-yl]amino}-N-{5-[(dimethylamino)methyl]-2-methylphenyl}benzamide |

TABLE 1-continued

| Cmpd No. | Structure | Name |
|---|---|---|
| 54 | 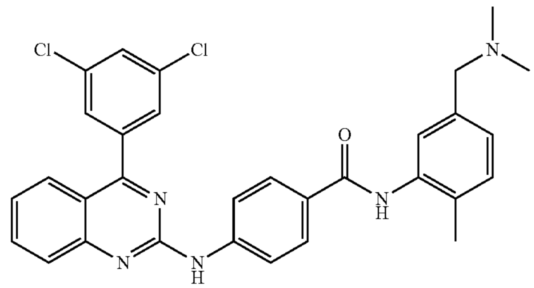 [SMILES: Cc1ccc(CN(C)C)cc1NC(=O)c1ccc(Nc2nc(-c3cc(Cl)cc(Cl)c3)c3ccccc3n2)cc1] | 4-{[4-(3,5-dichlorophenyl)quinazolin-2-yl]amino}-N-{5-[(dimethylamino)methyl]-2-methylphenyl}benzamide |
| 55 | 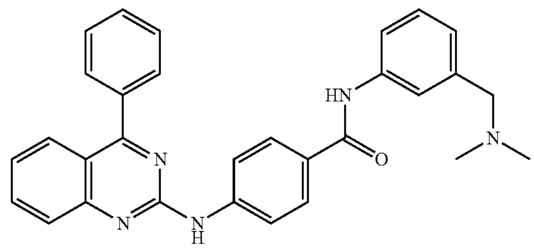 [SMILES: CN(C)Cc1cccc(NC(=O)c2ccc(Nc3nc(-c4ccccc4)c4ccccc4n3)cc2)c1] | N-{3-[(dimethylamino)methyl]phenyl}-4-[(4-phenylquinazolin-2-yl)amino]benzamide |
| 56 | 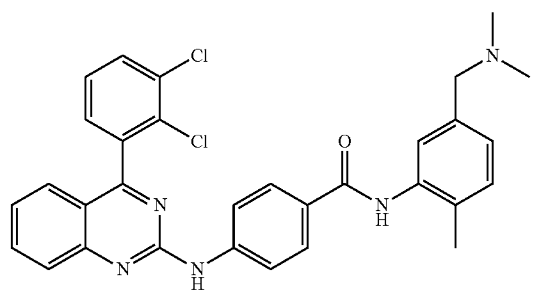 [SMILES: Cc1ccc(CN(C)C)cc1NC(=O)c1ccc(Nc2nc(-c3cccc(Cl)c3Cl)c3ccccc3n2)cc1] | 4-{[4-(2,3-dichlorophenyl)quinazolin-2-yl]amino}-N-{5-[(dimethylamino)methyl]-2-methylphenyl}benzamide |
| 57 | 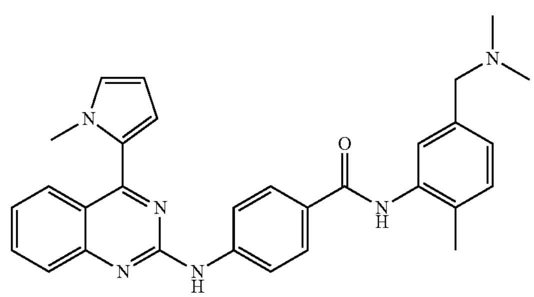 [SMILES: Cc1ccc(CN(C)C)cc1NC(=O)c1ccc(Nc2nc(-c3cccn3C)c3ccccc3n2)cc1] | N-{5-[(dimethylamino)methyl]-2-methylphenyl}-4-{[4-(1-methyl-1H-pyrrol-2-yl)quinazolin-2-yl]amino}benzamide |
| 58 | 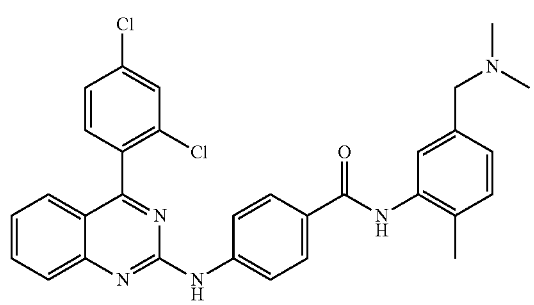 [SMILES: Cc1ccc(CN(C)C)cc1NC(=O)c1ccc(Nc2nc(-c3ccc(Cl)cc3Cl)c3ccccc3n2)cc1] | 4-{[4-(2,4-dichlorophenyl)quinazolin-2-yl]amino}-N-{5-[(dimethylamino)methyl]-2-methylphenyl}benzamide |

TABLE 1-continued

| Cmpd No. | Structure | Name |
|---|---|---|
| 59 | 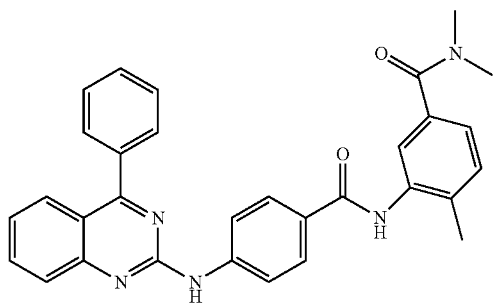 [SMILES: Cc1ccc(C(=O)N(C)C)cc1NC(=O)c1ccc(Nc2nc(-c3ccccc3)c3ccccc3n2)cc1] | N,N,4-trimethyl-3-[({4-[(4-phenylquinazolin-2-yl)amino]phenyl}carbonyl)amino]benzamide |
| 60 | 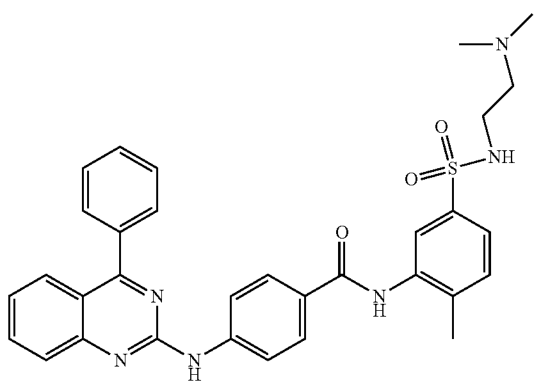 [SMILES: Cc1ccc(S(=O)(=O)NCCN(C)C)cc1NC(=O)c1ccc(Nc2nc(-c3ccccc3)c3ccccc3n2)cc1] | N-[5-({[2-(dimethylamino)ethyl]amino}sulfonyl)-2-methylphenyl]-4-[(4-phenylquinazolin-2-yl)amino]benzamide |
| 61 | 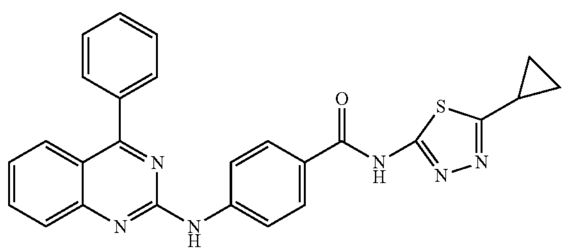 [SMILES: O=C(Nc1nnc(C2CC2)s1)c1ccc(Nc2nc(-c3ccccc3)c3ccccc3n2)cc1] | N-(5-cyclopropyl-1,3,4-thiadiazol-2-yl)-4-[(4-phenylquinazolin-2-yl)amino]benzamide |
| 62 | 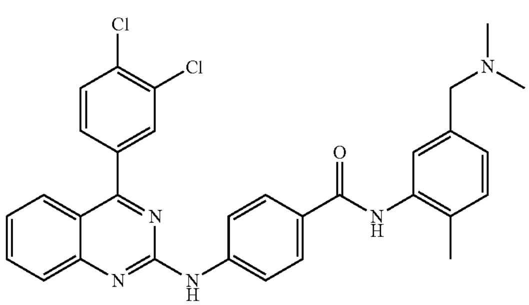 [SMILES: Cc1ccc(CN(C)C)cc1NC(=O)c1ccc(Nc2nc(-c3ccc(Cl)c(Cl)c3)c3ccccc3n2)cc1] | 4-{[4-(3,4-dichlorophenyl)quinazolin-2-yl]amino}-N-{5-[(dimethylamino)methyl]-2-methylphenyl}benzamide |
| 63 | 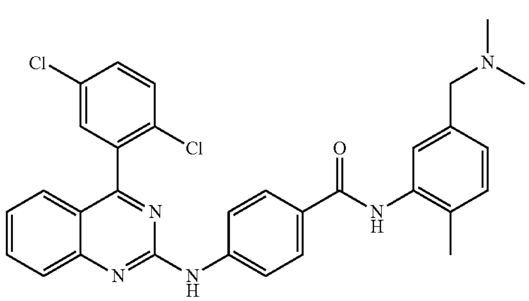 [SMILES: Cc1ccc(CN(C)C)cc1NC(=O)c1ccc(Nc2nc(-c3cc(Cl)ccc3Cl)c3ccccc3n2)cc1] | 4-{[4-(2,5-dichlorophenyl)quinazolin-2-yl]amino}-N-{5-[(dimethylamino)methyl]-2-methylphenyl}benzamide |

TABLE 1-continued

| Cmpd No. | Structure | Name |
|---|---|---|
| 64 | 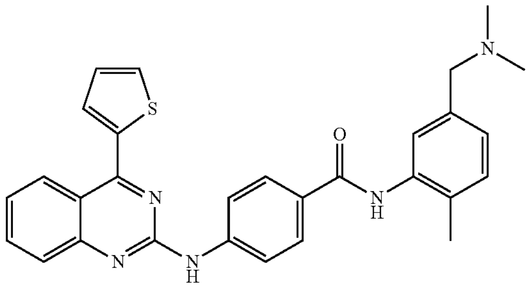 [SMILES: Cc1ccc(CN(C)C)cc1NC(=O)c1ccc(Nc2nc(-c3cccs3)c3ccccc3n2)cc1] | N-{5-[(dimethylamino)methyl]-2-methylphenyl}-4-{[4-(2-thienyl)quinazolin-2-yl]amino}benzamide |
| 65 | 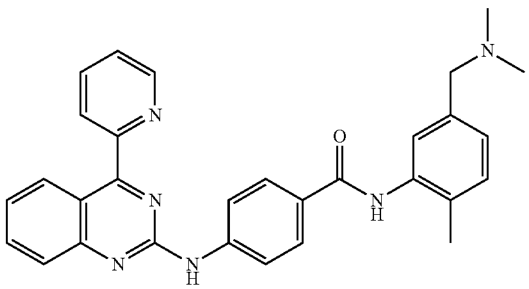 [SMILES: Cc1ccc(CN(C)C)cc1NC(=O)c1ccc(Nc2nc(-c3ccccn3)c3ccccc3n2)cc1] | N-{5-[(dimethylamino)methyl]-2-methylphenyl}-4-[(4-pyridin-2-ylquinazolin-2-yl)amino]benzamide |
| 66 | 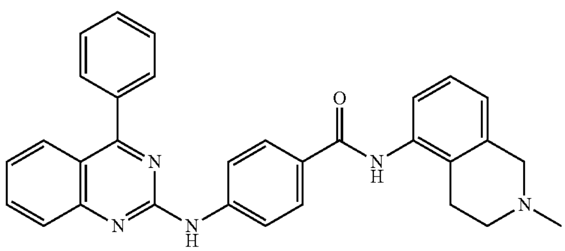 [SMILES: CN1CCc2c(cccc2NC(=O)c2ccc(Nc3nc(-c4ccccc4)c4ccccc4n3)cc2)C1] | N-(2-methyl-1,2,3,4-tetrahydroisoquinolin-5-yl)-4-[(4-phenylquinazolin-2-yl)amino]benzamide |
| 67 | 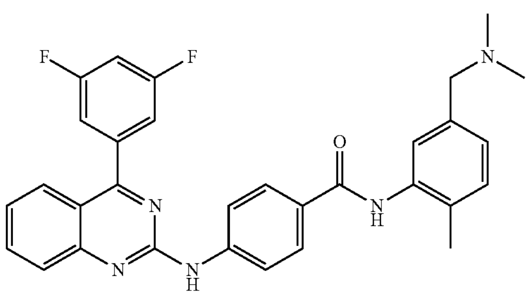 [SMILES: Cc1ccc(CN(C)C)cc1NC(=O)c1ccc(Nc2nc(-c3cc(F)cc(F)c3)c3ccccc3n2)cc1] | 4-{[4-(3,5-difluorophenyl)quinazolin-2-yl]amino}-N-{5-[(dimethylamino)methyl]-2-methylphenyl}benzamide |
| 68 | 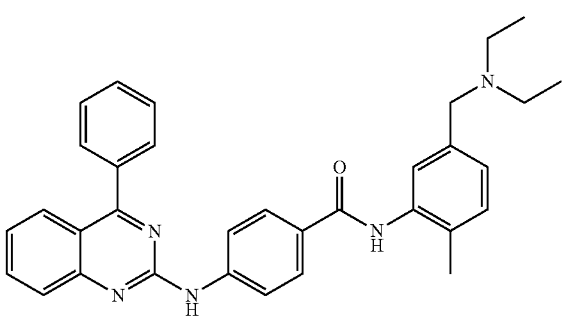 [SMILES: CCN(CC)Cc1ccc(C)c(NC(=O)c2ccc(Nc3nc(-c4ccccc4)c4ccccc4n3)cc2)c1] | N-{5-[(diethylamino)methyl]-2-methylphenyl}-4-[(4-phenylquinazolin-2-yl)amino]benzamide |

TABLE 1-continued

| Cmpd No. | Structure | Name |
|---|---|---|
| 69 | 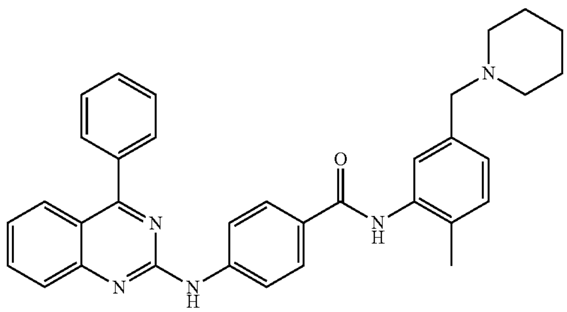 [SMILES: Cc1ccc(CN2CCCCC2)cc1NC(=O)c1ccc(Nc2nc(-c3ccccc3)c3ccccc3n2)cc1] | N-[2-methyl-5-(piperidin-1-ylmethyl)phenyl]-4-[(4-phenylquinazolin-2-yl)amino]benzamide |
| 70 | 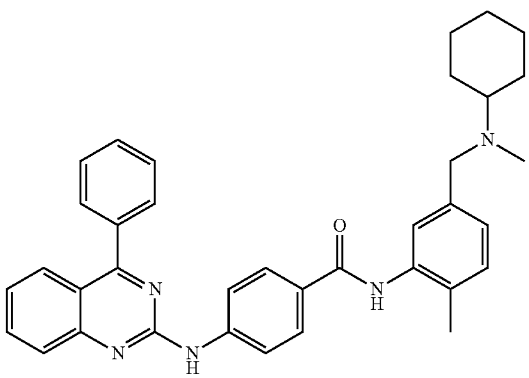 [SMILES: Cc1ccc(CN(C)C2CCCCC2)cc1NC(=O)c1ccc(Nc2nc(-c3ccccc3)c3ccccc3n2)cc1] | N-(5-{[cyclohexyl(methyl)amino]methyl}-2-methylphenyl)-4-[(4-phenylquinazolin-2-yl)amino]benzamide |
| 71 | 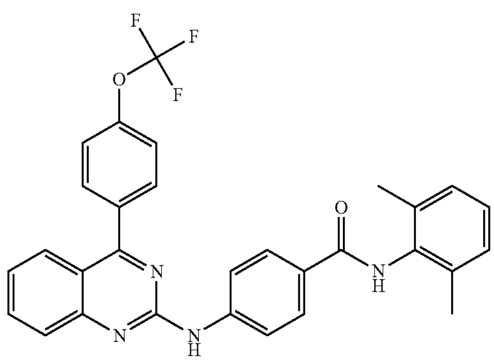 [SMILES: Cc1cccc(C)c1NC(=O)c1ccc(Nc2nc(-c3ccc(OC(F)(F)F)cc3)c3ccccc3n2)cc1] | N-(2,6-dimethylphenyl)-4-[(4-{4-[(trifluoromethyl)oxy]phenyl}quinazolin-2-yl)amino]benzamide |
| 72 | 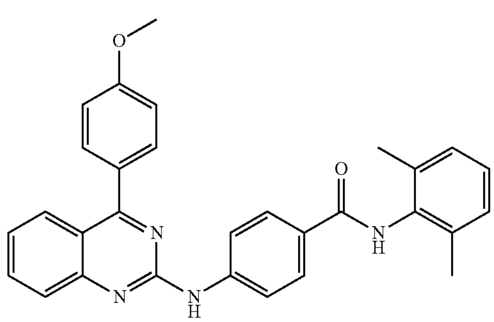 [SMILES: COc1ccc(-c2nc(Nc3ccc(C(=O)Nc4c(C)cccc4C)cc3)nc3ccccc23)cc1] | N-(2,6-dimethylphenyl)-4-({4-[4-(methyloxy)phenyl]quinazolin-2-yl}amino)benzamide |
| 73 | 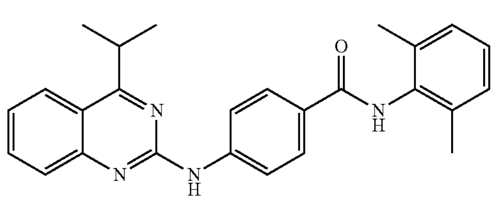 [SMILES: Cc1cccc(C)c1NC(=O)c1ccc(Nc2nc(C(C)C)c3ccccc3n2)cc1] | N-(2,6-dimethylphenyl)-4-{[4-(1-methylethyl)quinazolin-2-yl]amino}benzamide |

TABLE 1-continued

| Cmpd No. | Structure | Name |
|---|---|---|
| 74 | 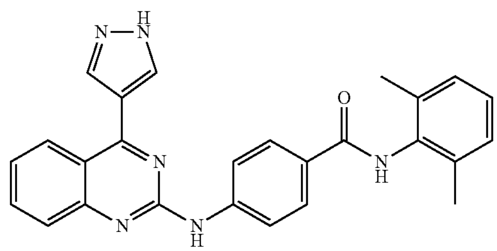 [SMILES: Cc1cccc(C)c1NC(=O)c1ccc(Nc2nc(-c3cn[nH]c3)c3ccccc3n2)cc1] | N-(2,6-dimethylphenyl)-4-{[4-(1H-pyrazol-4-yl)quinazolin-2-yl]amino}benzamide |
| 75 | 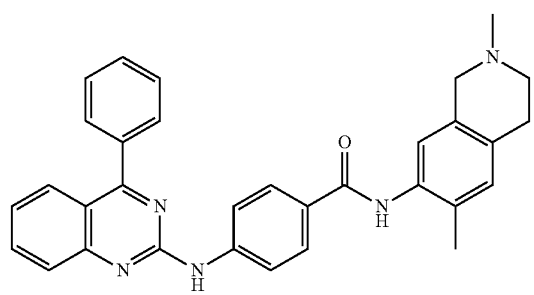 [SMILES: Cc1cc2c(cc1NC(=O)c1ccc(Nc3nc(-c4ccccc4)c4ccccc4n3)cc1)CN(C)CC2] | N-(2,6-dimethyl-1,2,3,4-tetrahydroisoquinolin-7-yl)-4-[(4-phenylquinazolin-2-yl)amino]benzamide |
| 76 | 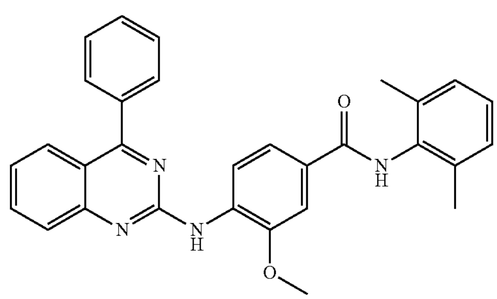 [SMILES: COc1cc(C(=O)Nc2c(C)cccc2C)ccc1Nc1nc(-c2ccccc2)c2ccccc2n1] | N-(2,6-dimethylphenyl)-3-(methyloxy)-4-[(4-phenylquinazolin-2-yl)amino]benzamide |
| 77 | 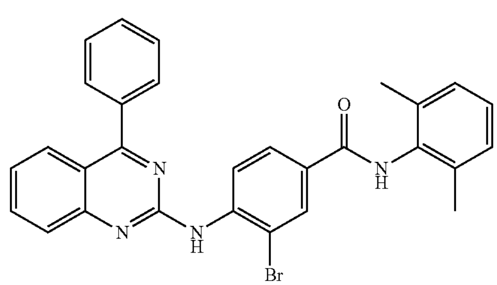 [SMILES: Cc1cccc(C)c1NC(=O)c1ccc(Nc2nc(-c3ccccc3)c3ccccc3n2)c(Br)c1] | 3-bromo-N-(2,6-dimethylphenyl)-4-[(4-phenylquinazolin-2-yl)amino]benzamide |
| 78 | 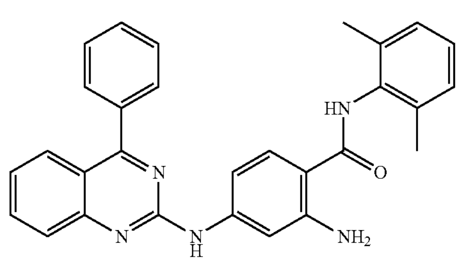 [SMILES: Cc1cccc(C)c1NC(=O)c1ccc(Nc2nc(-c3ccccc3)c3ccccc3n2)cc1N] | 2-amino-N-(2,6-dimethylphenyl)-4-[(4-phenylquinazolin-2-yl)amino]benzamide |

TABLE 1-continued

| Cmpd No. | Structure | Name |
|---|---|---|
| 79 | 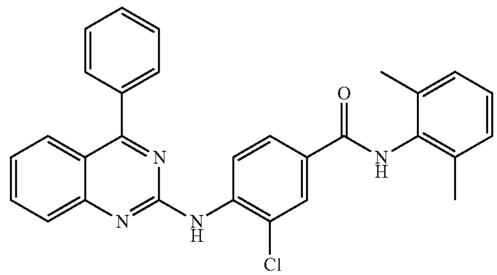 [SMILES: Cc1cccc(C)c1NC(=O)c1ccc(Nc2nc(-c3ccccc3)c3ccccc3n2)c(Cl)c1] | 3-chloro-N-(2,6-dimethylphenyl)-4-[(4-phenylquinazolin-2-yl)amino]benzamide |
| 80 | 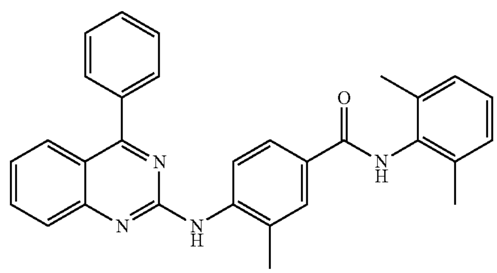 [SMILES: Cc1cc(C(=O)Nc2c(C)cccc2C)ccc1Nc1nc(-c2ccccc2)c2ccccc2n1] | N-(2,6-dimethylphenyl)-3-methyl-4-[(4-phenylquinazolin-2-yl)amino]benzamide |
| 81 | 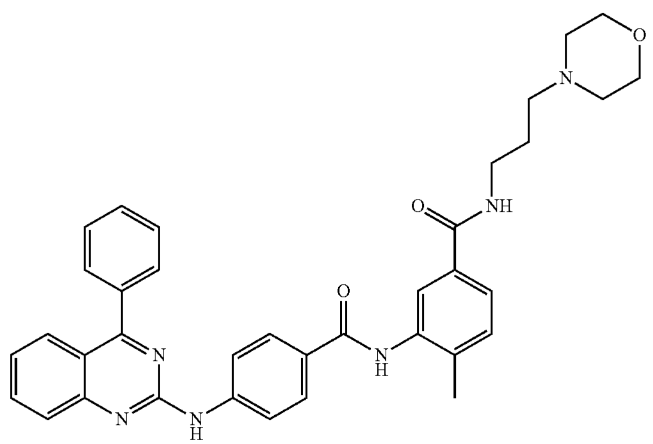 [SMILES: Cc1ccc(C(=O)NCCCN2CCOCC2)cc1NC(=O)c1ccc(Nc2nc(-c3ccccc3)c3ccccc3n2)cc1] | 4-methyl-N-(3-morpholin-4-ylpropyl)-3-[({4-[(4-phenylquinazolin-2-yl)amino]phenyl}carbonyl)amino]benzamide |
| 82 | 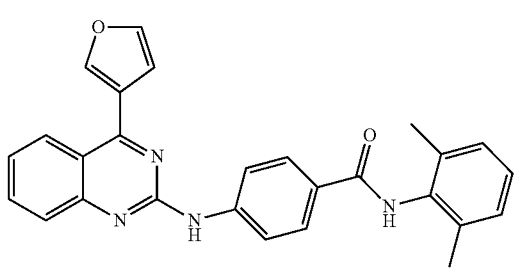 [SMILES: Cc1cccc(C)c1NC(=O)c1ccc(Nc2nc(-c3ccoc3)c3ccccc3n2)cc1] | N-(2,6-dimethylphenyl)-4-[(4-furan-3-ylquinazolin-2-yl)amino]benzamide |
| 83 | 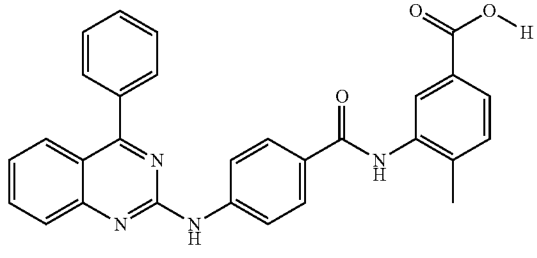 [SMILES: Cc1ccc(C(=O)O)cc1NC(=O)c1ccc(Nc2nc(-c3ccccc3)c3ccccc3n2)cc1] | 4-methyl-3-[({4-[(4-phenylquinazolin-2-yl)amino]phenyl}carbonyl)amino]benzoic acid |

TABLE 1-continued

| Cmpd No. | Structure | Name |
|---|---|---|
| 84 | 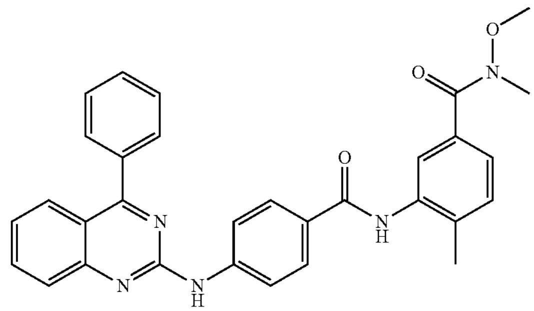 [SMILES: CON(C)C(=O)c1ccc(C)c(NC(=O)c2ccc(Nc3nc(-c4ccccc4)c4ccccc4n3)cc2)c1] | N,4-dimethyl-N-(methyloxy)-3-[({4-[(4-phenylquinazolin-2-yl)amino]phenyl}carbonyl)amino]benzamide |
| 85 | 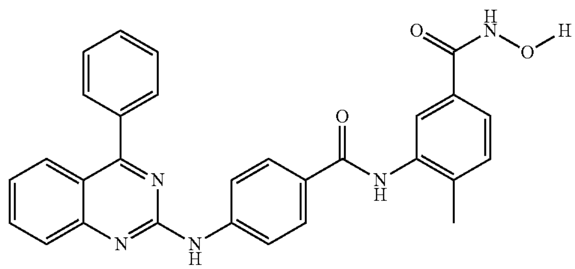 [SMILES: Cc1ccc(C(=O)NO)cc1NC(=O)c1ccc(Nc2nc(-c3ccccc3)c3ccccc3n2)cc1] | N-hydroxy-4-methyl-3-[({4-[(4-phenylquinazolin-2-yl)amino]phenyl}carbonyl)amino]benzamide |
| 86 | 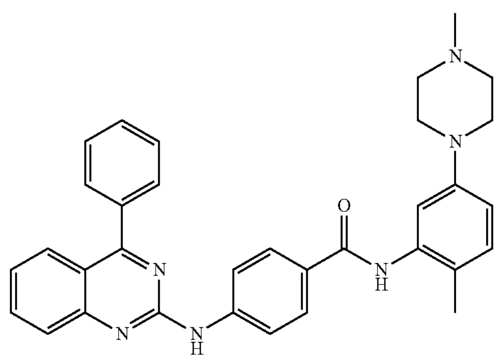 [SMILES: Cc1ccc(N2CCN(C)CC2)cc1NC(=O)c1ccc(Nc2nc(-c3ccccc3)c3ccccc3n2)cc1] | N-[2-methyl-5-(4-methylpiperazin-1-yl)phenyl]-4-[(4-phenylquinazolin-2-yl)amino]benzamide |
| 87 | 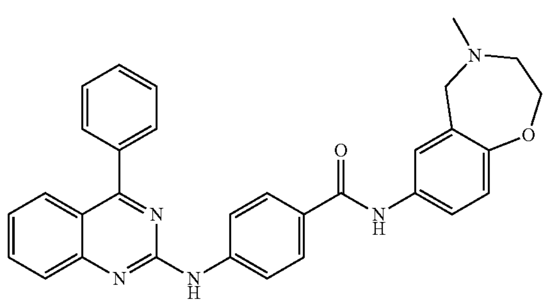 [SMILES: CN1CCOc2ccc(NC(=O)c3ccc(Nc4nc(-c5ccccc5)c5ccccc5n4)cc3)cc2C1] | N-(4-methyl-2,3,4,5-tetrahydro-1,4-benzoxazepin-7-yl)-4-[(4-phenylquinazolin-2-yl)amino]benzamide |
| 88 | 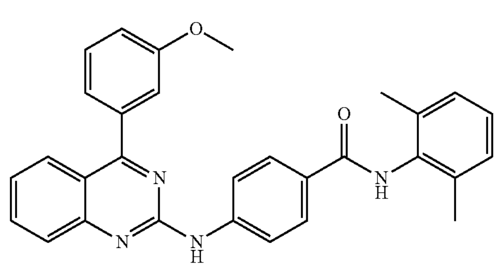 [SMILES: COc1cccc(-c2nc(Nc3ccc(C(=O)Nc4c(C)cccc4C)cc3)nc3ccccc23)c1] | N-(2,6-dimethylphenyl)-4-({4-[3-(methyloxy)phenyl]quinazolin-2-yl}amino)benzamide |

TABLE 1-continued

| Cmpd No. | Structure | Name |
|---|---|---|
| 89 | 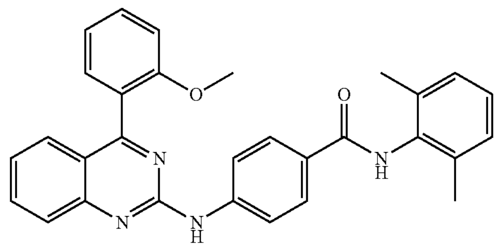 [SMILES: COc1ccccc1-c1nc(Nc2ccc(C(=O)Nc3c(C)cccc3C)cc2)nc2ccccc12] | N-(2,6-dimethylphenyl)-4-({4-[2-(methyloxy)phenyl]quinazolin-2-yl}amino)benzamide |
| 90 | 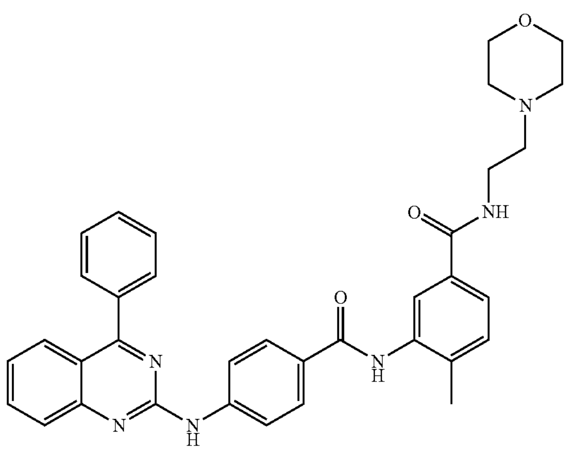 [SMILES: Cc1ccc(C(=O)NCCN2CCOCC2)cc1NC(=O)c1ccc(Nc2nc(-c3ccccc3)c3ccccc3n2)cc1] | 4-methyl-N-(2-morpholin-4-ylethyl)-3-[({4-[(4-phenylquinazolin-2-yl)amino]phenyl}carbonyl)amino]benzamide |
| 91 | 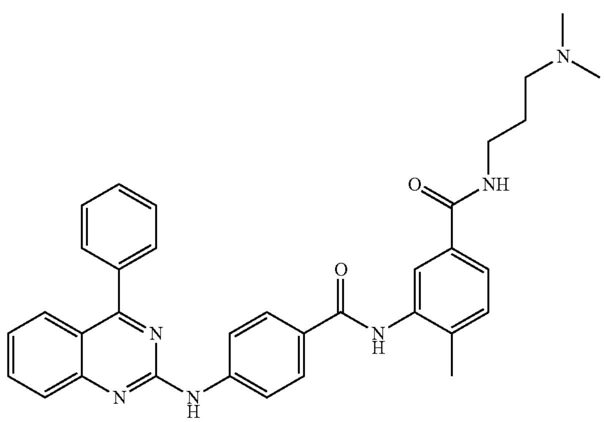 [SMILES: Cc1ccc(C(=O)NCCCN(C)C)cc1NC(=O)c1ccc(Nc2nc(-c3ccccc3)c3ccccc3n2)cc1] | N-[3-(dimethylamino)propyl]-4-methyl-3-[({4-[(4-phenylquinazolin-2-yl)amino]phenyl}carbonyl)amino]benzamide |
| 92 | 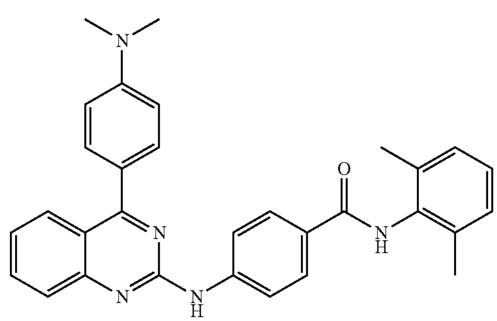 [SMILES: Cc1cccc(C)c1NC(=O)c1ccc(Nc2nc(-c3ccc(N(C)C)cc3)c3ccccc3n2)cc1] | 4-({4-[4-(dimethylamino)phenyl]quinazolin-2-yl}amino)-N-(2,6-dimethylphenyl)benzamide |

| Cmpd No. | Structure | Name |
|---|---|---|
| 93 | 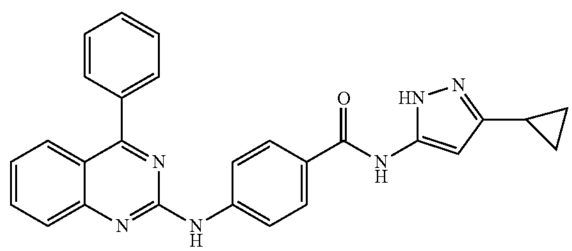 [SMILES: O=C(Nc1cc(C2CC2)n[nH]1)c1ccc(Nc2nc(-c3ccccc3)c3ccccc3n2)cc1] | N-(3-cyclopropyl-1H-pyrazol-5-yl)-4-[(4-phenylquinazolin-2-yl)amino]benzamide |
| 94 | 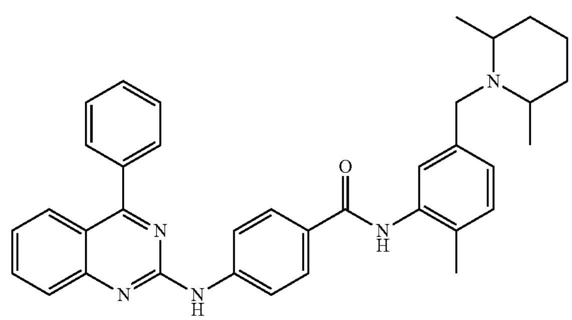 [SMILES: Cc1ccc(CN2C(C)CCCC2C)cc1NC(=O)c1ccc(Nc2nc(-c3ccccc3)c3ccccc3n2)cc1] | N-{5-[(2,6-dimethylpiperidin-1-yl)methyl]-2-methylphenyl}-4-[(4-phenylquinazolin-2-yl)amino]benzamide |
| 95 | 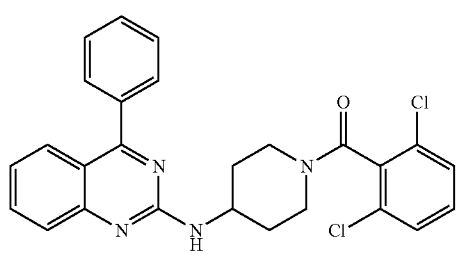 [SMILES: O=C(c1c(Cl)cccc1Cl)N1CCC(Nc2nc(-c3ccccc3)c3ccccc3n2)CC1] | N-{1-[(2,6-dichlorophenyl)carbonyl]piperidin-4-yl}-4-phenylquinazolin-2-amine |
| 96 | 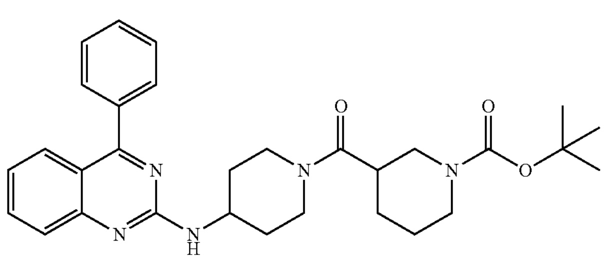 [SMILES: CC(C)(C)OC(=O)N1CCCC(C(=O)N2CCC(Nc3nc(-c4ccccc4)c4ccccc4n3)CC2)C1] | 1,1-dimethylethyl 3-({4-[(4-phenylquinazolin-2-yl)amino]piperidin-1-yl}carbonyl)piperidine-1-carboxylate |
| 97 | 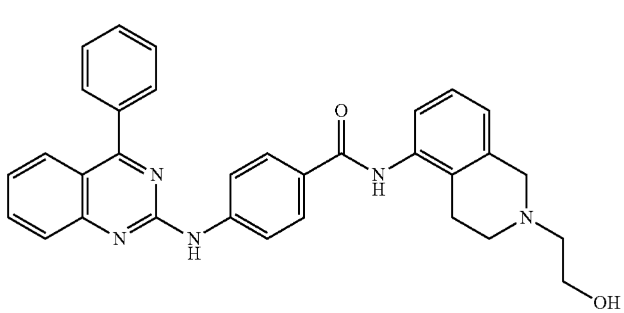 [SMILES: O=C(Nc1cccc2c1CCN(CCO)C2)c1ccc(Nc2nc(-c3ccccc3)c3ccccc3n2)cc1] | N-[2-(2-hydroxyethyl)-1,2,3,4-tetrahydroisoquinolin-5-yl]-4-[(4-phenylquinazolin-2-yl)amino]benzamide |

TABLE 1-continued

| Cmpd No. | Structure | Name |
|---|---|---|
| 98 | 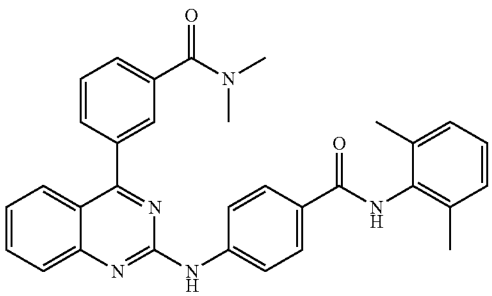 [SMILES: Cc1cccc(C)c1NC(=O)c1ccc(Nc2nc(-c3cccc(C(=O)N(C)C)c3)c3ccccc3n2)cc1] | 3-{2-[(4-{[(2,6-dimethylphenyl)amino]carbonyl}phenyl)amino]quinazolin-4-yl}-N,N-dimethylbenzamide |
| 99 | 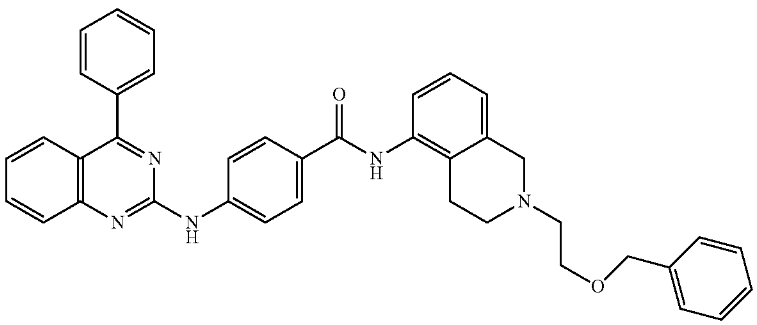 [SMILES: O=C(Nc1cccc2c1CCN(CCOCc1ccccc1)C2)c1ccc(Nc2nc(-c3ccccc3)c3ccccc3n2)cc1] | N-(2-{2-[(phenylmethyl)oxy]ethyl}-1,2,3,4-tetrahydroisoquinolin-5-yl)-4-[(4-phenylquinazolin-2-yl)amino]benzamide |
| 100 | 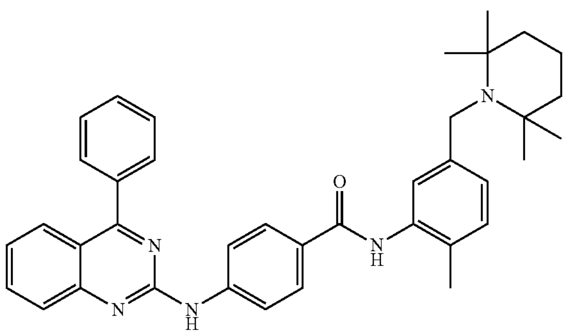 [SMILES: Cc1ccc(CN2C(C)(C)CCCC2(C)C)cc1NC(=O)c1ccc(Nc2nc(-c3ccccc3)c3ccccc3n2)cc1] | N-{2-methyl-5-[(2,2,6,6-tetramethylpiperidin-1-yl)methyl]phenyl}-4-[(4-phenylquinazolin-2-yl)amino]benzamide |
| 101 | 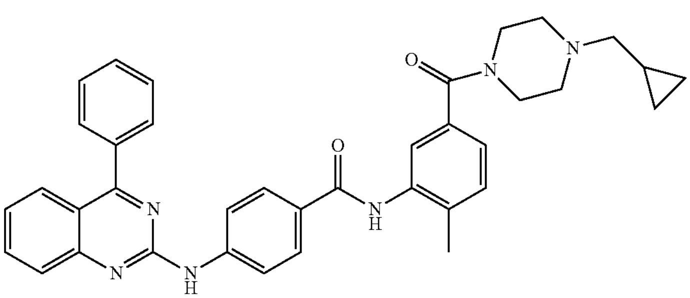 [SMILES: Cc1ccc(C(=O)N2CCN(CC3CC3)CC2)cc1NC(=O)c1ccc(Nc2nc(-c3ccccc3)c3ccccc3n2)cc1] | N-(5-{[4-(cyclopropylmethyl)piperazin-1-yl]carbonyl}-2-methylphenyl)-4-[(4-phenylquinazolin-2-yl)amino]benzamide |
| 102 | 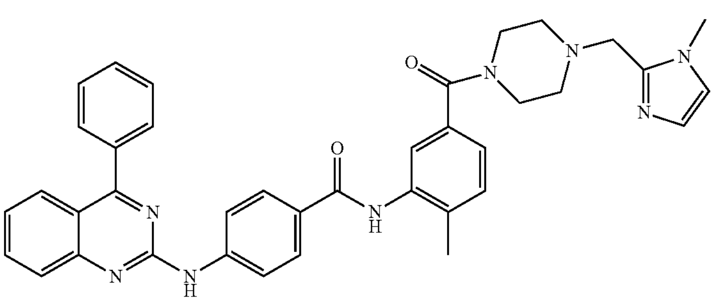 [SMILES: Cc1ccc(C(=O)N2CCN(Cc3nccn3C)CC2)cc1NC(=O)c1ccc(Nc2nc(-c3ccccc3)c3ccccc3n2)cc1] | N-[2-methyl-5-({4-[(1-methyl-1H-imidazol-2-yl)methyl]piperazin-1-yl}carbonyl)phenyl]-4-[(4-phenylquinazolin-2-yl)amino]benzamide |

TABLE 1-continued

| Cmpd No. | Structure | Name |
|---|---|---|
| 103 | 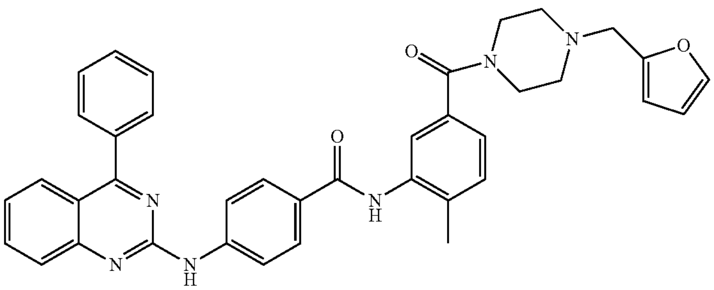 [SMILES: Cc1ccc(C(=O)N2CCN(Cc3ccco3)CC2)cc1NC(=O)c1ccc(Nc2nc(-c3ccccc3)c3ccccc3n2)cc1] | N-(5-{[4-(furan-2-ylmethyl)piperazin-1-yl]carbonyl}-2-methylphenyl)-4-[(4-phenylquinazolin-2-yl)amino]benzamide |
| 104 | 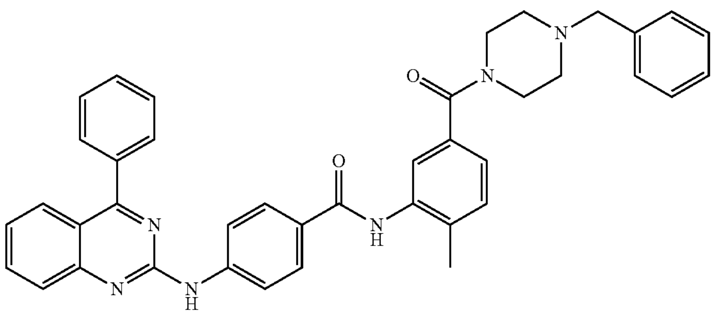 [SMILES: Cc1ccc(C(=O)N2CCN(Cc3ccccc3)CC2)cc1NC(=O)c1ccc(Nc2nc(-c3ccccc3)c3ccccc3n2)cc1] | N-(2-methyl-5-{[4-(phenylmethyl)piperazin-1-yl]carbonyl}phenyl)-4-[(4-phenylquinazolin-2-yl)amino]benzamide |
| 105 | 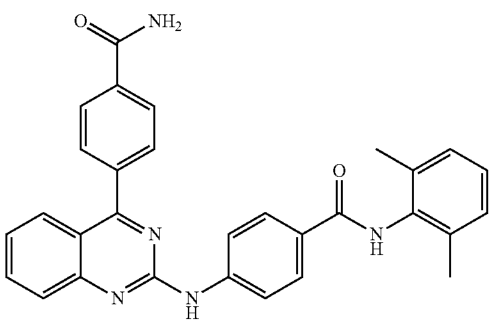 [SMILES: Cc1cccc(C)c1NC(=O)c1ccc(Nc2nc(-c3ccc(C(N)=O)cc3)c3ccccc3n2)cc1] | 4-({4-[4-(aminocarbonyl)phenyl]quinazolin-2-yl}amino)-N-(2,6-dimethylphenyl)benzamide |
| 106 | 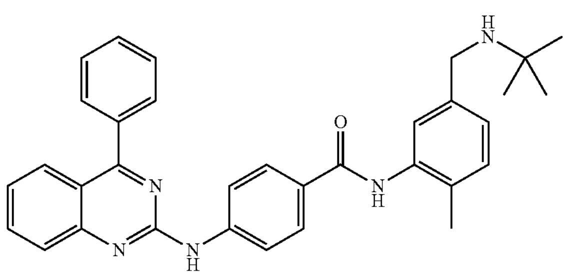 [SMILES: Cc1ccc(CNC(C)(C)C)cc1NC(=O)c1ccc(Nc2nc(-c3ccccc3)c3ccccc3n2)cc1] | N-(5-{[(1,1-dimethylethyl)amino]methyl}-2-methylphenyl)-4-[(4-phenylquinazolin-2-yl)amino]benzamide |
| 107 | 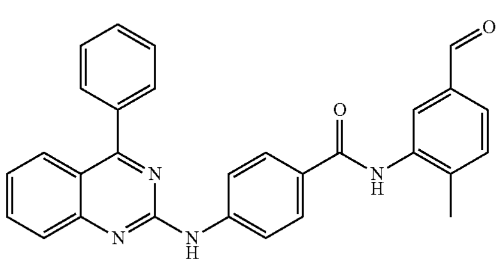 [SMILES: Cc1ccc(C=O)cc1NC(=O)c1ccc(Nc2nc(-c3ccccc3)c3ccccc3n2)cc1] | N-(5-formyl-2-methylphenyl)-4-[(4-phenylquinazolin-2-yl)amino]benzamide |

TABLE 1-continued

| Cmpd No. | Structure | Name |
|---|---|---|
| 108 | 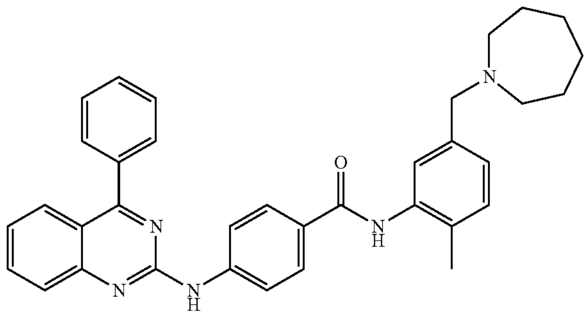 [SMILES: Cc1ccc(CN2CCCCCC2)cc1NC(=O)c1ccc(Nc2nc(-c3ccccc3)c3ccccc3n2)cc1] | N-[5-(azepan-1-ylmethyl)-2-methylphenyl]-4-[(4-phenylquinazolin-2-yl)amino]benzamide |
| 109 | 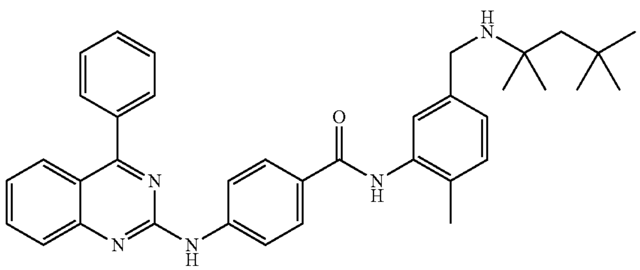 [SMILES: Cc1ccc(CNC(C)(C)CC(C)(C)C)cc1NC(=O)c1ccc(Nc2nc(-c3ccccc3)c3ccccc3n2)cc1] | N-(2-methyl-5-{[(1,1,3,3-tetramethylbutyl)amino]methyl}phenyl)-4-[(4-phenylquinazolin-2-yl)amino]benzamide |
| 110 | 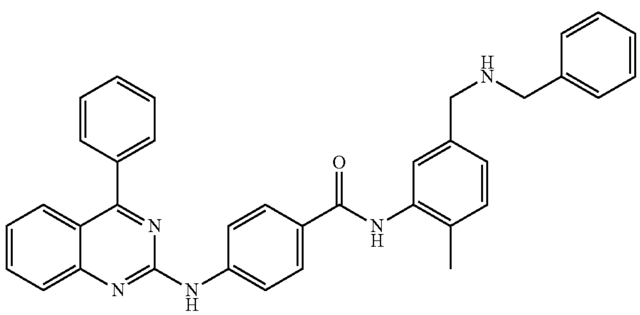 [SMILES: Cc1ccc(CNCc2ccccc2)cc1NC(=O)c1ccc(Nc2nc(-c3ccccc3)c3ccccc3n2)cc1] | N-(2-methyl-5-{[(phenylmethyl)amino]methyl}phenyl)-4-[(4-phenylquinazolin-2-yl)amino]benzamide |
| 111 | 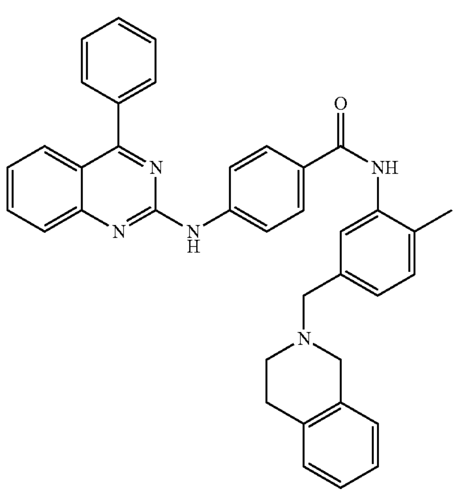 [SMILES: Cc1ccc(CN2CCc3ccccc3C2)cc1NC(=O)c1ccc(Nc2nc(-c3ccccc3)c3ccccc3n2)cc1] | N-[5-(3,4-dihydroisoquinolin-2(1H)-ylmethyl)-2-methylphenyl]-4-[(4-phenylquinazolin-2-yl)amino]benzamide |

TABLE 1-continued

| Cmpd No. | Structure | Name |
|---|---|---|
| 112 | 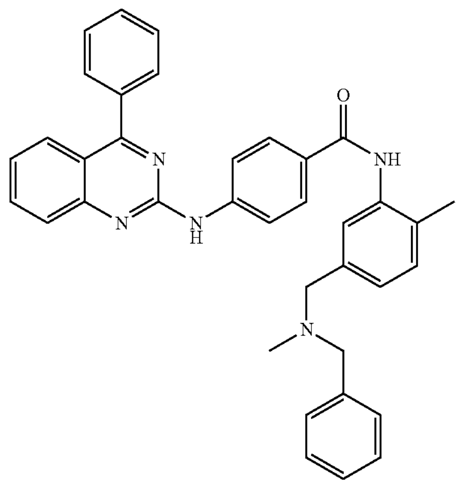 [SMILES: Cc1ccc(CN(C)Cc2ccccc2)cc1NC(=O)c1ccc(Nc2nc(-c3ccccc3)c3ccccc3n2)cc1] | N-(2-methyl-5-{[methyl(phenylmethyl)amino]methyl}phenyl)-4-[(4-phenylquinazolin-2-yl)amino]benzamide |
| 113 | 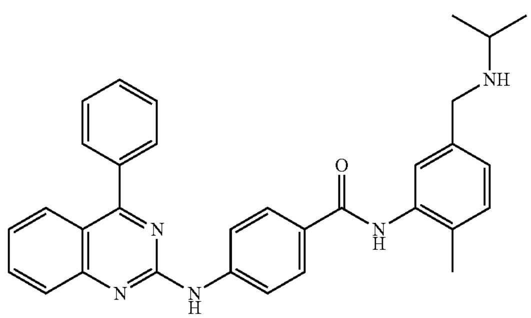 [SMILES: Cc1ccc(CNC(C)C)cc1NC(=O)c1ccc(Nc2nc(-c3ccccc3)c3ccccc3n2)cc1] | N-(2-methyl-5-{[(1-methylethyl)amino]methyl}phenyl)-4-[(4-phenylquinazolin-2-yl)amino]benzamide |
| 114 | 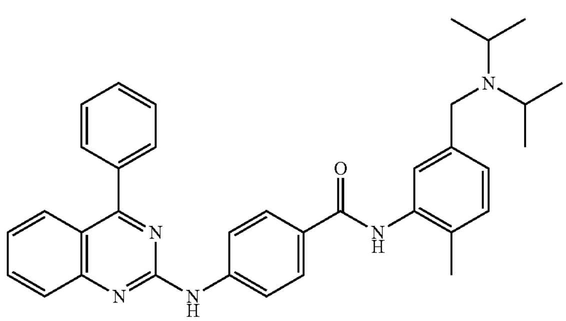 [SMILES: Cc1ccc(CN(C(C)C)C(C)C)cc1NC(=O)c1ccc(Nc2nc(-c3ccccc3)c3ccccc3n2)cc1] | N-(5-{[bis(1-methylethyl)amino]methyl}-2-methylphenyl)-4-[(4-phenylquinazolin-2-yl)amino]benzamide |
| 115 | 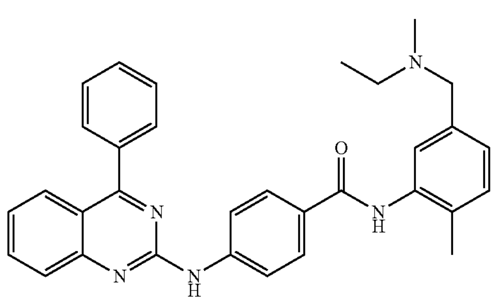 [SMILES: CCN(C)Cc1ccc(C)c(NC(=O)c2ccc(Nc3nc(-c4ccccc4)c4ccccc4n3)cc2)c1] | N-(5-{[ethyl(methyl)amino]methyl}-2-methylphenyl)-4-[(4-phenylquinazolin-2-yl)amino]benzamide |

TABLE 1-continued

| Cmpd No. | Structure | Name |
|---|---|---|
| 116 | 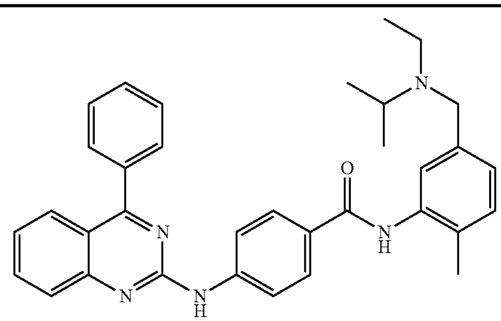 | N-(5-{[ethyl(1-methylethyl)amino]methyl}-2-methylphenyl)-4-[(4-phenylquinazolin-2-yl)amino]benzamide |
| 117 | 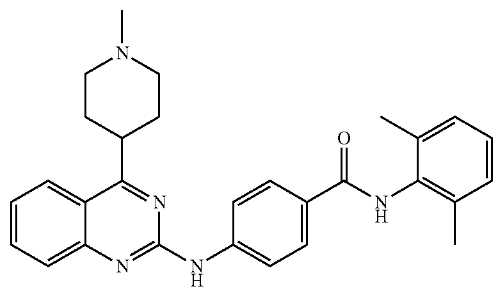 [SMILES: Cc1cccc(C)c1NC(=O)c1ccc(Nc2nc(C3CCN(C)CC3)c3ccccc3n2)cc1] | N-(2,6-dimethylphenyl)-4-{[4-(1-methylpiperidin-4-yl)quinazolin-2-yl]amino}benzamide |
| 118 | 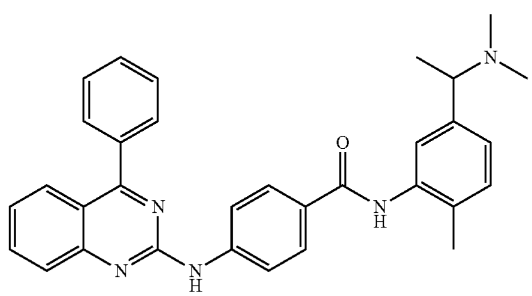 [SMILES: Cc1ccc(C(C)N(C)C)cc1NC(=O)c1ccc(Nc2nc(-c3ccccc3)c3ccccc3n2)cc1] | N-{5-[1-(dimethylamino)ethyl]-2-methylphenyl}-4-[(4-phenylquinazolin-2-yl)amino]benzamide |
| 119 | 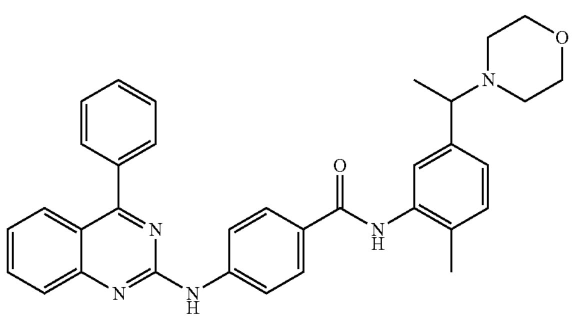 [SMILES: Cc1ccc(C(C)N2CCOCC2)cc1NC(=O)c1ccc(Nc2nc(-c3ccccc3)c3ccccc3n2)cc1] | N-[2-methyl-5-(1-morpholin-4-ylethyl)phenyl]-4-[(4-phenylquinazolin-2-yl)amino]benzamide |
| 120 | 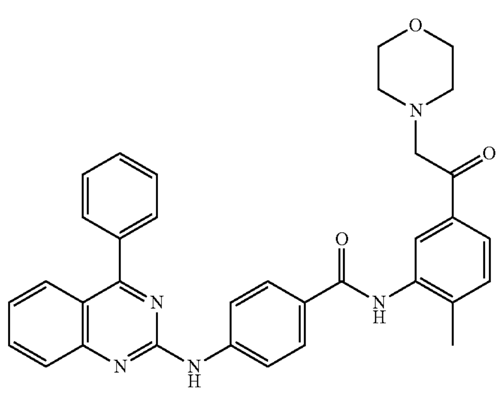 [SMILES: Cc1ccc(C(=O)CN2CCOCC2)cc1NC(=O)c1ccc(Nc2nc(-c3ccccc3)c3ccccc3n2)cc1] | N-[2-methyl-5-(morpholin-4-ylacetyl)phenyl]-4-[(4-phenylquinazolin-2-yl)amino]benzamide |

TABLE 1-continued

| Cmpd No. | Structure | Name |
|---|---|---|
| 121 | 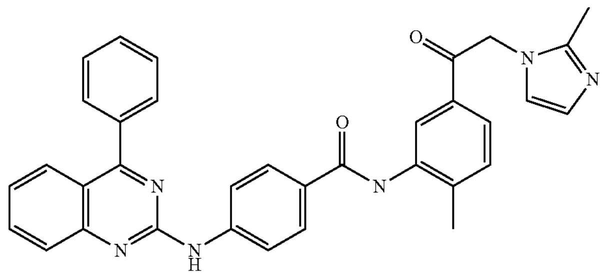 [SMILES: Cc1ccc(C(=O)Cn2ccnc2C)cc1NC(=O)c1ccc(Nc2nc(-c3ccccc3)c3ccccc3n2)cc1] | N-{2-methyl-5-[(2-methyl-1H-imidazol-1-yl)acetyl]phenyl}-4-[(4-phenylquinazolin-2-yl)amino]benzamide |
| 122 | 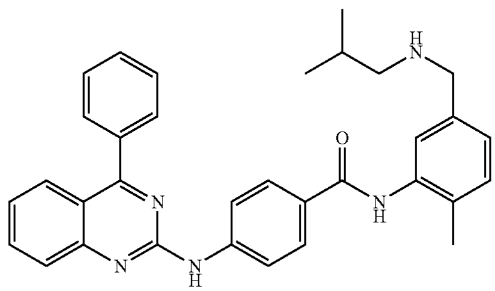 [SMILES: Cc1ccc(CNCC(C)C)cc1NC(=O)c1ccc(Nc2nc(-c3ccccc3)c3ccccc3n2)cc1] | N-(2-methyl-5-{[(2-methylpropyl)amino]methyl}phenyl)-4-[(4-phenylquinazolin-2-yl)amino]benzamide |
| 123 | 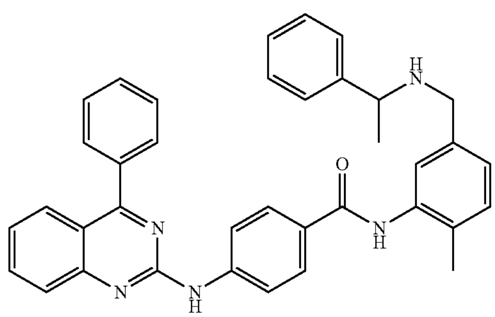 [SMILES: Cc1ccc(CNC(C)c2ccccc2)cc1NC(=O)c1ccc(Nc2nc(-c3ccccc3)c3ccccc3n2)cc1] | N-(2-methyl-5-{[(1-phenylethyl)amino]methyl}phenyl)-4-[(4-phenylquinazolin-2-yl)amino]benzamide |
| 124 | 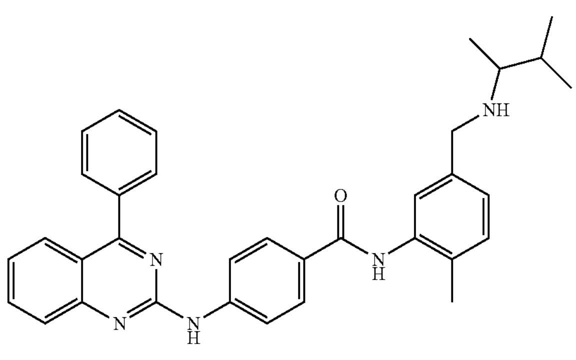 [SMILES: Cc1ccc(CNC(C)C(C)C)cc1NC(=O)c1ccc(Nc2nc(-c3ccccc3)c3ccccc3n2)cc1] | N-(5-{[(1,2-dimethylpropyl)amino]methyl}-2-methylphenyl)-4-[(4-phenylquinazolin-2-yl)amino]benzamide |
| 125 | 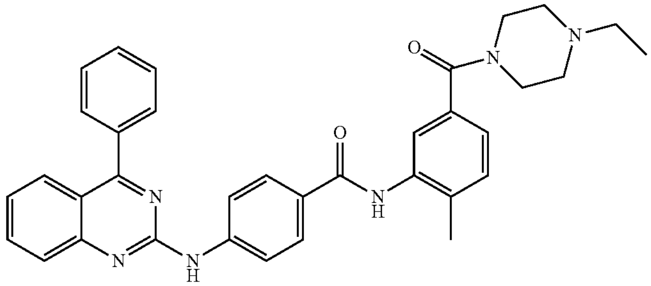 [SMILES: CCN1CCN(C(=O)c2ccc(C)c(NC(=O)c3ccc(Nc4nc(-c5ccccc5)c5ccccc5n4)cc3)c2)CC1] | N-{5-[(4-ethylpiperazin-1-yl)carbonyl]-2-methylphenyl}-4-[(4-phenylquinazolin-2-yl)amino]benzamide |

TABLE 1-continued

| Cmpd No. | Structure | Name |
|---|---|---|
| 126 | 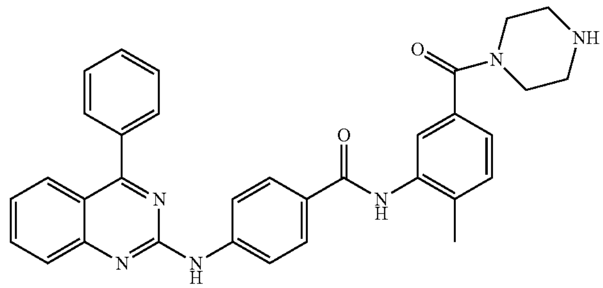 [SMILES: Cc1ccc(C(=O)N2CCNCC2)cc1NC(=O)c1ccc(Nc2nc(-c3ccccc3)c3ccccc3n2)cc1] | N-[2-methyl-5-(piperazin-1-ylcarbonyl)phenyl]-4-[(4-phenylquinazolin-2-yl)amino]benzamide |
| 127 | 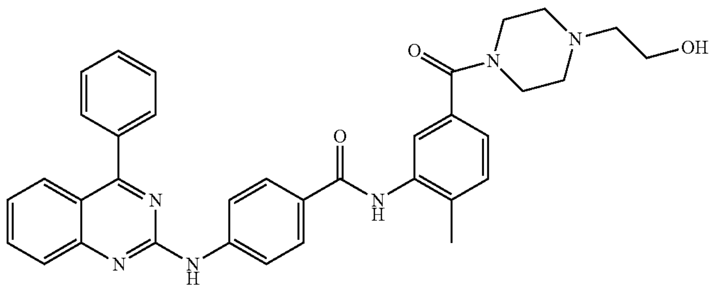 [SMILES: Cc1ccc(C(=O)N2CCN(CCO)CC2)cc1NC(=O)c1ccc(Nc2nc(-c3ccccc3)c3ccccc3n2)cc1] | N-(5-{[4-(2-hydroxyethyl)piperazin-1-yl]carbonyl}-2-methylphenyl)-4-[(4-phenylquinazolin-2-yl)amino]benzamide |
| 128 | 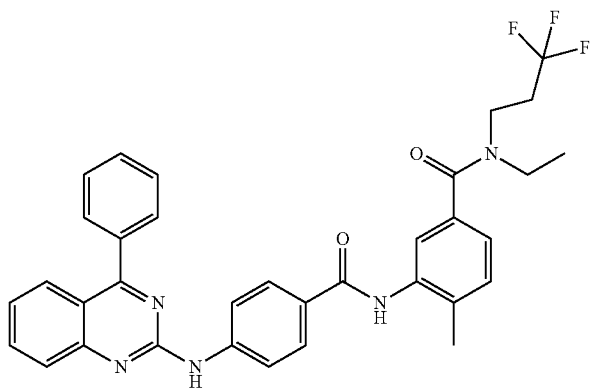 [SMILES: CCN(CCC(F)(F)F)C(=O)c1ccc(C)c(NC(=O)c2ccc(Nc3nc(-c4ccccc4)c4ccccc4n3)cc2)c1] | N-(5-{1-[ethyl(3,3,3-trifluoropropyl)amino]ethyl}-2-methylphenyl)-4-[(4-phenylquinazolin-2-yl)amino]benzamide |
| 129 | 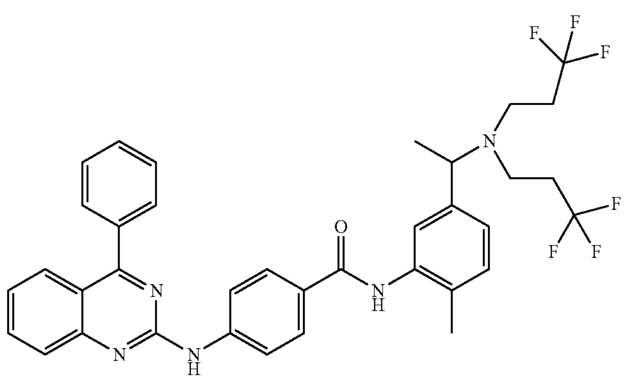 [SMILES: Cc1ccc(C(C)N(CCC(F)(F)F)CCC(F)(F)F)cc1NC(=O)c1ccc(Nc2nc(-c3ccccc3)c3ccccc3n2)cc1] | N-(5-{1-[bis(3,3,3-trifluoropropyl)amino]ethyl}-2-methylphenyl)-4-[(4-phenylquinazolin-2-yl)amino]benzamide |
| 130 | 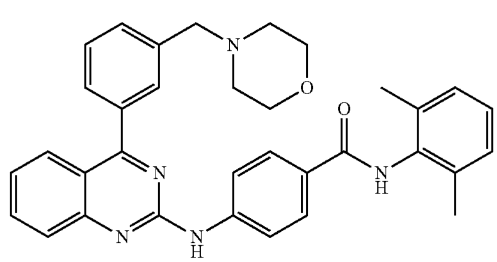 [SMILES: Cc1cccc(C)c1NC(=O)c1ccc(Nc2nc(-c3cccc(CN4CCOCC4)c3)c3ccccc3n2)cc1] | N-(2,6-dimethylphenyl)-4-({4-[3-(morpholin-4-ylmethyl)phenyl]quinazolin-2-yl}amino)benzamide |

TABLE 1-continued

| Cmpd No. | Structure | Name |
|---|---|---|
| 131 | 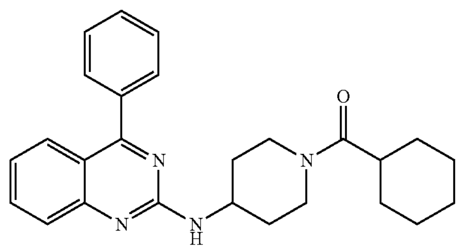 [SMILES: O=C(C1CCCCC1)N1CCC(Nc2nc(-c3ccccc3)c3ccccc3n2)CC1] | N-[1-(cyclohexylcarbonyl)piperidin-4-yl]-4-phenylquinazolin-2-amine |
| 132 | 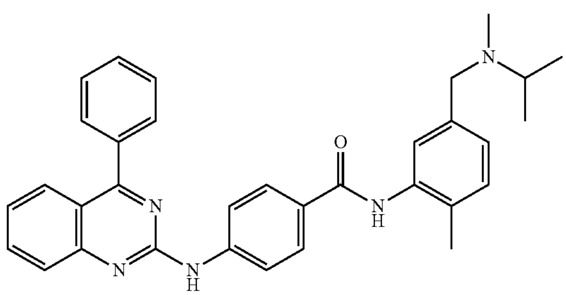 [SMILES: Cc1ccc(CN(C)C(C)C)cc1NC(=O)c1ccc(Nc2nc(-c3ccccc3)c3ccccc3n2)cc1] | N-(2-methyl-5-{[methyl(1-methylethyl)amino]methyl}phenyl)-4-[(4-phenylquinazolin-2-yl)amino]benzamide |
| 133 | 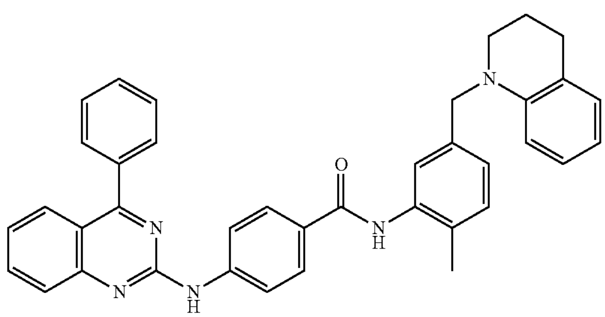 [SMILES: Cc1ccc(CN2CCCc3ccccc32)cc1NC(=O)c1ccc(Nc2nc(-c3ccccc3)c3ccccc3n2)cc1] | N-[5-(3,4-dihydroquinolin-1(2H)-ylmethyl)-2-methylphenyl]-4-[(4-phenylquinazolin-2-yl)amino]benzamide |
| 134 | 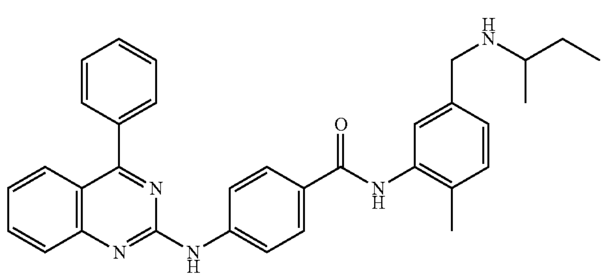 [SMILES: CCC(C)NCc1ccc(C)c(NC(=O)c2ccc(Nc3nc(-c4ccccc4)c4ccccc4n3)cc2)c1] | N-(2-methyl-5-{[(1-methylpropyl)amino]methyl}phenyl)-4-[(4-phenylquinazolin-2-yl)amino]benzamide |
| 135 | 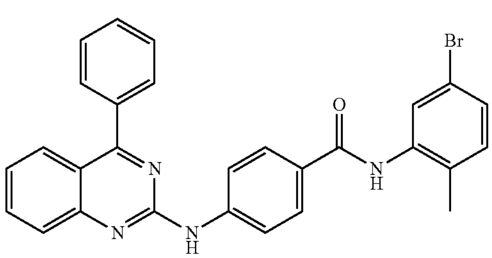 [SMILES: Cc1ccc(Br)cc1NC(=O)c1ccc(Nc2nc(-c3ccccc3)c3ccccc3n2)cc1] | N-(5-bromo-2-methylphenyl)-4-[(4-phenylquinazolin-2-yl)amino]benzamide |

TABLE 1-continued

| Cmpd No. | Structure | Name |
|---|---|---|
| 136 | 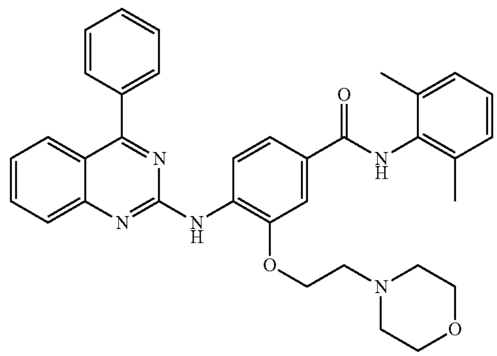 [SMILES: Cc1cccc(C)c1NC(=O)c1ccc(Nc2nc(-c3ccccc3)c3ccccc3n2)c(OCCN2CCOCC2)c1] | N-(2,6-dimethylphenyl)-3-[(2-morpholin-4-ylethyl)oxy]-4-[(4-phenylquinazolin-2-yl)amino]benzamide |
| 137 | 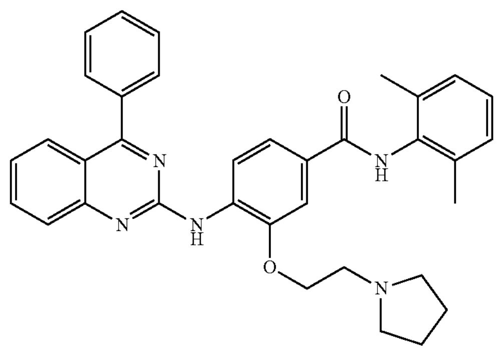 [SMILES: Cc1cccc(C)c1NC(=O)c1ccc(Nc2nc(-c3ccccc3)c3ccccc3n2)c(OCCN2CCCC2)c1] | N-(2,6-dimethylphenyl)-4-[(4-phenylquinazolin-2-yl)amino]-3-[(2-pyrrolidin-1-ylethyl)oxy]benzamide |
| 138 | 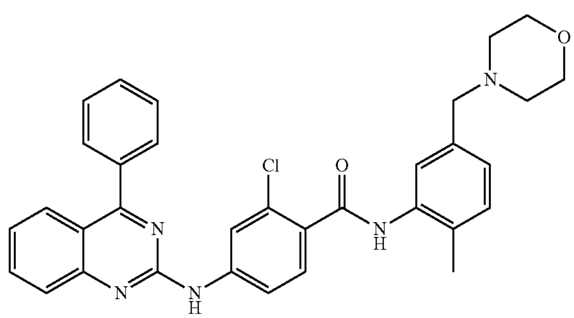 [SMILES: Cc1ccc(CN2CCOCC2)cc1NC(=O)c1ccc(Nc2nc(-c3ccccc3)c3ccccc3n2)cc1Cl] | 2-chloro-N-[2-methyl-5-(morpholin-4-ylmethyl)phenyl]-4-[(4-phenylquinazolin-2-yl)amino]benzamide |
| 139 | 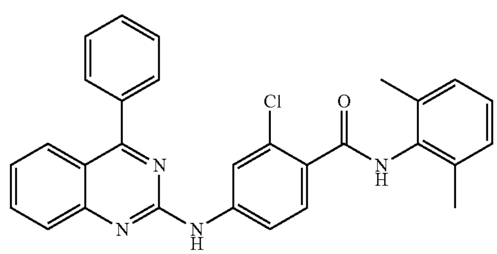 [SMILES: Cc1cccc(C)c1NC(=O)c1ccc(Nc2nc(-c3ccccc3)c3ccccc3n2)cc1Cl] | 2-chloro-N-(2,6-dimethylphenyl)-4-[(4-phenylquinazolin-2-yl)amino]benzamide |
| 140 | 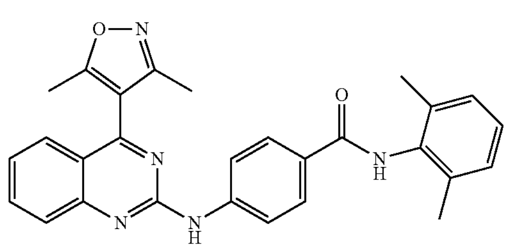 [SMILES: Cc1cccc(C)c1NC(=O)c1ccc(Nc2nc(-c3c(C)noc3C)c3ccccc3n2)cc1] | 4-{[4-(3,5-dimethylisoxazol-4-yl)quinazolin-2-yl]amino}-N-(2,6-dimethylphenyl)benzamide |

TABLE 1-continued

| Cmpd No. | Structure | Name |
|---|---|---|
| 141 | 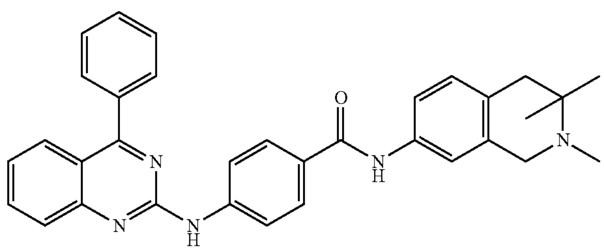 | 4-[(4-phenylquinazolin-2-yl)amino]-N-(2,3,3-trimethyl-1,2,3,4-tetrahydroisoquinolin-7-yl)benzamide |
| 142 | 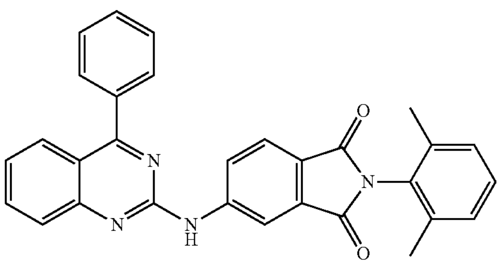 [SMILES: Cc1cccc(C)c1N1C(=O)c2ccc(Nc3nc(-c4ccccc4)c4ccccc4n3)cc2C1=O] | 2-(2,6-dimethylphenyl)-5-[(4-phenylquinazolin-2-yl)amino]-1H-isoindole-1,3(2H)-dione |
| 143 | 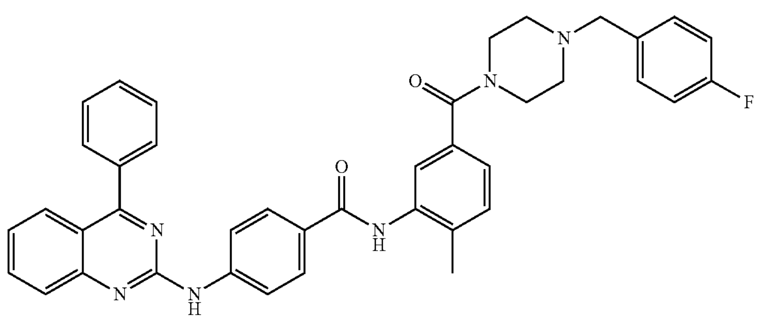 [SMILES: Cc1ccc(C(=O)N2CCN(Cc3ccc(F)cc3)CC2)cc1NC(=O)c1ccc(Nc2nc(-c3ccccc3)c3ccccc3n2)cc1] | N-[5-({4-[(4-fluorophenyl)methyl]piperazin-1-yl}carbonyl)-2-methylphenyl]-4-[(4-phenylquinazolin-2-yl)amino]benzamide |
| 144 | 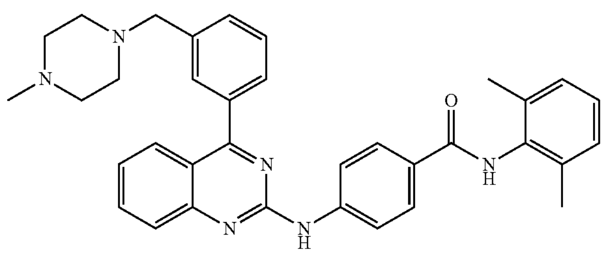 [SMILES: Cc1cccc(C)c1NC(=O)c1ccc(Nc2nc(-c3cccc(CN4CCN(C)CC4)c3)c3ccccc3n2)cc1] | N-(2,6-dimethylphenyl)-4-[(4-{3-[(4-methylpiperazin-1-yl)methyl]phenyl}quinazolin-2-yl)amino]benzamide |
| 145 | 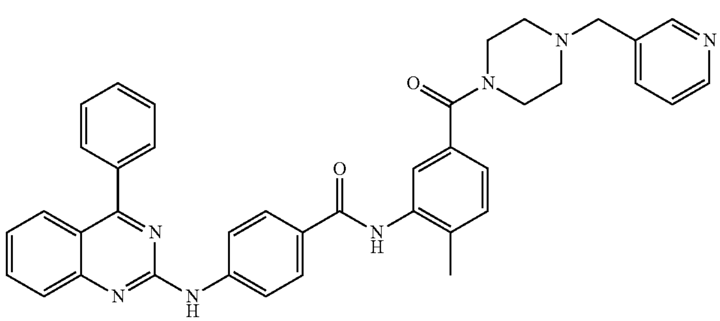 [SMILES: Cc1ccc(C(=O)N2CCN(Cc3cccnc3)CC2)cc1NC(=O)c1ccc(Nc2nc(-c3ccccc3)c3ccccc3n2)cc1] | N-(2-methyl-5-{[4-(pyridin-3-ylmethyl)piperazin-1-yl]carbonyl}phenyl)-4-[(4-phenylquinazolin-2-yl)amino]benzamide |

TABLE 1-continued

| Cmpd No. | Structure | Name |
|---|---|---|
| 146 | 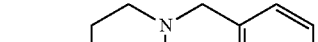 | N-(2-methyl-5-{[4-(pyridin-4-ylmethyl)piperazin-1-yl]carbonyl}phenyl)-4-[(4-phenylquinazolin-2-yl)amino]benzamide |
| 147 | 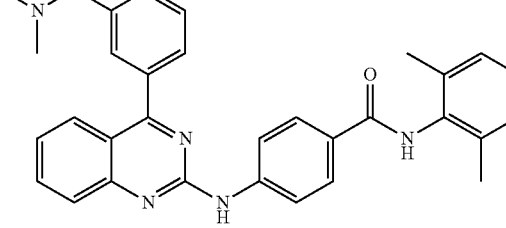 | 4-[(4-{3-[(dimethylamino)methyl]phenyl}quinazolin-2-yl)amino]-N-(2,6-dimethylphenyl)benzamide |
| 148 | 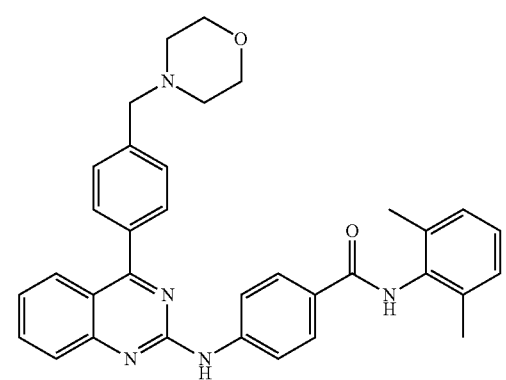 [SMILES: Cc1cccc(C)c1NC(=O)c1ccc(Nc2nc(-c3ccc(CN4CCOCC4)cc3)c3ccccc3n2)cc1] | N-(2,6-dimethylphenyl)-4-({4-[4-(morpholin-4-ylmethyl)phenyl]quinazolin-2-yl}amino)benzamide |
| 149 | 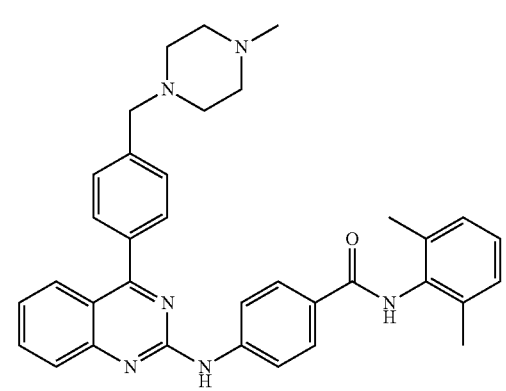 [SMILES: Cc1cccc(C)c1NC(=O)c1ccc(Nc2nc(-c3ccc(CN4CCN(C)CC4)cc3)c3ccccc3n2)cc1] | N-(2,6-dimethylphenyl)-4-[(4-{4-[(4-methylpiperazin-1-yl)methyl]phenyl}quinazolin-2-yl)amino]benzamide |

TABLE 1-continued

| Cmpd No. | Structure | Name |
|---|---|---|
| 150 | 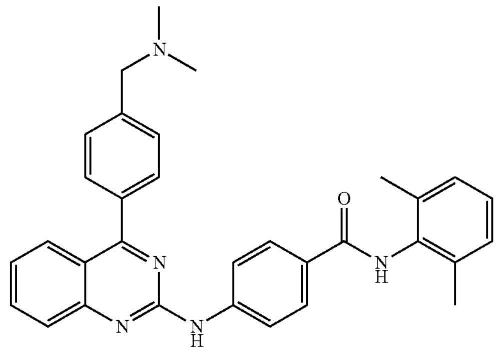 [SMILES: Cc1cccc(C)c1NC(=O)c1ccc(Nc2nc(-c3ccc(CN(C)C)cc3)c3ccccc3n2)cc1] | 4-[(4-{4-[(dimethylamino)methyl]phenyl}quinazolin-2-yl)amino]-N-(2,6-dimethylphenyl)benzamide |
| 151 | 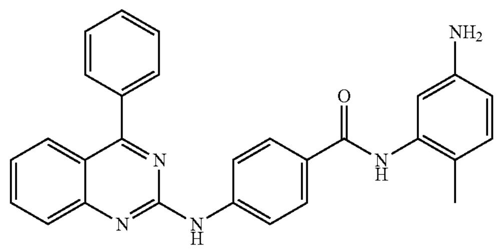 | N-(5-amino-2-methylphenyl)-4-[(4-phenylquinazolin-2-yl)amino]benzamide |
| 152 | 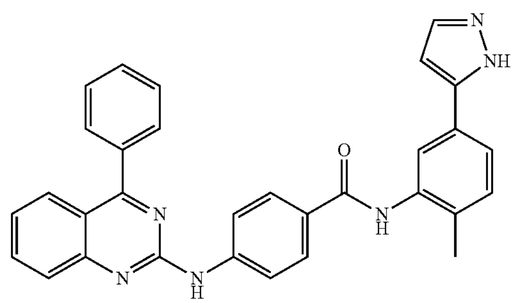 [SMILES: Cc1ccc(-c2ccn[nH]2)cc1NC(=O)c1ccc(Nc2nc(-c3ccccc3)c3ccccc3n2)cc1] | N-[2-methyl-5-(1H-pyrazol-5-yl)phenyl]-4-[(4-phenylquinazolin-2-yl)amino]benzamide |
| 153 | 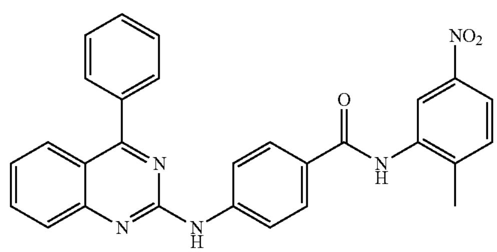 [SMILES: Cc1ccc([N+](=O)[O-])cc1NC(=O)c1ccc(Nc2nc(-c3ccccc3)c3ccccc3n2)cc1] | N-(2-methyl-5-nitrophenyl)-4-[(4-phenylquinazolin-2-yl)amino]benzamide |
| 154 | 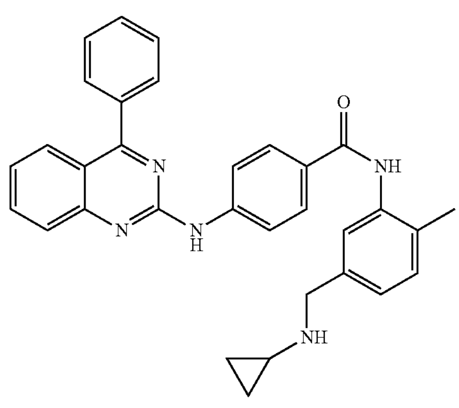 [SMILES: Cc1ccc(CNC2CC2)cc1NC(=O)c1ccc(Nc2nc(-c3ccccc3)c3ccccc3n2)cc1] | N-{5-[(cyclopropylamino)methyl]-2-methylphenyl}-4-[(4-phenylquinazolin-2-yl)amino]benzamide |

TABLE 1-continued

| Cmpd No. | Structure | Name |
|---|---|---|
| 155 | 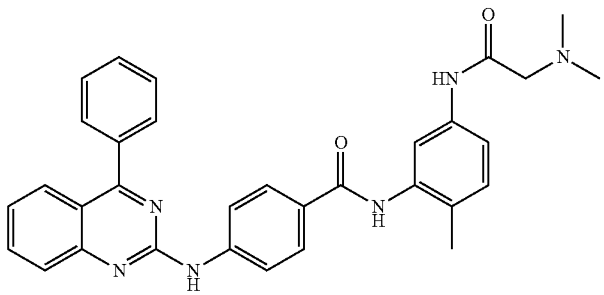 [SMILES: Cc1ccc(NC(=O)CN(C)C)cc1NC(=O)c1ccc(Nc2nc(-c3ccccc3)c3ccccc3n2)cc1] | N-[5-[{N,N-dimethylglycyl)amino]-2-methylphenyl}-4-[(4-phenylquinazolin-2-yl)amino]benzamide |
| 156 | 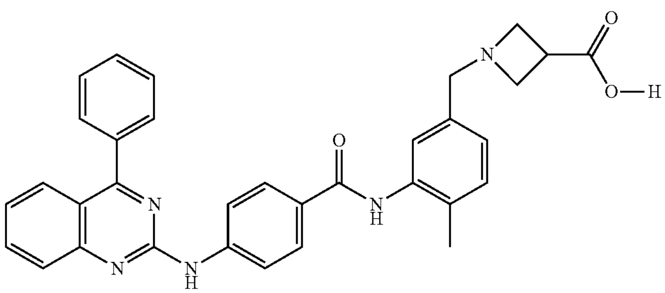 [SMILES: Cc1ccc(CN2CC(C(=O)O)C2)cc1NC(=O)c1ccc(Nc2nc(-c3ccccc3)c3ccccc3n2)cc1] | 1-({4-methyl-3-[({4-[(4-phenylquinazolin-2-yl)amino]phenyl}carbonyl)amino]phenyl}methyl)azetidine-3-carboxylic acid |
| 157 | 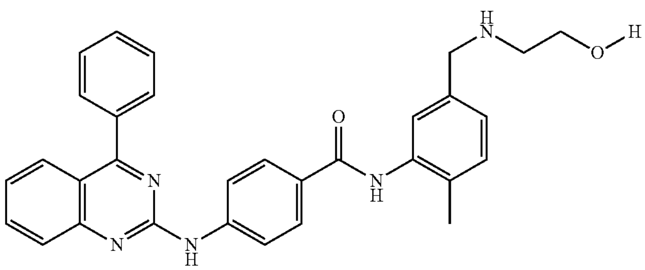 [SMILES: Cc1ccc(CNCCO)cc1NC(=O)c1ccc(Nc2nc(-c3ccccc3)c3ccccc3n2)cc1] | N-(5-{[(2-hydroxyethyl)amino]methyl}-2-methylphenyl)-4-[(4-phenylquinazolin-2-yl)amino]benzamide |
| 158 | 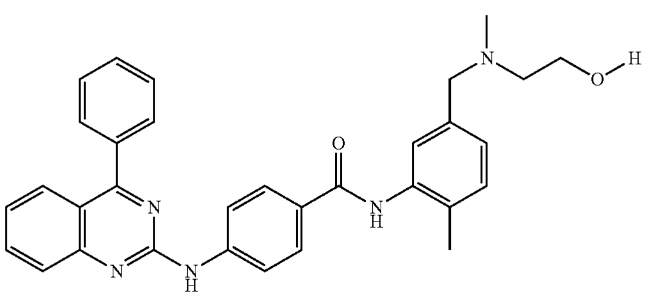 [SMILES: Cc1ccc(CN(C)CCO)cc1NC(=O)c1ccc(Nc2nc(-c3ccccc3)c3ccccc3n2)cc1] | N-(5-{[(2-hydroxyethyl)(methyl)amino]methyl}-2-methylphenyl)-4-[(4-phenylquinazolin-2-yl)amino]benzamide |
| 159 | 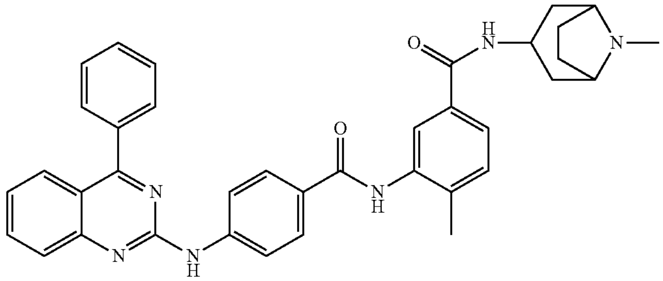 [SMILES: Cc1ccc(C(=O)NC2CC3CCC(C2)N3C)cc1NC(=O)c1ccc(Nc2nc(-c3ccccc3)c3ccccc3n2)cc1] | 4-methyl-N-(8-methyl-8-azabicyclo[3.2.1]oct-3-yl)-3-[({4-[(4-phenylquinazolin-2-yl)amino]phenyl}carbonyl)amino]benzamide |

TABLE 1-continued

| Cmpd No. | Structure | Name |
|---|---|---|
| 160 | 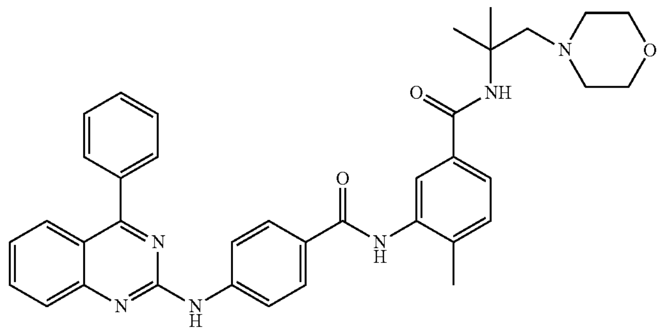 [SMILES: Cc1ccc(C(=O)NC(C)(C)CN2CCOCC2)cc1NC(=O)c1ccc(Nc2nc(-c3ccccc3)c3ccccc3n2)cc1] | N-(1,1-dimethyl-2-morpholin-4-ylethyl)-4-methyl-3-[({4-[(4-phenylquinazolin-2-yl)amino]phenyl}carbonyl)amino]benzamide |
| 161 | 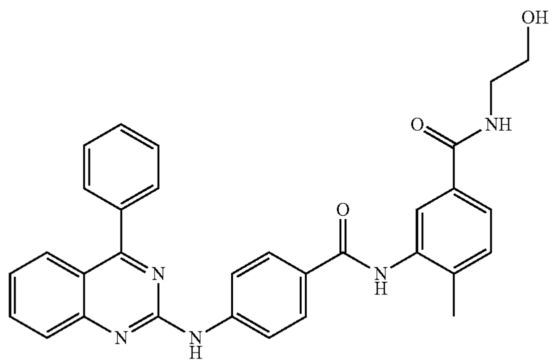 [SMILES: Cc1ccc(C(=O)NCCO)cc1NC(=O)c1ccc(Nc2nc(-c3ccccc3)c3ccccc3n2)cc1] | N-(2-hydroxyethyl)-4-methyl-3-[({4-[(4-phenylquinazolin-2-yl)amino]phenyl}carbonyl)amino]benzamide |
| 162 | 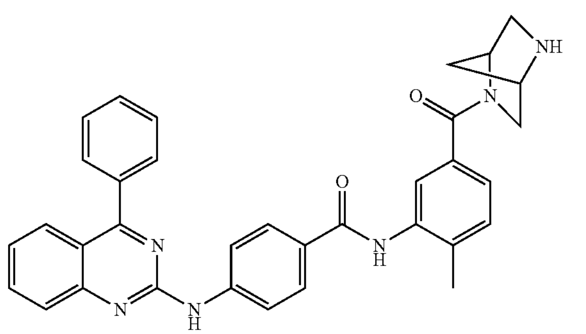 [SMILES: Cc1ccc(C(=O)N2CC3CC2CN3)cc1NC(=O)c1ccc(Nc2nc(-c3ccccc3)c3ccccc3n2)cc1] | N-[5-(2,5-diazabicyclo[2.2.1]hept-2-ylcarbonyl)-2-methylphenyl]-4-[(4-phenylquinazolin-2-yl)amino]benzamide |
| 163 | 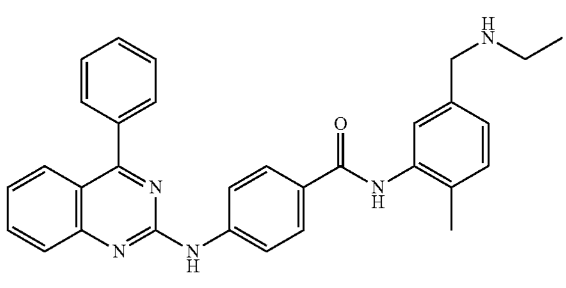 [SMILES: CCNCc1ccc(C)c(NC(=O)c2ccc(Nc3nc(-c4ccccc4)c4ccccc4n3)cc2)c1] | N-{5-[(ethylamino)methyl]-2-methylphenyl}-4-[(4-phenylquinazolin-2-yl)amino]benzamide |
| 164 | 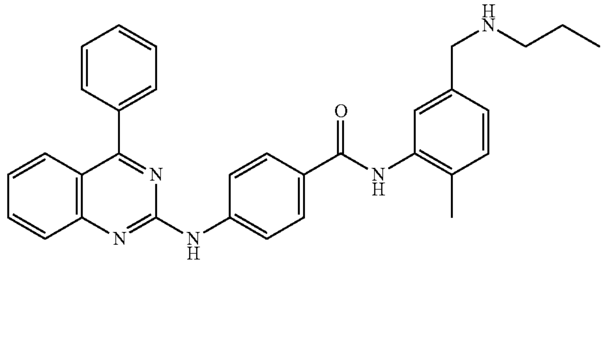 [SMILES: CCCNCc1ccc(C)c(NC(=O)c2ccc(Nc3nc(-c4ccccc4)c4ccccc4n3)cc2)c1] | N-{2-methyl-5-[(propylamino)methyl]phenyl}-4-[(4-phenylquinazolin-2-yl)amino]benzamide |

TABLE 1-continued

| Cmpd No. | Structure | Name |
|---|---|---|
| 165 | 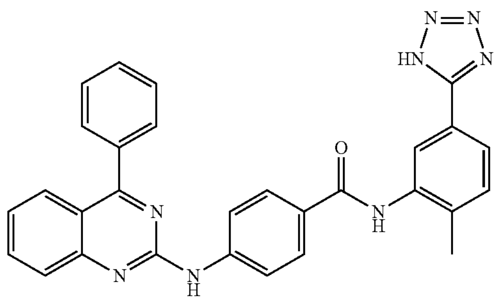 [SMILES: Cc1ccc(-c2nnn[nH]2)cc1NC(=O)c1ccc(Nc2nc(-c3ccccc3)c3ccccc3n2)cc1] | N-[2-methyl-5-(1H-tetrazol-5-yl)phenyl]-4-[(4-phenylquinazolin-2-yl)amino]benzamide |
| 166 | 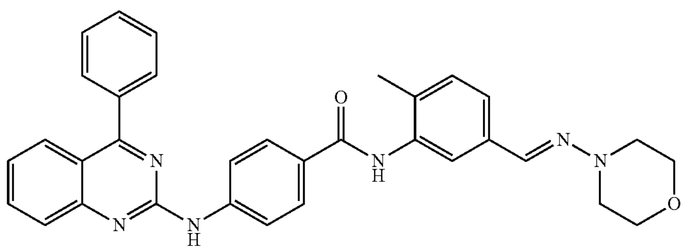 [SMILES: Cc1ccc(/C=N/N2CCOCC2)cc1NC(=O)c1ccc(Nc2nc(-c3ccccc3)c3ccccc3n2)cc1] | N-{2-methyl-5-[(E)-(morpholin-4-ylimino)methyl]phenyl}-4-[(4-phenylquinazolin-2-yl)amino]benzamide |
| 167 | 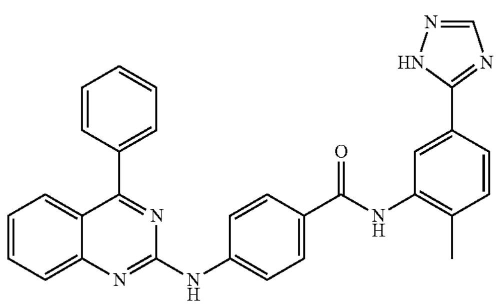 [SMILES: Cc1ccc(-c2ncn[nH]2)cc1NC(=O)c1ccc(Nc2nc(-c3ccccc3)c3ccccc3n2)cc1] | N-[2-methyl-5-(1H-1,2,4-triazol-5-yl)phenyl]-4-[(4-phenylquinazolin-2-yl)amino]benzamide |
| 168 | 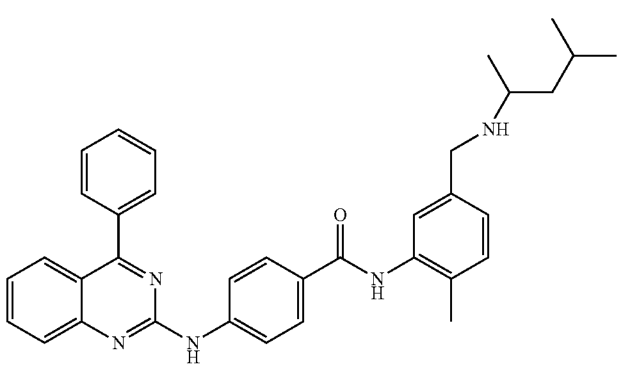 [SMILES: Cc1ccc(CNC(C)CC(C)C)cc1NC(=O)c1ccc(Nc2nc(-c3ccccc3)c3ccccc3n2)cc1] | N-(5-{[(1,3-dimethylbutyl)amino]methyl}-2-methylphenyl)-4-[(4-phenylquinazolin-2-yl)amino]benzamide |
| 169 | 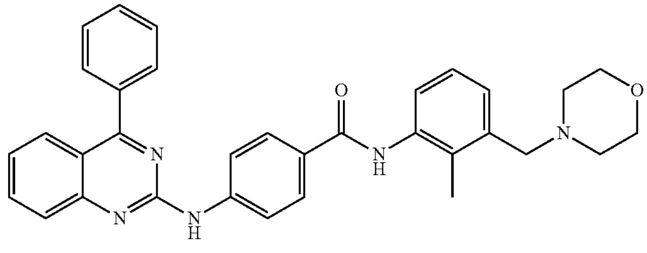 [SMILES: Cc1c(CN2CCOCC2)cccc1NC(=O)c1ccc(Nc2nc(-c3ccccc3)c3ccccc3n2)cc1] | N-[2-methyl-3-(morpholin-4-ylmethyl)phenyl]-4-[(4-phenylquinazolin-2-yl)amino]benzamide |

TABLE 1-continued

| Cmpd No. | Structure | Name |
|---|---|---|
| 170 | 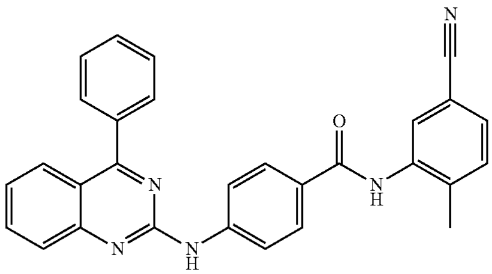 [SMILES: Cc1ccc(C#N)cc1NC(=O)c1ccc(Nc2nc(-c3ccccc3)c3ccccc3n2)cc1] | N-(5-cyano-2-methylphenyl)-4-[(4-phenylquinazolin-2-yl)amino]benzamide |
| 171 | 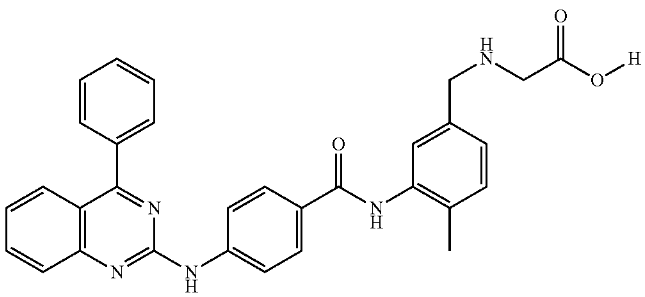 [SMILES: Cc1ccc(CNCC(=O)O)cc1NC(=O)c1ccc(Nc2nc(-c3ccccc3)c3ccccc3n2)cc1] | N-({4-methyl-3-[({4-[(4-phenylquinazolin-2-yl)amino]phenyl}carbonyl)amino]phenyl}methyl)glycine |
| 172 | 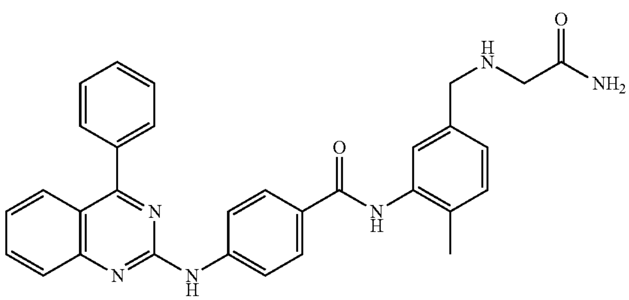 [SMILES: Cc1ccc(CNCC(N)=O)cc1NC(=O)c1ccc(Nc2nc(-c3ccccc3)c3ccccc3n2)cc1] | N-(5-{[(2-amino-2-oxoethyl)amino]methyl}-2-methylphenyl)-4-[(4-phenylquinazolin-2-yl)amino]benzamide |
| 173 | 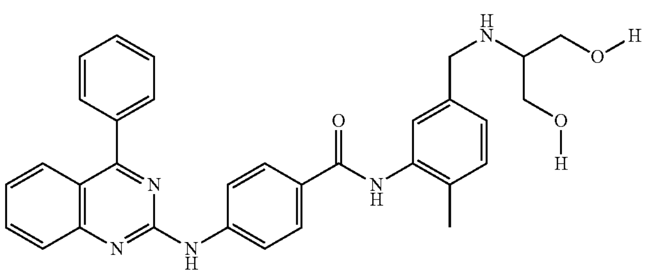 [SMILES: Cc1ccc(CNC(CO)CO)cc1NC(=O)c1ccc(Nc2nc(-c3ccccc3)c3ccccc3n2)cc1] | N-[5-({[2-hydroxy-1-(hydroxymethyl)ethyl]amino}methyl)-2-methylphenyl]-4-[(4-phenylquinazolin-2-yl)amino]benzamide |
| 174 | 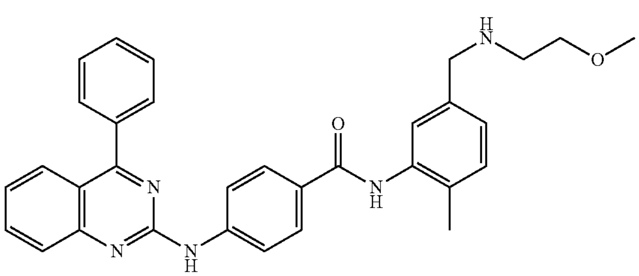 [SMILES: COCCNCc1ccc(C)c(NC(=O)c2ccc(Nc3nc(-c4ccccc4)c4ccccc4n3)cc2)c1] | N-[2-methyl-5-({[2-(methyloxy)ethyl]amino}methyl)phenyl]-4-[(4-phenylquinazolin-2-yl)amino]benzamide |

TABLE 1-continued

| Cmpd No. | Structure | Name |
|---|---|---|
| 175 | 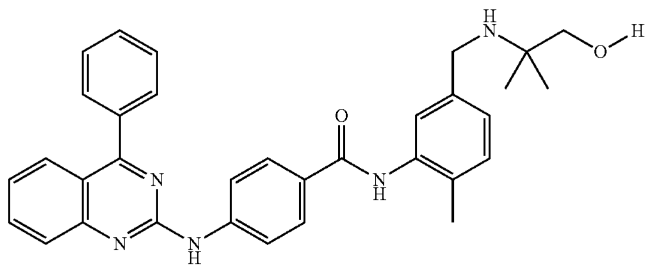 [SMILES: Cc1ccc(CNC(C)(C)CO)cc1NC(=O)c1ccc(Nc2nc(-c3ccccc3)c3ccccc3n2)cc1] | N-(5-{[(2-hydroxy-1,1-dimethylethyl)amino]methyl}-2-methylphenyl)-4-[(4-phenylquinazolin-2-yl)amino]benzamide |
| 176 | 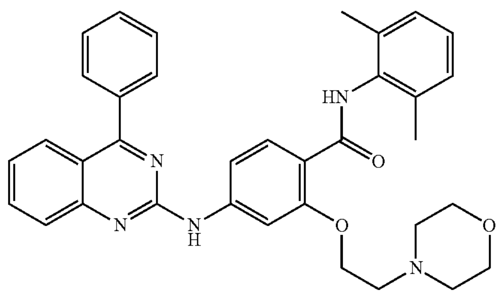 [SMILES: Cc1cccc(C)c1NC(=O)c1ccc(Nc2nc(-c3ccccc3)c3ccccc3n2)cc1OCCN1CCOCC1] | N-(2,6-dimethylphenyl)-2-[(2-morpholin-4-ylethyl)oxy]-4-[(4-phenylquinazolin-2-yl)amino]benzamide |
| 177 | 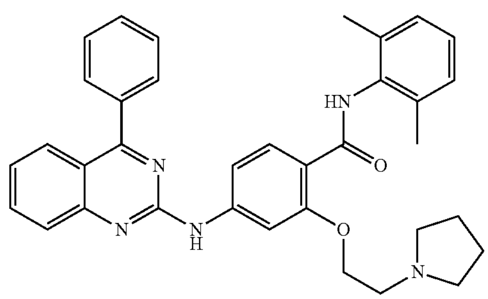 [SMILES: Cc1cccc(C)c1NC(=O)c1ccc(Nc2nc(-c3ccccc3)c3ccccc3n2)cc1OCCN1CCCC1] | N-(2,6-dimethylphenyl)-4-[(4-phenylquinazolin-2-yl)amino]-2-[(2-pyrrolidin-1-ylethyl)oxy]benzamide |
| 178 | 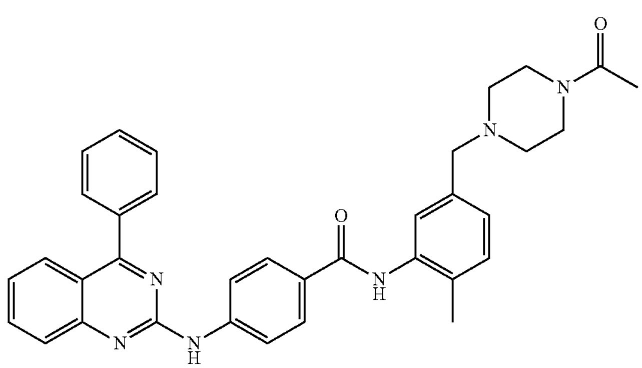 [SMILES: CC(=O)N1CCN(Cc2ccc(C)c(NC(=O)c3ccc(Nc4nc(-c5ccccc5)c5ccccc5n4)cc3)c2)CC1] | N-{5-[(4-acetylpiperazin-1-yl)methyl]-2-methylphenyl}-4-[(4-phenylquinazolin-2-yl)amino]benzamide |
| 179 | 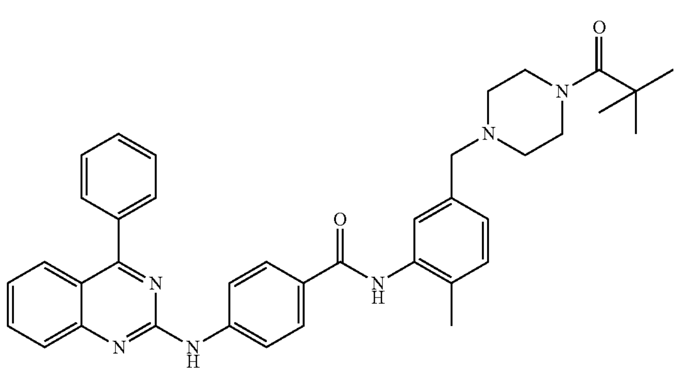 [SMILES: Cc1ccc(CN2CCN(C(=O)C(C)(C)C)CC2)cc1NC(=O)c1ccc(Nc2nc(-c3ccccc3)c3ccccc3n2)cc1] | N-(5-{[4-(2,2-dimethylpropanoyl)piperazin-1-yl]methyl}-2-methylphenyl)-4-[(4-phenylquinazolin-2-yl)amino]benzamide |

TABLE 1-continued

| Cmpd No. | Structure | Name |
|---|---|---|
| 180 | 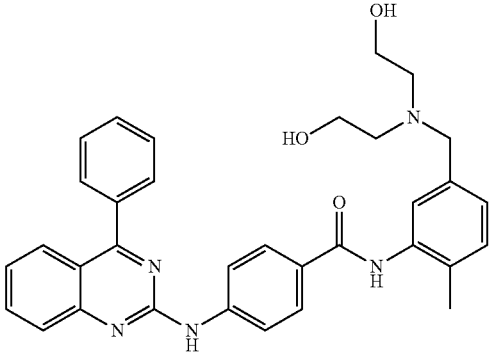 [SMILES: Cc1ccc(CN(CCO)CCO)cc1NC(=O)c1ccc(Nc2nc(-c3ccccc3)c3ccccc3n2)cc1] | N-(5-{[bis(2-hydroxyethyl)amino]methyl}-2-methylphenyl)-4-[(4-phenylquinazolin-2-yl)amino]benzamide |
| 181 | 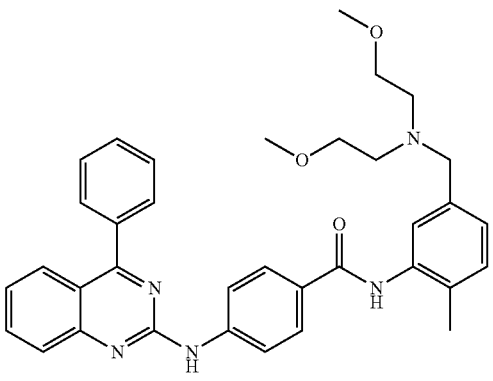 [SMILES: COCCN(CCOC)Cc1ccc(C)c(NC(=O)c2ccc(Nc3nc(-c4ccccc4)c4ccccc4n3)cc2)c1] | N-[5-({bis[2-(methyloxy)ethyl]amino}methyl)-2-methylphenyl]-4-[(4-phenylquinazolin-2-yl)amino]benzamide |
| 182 | 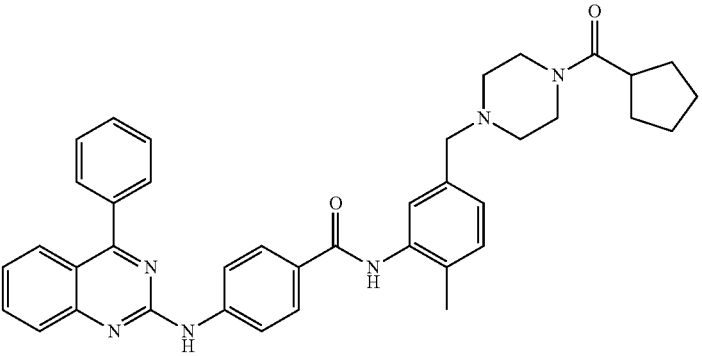 [SMILES: Cc1ccc(CN2CCN(C(=O)C3CCCC3)CC2)cc1NC(=O)c1ccc(Nc2nc(-c3ccccc3)c3ccccc3n2)cc1] | N-(5-{[4-(cyclopentylcarbonyl)piperazin-1-yl]methyl}-2-methylphenyl)-4-[(4-phenylquinazolin-2-yl)amino]benzamide |
| 183 | 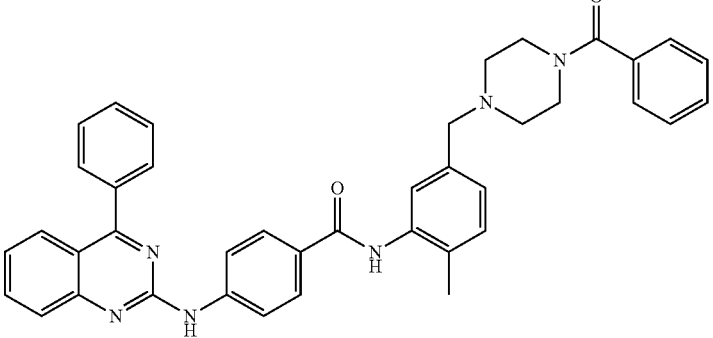 | N-(2-methyl-5-{[4-(phenylcarbonyl)piperazin-1-yl]methyl}phenyl)-4-[(4-phenylquinazolin-2-yl)amino]benzamide |

TABLE 1-continued

| Cmpd No. | Structure | Name |
|---|---|---|
| 184 | 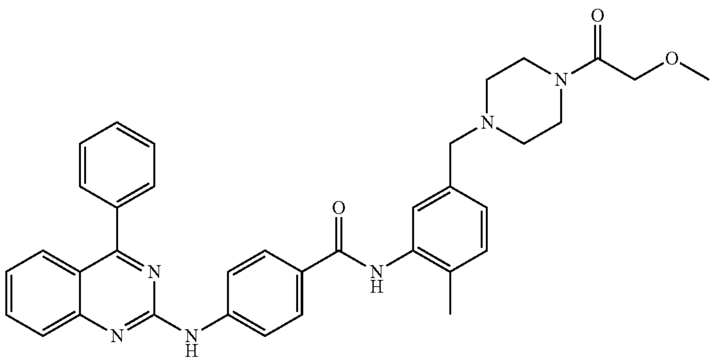 [SMILES: COCC(=O)N1CCN(Cc2ccc(C)c(NC(=O)c3ccc(Nc4nc(-c5ccccc5)c5ccccc5n4)cc3)c2)CC1] | N-[2-methyl-5-({4-[(methyloxy)acetyl]piperazin-1-yl}methyl)phenyl]-4-[(4-phenylquinazolin-2-yl)amino]benzamide |
| 185 | 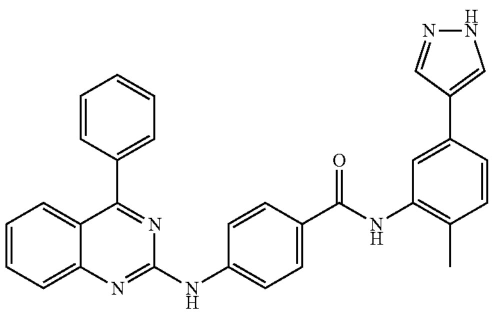 [SMILES: Cc1ccc(-c2cn[nH]c2)cc1NC(=O)c1ccc(Nc2nc(-c3ccccc3)c3ccccc3n2)cc1] | N-[2-methyl-5-(1H-pyrazol-4-yl)phenyl]-4-[(4-phenylquinazolin-2-yl)amino]benzamide |
| 186 | 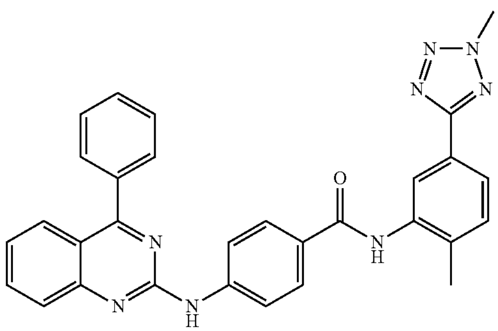 [SMILES: Cc1ccc(-c2nnn(C)n2)cc1NC(=O)c1ccc(Nc2nc(-c3ccccc3)c3ccccc3n2)cc1] | N-[2-methyl-5-(2-methyl-2H-tetrazol-5-yl)phenyl]-4-[(4-phenylquinazolin-2-yl)amino]benzamide |
| 187 | 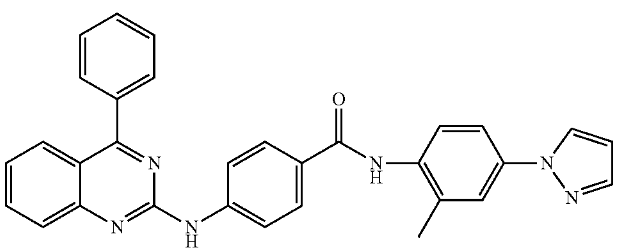 [SMILES: Cc1cc(-n2cccn2)ccc1NC(=O)c1ccc(Nc2nc(-c3ccccc3)c3ccccc3n2)cc1] | N-[2-methyl-4-(1H-pyrazol-1-yl)phenyl]-4-[(4-phenylquinazolin-2-yl)amino]benzamide |
| 188 | 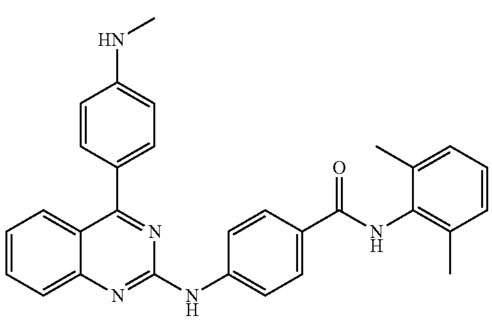 [SMILES: CNc1ccc(-c2nc(Nc3ccc(C(=O)Nc4c(C)cccc4C)cc3)nc3ccccc23)cc1] | N-(2,6-dimethylphenyl)-4-({4-[4-(methylamino)phenyl]quinazolin-2-yl}amino)benzamide |

TABLE 1-continued

| Cmpd No. | Structure | Name |
|---|---|---|
| 189 | 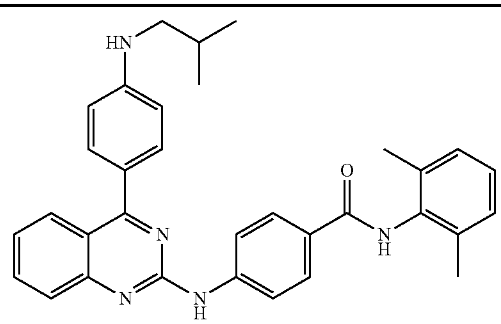 | N-(2,6-dimethylphenyl)-4-[(4-{4-[(2-methylpropyl)amino]phenyl}quinazolin-2-yl)amino]benzamide |
| 190 | 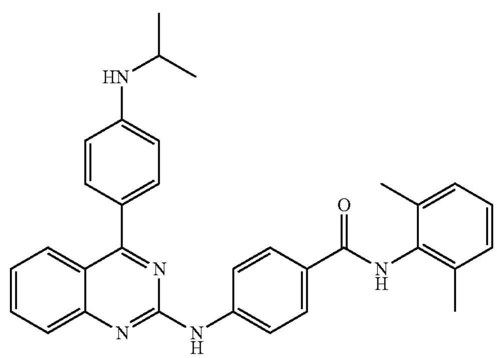 [SMILES: Cc1cccc(C)c1NC(=O)c1ccc(Nc2nc(-c3ccc(NC(C)C)cc3)c3ccccc3n2)cc1] | N-(2,6-dimethylphenyl)-4-[(4-{4-[(1-methylethyl)amino]phenyl}quinazolin-2-yl)amino]benzamide |
| 191 | 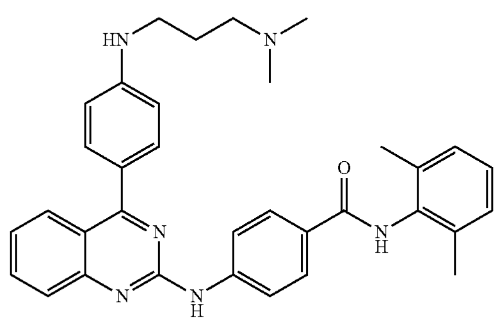 [SMILES: Cc1cccc(C)c1NC(=O)c1ccc(Nc2nc(-c3ccc(NCCCN(C)C)cc3)c3ccccc3n2)cc1] | 4-{[4-(4-{[3-(dimethylamino)propyl]amino}phenyl)quinazolin-2-yl]amino}-N-(2,6-dimethylphenyl)benzamide |
| 192 | 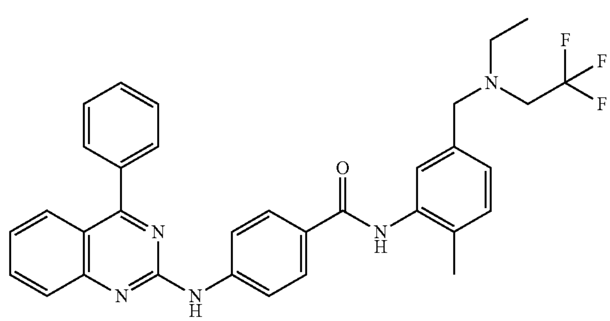 [SMILES: CCN(Cc1ccc(C)c(NC(=O)c2ccc(Nc3nc(-c4ccccc4)c4ccccc4n3)cc2)c1)CC(F)(F)F] | N-(5-{[ethyl(2,2,2-trifluoroethyl)amino]methyl}-2-methylphenyl)-4-[(4-phenylquinazolin-2-yl)amino]benzamide |
| 193 | 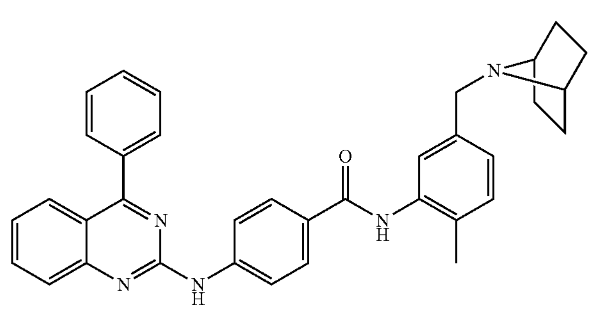 [SMILES: Cc1ccc(CN2C3CCC2CC3)cc1NC(=O)c1ccc(Nc2nc(-c3ccccc3)c3ccccc3n2)cc1] | N-[5-(7-azabicyclo[2.2.1]hept-7-ylmethyl)-2-methylphenyl]-4-[(4-phenylquinazolin-2-yl)amino]benzamide |

TABLE 1-continued

| Cmpd No. | Structure | Name |
|---|---|---|
| 194 | 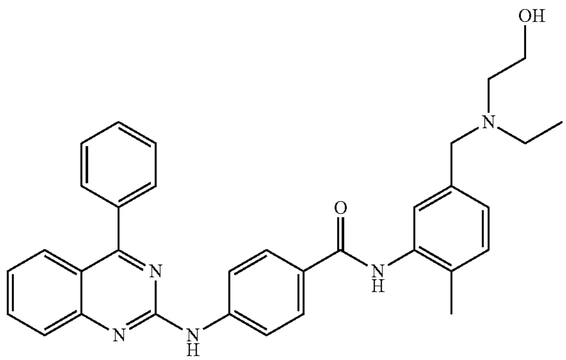 [SMILES: CCN(CCO)Cc1ccc(C)c(NC(=O)c2ccc(Nc3nc(-c4ccccc4)c4ccccc4n3)cc2)c1] | N-(5-{[ethyl(2-hydroxyethyl)amino]methyl}-2-methylphenyl)-4-[(4-phenylquinazolin-2-yl)amino]benzamide |
| 195 | 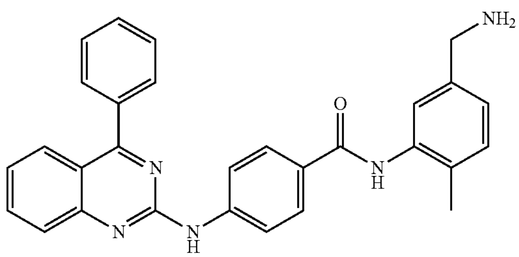 [SMILES: Cc1ccc(CN)cc1NC(=O)c1ccc(Nc2nc(-c3ccccc3)c3ccccc3n2)cc1] | N-[5-(aminomethyl)-2-methylphenyl]-4-[(4-phenylquinazolin-2-yl)amino]benzamide |
| 196 | 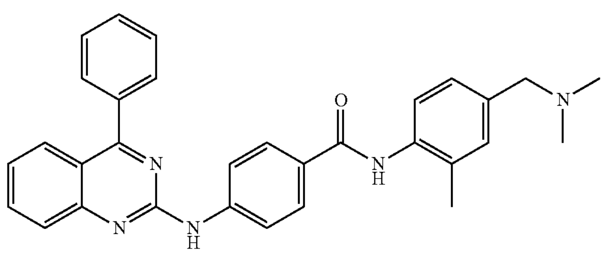 [SMILES: Cc1cc(CN(C)C)ccc1NC(=O)c1ccc(Nc2nc(-c3ccccc3)c3ccccc3n2)cc1] | N-{4-[(dimethylamino)methyl]-2-methylphenyl}-4-[(4-phenylquinazolin-2-yl)amino]benzamide |
| 197 | 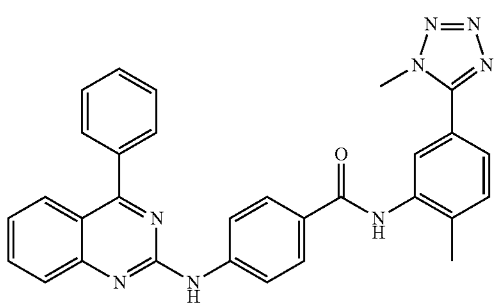 [SMILES: Cc1ccc(-c2nnnn2C)cc1NC(=O)c1ccc(Nc2nc(-c3ccccc3)c3ccccc3n2)cc1] | N-[2-methyl-5-(1-methyl-1H-tetrazol-5-yl)phenyl]-4-[(4-phenylquinazolin-2-yl)amino]benzamide |
| 198 | 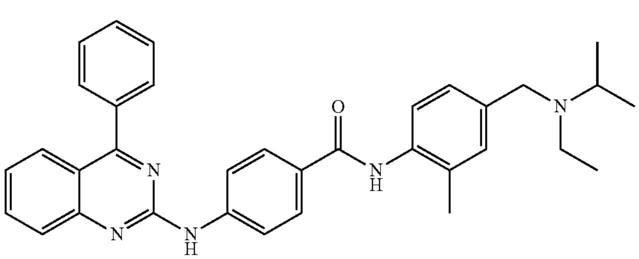 [SMILES: CCN(Cc1ccc(NC(=O)c2ccc(Nc3nc(-c4ccccc4)c4ccccc4n3)cc2)c(C)c1)C(C)C] | N-(4-{[ethyl(1-methylethyl)amino]methyl}-2-methylphenyl)-4-[(4-phenylquinazolin-2-yl)amino]benzamide |

| Cmpd No. | Structure | Name |
|---|---|---|
| 199 | 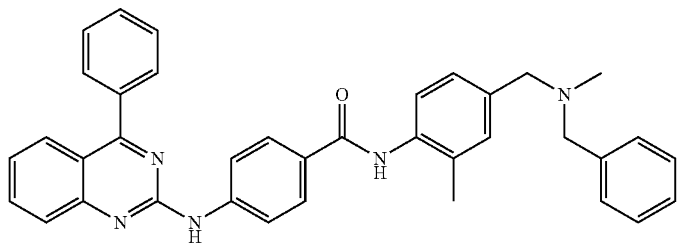 [SMILES: Cc1cc(CN(C)Cc2ccccc2)ccc1NC(=O)c1ccc(Nc2nc(-c3ccccc3)c3ccccc3n2)cc1] | N-(2-methyl-4-{[methyl(phenylmethyl)amino]methyl}phenyl)-4-[(4-phenylquinazolin-2-yl)amino]benzamide |
| 200 | 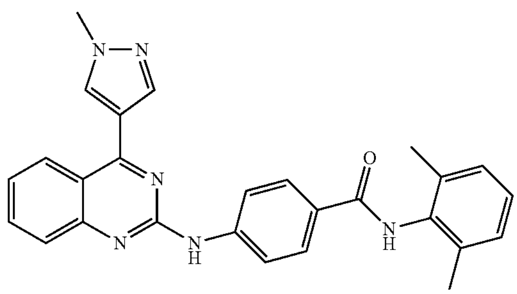 [SMILES: Cc1cccc(C)c1NC(=O)c1ccc(Nc2nc(-c3cnn(C)c3)c3ccccc3n2)cc1] | N-(2,6-dimethylphenyl)-4-{[4-(1-methyl-1H-pyrazol-4-yl)quinazolin-2-yl]amino}benzamide |
| 201 | 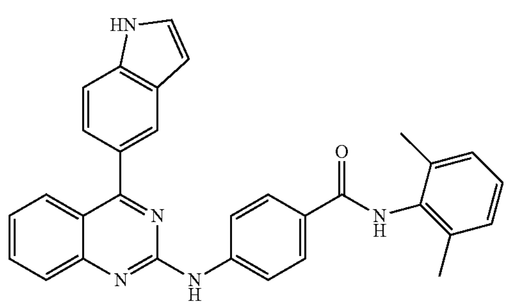 [SMILES: Cc1cccc(C)c1NC(=O)c1ccc(Nc2nc(-c3ccc4[nH]ccc4c3)c3ccccc3n2)cc1] | N-(2,6-dimethylphenyl)-4-{[4-(1H-indol-5-yl)quinazolin-2-yl]amino}benzamide |
| 202 | 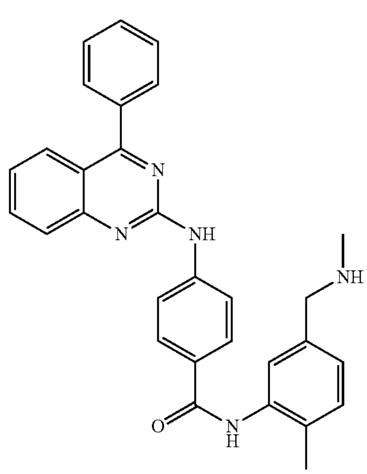 [SMILES: CNCc1ccc(C)c(NC(=O)c2ccc(Nc3nc(-c4ccccc4)c4ccccc4n3)cc2)c1] | N-{2-methyl-5-[(methylamino)methyl]phenyl}-4-[(4-phenylquinazolin-2-yl)amino]benzamide |

TABLE 1-continued

| Cmpd No. | Structure | Name |
|---|---|---|
| 203 | 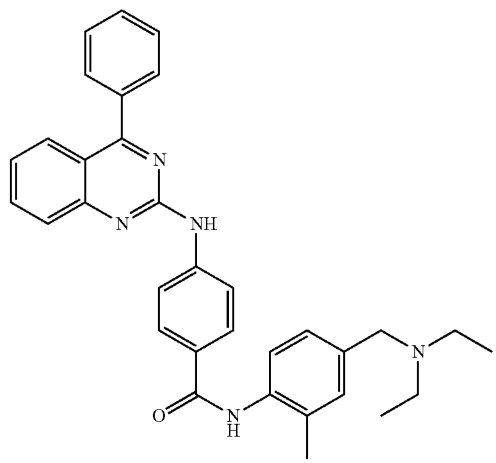 [SMILES: CCN(CC)Cc1ccc(NC(=O)c2ccc(Nc3nc(-c4ccccc4)c4ccccc4n3)cc2)c(C)c1] | N-{4-[(diethylamino)methyl]-2-methylphenyl}-4-[(4-phenylquinazolin-2-yl)amino]benzamide |
| 204 | 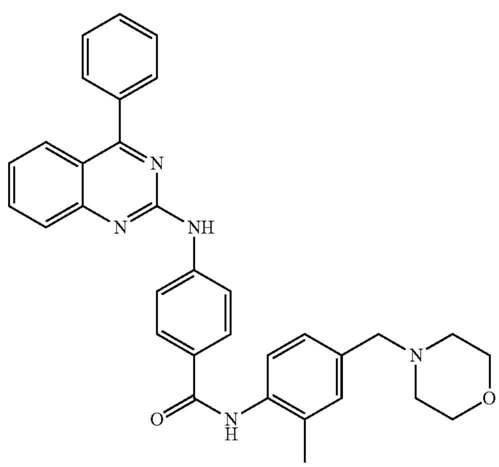 [SMILES: Cc1cc(CN2CCOCC2)ccc1NC(=O)c1ccc(Nc2nc(-c3ccccc3)c3ccccc3n2)cc1] | N-[2-methyl-4-(morpholin-4-ylmethyl)phenyl]-4-[(4-phenylquinazolin-2-yl)amino]benzamide |
| 205 | 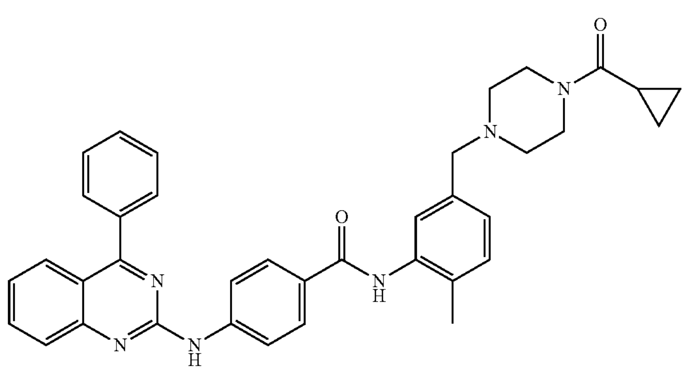 [SMILES: Cc1ccc(CN2CCN(C(=O)C3CC3)CC2)cc1NC(=O)c1ccc(Nc2nc(-c3ccccc3)c3ccccc3n2)cc1] | N-(5-{[4-(cyclopropylcarbonyl)piperazin-1-yl]methyl}-2-methylphenyl)-4-[(4-phenylquinazolin-2-yl)amino]benzamide |
| 206 | 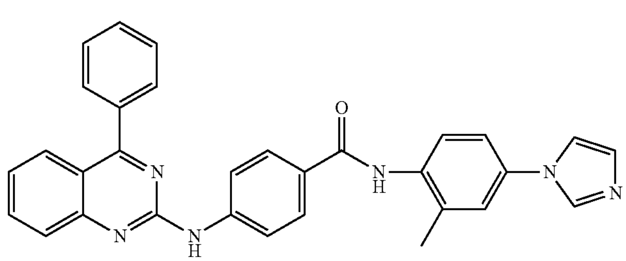 [SMILES: Cc1cc(-n2ccnc2)ccc1NC(=O)c1ccc(Nc2nc(-c3ccccc3)c3ccccc3n2)cc1] | N-[4-(1H-imidazol-1-yl)-2-methylphenyl]-4-[(4-phenylquinazolin-2-yl)amino]benzamide |

TABLE 1-continued

| Cmpd No. | Structure | Name |
|---|---|---|
| 207 | 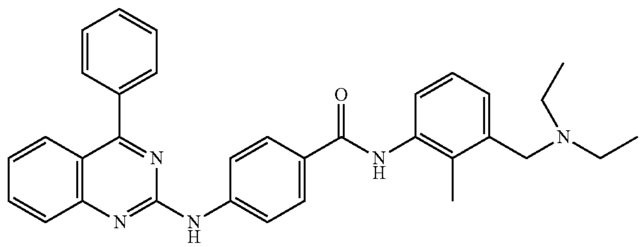 [SMILES: CCN(CC)Cc1cccc(NC(=O)c2ccc(Nc3nc(-c4ccccc4)c4ccccc4n3)cc2)c1C] | N-{3-[(diethylamino)methyl]-2-methylphenyl}-4-[(4-phenylquinazolin-2-yl)amino]benzamide |
| 208 | 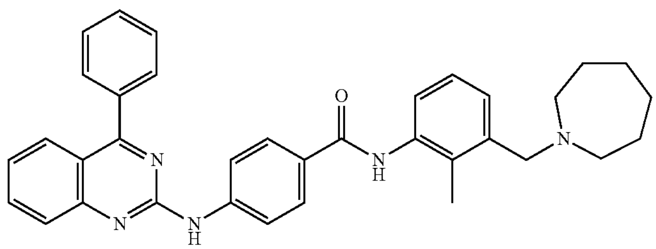 [SMILES: Cc1c(CN2CCCCCC2)cccc1NC(=O)c1ccc(Nc2nc(-c3ccccc3)c3ccccc3n2)cc1] | N-[3-(azepan-1-ylmethyl)-2-methylphenyl]-4-[(4-phenylquinazolin-2-yl)amino]benzamide |
| 209 | 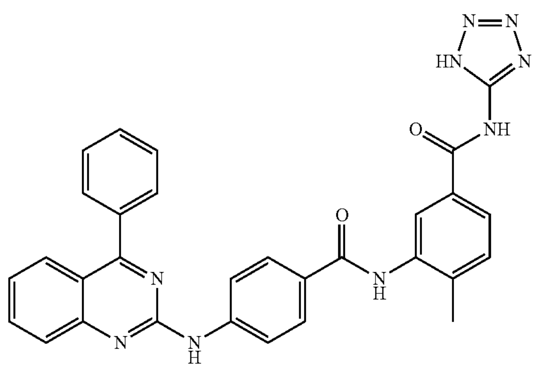 [SMILES: Cc1ccc(C(=O)Nc2nnn[nH]2)cc1NC(=O)c1ccc(Nc2nc(-c3ccccc3)c3ccccc3n2)cc1] | 4-methyl-3-[({4-[(4-phenylquinazolin-2-yl)amino]phenyl}carbonyl)amino]-N-1H-tetrazol-5-ylbenzamide |
| 210 | 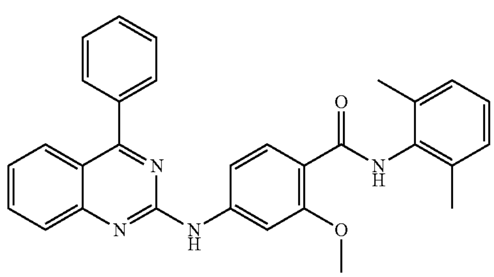 [SMILES: COc1cc(Nc2nc(-c3ccccc3)c3ccccc3n2)ccc1C(=O)Nc1c(C)cccc1C] | N-(2,6-dimethylphenyl)-2-(methyloxy)-4-[(4-phenylquinazolin-2-yl)amino]benzamide |
| 211 | 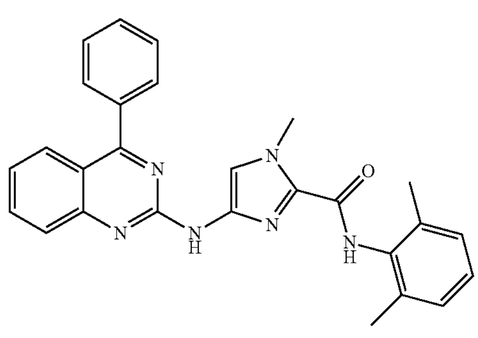 [SMILES: Cc1cccc(C)c1NC(=O)c1nc(Nc2nc(-c3ccccc3)c3ccccc3n2)cn1C] | N-(2,6-dimethylphenyl)-1-methyl-4-[(4-phenylquinazolin-2-yl)amino]-1H-imidazole-2-carboxamide |

TABLE 1-continued

| Cmpd No. | Structure | Name |
|---|---|---|
| 212 | 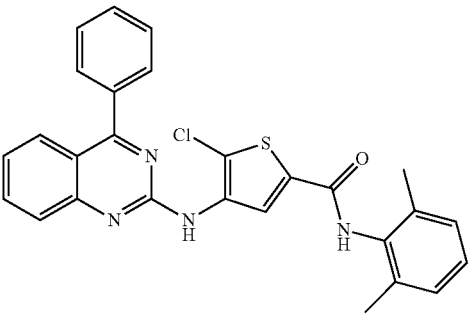 [SMILES: Cc1cccc(C)c1NC(=O)c1cc(Nc2nc(-c3ccccc3)c3ccccc3n2)c(Cl)s1] | 5-chloro-N-(2,6-dimethylphenyl)-4-[(4-phenylquinazolin-2-yl)amino]thiophene-2-carboxamide |
| 213 | 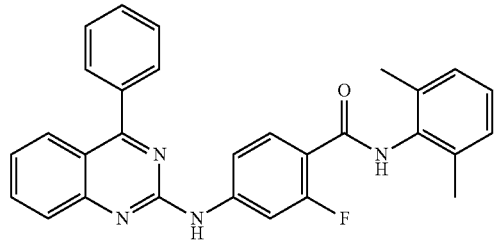 [SMILES: Cc1cccc(C)c1NC(=O)c1ccc(Nc2nc(-c3ccccc3)c3ccccc3n2)cc1F] | N-(2,6-dimethylphenyl)-2-fluoro-4-[(4-phenylquinazolin-2-yl)amino]benzamide |
| 214 | 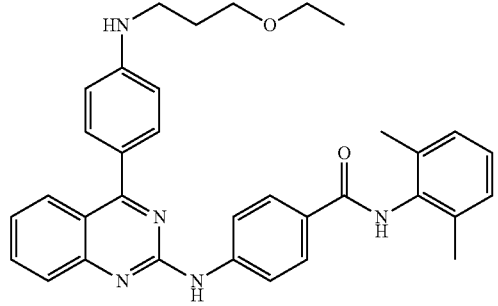 [SMILES: CCOCCCNc1ccc(-c2nc(Nc3ccc(C(=O)Nc4c(C)cccc4C)cc3)nc3ccccc23)cc1] | N-(2,6-dimethylphenyl)-4-{[4-(4-{[3-(ethyloxy)propyl]amino}phenyl)quinazolin-2-yl]amino}benzamide |
| 215 | 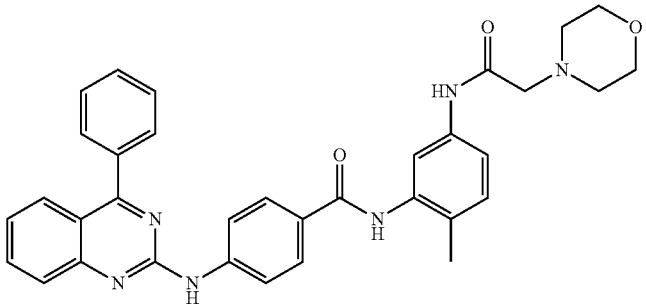 [SMILES: Cc1ccc(NC(=O)CN2CCOCC2)cc1NC(=O)c1ccc(Nc2nc(-c3ccccc3)c3ccccc3n2)cc1] | N-{2-methyl-5-[(morpholin-4-ylacetyl)amino]phenyl}-4-[(4-phenylquinazolin-2-yl)amino]benzamide |
| 216 | 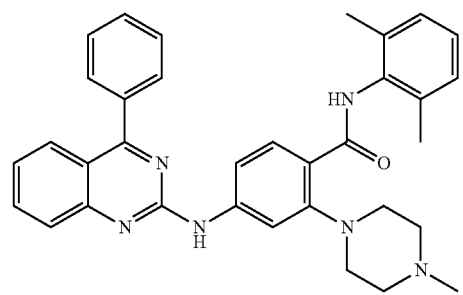 [SMILES: Cc1cccc(C)c1NC(=O)c1ccc(Nc2nc(-c3ccccc3)c3ccccc3n2)cc1N1CCN(C)CC1] | N-(2,6-dimethylphenyl)-2-(4-methylpiperazin-1-yl)-4-[(4-phenylquinazolin-2-yl)amino]benzamide |

TABLE 1-continued

| Cmpd No. | Structure | Name |
|---|---|---|
| 217 | 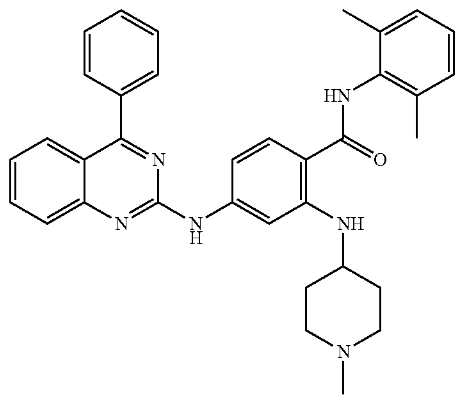 [SMILES: Cc1cccc(C)c1NC(=O)c1ccc(Nc2nc(-c3ccccc3)c3ccccc3n2)cc1NC1CCN(C)CC1] | N-(2,6-dimethylphenyl)-2-[(1-methylpiperidin-4-yl)amino]-4-[(4-phenylquinazolin-2-yl)amino]benzamide |
| 218 | 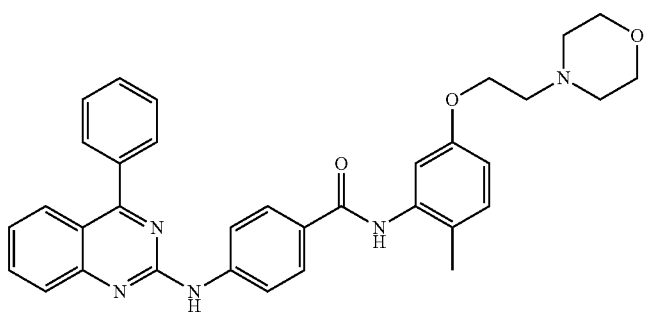 [SMILES: Cc1ccc(OCCN2CCOCC2)cc1NC(=O)c1ccc(Nc2nc(-c3ccccc3)c3ccccc3n2)cc1] | N-{2-methyl-5-[(2-morpholin-4-ylethyl)oxy]phenyl}-4-[(4-phenylquinazolin-2-yl)amino]benzamide |
| 219 | 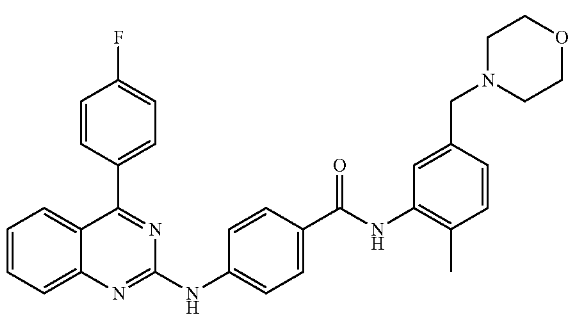 [SMILES: Cc1ccc(CN2CCOCC2)cc1NC(=O)c1ccc(Nc2nc(-c3ccc(F)cc3)c3ccccc3n2)cc1] | 4-{[4-(4-fluorophenyl)quinazolin-2-yl]amino}-N-[2-methyl-5-(morpholin-4-ylmethyl)phenyl]benzamide |
| 220 | 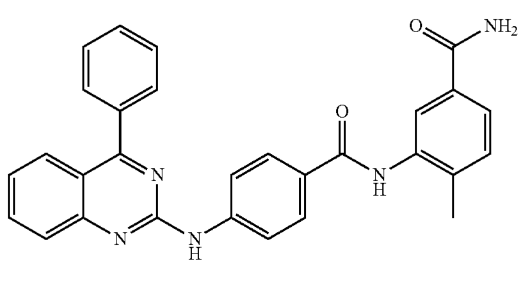 [SMILES: Cc1ccc(C(N)=O)cc1NC(=O)c1ccc(Nc2nc(-c3ccccc3)c3ccccc3n2)cc1] | 4-methyl-3-[({4-[(4-phenylquinazolin-2-yl)amino]phenyl}carbonyl)amino]benzamide |

TABLE 1-continued

| Cmpd No. | Structure | Name |
|---|---|---|
| 221 | 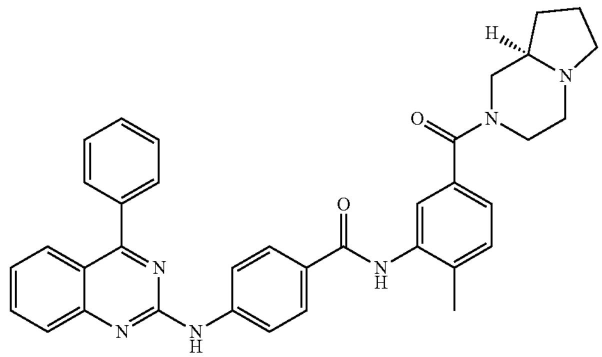 [SMILES: Cc1ccc(C(=O)N2CCN3CCC[C@@H]3C2)cc1NC(=O)c1ccc(Nc2nc(-c3ccccc3)c3ccccc3n2)cc1] | N-(5-[(8aR)-hexahydropyrrolo[1,2-a]pyrazin-2(1H)-ylcarbonyl]-2-methylphenyl}-4-[(4-phenylquinazolin-2-yl)amino]benzamide |
| 222 | 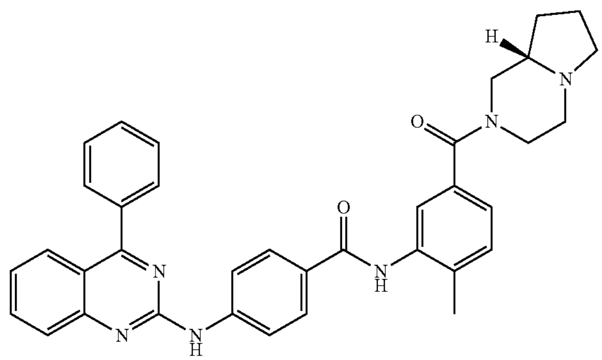 [SMILES: Cc1ccc(C(=O)N2CCN3CCC[C@H]3C2)cc1NC(=O)c1ccc(Nc2nc(-c3ccccc3)c3ccccc3n2)cc1] | N-{5-[(8aS)-hexahydropyrrolo[1,2-a]pyrazin-2(1H)-ylcarbonyl]-2-methylphenyl}-4-[(4-phenylquinazolin-2-yl)amino]benzamide |
| 223 | 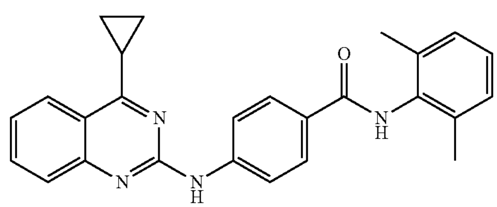 [SMILES: Cc1cccc(C)c1NC(=O)c1ccc(Nc2nc(C3CC3)c3ccccc3n2)cc1] | 4-[(4-cyclopropylquinazolin-2-yl)amino]-N-(2,6-dimethylphenyl)benzamide |
| 224 | 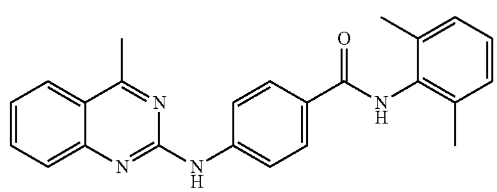 [SMILES: Cc1cccc(C)c1NC(=O)c1ccc(Nc2nc(C)c3ccccc3n2)cc1] | N-(2,6-dimethylphenyl)-4-[(4-methylquinazolin-2-yl)amino]benzamide |
| 225 | 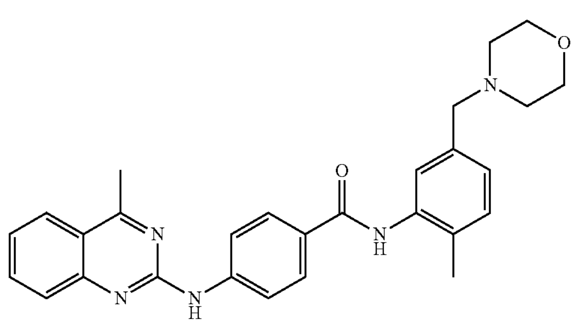 [SMILES: Cc1ccc(CN2CCOCC2)cc1NC(=O)c1ccc(Nc2nc(C)c3ccccc3n2)cc1] | N-[2-methyl-5-(morpholin-4-ylmethyl)phenyl]-4-[(4-methylquinazolin-2-yl)amino]benzamide |

TABLE 1-continued

| Cmpd No. | Structure | Name |
|---|---|---|
| 226 | 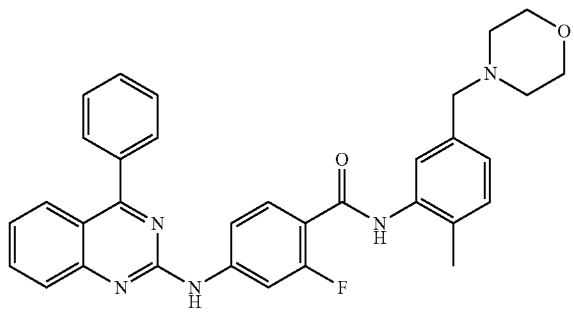 [SMILES: Cc1ccc(CN2CCOCC2)cc1NC(=O)c1ccc(Nc2nc(-c3ccccc3)c3ccccc3n2)cc1F] | 2-fluoro-N-[2-methyl-5-(morpholin-4-ylmethyl)phenyl]-4-[(4-phenylquinazolin-2-yl)amino]benzamide |
| 227 | 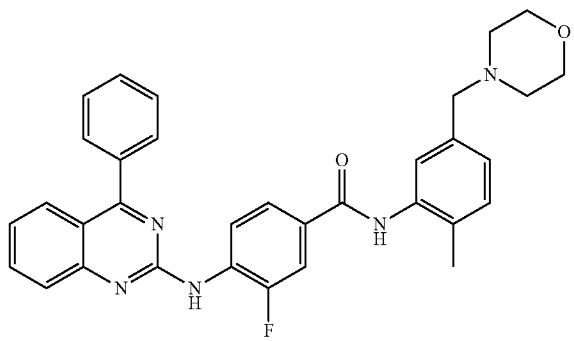 [SMILES: Cc1ccc(CN2CCOCC2)cc1NC(=O)c1ccc(Nc2nc(-c3ccccc3)c3ccccc3n2)c(F)c1] | 3-fluoro-N-[2-methyl-5-(morpholin-4-ylmethyl)phenyl]-4-[(4-phenylquinazolin-2-yl)amino]benzamide |
| 228 | 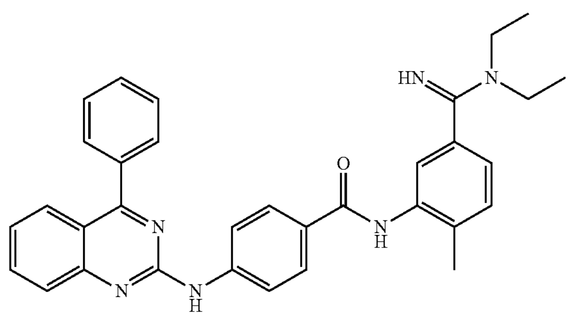 [SMILES: CCN(CC)C(=N)c1ccc(C)c(NC(=O)c2ccc(Nc3nc(-c4ccccc4)c4ccccc4n3)cc2)c1] | N-{5-[(diethylamino)(imino)methyl]-2-methylphenyl}-4-[(4-phenylquinazolin-2-yl)amino]benzamide |
| 229 | 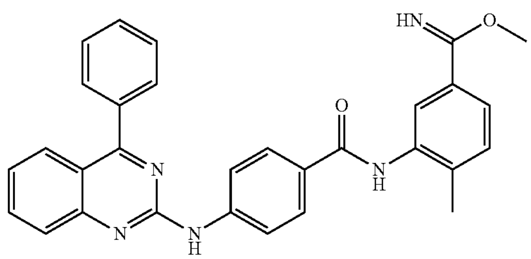 [SMILES: COC(=N)c1ccc(C)c(NC(=O)c2ccc(Nc3nc(-c4ccccc4)c4ccccc4n3)cc2)c1] | methyl 4-methyl-3-[({4-[(4-phenylquinazolin-2-yl)amino]phenyl}carbonyl)amino]benzenecarboximidoate |
| 230 | 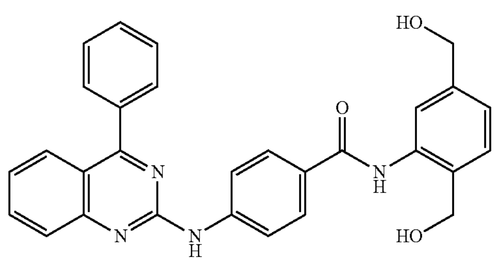 [SMILES: O=C(Nc1cc(CO)ccc1CO)c1ccc(Nc2nc(-c3ccccc3)c3ccccc3n2)cc1] | N-[2,5-bis(hydroxymethyl)phenyl]-4-[(4-phenylquinazolin-2-yl)amino]benzamide |

TABLE 1-continued
| Cmpd No. | Structure | Name |
|---|---|---|
| 231 | 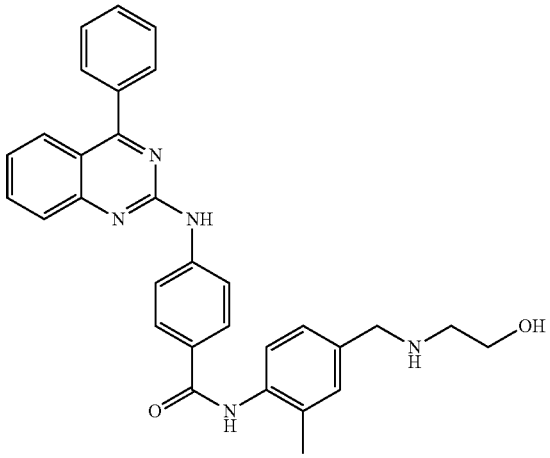 [SMILES: Cc1cc(CNCCO)ccc1NC(=O)c1ccc(Nc2nc(-c3ccccc3)c3ccccc3n2)cc1] | N-(4-{[(2-hydroxyethyl)amino]methyl}-2-methylphenyl)-4-[(4-phenylquinazolin-2-yl)amino]benzamide |
| 232 | 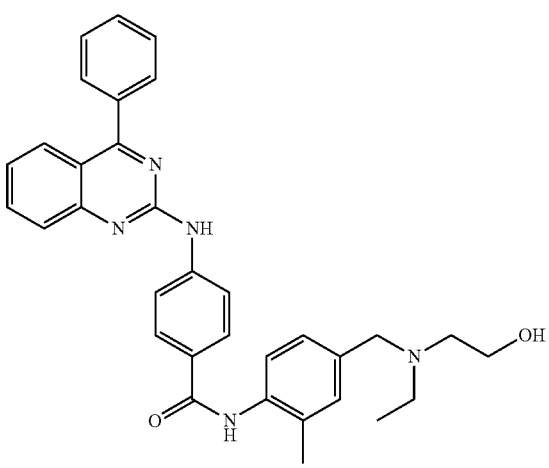 [SMILES: CCN(CCO)Cc1ccc(NC(=O)c2ccc(Nc3nc(-c4ccccc4)c4ccccc4n3)cc2)c(C)c1] | N-(4-{[ethyl(2-hydroxyethyl)amino]methyl}-2-methylphenyl)-4-[(4-phenylquinazolin-2-yl)amino]benzamide |
| 233 | 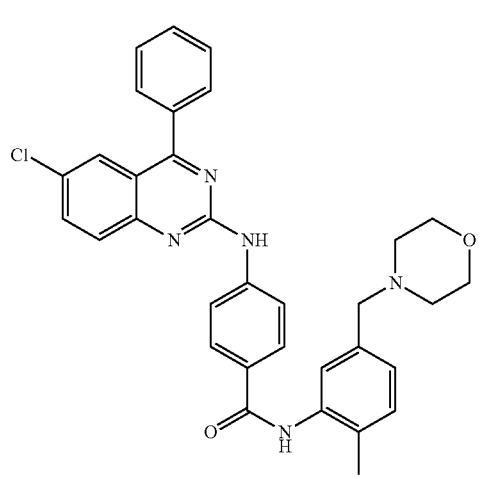 [SMILES: Cc1ccc(CN2CCOCC2)cc1NC(=O)c1ccc(Nc2nc(-c3ccccc3)c3cc(Cl)ccc3n2)cc1] | 4-[(6-chloro-4-phenylquinazolin-2-yl)amino]-N-[2-methyl-5-(morpholin-4-ylmethyl)phenyl]benzamide |

TABLE 1-continued

| Cmpd No. | Structure | Name |
|---|---|---|
| 234 | 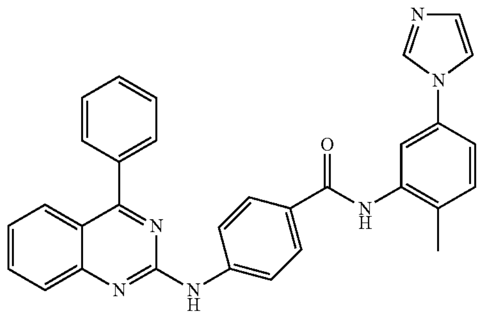 [SMILES: Cc1ccc(-n2ccnc2)cc1NC(=O)c1ccc(Nc2nc(-c3ccccc3)c3ccccc3n2)cc1] | N-[5-(1H-imidazol-1-yl)-2-methylphenyl]-4-[(4-phenylquinazolin-2-yl)amino]benzamide |
| 235 | 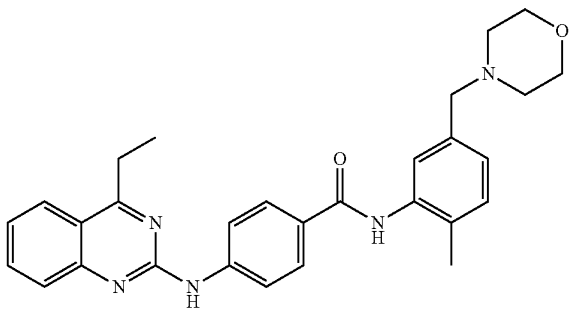 [SMILES: CCc1nc(Nc2ccc(C(=O)Nc3cc(CN4CCOCC4)ccc3C)cc2)nc2ccccc12] | 4-[(4-ethylquinazolin-2-yl)amino]-N-[2-methyl-5-(morpholin-4-ylmethyl)phenyl]benzamide |
| 236 | 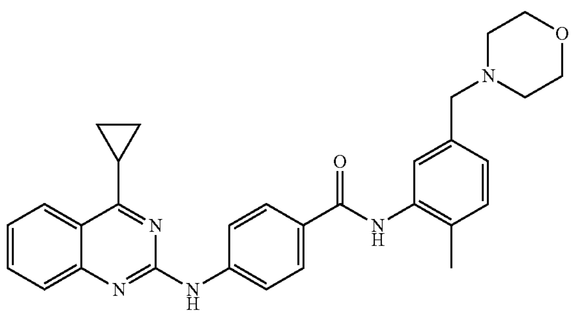 [SMILES: Cc1ccc(CN2CCOCC2)cc1NC(=O)c1ccc(Nc2nc(C3CC3)c3ccccc3n2)cc1] | 4-[(4-cyclopropylquinazolin-2-yl)amino]-N-[2-methyl-5-(morpholin-4-ylmethyl)phenyl]benzamide |
| 237 | 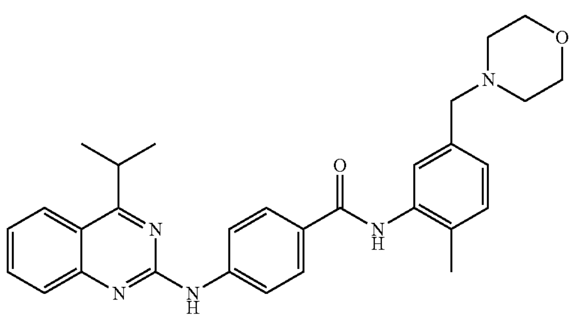 [SMILES: Cc1ccc(CN2CCOCC2)cc1NC(=O)c1ccc(Nc2nc(C(C)C)c3ccccc3n2)cc1] | 4-{[4-(1-methylethyl)quinazolin-2-yl]amino}-N-[2-methyl-5-(morpholin-4-ylmethyl)phenyl]benzamide |
| 238 | 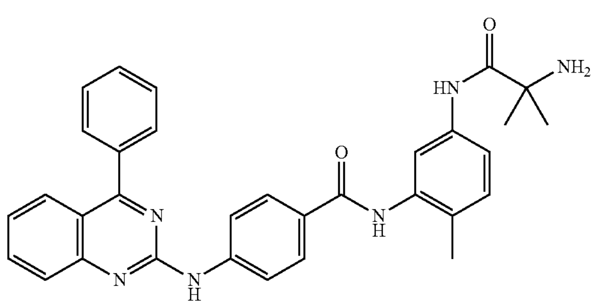 [SMILES: Cc1ccc(NC(=O)C(C)(C)N)cc1NC(=O)c1ccc(Nc2nc(-c3ccccc3)c3ccccc3n2)cc1] | N-{2-methyl-5-[(2-methylalanyl)amino]phenyl}-4-[(4-phenylquinazolin-2-yl)amino]benzamide |

TABLE 1-continued

| Cmpd No. | Structure | Name |
|---|---|---|
| 239 | 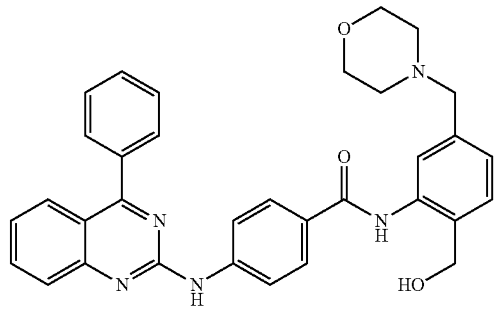 [SMILES: O=C(Nc1cc(CN2CCOCC2)ccc1CO)c1ccc(Nc2nc(-c3ccccc3)c3ccccc3n2)cc1] | N-[2-(hydroxymethyl)-5-(morpholin-4-ylmethyl)phenyl]-4-[(4-phenylquinazolin-2-yl)amino]benzamide |
| 240 | 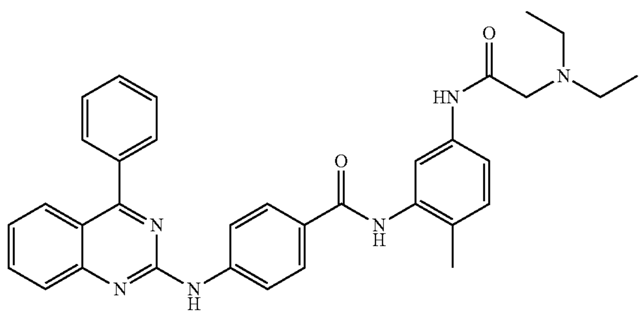 [SMILES: CCN(CC)CC(=O)Nc1ccc(C)c(NC(=O)c2ccc(Nc3nc(-c4ccccc4)c4ccccc4n3)cc2)c1] | N-{5-[(N,N-diethylglycyl)amino]-2-methylphenyl}-4-[(4-phenylquinazolin-2-yl)amino]benzamide |
| 241 | 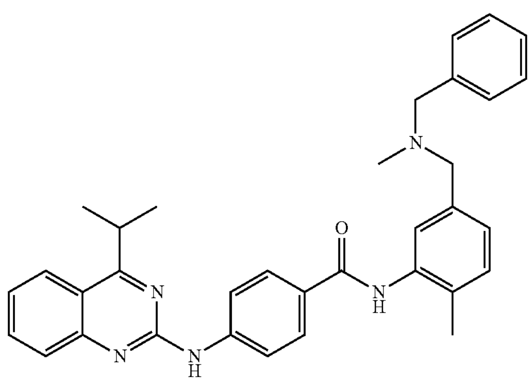 [SMILES: Cc1ccc(CN(C)Cc2ccccc2)cc1NC(=O)c1ccc(Nc2nc(C(C)C)c3ccccc3n2)cc1] | 4-{[4-(1-methylethyl)quinazolin-2-yl]amino}-N-(2-methyl-5-{[methyl(phenylmethyl)amino]methyl}phenyl)benzamide |
| 242 | 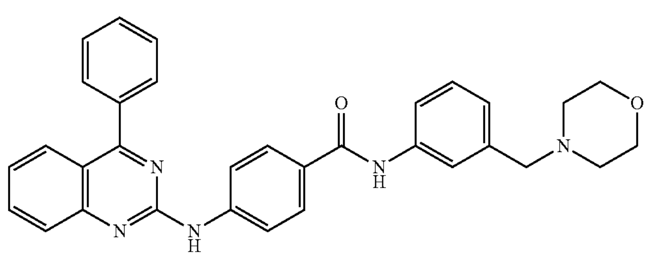 [SMILES: O=C(Nc1cccc(CN2CCOCC2)c1)c1ccc(Nc2nc(-c3ccccc3)c3ccccc3n2)cc1] | N-[3-(morpholin-4-ylmethyl)phenyl]-4-[(4-phenylquinazolin-2-yl)amino]benzamide |

TABLE 1-continued

| Cmpd No. | Structure | Name |
|---|---|---|
| 243 | 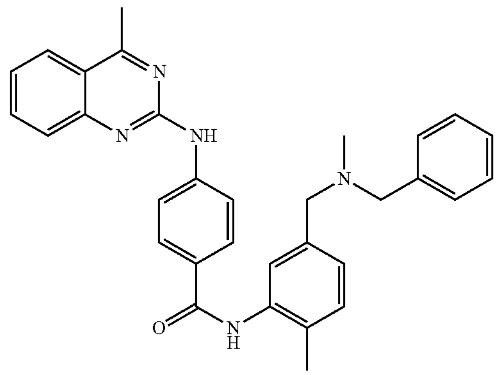 [SMILES: Cc1ccc(CN(C)Cc2ccccc2)cc1NC(=O)c1ccc(Nc2nc(C)c3ccccc3n2)cc1] | N-(2-methyl-5-{[methyl(phenylmethyl)amino]methyl}phenyl)-4-[(4-methylquinazolin-2-yl)amino]benzamide |
| 244 | 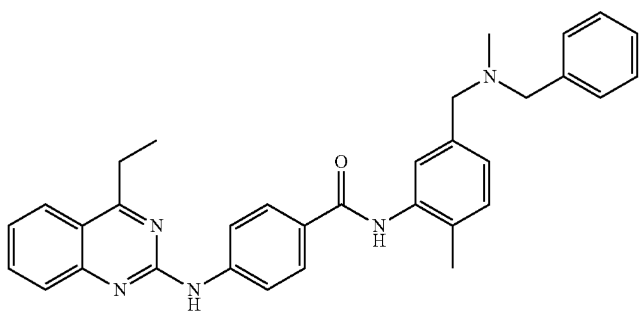 [SMILES: CCc1nc(Nc2ccc(C(=O)Nc3cc(CN(C)Cc4ccccc4)ccc3C)cc2)nc2ccccc12] | 4-[(4-ethylquinazolin-2-yl)amino]-N-(2-methyl-5-{[methyl(phenylmethyl)amino]methyl}phenyl)benzamide |
| 245 | 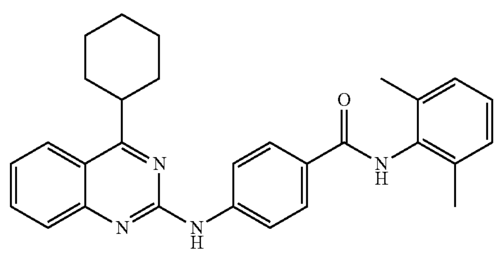 [SMILES: Cc1cccc(C)c1NC(=O)c1ccc(Nc2nc(C3CCCCC3)c3ccccc3n2)cc1] | 4-[(4-cyclohexylquinazolin-2-yl)amino]-N-(2,6-dimethylphenyl)benzamide |
| 246 | 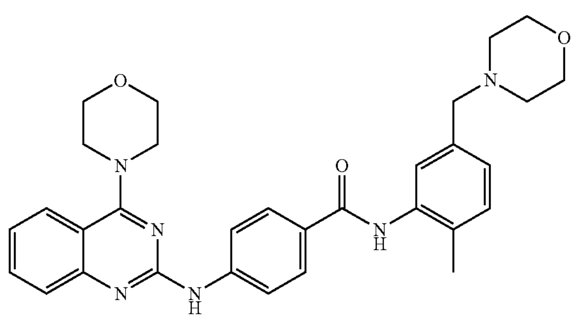 [SMILES: Cc1ccc(CN2CCOCC2)cc1NC(=O)c1ccc(Nc2nc(N3CCOCC3)c3ccccc3n2)cc1] | N-[2-methyl-5-(morpholin-4-ylmethyl)phenyl]-4-[(4-morpholin-4-ylquinazolin-2-yl)amino]benzamide |
| 247 | 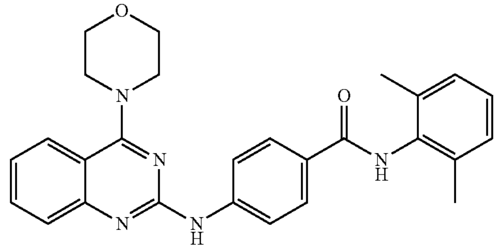 [SMILES: Cc1cccc(C)c1NC(=O)c1ccc(Nc2nc(N3CCOCC3)c3ccccc3n2)cc1] | N-(2,6-dimethylphenyl)-4-[(4-morpholin-4-ylquinazolin-2-yl)amino]benzamide |

TABLE 1-continued

| Cmpd No. | Structure | Name |
|---|---|---|
| 248 | 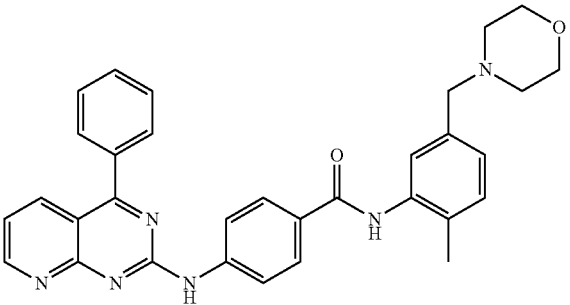 [SMILES: Cc1ccc(CN2CCOCC2)cc1NC(=O)c1ccc(Nc2nc(-c3ccccc3)c3cccnc3n2)cc1] | N-[2-methyl-5-(morpholin-4-ylmethyl)phenyl]-4-[(4-phenylpyrido[2,3-d]pyrimidin-2-yl)amino]benzamide |
| 249 | 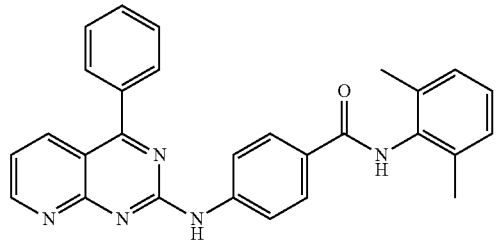 [SMILES: Cc1cccc(C)c1NC(=O)c1ccc(Nc2nc(-c3ccccc3)c3cccnc3n2)cc1] | N-(2,6-dimethylphenyl)-4-[(4-phenylpyrido[2,3-d]pyrimidin-2-yl)amino]benzamide |
| 250 | 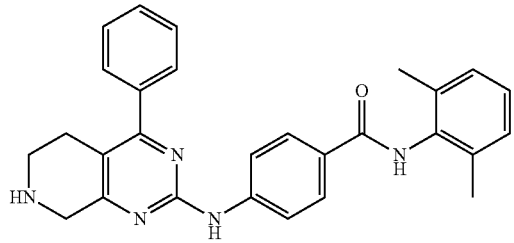 [SMILES: Cc1cccc(C)c1NC(=O)c1ccc(Nc2nc3c(c(-c4ccccc4)n2)CCNC3)cc1] | N-(2,6-dimethylphenyl)-4-[(4-phenyl-5,6,7,8-tetrahydropyrido[3,4-d]pyrimidin-2-yl)amino]benzamide |
| 251 | 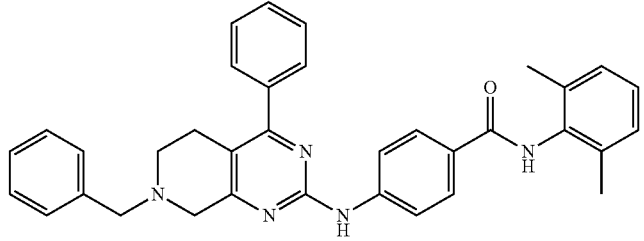 [SMILES: Cc1cccc(C)c1NC(=O)c1ccc(Nc2nc3c(c(-c4ccccc4)n2)CCN(Cc2ccccc2)C3)cc1] | N-(2,6-dimethylphenyl)-4-{[4-phenyl-7-(phenylmethyl)-5,6,7,8-tetrahydropyrido[3,4-d]pyrimidin-2-yl]amino}benzamide |
| 252 | 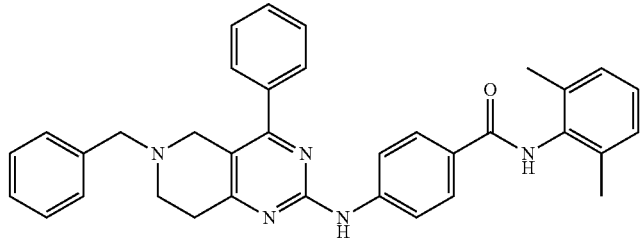 [SMILES: Cc1cccc(C)c1NC(=O)c1ccc(Nc2nc3c(c(-c4ccccc4)n2)CN(Cc2ccccc2)CC3)cc1] | N-(2,6-dimethylphenyl)-4-{[4-phenyl-6-(phenylmethyl)-5,6,7,8-tetrahydropyrido[4,3-d]pyrimidin-2-yl]amino}benzamide |
| 253 | 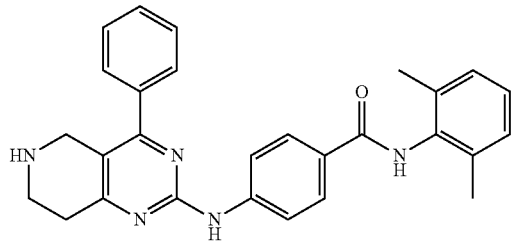 [SMILES: Cc1cccc(C)c1NC(=O)c1ccc(Nc2nc3c(c(-c4ccccc4)n2)CNCC3)cc1] | N-(2,6-dimethylphenyl)-4-[(4-phenyl-5,6,7,8-tetrahydropyrido[4,3-d]pyrimidin-2-yl)amino]benzamide |

TABLE 1-continued

| Cmpd No. | Structure | Name |
|---|---|---|
| 254 | 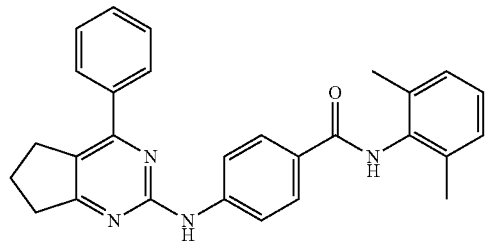 [SMILES: Cc1cccc(C)c1NC(=O)c1ccc(Nc2nc3c(c(-c4ccccc4)n2)CCC3)cc1] | N-(2,6-dimethylphenyl)-4-[(4-phenyl-6,7-dihydro-5H-cyclopenta[d]pyrimidin-2-yl)amino]benzamide |
| 255 | 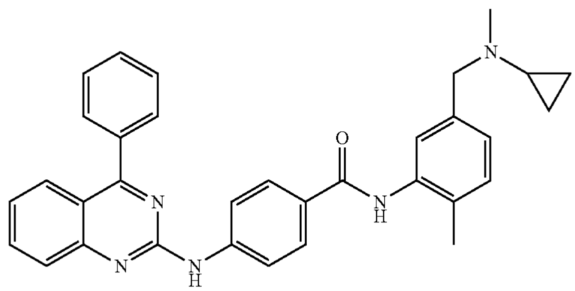 [SMILES: Cc1ccc(CN(C)C2CC2)cc1NC(=O)c1ccc(Nc2nc(-c3ccccc3)c3ccccc3n2)cc1] | N-(5-{[cyclopropyl(methyl)amino]methyl}-2-methylphenyl)-4-[(4-phenylquinazolin-2-yl)amino]benzamide |
| 256 | 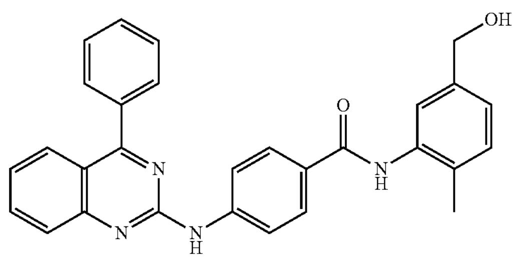 [SMILES: Cc1ccc(CO)cc1NC(=O)c1ccc(Nc2nc(-c3ccccc3)c3ccccc3n2)cc1] | N-[5-(hydroxymethyl)-2-methylphenyl]-4-[(4-phenylquinazolin-2-yl)amino]benzamide |
| 257 | 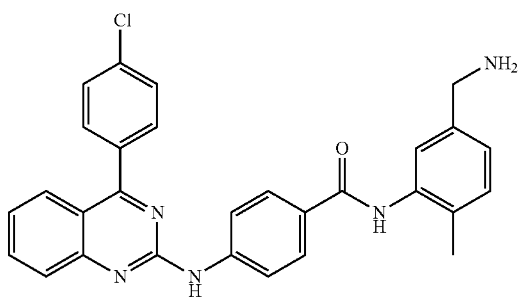 [SMILES: Cc1ccc(CN)cc1NC(=O)c1ccc(Nc2nc(-c3ccc(Cl)cc3)c3ccccc3n2)cc1] | N-[5-(aminomethyl)-2-methylphenyl]-4-{[4-(4-chlorophenyl)quinazolin-2-yl]amino}benzamide |
| 258 | 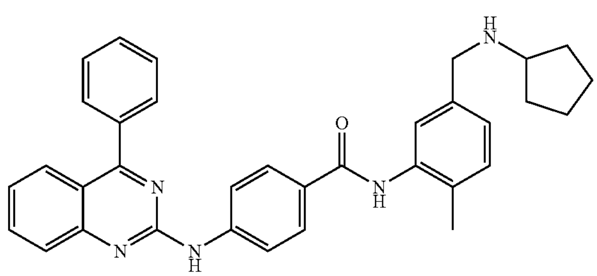 [SMILES: Cc1ccc(CNC2CCCC2)cc1NC(=O)c1ccc(Nc2nc(-c3ccccc3)c3ccccc3n2)cc1] | N-{5-[(cyclopentylamino)methyl]-2-methylphenyl}-4-[(4-phenylquinazolin-2-yl)amino]benzamide |

In another embodiment of the invention, the Compound in Table 1 is a pharmaceutically acceptable salt, hydrate, solvate or combination thereof. In another embodiment of the invention, the Compound in Table 1 is a pharmaceutically acceptable salt, hydrate, solvate or combination thereof, where the pharmaceutically acceptable salt is formed with one or two acids independently selected from hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid.

Abbreviations and Definitions

The following abbreviations and terms have the indicated meanings throughout:

| Abbreviation | Meaning |
| --- | --- |
| br | broad |
| ° C. | degrees Celsius |
| CBZ | CarboBenZoxy = benzyloxycarbonyl |
| d | doublet |
| dd | doublet of doublet |
| dt | doublet of triplet |
| EI | Electron Impact ionization |
| Et | Ethyl |
| g | gram(s) |
| GC | gas chromatography |
| h or hr | hour(s) |
| HATU | 2-(1H-7-azabenzotriazol-1-yl)--1,1,3,3-tetramethyl uronium hexafluorophosphate methanaminium |
| HPLC | high pressure liquid chromatography |
| L | liter(s) |
| M | molar or molarity |
| m | Multiplet |
| mg | milligram(s) |
| MHz | megahertz (frequency) |
| Min | minute(s) |
| mL | milliliter(s) |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| s- | Secondary |
| t- | Tertiary |
| t or tr | Triplet |
| TFA | trifluoroacetic acid |
| THF | Tetrahydrofuran |
| μL | microliter(s) |
| μM | Micromole(s) or micromolar |

Optional substituents, as defined in the Summary of the Invention for a Compound of Formula I, are located at the 5-, 6-, 7-, and 8-positions of the quinazolinyl ring formed by $R^2$ and $R^3$ together with the pyrimidinyl to which $R^2$ and $R^3$ are attached. The 5-, 6-, 7-, and 8-positions are depicted in the following structure (a).

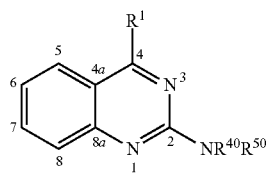

(a)

Optional substituents, as defined in the Summary of the Invention for a Compound of Formula I, are located at the 5-, 6-, 7-, and 8-positions of the pyrido[3,2-d]pyrimidinyl, pyrido[4,3-d]pyrimidinyl, pyrido[3,4-d]pyrimidinyl, and pyrido[2,3-d]pyrimidinyl rings formed by $R^2$ and $R^3$ together with the pyrimidinyl to which $R^2$ and $R^3$ are attached. The 5-, 6-, 7-, and 8-positions are depicted in the following structures (b), (c), (d), and (e).

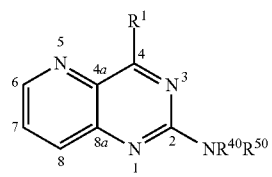

(b)

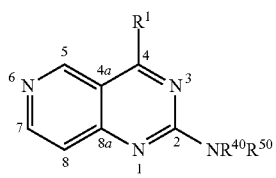

(c)

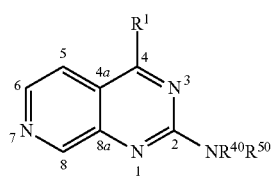

(d)

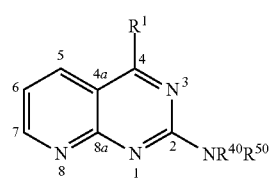

(e)

It is understood by one of ordinary skill in the art that when the atom at the 5-, 6-, 7-, or 8-position is a nitrogen then it is not substituted.

The symbol "—" means a single bond, "=" means a double bond, "≡" means a triple bond, and " $\stackrel{\scriptscriptstyle ---}{\scriptscriptstyle ---}$ " means a single bond and optionally a double bond. When chemical structures are depicted or described, unless explicitly stated otherwise, all carbons are assumed to have hydrogen substitution to conform to a valence of four.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a straight or branched hydrocarbon radical having from 2 to 8 carbon atoms and at least one double bond and includes ethenyl, propenyl, 1-but-3-enyl, 1-pent-3-enyl, 1-hex-5-enyl and the like. "Lower alkenyl" means an alkenyl group having one to six carbon atoms.

"Alkenylcarbonyl" means a C(O)R group where R is alkenyl, as defined herein.

"Alkenyloxy" or "lower alkenyloxy" means an —OR group where R is alkenyl, as defined herein. Representative examples include methoxy, ethoxy, 1-methoxyprop-1-en-3-yl, propoxy, isopropoxy, cyclopropyloxy, cyclohexyloxy and the like.

"Alkoxy," "lower alkoxy," or "alkyloxy" means an —OR group where R is alkyl, as defined herein. Representative examples include methoxy, ethoxy, 1-methoxyprop-1-en-3-yl, propoxy, isopropoxy, and the like.

"Alkoxyalkyl" means an alkyl group, as defined herein, substituted with one, two, or three alkoxy groups, as defined herein.

"Alkoxycarbonyl" means a —C(O)OR group where R is alkyl, as defined herein.

"Alkoxyalkylcarbonyl" means a —C(O)R group where R is alkoxyalkyl as defined herein.

"Alkyl" means a linear or branched hydrocarbon group having one to eight carbon atoms. "Lower alkyl" means an alkyl group having one to six carbon atoms. Examples of lower alkyl groups include methyl, ethyl, propyl, isopropyl, butyl, s-butyl, t-butyl, isobutyl, pentyl, hexyl and the like. A "$C_0$ alkyl" (as in "$C_0$-$C_6$-alkyl") is a covalent bond. "$C_6$ alkyl" refers to, for example, n-hexyl, iso-hexyl, and the like.

"Alkylamino" means a —NHR radical where R is alkyl as defined herein, or an N-oxide derivative thereof, e.g., methylamino, ethylamino, n-, iso-propylamino, n-, iso-, tert-butylamino, or methylamino-N-oxide, and the like.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylaminocarbonyl" means a —C(O)R group where R is alkylamino, as defined herein.

"Alkylaminocarbonylalkyl" means an alkyl group, as defined herein, substituted with at least one, for example one or two, alkylaminocarbonyl, as defined herein.

"Alkylcarbonyl" means a —C(O)R group where R is alkyl as defined herein.

"Alkylcarbonylamino" means a —NRC(O)R' group where R is hydrogen or alkyl, as defined herein, and R' is alkyl, as defined herein.

"Alkylene" refers to straight or branched divalent hydrocarbon, containing no unsaturation and having from two to eight carbon atoms. Examples of alkylene include eth-diyl (—CH$_2$CH$_2$—), prop-1,3-diyl (—CH$_2$CH$_2$CH$_2$—), 2,2-dimethylprop-1,3-diyl (—CH$_2$C(CH$_3$)$_2$CH$_2$—), and the like.

"Alkylsulfonyl" means a —S(O)$_2$R group where R is alkyl, as defined herein.

"Alkynyl" means a straight or branched hydrocarbon radical having from 2 to 8 carbon atoms and at least one triple bond and includes ethynyl, propynyl, butynyl, pentyn-2-yl and the like. "Lower alkynyl" means an alkynyl group having one to six carbon atoms.

"Amino" means a —NH$_2$.

"Aminoalkyl" means an alkyl group substituted with at least one, for example one, two, or three, amino groups.

"Aminoalkyloxy" means an —OR group where R is aminoalkyl, as defined herein.

"Aminocarbonyl" means a —C(O)NH$_2$ group.

"Aminocarbonylalkyl" means an alkyl group, as defined herein, substituted at least one, for example one or two, aminocarbonyl group(s), as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Arylalkyl" means an alkyl group, as defined herein, substituted with one or two aryl groups, as defined herein. Examples include benzyl, phenethyl, phenylvinyl, phenylallyl and the like.

"Arylalkylamino means a —NHR group where R is arylalkyl as defined herein.

"Arylalkyl(alkyl)amino" means a —NRR' group where R is alkyl as defined herein and R' is arylalkyl as defined herein.

"Arylcarbonyl" means a —C(O)R group where R is aryl as defined herein.

"Aryloxy" means a —OR group where R is aryl as defined herein.

"Arylalkyloxy" means a —OR group where R is arylalkyl as defined herein.

"Arylsulfonyl" means a —SO$_2$R group where R is aryl as defined herein.

"Carboxyalkyl" means an alkyl group, as defined herein, substituted with one, two, or three —C(O)OH groups.

"Carboxy ester" means a —C(O)OR group where R is lower alkyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Cyanoalkyl" means an alkyl, alkenyl, or alkynyl radical, as defined herein, substituted with at least one, for example one, two, or three, cyano groups.

"Cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl and cyclohexyl.

"Cycloalkylalkyl" means alkyl group substituted with one or two cycloalkyl group(s), as defined herein. Representative examples include cyclopropylmethyl and 2-cyclobutyl-ethyl, and the like.

"Cycloalkylcarbonyl" means a —C(O)R group where R is cycloalkyl as defined herein.

"Dialkylamino" means an —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with at least one, for example one or two, dialkylamino group(s), as defined herein.

"Dialkylaminoalkyloxy" means an —OR group where R is dialkylaminoalkyl, as defined herein.

"Dialkylaminocarbonyl" means a —C(O)R group where R is dialkylamino, as defined herein.

"Dialkylaminocarbonylalkyl" means an alkyl group, as defined herein, substituted with at least one, for example one or two, dialkylaminocarbonyl, as defined herein.

"Di(arylalkyl)amino" means a —NRR' group where R and R' are arylalkyl as defined herein.

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloalkoxy" means an —OR' group where R' is haloalkyl as defined herein, e.g., trifluoromethoxy or 2,2,2-trifluoroethoxy, and the like.

"Haloalkoxyalkyl" means an alkyl group, as defined herein, substituted with one, two, or three haloalkoxy, as defined herein.

"Halogen" or "halo" means fluoro, chloro, bromo and iodo.

"Haloalkenyl means an alkenyl group, as defined herein, substituted with one or more halogens, for example one to five halo atoms.

"Haloalkyl" means an alkyl group, as defined herein, substituted with one or more halogens, for example one, two, three, four, or five halo atoms. Representative examples includes 2,2-difluoroethyl, trifluoromethyl, and 2-chloro-1-fluoroethyl, and the like.

"Heteroaryl" means a monocyclic, fused bicyclic, or fused tricyclic, monovalent radical of 5 to 14 ring atoms containing one or more, for example one, two, three, or four ring heteroatoms independently selected from —O—, —S(O)$_n$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on the nitrogen, R$^x$ is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Hetereoarylalkyl" means an alkyl group substituted with one or two heteroaryl group(s) as defined herein.

"Heterocycloalkyl" means a saturated or partially unsaturated monovalent monocyclic group of 3 to 9 ring atoms or a saturated or partially unsaturated monovalent fused bicyclic group of 5 to 12 ring atoms in which one or more, for example one, two, three, or four ring heteroatoms independently selected from —O—, —S(O)$_n$— (n is 0, 1, or 2), —N=, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. In particular, when the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl group, as defined herein, substituted with one or two heterocycloalkyl group(s), as defined herein.

"Heterocycloalkylalkyloxy" means an OR group where R is heterocycloalkylalkyl as defined herein.

"Hydroxyalkyl" means an alkyl radical, as defined herein, substituted with at least one, for example one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, 2-hydroxyethyl, 2,3-dihydroxypropyl, or 1-(hydroxymethyl)-2-hydroxyethyl, and the like.

"Hydroxyamino" means a —NH(OH) group.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC$_{1-8}$ alkyl," both the "C$_{1-8}$ alkyl" portion and the "aryl" portion of the molecule may or may not be substituted. A list of exemplary optional substitutions is presented below in the definition of "substituted."

"Optionally substituted alkyl" means an alkyl radical, as defined herein, optionally substituted with one or more group(s), for example one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^S$— (where R$^c$ is hydrogen, alkyl, optionally substituted alkenyl, optionally substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, optionally substituted alkenyl, optionally substituted alkynyl, hydroxy, alkoxy, alkenyloxy, or cyanoalkyl).

"Optionally substituted alkenyl" means an alkenyl radical, as defined herein, optionally substituted with one or more group(s), for example one, two, or three groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, optionally substituted alkyl, optionally substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, optionally substituted alkyl, alkenyl, optionally substituted alkynyl, hydroxy, alkoxy, or alkenyloxy).

"Optionally substituted aryl" means an aryl group, as defined herein, which is optionally substituted with one, two, three, four, of five groups selected from halo, haloalkyl, haloalkoxy, hydroxy, lower alkyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted cycloalkyl" means a cycloalkyl, as defined herein, optionally substituted with one, two, three, four, or five groups selected from halo, haloalkyl, haloalkoxy, hydroxy, oxo, lower alkyl, lower alkenyl, lower alkynyl, alkoxy, optionally substituted heterocycloalkyl, cycloalkyl, optionally substituted phenyl, optionally substituted heteroaryl, alkylaminoalkyl, dialkylaminoalkyl, alkylcarbonyl, carboxy, alkoxycarbonyl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), amino, alkylamino, dialkylamino, and —NHS(O)$_2$R' (where R' is alkyl, aryl, or heteroaryl).

"Optionally substituted cycloalkylalkyl" means an alkyl group substituted with one or two optionally substituted cycloalkyl groups as defined herein.

"Optionally substituted heteroaryl" means a heteroaryl group, as defined herein, optionally substituted with one, two, three, four, or five groups selected from halo, haloalkyl, haloalkoxy, lower alkyl, lower alkenyl, lower alkynyl, alkoxy, hydroxy, oxo (valency rules permitting), alkylcarbonyl, carboxy, alkoxycarbonyl, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heteroarylalkyl" means an alkyl group substituted with one optionally substituted heteroaryl as defined herein.

"Optionally substituted heterocycloalkyl" means a heterocycloalkyl, as defined herein, optionally substituted with one, two, three, four, or five groups selected from halo, haloalkyl, haloalkoxy, hydroxy, hydroxyalkyl, oxo, lower alkyl, lower alkenyl, lower alkynyl, alkoxy, optionally substituted cycloalkyl, optionally substituted cycloalkylalkyl, heterocycloalkyl, optionally substituted aryl, optionally substituted heteroaryl, optionally substituted heteroarylalkyl, alkylaminoalkyl, dialkylaminoalkyl, alkylcarbonyl, cycloalkylcarbonyl, phenylcarbonyl, carboxy, alkoxycarbonyl, alkoxyalkylcarbonyl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), amino, alkylamino, dialkylamino, and —NHS(O)$_2$R' (where R' is alkyl, aryl, or heteroaryl).

"Optionally substituted heterocycloalkylalkyl" means an alkyl group substituted with one optionally substituted heterocycloalkyl group, as defined herein.

"Optionally substituted heterocycloalkylalkyloxy" means a —OR group where R is optionally substituted heterocycloalkylalkyl, as defined herein.

"Optionally substituted phenyl" means a phenyl group which is optionally substituted with one, two, three, four, of five groups selected from halo, haloalkyl, haloalkoxy, hydroxy, lower alkyl, lower alkenyl, lower alkynyl, alkoxy, alkylcarbonyl, carboxy, alkoxycarbonyl, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted phenylalkyl" means an alkyl group substituted with one optionally substituted phenyl as defined herein.

"Phenylalkyl" means an alkyl group substituted with one or two phenyl groups.

"Phenylalkyloxyalkyl" means an alkyl group substituted with one —OR group where R is phenylalkyl as defined herein.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings C and C'), but not a bridgehead atom, can be a shared atom between the saturated bridged ring system and a spirocyclyl (ring D) attached thereto. A spirocyclyl can be carbocyclic or heteroalicyclic

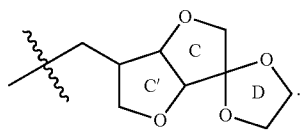

"Aminoalkylamino" means an —NHR group where R is aminoalkyl as defined herein.

"Alkylaminoalkylamino" means an —NHR group where R is alkylaminoalkyl as defined herein.

"Dialkylaminoalkylamino" means an —NHR group where R is dialkylaminoalkyl as defined herein.

"Alkyloxyalkyl" means an alkyl group, as defined herein, substituted with one, two, or three alkyloxy groups as defined herein.

"Alkyloxyalkylamino" means a —NHR group where R is alkyloxyalkyl as defined herein.

"Halophenyl" means a phenyl group substituted with 1, 2, 3, 4, or 5 halo groups.

"Heterocycloalkylamino" means an —NHR group where R is heterocycloalkyl as defined herein.

"Phenylalkylamino" means a —NHR group where R is phenylalkyl as defined herein.

"Phenylcarbonyl" means a —C(O)R group where R is phenyl.

"Optionally substituted phenylcarbonyl" means a —C(O)R group where R is optionally substituted phenyl as defined herein.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast. Thus, the term "cancerous cell" as provided herein, includes a cell afflicted by any one of the above-identified conditions.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

General Administration

In one aspect, the invention provides pharmaceutical compositions comprising a modulator of the Hedgehog pathway according to the invention and a pharmaceutically acceptable carrier, excipient, or diluent. In certain other embodiments, administration may be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, in unit dosage forms suitable for simple administration of precise dosages. When treating brain cancers, including glioblastomas, the administration may be by placing a gliadel, a dissolvable material that contains the chemotherapy drug (in particular BCNU), directly into brain tumors during an operation.

The compositions will include a compound of Formula I or II as the/an active agent and can include a conventional pharmaceutical carrier or excipient and in addition may include other medicinal agents and pharmaceutical agents that are generally administered to a patient being treated for cancer.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt, hydrate, solvate or combination thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt, hydrate, solvate or combination thereof, and 99% to 1% by weight of a suitable pharmaceutical excipient. In one example, the composition will be between about 5% and about 75% by weight of a compound(s) of the invention, or a pharmaceutically acceptable salt, hydrate, solvate or combination thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt, hydrate, solvate or combination thereof, for treatment of a disease-state in accordance with the teachings of this invention.

The compounds of the invention, or their pharmaceutically acceptable salts, hydrates, solvates or combinations thereof, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 300 mg per kilogram of body weight per day is an example. In another example the dose range is 3-100 mg/kg of body weight per day. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Representative pharmaceutical formulations containing a compound of Formula I or II are described below in the Pharmaceutical Composition Examples.

Utility

Certain compounds of Formula I have been tested using the assay described in Biological Examples 1 and 2 and have been determined to be modulators of the Hedgehog pathway. As such compounds of Formula I are useful for treating diseases, particularly cancer in which Hedgehog pathway activity contributes to the pathology and/or symptomatology of the disease. For example, cancer in which Hedgehog pathway activity contributes to its pathology and/or symptomatology include basal cell carcinomas, medulloblastomas, rhabdomyosaracomas, breast carcinomas, meningiomas, pancreatic cancers, stomach cancers, esophageal cancers, biliary tract cancers, prostate cancers, small cell lung cancers, non-small cell lung cancers, glial cell cancers, multiple myelomas, and colon cancers, and the like.

Suitable in vitro assays for measuring Hedgehog pathway activity and the inhibition thereof by compounds are known. For example, see Chen et al., *Proc Natl Acad Sci USA* 2002, 99, 14071-14076. Also see Chen et. al. *Genes Dev* 2002, 16, 2743-2748. For further details of in vitro assays for measuring cellular activity, see Biological Examples 1, 2, 3, 4, and 5, infra. Suitable in vivo models of cancer are known to those of ordinary skill in the art. For further details of in vivo assays see Biological Examples 6-9, infra. A pharmacodynamic assay is described in Biological Example 10. Efficacy models are described in Examples 11-12. Following the examples disclosed herein, as well as that disclosed in the art, a person of ordinary skill in the art can determine the ability of a compound of this invention to modulate Hedgehog pathway activity.

Preparations of the Intermediates and Compounds of the Invention

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, hydrates, solvates or combinations thereof, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. When the term "single isomer" is used, it includes the terms stereoisomer, enantiomer, diastereomer, geometric isomer, and atrope isomer.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Compounds of Formula I can be prepared using methods known to one of ordinary skill in the art. Unless specified to the contrary, the reactions described herein take place at atmospheric pressure and over a temperature range from about −78° C. to about 150° C., in another example from about 0° C. to about 125° C. and in another example at about room (or ambient) temperature, e.g., about 20° C. Unless otherwise stated (as in the case of an hydrogenation), all reactions are performed under an atmosphere of nitrogen.

A Compound of Formula I where $R^1$ is phenyl or pyridinyl, where the phenyl and pyridinyl are optionally substituted with 1, 2, or 3 $R^6$, $R^{50}$ is

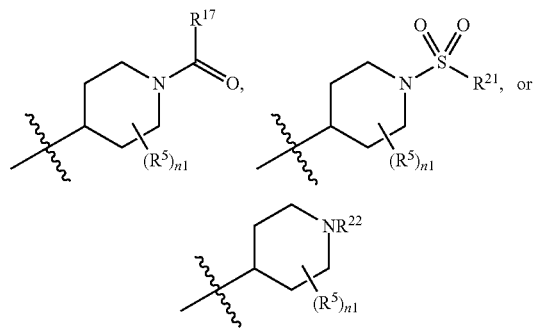

and all other groups are as defined in the Summary of the Invention for a Compound of Formula I can be prepared as follows.

An intermediate of formula 3 where $R^1$ is phenyl or pyridinyl, where the phenyl and pyridinyl are optionally substituted with 1, 2, or 3 $R^6$, can be prepared using the following schemes to prepare a Compound of Formula I where all other groups are as defined in the Summary of the Invention for a Compound of Formula I.

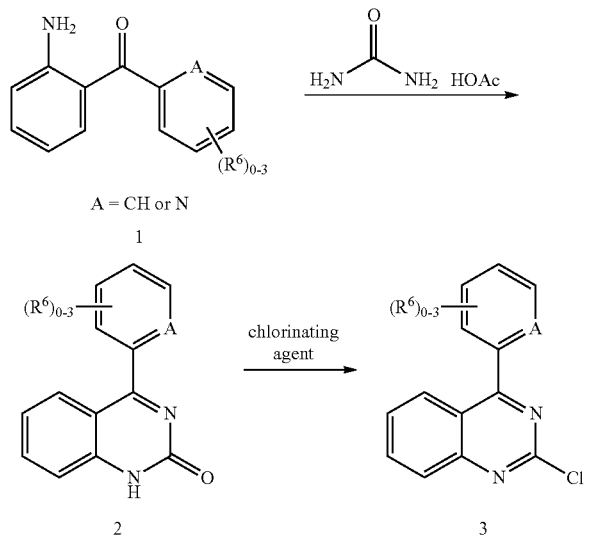

The keteone 1 (where A is CH or N) is reacted with urea in the presence of acetic acid at a temperature of about 105-110° C. and is allowed to react for about 18 hours to yield 2 as a solid which is then optionally washed and dried. Intermediate 2 is then reacted with a chlorinating agent such as $POCl_3$ and the like carried out at about reflux for about 30 min. The reaction mixture is then optionally worked up by pouring over ice/water mixture and filtering to collect the resulting solid.

An intermediate of formula 5 where $R^1$ is phenyl or pyridinyl, where the phenyl and pyridinyl are optionally substituted with 1, 2, or 3 $R^6$, and $R^{50}$ is

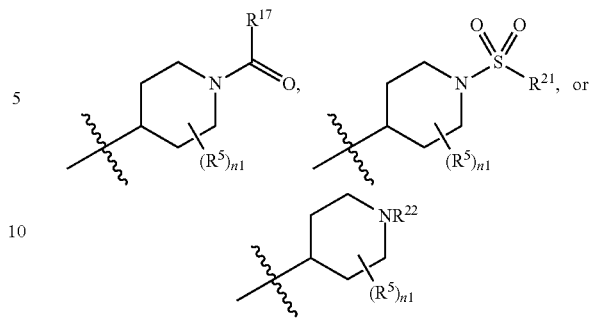

where $R^{17}$, $R^{21}$, $R^{22}$, $R^5$, and n1 are as defined in the Summary of the Invention for a Compound of Formula I for a Compound of Formula I can be prepared using the following Schemes B and C.

Scheme B

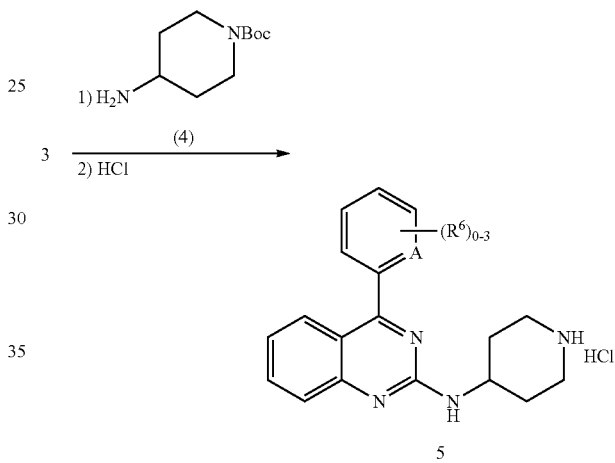

Intermediate 3 is treated with intermediate 4 in a solvent such as n-butanol. After removal of the n-butanol on a rotary evaporator, a solvent such as dichloromethane is added and the suspension is sonicated and filtered, followed by removal of the solvent. The product can be purified by column chromatography and is then treated with 4 N HCl in 1,4-dioxane at a temperature of about 100° C. for about 1 h to yield intermediate 5 (where A is CH or N and $R^6$ is as defined in the Summary of the Invention for a Compound of Formula I).

Scheme C

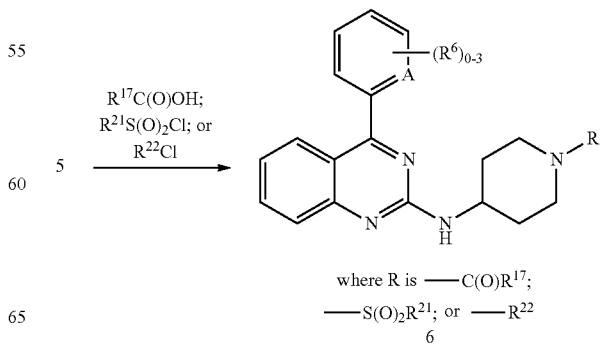

where R is —C(O)$R^{17}$;
—S(O)$_2R^{21}$; or —$R^{22}$

6

The intermediate of formula 5 can be reacted with an intermediate of formula R$^{17}$C(O)OH, where R$^{17}$ is as defined in the Summary of the Invention for a Compound of Formula I, in a solvent such as DMF, and in the presence of a coupling reagent such as HATU and a base such as triethylamine. Alternatively, the intermediate of formula 5 can be reacted with an intermediate of formula R$^{21}$S(O)$_2$Cl where R$^{21}$ as defined in the Summary of the Invention for a Compound of Formula I using conditions known to one of ordinary skill in the art. Alternatively, the intermediate of formula 5 can be reacted with an intermediate of formula R$^{22}$Cl where R$^{22}$ as defined in the Summary of the Invention for a Compound of Formula I using conditions known to one of ordinary skill in the art.

A Compound of Formula I where R$^1$ is phenyl or pyridinyl, where the phenyl and pyridinyl are optionally substituted with 1, 2, or 3 R$^6$, R$^{50}$ is

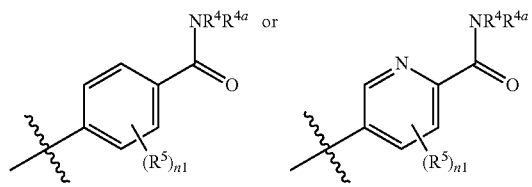

and all other groups are as defined in the Summary of the Invention for a Compound of Formula I can be prepared as follows.

Scheme D

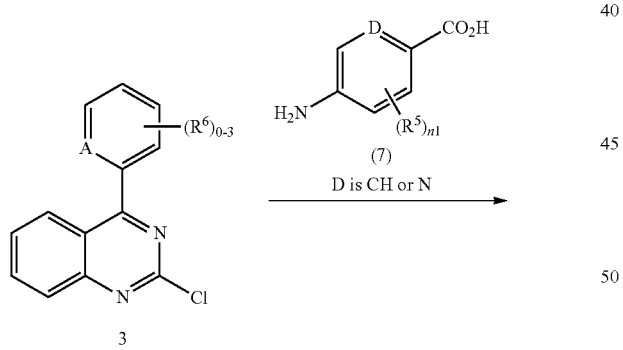

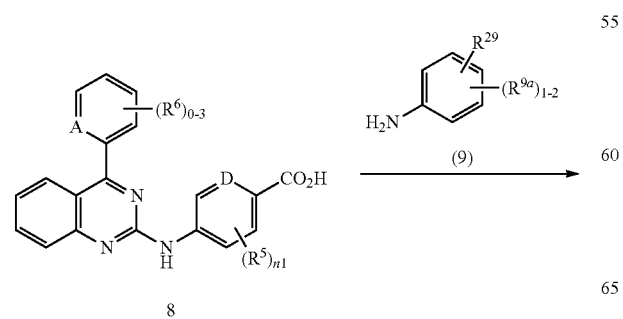

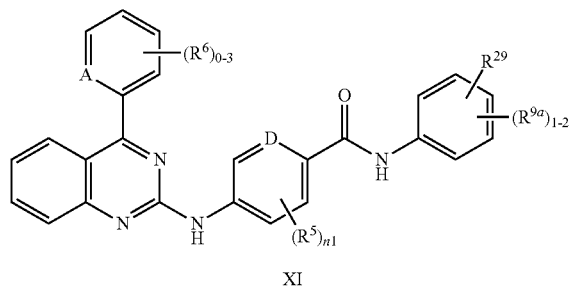

An intermediate of formula 3 (where A is CH or N and R$^6$ is as defined in the Summary of the Invention for a Compound of Formula I), prepared as described above in Scheme A, is reacted with an intermediate of formula 7 (where D is CH or N and R$^5$ and n1 are as defined in the Summary of the Invention for a Compound of Formula I) in a solvent such as isopropanol at about reflux for about 4 h to yield an intermediate of formula 8.

8 is then reacted with an aniline of formula 9 (where R$^{29}$ and R$^{9a}$ are as defined in the Summary of the Invention for a Compound of Formula I) in a solvent such as DMF, in the presence of a coupling agent such as HATU and a base such as N,N-diethyl-N-isopropyl-amine to yield a Compound of the Invention of formula XI. Alternatively, 8 is treated with a chlorinating agent such as SOCl$_2$, in a solvent such as DMF at room temperature to yield the acid chloride which is then treated with an aniline as described above to yield a Compound of the Invention of formula XI.

A Compound of Formula I where R$^1$ is phenyl or pyridinyl, where the phenyl and pyridinyl are optionally substituted with 1, 2, or 3 R$^6$ and R$^{50}$ is

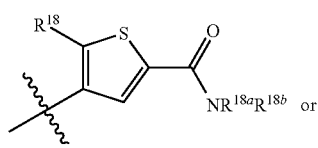

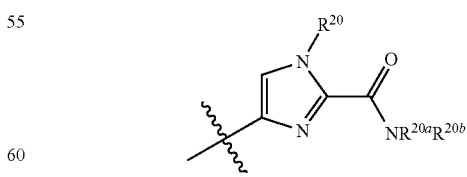

where R$^6$, R$^{18}$, R$^{18a}$, R$^{18b}$, R$^{20}$, R$^{20a}$, and R$^{20b}$ are as defined in the Summary of the Invention for a Compound of Formula I can be prepared according to Scheme S.

Scheme S

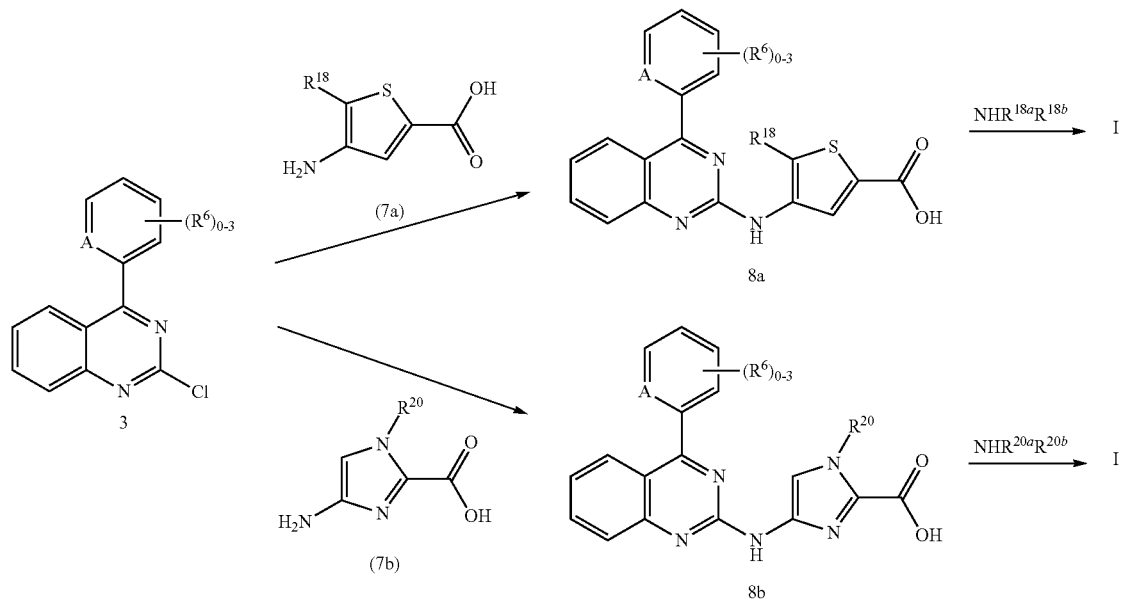

In Scheme S, intermediate 3 where A is CH or N and $R^6$ is as defined in the Summary of the Invention for a Compound of Formula I, prepared as described above in Scheme A, can be treated using the conditions in Scheme D, except that intermediate 7 in Scheme D is substituted with intermediate 7a or 7b and the intermediate of formula 9 in Scheme D is replaced with intermediates of formula $NHR^{18a}R^{18b}$ or $NHR^{20a}R^{20b}$ to yield a Compound of the Invention of Formula I where $R^{18}a$, $R^{18b}$, $R^{20a}$, $R^{20b}$, are as defined in the Summary of the Invention for a Compound of Formula I.

A Compound of Formula I where $R^1$ is phenyl or pyridinyl, where the phenyl and pyridinyl are optionally substituted with 1, 2, or 3 $R^6$, $R^{50}$ is and all other groups are as defined in the Summary of the Invention for a Compound of Formula I can be prepared as follows.

Scheme E

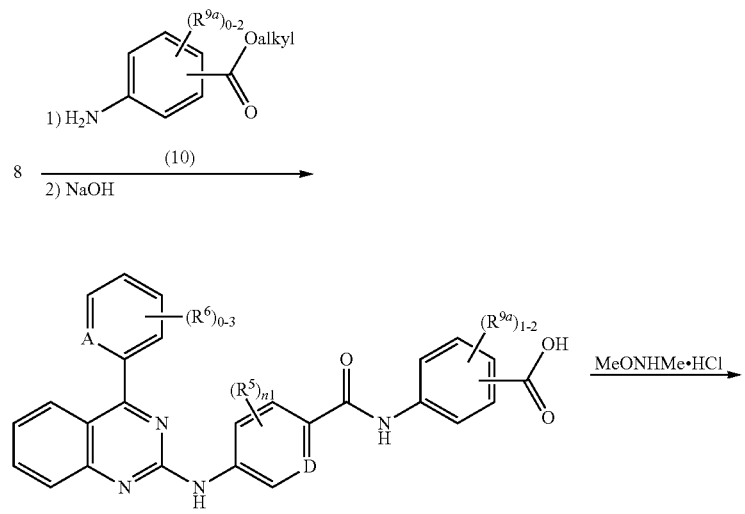

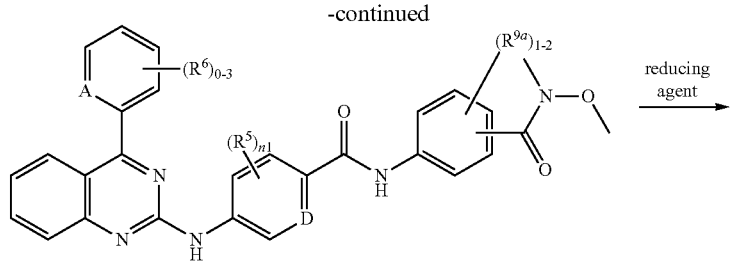

12

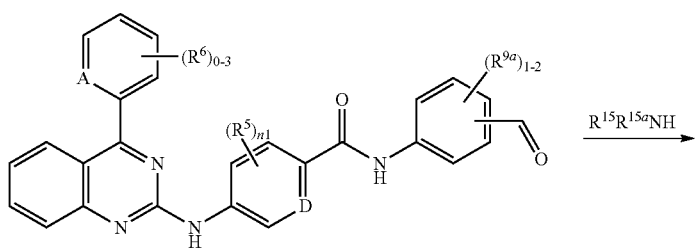

13

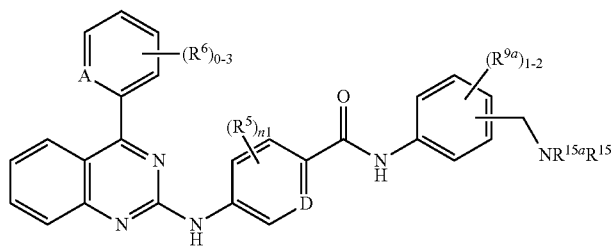

XII

Intermediate 8, prepared as described in Scheme D, is 1) treated with an aniline of formula 10 (where $R^{9a}$ is as defined in the Summary of the Invention for a Compound of Formula I) in the presence of a base such as Hunig's base and a coupling agent such as HATU in a solvent such as DMF at a temperature of about 60° C. for approximately overnight, 2) worked up and taken up in a mixture of THF and ACN, and 3) saponified with a base such as NaOH at about 70° C. for about 3 h to yield the free acid of formula II (where A and D are independently CH or N, and n1, $R^5$, and $R^6$ are as defined in the Summary of the Invention for a Compound of Formula I).

Intermediate 11 is then treated with N,O-dimethylhydroxylamine hydrochloride in the presence of a coupling agent such as HATU and a base such as Hunig's base in a solvent such as DMF for about 2 hours at room temperature and subsequently worked up to yield the Weinreb amide 12. Intermediate 12 is then treated with a reducing agent such as Dibal in a solvent such as DCM at a temperature of about −78° C. to yield an intermediate of formula 13. Methanol and then water is added carefully to the reaction mixture with vigorous stifling. 1 N hydrochloric acid is then added and the precipitates that formed are collected.

Reductive amination is carried out on intermediate 13 to in the presence of acetic acid and THF and a reducing agent such as $NaBH(OAc)_3$ in a solvent such as DCM for approximately overnight to yield a Compound of the Invention of Formula XII (where $R^{15}$ and $R^{15a}$ are as defined in the Summary of the Invention for a Compound of Formula I).

A Compound of Formula I where $R^1$ is phenyl or pyridinyl, where the phenyl and pyridinyl are optionally substituted with 1, 2, or 3 $R^6$, $R^{50}$ is where $R^4$ is phenyl substituted with $R^{29}$ which is $R^{9b}$ which is alkyl substituted with one $R^{11}$ where $R^{11}$ is —$NR^{15}R^{15a}$, and all other groups are as defined in the Summary of the Invention can be prepared as follows.

Scheme F

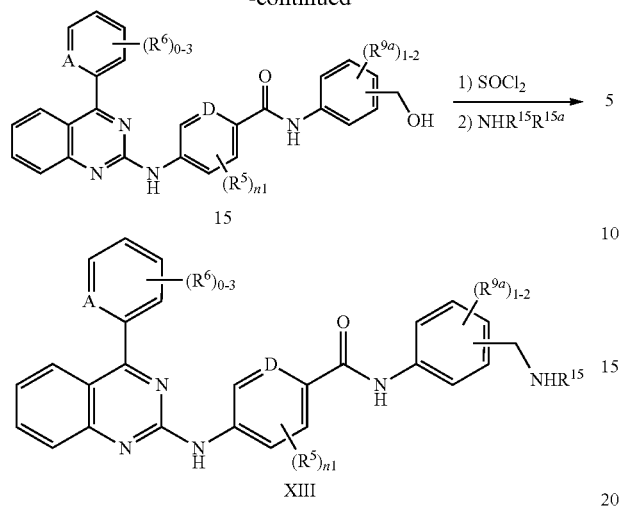

Intermediate 8, prepared as described in Scheme D, is treated with a chlorinating reagent such as thionyl chloride in a solvent such as dichloromethane (50 mL) and in the presence of a catalytic amount of DMF at rt to yield the acid chloride which is then treated with an aniline of formula 14 (where $R^{9a}$ is as defined in the Summary of the Invention for a Compound of Formula I) in the presence of a base such as triethylamine to yield an intermediate of formula 15 (where A and D are independently CH or N, $R^{9a}$ is as defiend in the Summary of the Invention for a Compound of Formula I). 15 is then treated with a chlorinating agent such as thionyl chloride in a solvent such as DCM at a temperature of about 0° C. for about 2 hours, followed by concentration, and treatment with an amine of formula $NHR^{15}R^{15a}$ (where $R^{15}$ and $R^{15a}$ are as defined in the Summary of the Invention for a Compound of Formula I) in a solvent such as THF at about 0° C.

An intermediate of formula 17 where $R^1$ is phenyl or heteroaryl, where the phenyl and heteroaryl are optionally substituted with 1, 2, or 3 $R^6$, can be prepared as follows and subsequently used to prepare a Compound of the Invention.

Scheme G

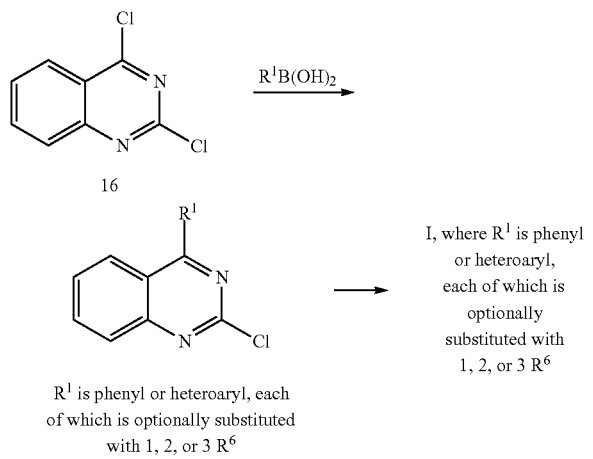

An intermediate of formula 16 is treated with a boronic acid of formula $R^1B(OH)_2$ in the presence of a catalyst such as dichloro-((bis-diphenylphosphino)ferrocenyl)-palladium (II) (complex with methylene chloride), and a base such as triethylamine in a solvent(s) such as dimethoxyethane/water at a temperature of about 80° C. for about 14 h to yield an intermediate of formula 17.

An intermediate of formula 19, which is useful in the synthesis of a Compound of the Invention of Formula I, where $R^{9a}$ is as defined in the Summary of the Invention for a Compound of Formula I and $R^{29}$ is —OR where R is optionally substituted heterocycloalkylalkyl, aminoalkyl, alkylaminoalkyl, or dialkylaminoalkyl can be prepared using the following scheme.

Scheme H

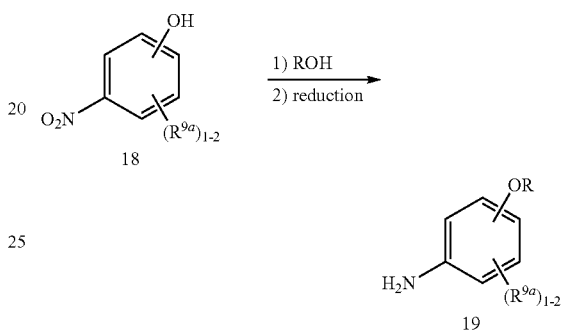

R is optionally substituted heterocycloalkylalkyl, aminoalkyl, alkylaminoalkyl, or dialkylaminoalkyl 18 is reacted with an intermediate of formula ROH where R is optionally substituted heterocycloalkylalkyl, aminoalkyl, alkylaminoalkyl, or dialkylaminoalkyl in a solvent such as dichloromethane, in the presence of triphenylphosphine and diisopropylazo dicarboxylate at room temperature under nitrogen for about 1 h, and then is treated with $H_2$ in the presence of a catalyst such as palladium on carbon and a drop of concentrated hydrochloric acid in a solvent such as ethanol to yield an intermediate of formula 19.

An intermediate of formula 21, which is useful in the synthesis of a Compound of the Invention, where $R^{9a}$ is as defined in the Summary of the Invention for a Compound of Formula I and $R^{29}$ is an optionally substituted heteroaryl can be prepared using the following scheme.

Scheme J

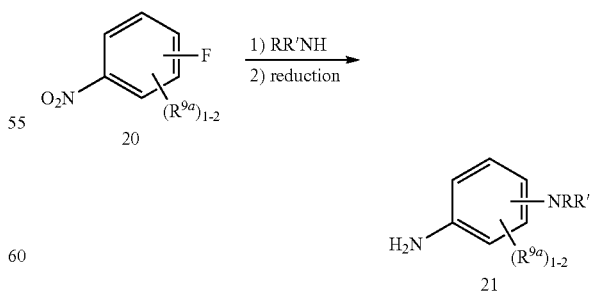

where R and R' together with the nitrogen to which they are attached form an optionally substituted heteroaryl ring The first step is carried out in the presence of a base such as potassium carbonate and in a solvent such as DMF at a temperature of about 100° C. The second step is carried out with $H_2$ in the presence of a catalyst such as palladium on carbon in a solvent such as ethanol.

A Compound of Formula I where $R^1$ is phenyl or pyridinyl, where the phenyl and pyridinyl are optionally substituted with 1, 2, or 3 $R^6$, $R^{50}$ is

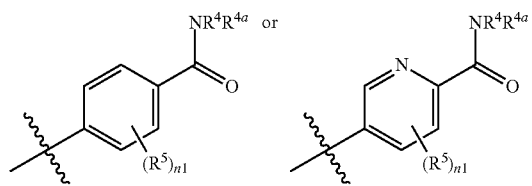

where $R^4$ is phenyl substituted with $R^{29}$ which is $R^{9b}$ which is —NHC(O)$R^{23a}$, and all other groups are as defined in the Summary of the Invention for a Compound of Formula I can be prepared as follows.

An intermediate of formula 22 is prepared as described in Scheme D. It is then treated with formic acid, potassium formate, and a catalyst such as platinum on carbon in a solvent(s) such as tetrahydrofuran/ethanol and is heated to about reflux for about 1 h to yield the intermediate of formula 23. Intermediate 23 is then treated with an acid of formula $R^{23a}$C(O)OH in the presence of a base such as Hunig's base in a solvent such as dimethylformamide and a coupling agent such as HATU and is heated to about 80° C. for about 1 h. to yield a Compound of Formula XIV.

A Compound of Formula I where $R^1$ is phenyl or pyridinyl, where the phenyl and pyridinyl are optionally substituted with 1, 2, or 3 $R^6$, $R^{50}$ is

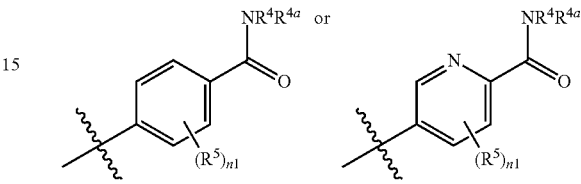

where $R^4$ is phenyl substituted with $R^{29}$ which is $R^{9b}$ which is optionally substituted heteroaryl, and all other groups are as defined in the Summary of the Invention for a Compound of Formula I can be prepared as follows.

Scheme K

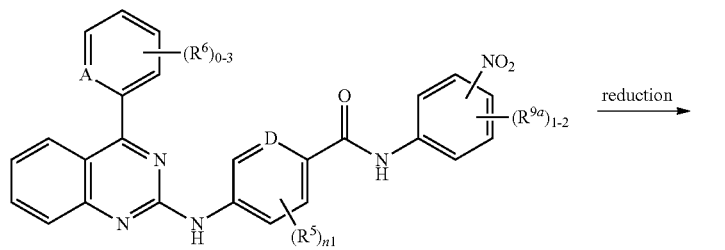

22

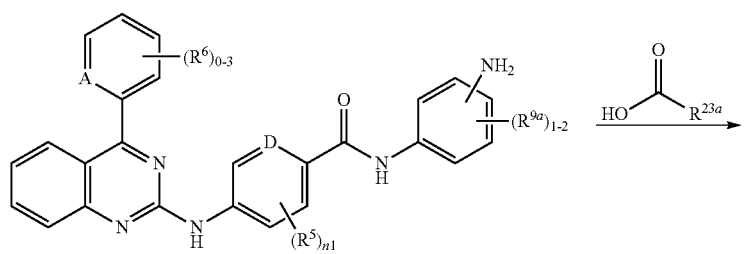

23

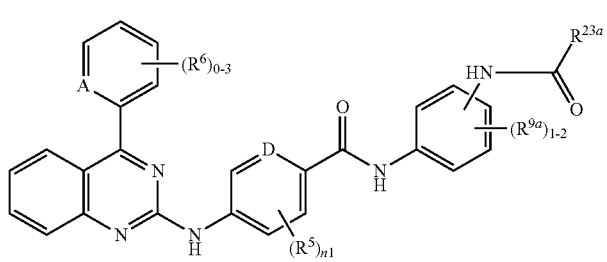

XIV

Scheme L

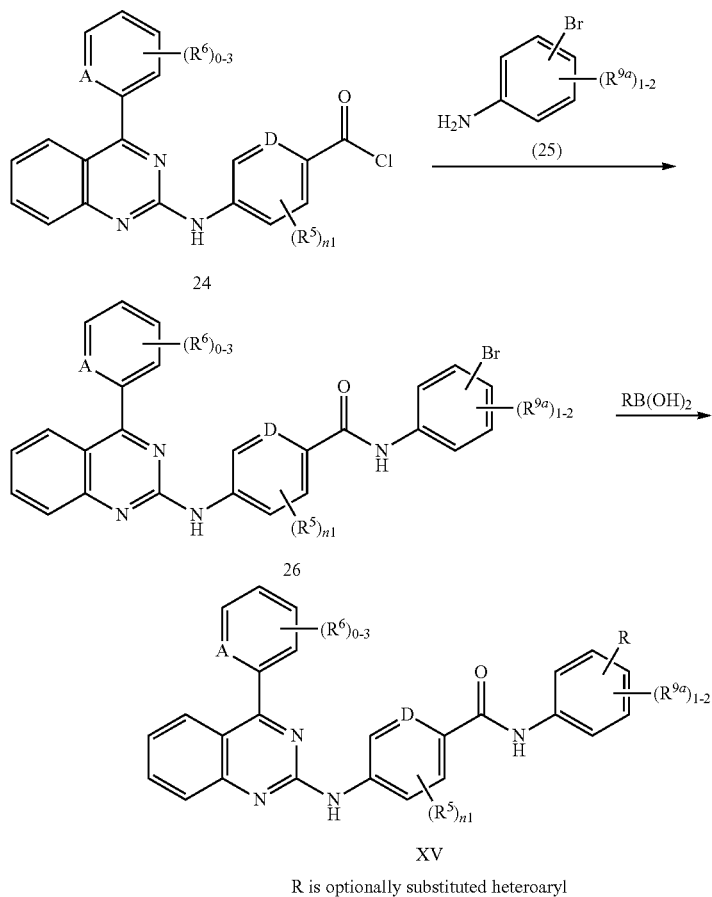

R is optionally substituted heteroaryl

Intermediate of formula 24 can be prepared as described in Scheme D where the acid chloride 24 is prepared from the acid of intermediate of formula 8. It is then treated with an aniline of formula 25 in the presence of a base such as Hunig's base and in a solvent such as THF at room temperature to yield an intermediate of formula 26. 26 is then treated with a boronic acid of formula $RB(OH)_2$ in the presence of a base such as $K_2CO_3$ and a catalyst such as $Pd(PPh_3)_4$ in a solvent such as dioxane and is heated to about 110° C. to yield a Compound of Formula XV.

Alternatively, an intermediate of formula 26 can be treated with an intermediate of formula RR'NH, where R and R' together with the nitrogen to which they are attached form an optionally substituted heteroaryl, in the presence of copper (I) iodide and a base such as cesium carbonate in a solvent such as DMF under an atmosphere of nitrogen and heated to about 110° C. to yield a Compound of Formula XV.

A Compound of Formula I where $R^1$ and $R^{19}$ are as defined in the Summary of the Invention for a Compound of Formula I can be prepared as follows.

Scheme M

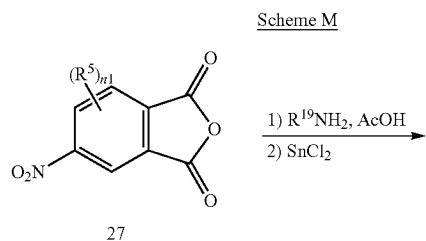

A mixture of intermediate 27 (where n1 and $R^5$ are as defined in the Summary of the Invention for a Compound of Formula I) and an intermediate of formula $R^{19}NH_2$ in acetic acid is heated at about 100° C. approximately overnight. The product is dissolved in a solvent such as ethanol, and tin (II) chloride is added. The mixture is heated to about reflux for approximately 5 h. The reaction mixture is cooled and made basic by adding, for example, aqueous 2 N sodium hydroxide. The product is then extracted into an organic solvent such as ethyl acetate, washed with water and saturated sodium chloride, dried over a drying agent such as anhydrous sodium sulfate, filtered, and concentrated under vacuum to give intermediate 28 which can be used without further purification.

A mixture of the intermediate of formula 28 and an intermediate of formula 17 in a solvent such as n-butanol is heated at about 120° C. until all of the solvent evaporates. Additional solvent is added and the process is repeated twice. After the reaction mixture is cooled, water is added. A precipitate which form is collected by suction filtration. N,N-Dimethylacetamide is added to dissolve the solid which can then be purified by preparative reverse-phase HPLC.

A Compound of Formula I where $R^1$ is cycloalkyl, D is carbon or nitrogen, and $R^{9a}$ and $R^{29}$ are as defined in the Summary of the Invention for a Compound of Formula I can be prepared as follows.

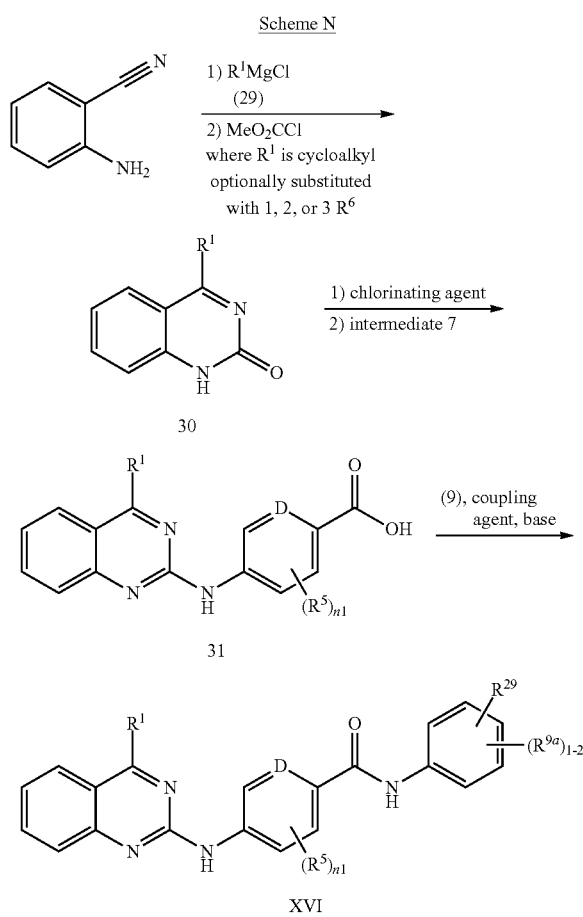

To a dried round-bottomed flask containing an intermediate of formula 29 in a solvent such as anhydrous ether is added dropwise a solution of 2-aminobenzonitrile in a solvent such as anhydrous ether. The mixture is stirred at rt for approximately 2 h, then cooled to about 0° C. A solution of methyl chloroformate in a solvent such as dry ether is added. The reaction mixture is returned to rt and stirred for approximately 2 d. The reaction is quenched with an acid such as 1 N hydrochloric acid and stirred for approximately 30 min to give an intermediate of formula 30.

A mixture of intermediate 30 and a chlorinating agent such as phosphorous oxychloride is heated to about reflux for approximately 1 h. The volatiles can be removed under reduced pressure and then the residue can be treated with ice water and extracted into ethyl acetate. To this are added intermediate 7, a base such as triethylamine, and a solvent such as n-butanol. This mixture is heated to about 140° C. for approximately 25 min. The mixture is cooled to rt and triturated with a solvent such as ether. The residual solid is collected via vacuum filtration, washed with a solvent such as ether, and dried to 31.

To a stirred mixture of intermediate 31, a coupling agent such as HATU, a base such as Hunig's base, and a solvent such as dimethylformamide is added an intermediate of formula 9. The reaction is heated to about 50° C. for approximately overnight. The mixture is cooled, diluted with a solvent such as water, and extracted into a solvent such as ethyl acetate. The combined organic extracts can be washed with a solution such as 1 N sodium bicarbonate and a 5% aqueous solution of lithium chloride. The product can then be extracted into a solvent such as 1 N hydrochloric acid. The combined acidic washes are neutralized with a base such as 1 N sodium hydroxide and extracted into a solvent such as dichloromethane. These combined organic extracts are dried, filtered, and concentrated under vacuum. The residue obtained can be purified by recrystallization from a solvent such as methanol to give a Compound of the Invention of Formula XVI.

A Compound of Formula XVIIa where $R^1$ is phenyl or heteroaryl each of which is optionally substituted with 1, 2, or 3 $R^6$; R is alkyl, alkoxycarbonyl, benzyloxycarbonyl, or optionally substituted phenylalkyl; and $R^{9a}$ and $R^{29}$ are as defined in the Summary of the Invention for a Compound of Formula I can be prepared as follows.

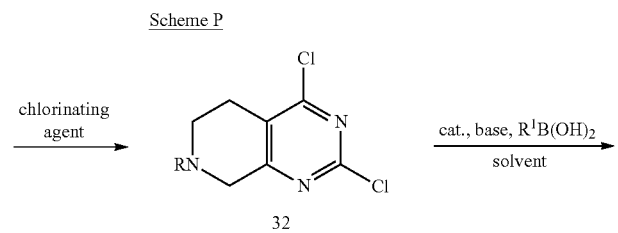

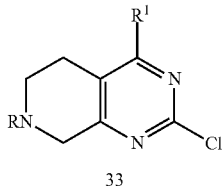

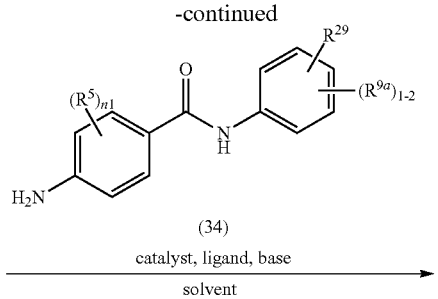

(34)

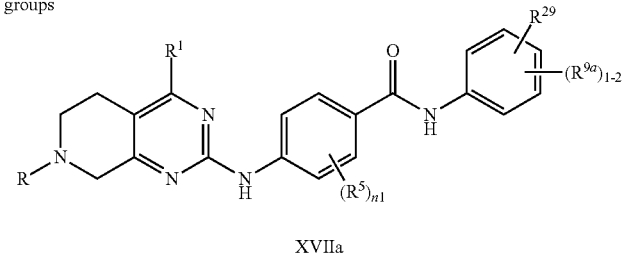

XVIIa

A solution of intermediate 31 (which is commercially available or can be prepared using procedures know to one of ordinary skill in the art), and a chlorinating agent such as phosphorus oxychloride is stirred at about 110° C. for approximately 18 h. The reaction mixture is cooled, concentrated, and treated with a base such as concentrated ammonium hydroxide until basic. The product can be extracted into ethyl acetate and washed with a solution such as saturated sodium chloride, dried, and concentrated under reduced pressure to give the intermediate of formula 32 which can be used without further purification.

To a round bottomed flask containing intermediate 32 is added $R^1B(OH)_2$, a catalyst such as dichloro-((bis-diphenylphosphino)ferrocenyl)-palladium (II) (complex with methylene chloride), a base such as triethylamine, dimethoxyethane, and water. The reaction mixture is heated to about 80° C. for approximately 14 h, then cooled to rt and diluted with a solvent such as ethyl acetate. The organic layer is washed with a solution such as saturated sodium bicarbonate, dried, filtered, and concentrated under reduced pressure. The material can be purified by flash column chromatography to afford intermediate 33.

To a round bottomed flask containing intermediate 33 is added an intermediate of formula 34 (which is commercially available or can be prepared using procedures know to one of ordinay skill in the art) a catalyst such as diacetoxypalladium (II), a ligand such as di-tert-butyl(phenyl)phosphine, a base such as cesium carbonate, and a solvent such as toluene. The reaction mixture is heated to about 100° C. for approximately 14 h, then cooled and diluted with a solvent such as ethyl acetate. The organic layer can be washed with a solution such as saturated sodium bicarbonate, dried, filtered, and concentrated under reduced pressure. The material can be purified by flash column chromatography to afford a Compound of Formula XVIIa.

A Compound of Formula XVIIb where $R^1$ is phenyl or heteroaryl each of which is optionally substituted with 1, 2, or 3 $R^6$; and $R^{9a}$ and $R^{29}$ are as defined in the Summary of the Invention for a Compound of Formula I can be prepared as follows.

Scheme Q

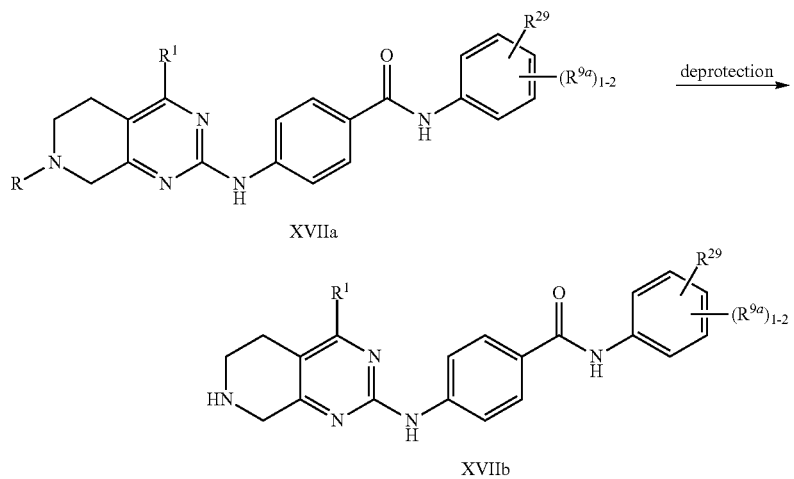

A Compound of Formula XVIIa where R is a benzyl group, prepared as described in Scheme P, can be treated with 1,4-cyclohexadiene, in the presence of a catalyst such as 10% palladium on carbon, in a solvent such as ethanol to remove the benzyl group. The reaction is heated to about 80° C. for approximately overnight. Upon cooling, the reaction mixture is filtered through celite and concentrated under reduced pressure. The resulting residue can be purified by preparative reverse phase HPLC to give a Compound of Formula XVIIb.

Alternatively, a Compound of Formula XVIIb can be used to make a Compound of Formula XVIIa where R is alkyl, alkoxycarbonyl, benzyloxycarbonyl, or optionally substituted phenylalkyl by reacting with the appropriate reagent, known to one of ordinary skill in the art.

An intermediate of formula 42 (where $R^1$ is phenyl or heteroaryl and the phenyl and heteroaryl are optionally substituted with 1, 2, or 3 $R^6$ groups), which is useful in the preparation of a Compound of Formula I, can be prepared using the conditions in Scheme R.

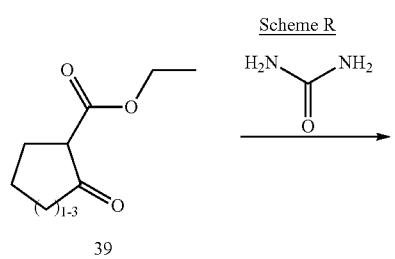

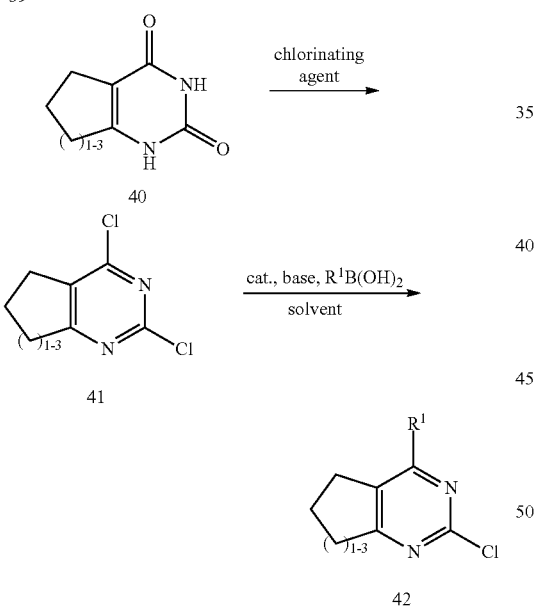

A solution of intermediate 39, urea, and hydrochloric acid (37%, aqueous) in a solvent such as EtOH is heated to about 80° C. for approximately 24 h. The mixture is cooled to rt, and the precipitate is collected by filtration and dried to afford intermediate 40.

A stirred mixture of intermediate 40 and a chlorinating agent such as phosphorus oxychloride is heated to about 105° C. for approximately 30 min. The reaction mixture is cooled to rt and slowly poured over an ice/water mixture. The solid that forms is collected by filtration, washed with water (50 mL) and dried under reduced pressure to give intermediate 41.

To a round bottomed flask containing intermediate 41 are added $R^1B(OH)_2$, a catalyst such as dichloro-((bis-diphenylphosphino)ferrocenyl)-palladium (II) (complex with methylene chloride), a base such as triethylamine, and a solvent mixture such as dimethylformamide and water. The reaction mixture is heated to about 80° C. for approximately 14 h, then cooled to rt and diluted with ethyl acetate. The organic layer is washed with a solution such as saturated sodium bicarbonate, dried, filtered, and concentrated under reduced pressure. The material can be purified by flash column chromatography to afford intermediate 42.

An intermediate for formula 35, which is useful in the preparation of a Compound of Formula I, can be prepared according to Scheme T where $R^1$ is as defined in the Summary of the Invention for a Compound of Formula I

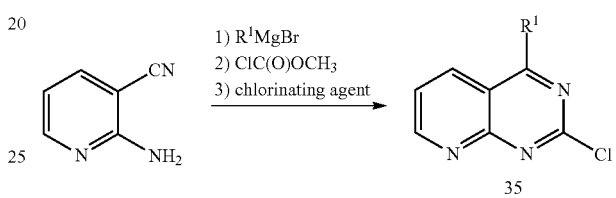

using conditions similar to those in Scheme N. Analogously, intermediates of formula 36, 37, and 38,

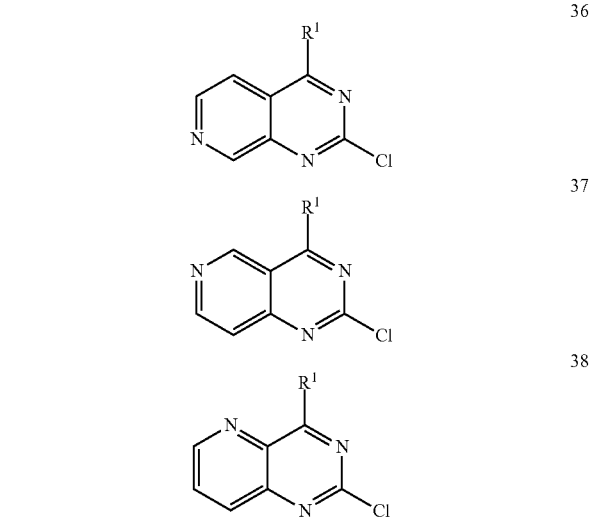

which are useful in the preparation of a Compound of Formula I, can be prepared using procedures similar to those in Scheme T. Intermediates of formula 35, 36, 37, 38, and 42 can then be used instead of intermediate 3 in Scheme B, continuing on with the resulting intermediate through the steps in Scheme C. In addition, intermediates of formula 35, 36, 37, 38, and 42 can be used instead of intermediate 3 in Scheme D, continuing on with the resulting intermediate through the steps in Schemes E, F, K, and L. In addition, intermediates of formula 35, 36, 37, 38, and 42 can be used instead of intermediate 17 in Scheme M.

A Compound of Formula I where $R^1$, $R^2$, $R^3$, $R^{40}$, and $R^{50}$ are described in the Summary of the Invention for a Compound of Formula I can be prepared as follows.

Scheme U

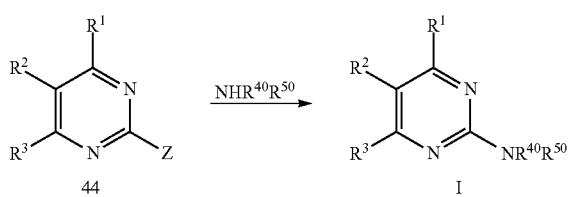

An intermediate of formula 44 where Z is a leaving group is treated with an intermediate of formula NHR$^{40}$R$^{50}$ using conditions known to one of ordinary skill in the art.

A Compound of Formula I where R$^1$, R$^2$, R$^3$, R$^4$, and R$^{4a}$ are described in the Summary of the Invention for a Compound of Formula I can be prepared as follows.

Scheme V

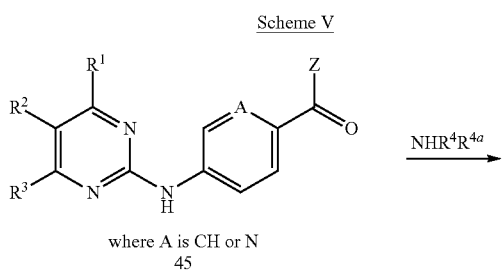

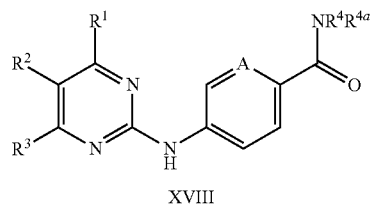

An intermediate of formula 45 where A is CH or N and Z is, for example, OH or halo is treated with an intermediate of formula NHR$^4$R$^{4a}$ using conditions known to one of ordinary skill in the art.

A Compound of Formula I where R$^1$, R$^2$, R$^3$, R$^{17}$, R$^{21}$, and R$^{22}$ are described in the Summary of the Invention for a Compound of Formula I can be prepared as follows.

Scheme W

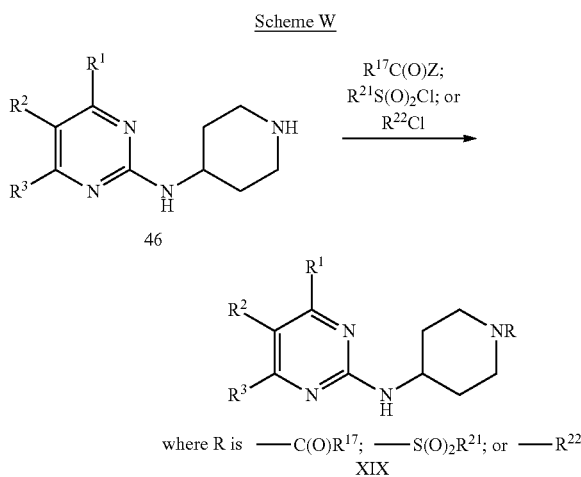

An intermediate of formula 45 where A is CH or N and Z is, for example, OH or halo is treated with an intermediate of formula NHR$^4$R$^{4a}$ using conditions known to one of ordinary skill in the art.

A Compound of Formula I where R$^1$, R$^2$, R$^3$, R$^{18}$, R$^{18a}$, and R$^{18b}$ are described in the Summary of the Invention for a Compound of Formula I can be prepared as follows.

Scheme X

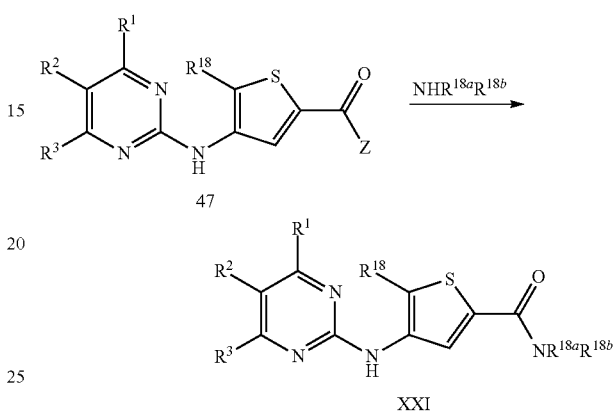

An intermediate of formula 47 where Z is, for example, OH or halo is treated with an intermediate of formula NHR$^{18a}$R$^{18b}$ using conditions known to one of ordinary skill in the art.

A Compound of Formula I where R$^1$, R$^2$, R$^3$, R$^{20}$, R$^{20a}$, and R$^{20b}$ are described in the Summary of the Invention for a Compound of Formula I can be prepared as follows.

Scheme Y

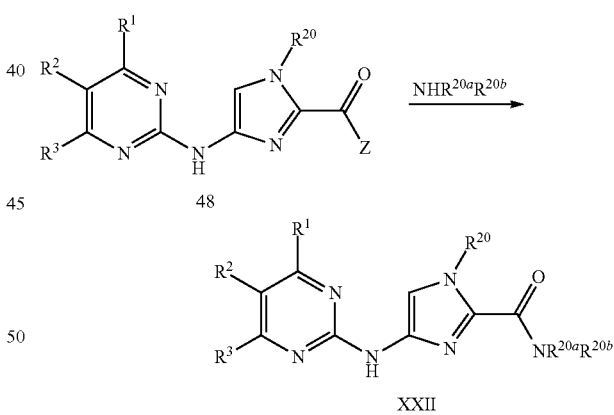

An intermediate of formula 48 where Z is, for example, OH or halo is treated with an intermediate of formula NHR$^{20a}$R$^{20b}$ using conditions known to one of ordinary skill in the art.

The synthesis of representative compounds of this invention is described in detailed procedures below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Each of the following compounds can be prepared as a pharmaceutically acceptable salt, solvate, and/or hydrate. In particular, the pharmaceutically acceptable salt can be formed with one or two acids independently selected from hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid.

Example 1

Scheme 1

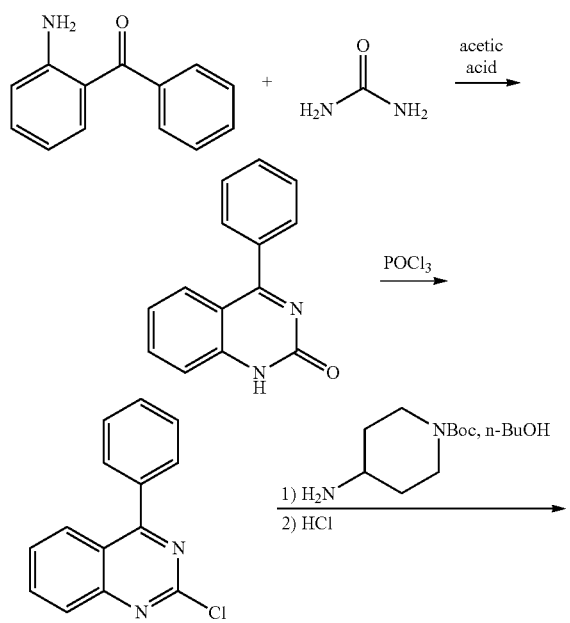

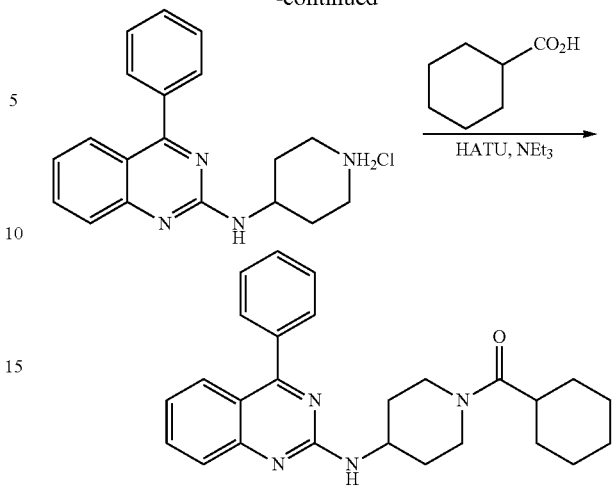

Example 1

N-[1-(cyclohexylcarbonyl)piperidin-4-yl]-4-phenylquinazolin-2-amine

A solution of 2-aminobenzophenone (100 g, 0.51 mol), urea (55 g, 0.93 mol) and acetic acid (300 mL) was stirred at 110° C. for 18 h. The reaction mixture was cooled to rt and filtered. The solid was washed with water and dried under reduced pressure. 4-Phenylquinazolin-2(1H)-one was isolated as a yellow solid and was used without further purification.

A flask was charged with 4-phenylquinazolin-2(1H)-one (110 g, 0.51 mol) and phosphorus oxychloride (300 mL), and the mixture was stirred at 105° C. for 30 min. The reaction mixture was cooled to rt and slowly poured over an ice/water mixture. The solid was collected by filtration, washed with water (50 mL) and dried under reduced pressure. The product, 2-chloro-4-phenylquinazoline, was isolated as an off-white solid (110 g, 91%).

A solution of 2-chloro-4-phenylquinazoline (1.38 g, 5.75 mmol), and tert-butyl 4-aminopiperidine-1-carboxylate (2.81 g, 14.1 mmol) was heated at reflux in n-butanol (20 mL) for 4 h. After removal of the n-butanol on a rotary evaporator, dichloromethane (100 mL) was added and the suspension was sonicated for 30 min and filtered. The solution was then concentrated on a rotary evaporator to give a brown residue. This residue was purified by column chromatography on silica gel (95:5 hexanes/ethyl acetate) to yield a green oil that was treated with 4M HCl in 1,4-dioxane (100 mL) at 100° C. for 1 h. The solvent was removed on a rotary evaporator to give 4-phenyl-N-(piperidine-4-yl)quinazolin-2-amine (2.05 g, 90%) as a dark yellow solid.

To a solution of 4-phenyl-N-(piperidine-4-yl)quinazolin-2-amine (0.34 g, 1.0 mmol), cyclohexanecarboxylic acid (0.15 g, 1.2 mmol), and triethylamine (1.38 mL, 10 mmol) in dimethylformamide (15 mL) was added O-(7-azabenzotriazol-1-yloxy)-N,N,N',N'-tetramethyluronium hexafluorophosphate (HATU, 0.57 g, 1.5 mmol) and the solution was stirred at rt for 16 h. An aqueous 5% solution of lithium chloride (100 mL) was added and the resulting solid was filtered and recrystallized in methanol/methyl-tert-butyl ether to yield N-[1-(cyclohexylcarbonyl)piperidin-4-yl]-4-phenylquinazolin-2-amine (0.32 g, 77%) as a yellow solid. $^1$H NMR (400 MHz, CDCl$_3$): δ 11.81 (d, 1H), 7.70-7.65 (m, 4H), 7.56-7.53 (m, 3H), 7.21-7.16 (m, 1H), 5.26 (d, 1H), 4.52 (m, 1H), 4.34-4.28 (m, 1H), 3.92 (m, 1H), 3.28 (t, 1H), 2.94 (t, 1H), 2.51 (tt, 2H), 2.29-2.16 (m, 2H), 1.83-1.69 (m, 5H), 1.57-1.44 (m, 4H), 1.30-1.26 (m, 2H). MS (EI) for $C_{26}H_{30}N_4O$: 415.3 (MH$^+$).

Using procedures described in Scheme 1, the following compounds were prepared.

Example 2

N-[(3,4-dichlorophenyl)methyl]-4-[(4-phenylquinazolin-2-yl)amino]piperidine-1-carboxamide. $^1$H NMR (400 MHz, CDCl$_3$): δ 7.82 (d, 1H), 7.70-7.66 (m, 4H), 7.55 (m, 3H), 7.40 (m, 2H), 7.16 (m, 2H), 5.26 (d, 1H), 4.89 (t, 1H), 4.39 (d, 2H), 4.26 (m, 1H), 3.93 (m, 2H), 3.12 (m, 2H), 2.21 (m, 2H), 1.52 (m, 2H). MS (EI) for $C_{27}H_{25}Cl_2N_5O$: 506.0 (MH$^+$).

Example 3

N-[1-(1H-benzimidazol-2-yl)piperidin-4-yl]-4-phenylquinazolin-2-amine. $^1$H NMR (400 MHz, DMSO-d$_6$): δ 11.33 (s, 1H), 7.72-7.54 (m, 8H), 7.21 (m, 3H), 6.92 (m, 2H), 4.21 (m, 1H), 4.11 (d, 2H), 2.08 (br d, 2H), 1.65 (m, 2H). MS (EI) for $C_{26}H_{24}N_6$: 421.2 (MH$^+$).

Example 4

4-phenyl-N-[1-(phenylcarbonyl)piperidin-4-yl]quinazolin-2-amine. $^1$H NMR (400 MHz, DMSO-d$_6$): δ 7.75 (m, 4H) 7.69 (m, 5H), 7.47 (m, 3H), 7.39 (m, 2H), 7.21 (t, 1H), 4.21 (br s, 1H), 4.14 (m, 1H), 3.60 (br s, 1H), 3.35 (br s, 1H), 3.18 (br s, 1H), 2.00 (br d, 2H), 1.50 (br s, 2H). MS (EI) for $C_{26}H_{24}N_4O$: 409.2 (MH$^+$).

Example 5

4-phenyl-N-[1-(phenylacetyl)piperidin-4-yl]quinazolin-2-amine. $^1$H NMR (400 MHz, DMSO-d$_6$): δ 7.70 (m, 3H), 7.67-7.50 (m, 5H), 7.33 (t, 2H), 7.24-7.16 (m, 4H), 4.30 (d, 1H), 4.15 (m, 1H), 4.00 (d, 1H), 3.75 (s, 2H), 3.30 (t, 1H), 2.85 (t, 1H), 1.95 (br s, 2H), 1.40 (m, 2H). MS (EI) for $C_{27}H_{26}N_4O$: 423.2 (MH$^+$).

Example 6

4-phenyl-N-[1-(2-phenylpropanoyl)piperidin-4-yl]quinazolin-2-amine. $^1$H NMR (400 MHz, DMSO-d$_6$): δ 7.81 (t, 1H), 7.79-7.59 (m, 4H), 7.52 (m, 3H), 7.33 (m, 2H), 7.26-7.13 (m, 3H), 5.31 (d, ½H), 5.02 (d, ½H), 4.67 (d, ½H), 4.45 (m, ½ H), 4.20 (m, 1H), 3.95-3.79 (m, 2H), 3.19-2.83 (m, 2H), 2.14 (d, 1H), 1.97 (d, 1H), 1.84 (d, 2H), 1.46 (m, 3H), 1.31 (m, 1H), 0.50 (m, 1H). MS (EI) for $C_{28}H_{28}N_4O$: 437.2 (MH$^+$).

Example 7

N-{1-[(3,5-dimethylisoxazol-4-yl)sulfonyl]piperidin-4-yl}-4-phenylquinazolin-2-amine. $^1$H NMR (400 MHz, CDCl$_3$): δ 7.82 (d, 1H), 7.70-7.62 (m, 4H), 7.54 (m, 3H), 7.18 (m, 1H), 5.23 (d, 1H), 4.17 (m, 1H), 3.71 (m, 2H), 2.88 (m, 2H), 2.67 (s, 3H), 2.43 (s, 3H), 2.26 (m, 2H), 1.74 (m, 1H). MS (EI) for $C_{24}H_{25}N_5O_3S$: 464.2 (MH$^+$).

Example 8

N-{1-[(2,6-dichlorophenyl)carbonyl]piperidin-4-yl}-4-phenylquinazolin-2-amine. $^1$H NMR (400 MHz, CD$_3$OD): δ 7.77 (d, 1H), 7.72-7.67 (m, 3H), 7.62-7.54 (m, 4H), 7.49-7.39 (m, 3H), 7.22-7.18 (m, 1H), 4.66-4.62 (m, 1H), 4.34-4.27 (m, 1H), 3.46-3.44 (m, 1H), 3.36 (m, 1H), 3.25-3.18 (m, 1H), 2.27-2.23 (m, 1H), 2.12-2.09 (m, 1H), 1.75-1.60 (m, 3H). MS (EI) for $C_{26}H_{22}Cl_2N_4O$: 477.1 (MH$^+$).

Example 9

1,1-dimethylethyl 3-({4-[(4-phenylquinazolin-2-yl)amino]piperidin-1-yl}carbonyl)piperidine-1-carboxylate. $^1$H NMR (400 MHz, CDCl$_3$): δ 8.03 (s, 1H), 7.81 (m, 1H), 7.67 (m, 4H), 7.44 (m, 3H), 7.18 (t, 1H), 4.65-3.95 (m, 8H), 3.29 (m, 1H), 2.98-1.68 (m, 9H), 1.41 (s, 9H). MS (EI) for $C_{30}H_{37}N_5O_3$: 516.4 (MH$^+$).

Example 10

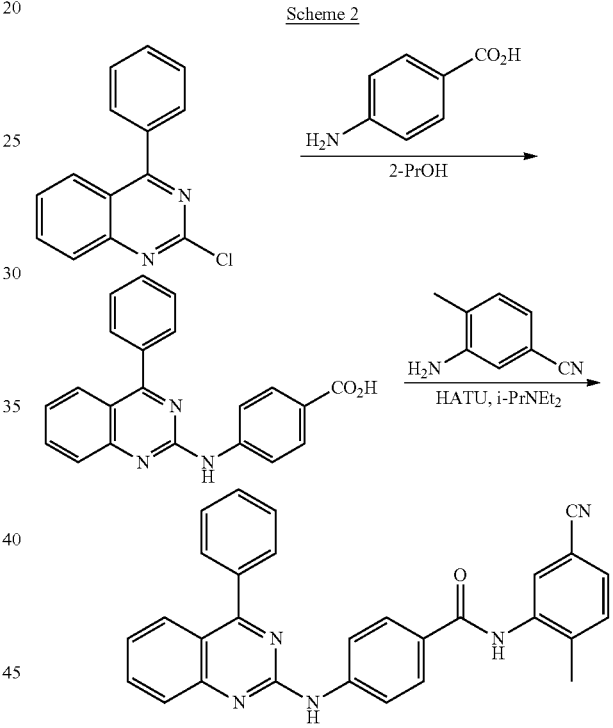

Scheme 2

Example 10

N-(5-cyano-2-methylphenyl)-4-[(4-phenylquinazolin-2-yl)amino]benzamide

To a solution of 2-chloro-4-phenylquinazoline (9.6 g, 40 mmol) in 2-propanol (130 mL) was added 4-aminobenzoic acid (8.2 g, 60 mmol) and the mixture was stirred at reflux for 4 h. The mixture was cooled to rt and the precipitate was collected by filtration and washed with 2-propanol. The product, 4-(4-phenylquinazolin-2-ylamino)benzoic acid, was isolated as a yellow solid (12.9 g, 95%).

To a stirred mixture of 4-(4-phenylquinazolin-2-ylamino) benzoic acid (1.37 g, 4.02 mmol), 3-amino-4-methylbenzonitrile (529 mg, 4.01 mmol), and Hunig's base (2.1 mL, 12 mmol) in dimethylformamide (10 mL) was added HATU (3.04 g, 8.00 mmol). The stirred mixture was heated to 80° C. overnight, then cooled to rt. The reaction was diluted with ethyl acetate and extracted with water. The organic layer was washed with saturated sodium bicarbonate and concentrated on a rotary evaporator. The residue was sonicated with acetonitrile and filtered to give a light yellow solid, which was again washed with water, acetonitrile, and dried under reduced pressure to give N-(5-cyano-2-methylphenyl)-4-[(4-phenylquinazolin-2-yl)amino]benzamide (1.18 g, 65%) as a light yellow solid. $^1$H NMR (400 MHz, DMSO-d$_6$): δ 10.36 (s, 1H), 9.87 (s, 1H), 8.19 (d, 2H), 8.00 (d, 2H), 7.91-7.78 (m, 6H), 7.66-7.62 (m, 4H), 7.51 (d, 1H), 7.42 (ddd, 1H), 2.36 (s, 3H). MS (EI) for C$_{29}$H$_{21}$N$_5$O: 456.1 (MH$^+$).

Using the procedures described in Scheme 2, the following compounds were prepared.

Example 11

N-(2,6-dimethylphenyl)-4-[(4-phenylquinazolin-2-yl)amino]benzamide. $^1$H NMR (400 MHz, DMSO-d$_6$): δ 10.31 (s, 1H), 9.61 (s, 1H), 8.18 (d, 2H), 8.02 (d, 2H), 7.88-7.79 (m, 5H), 7.64 (t, 3H), 7.41 (t, 1H), 7.13 (s, 3H), 2.20 (s, 6H). MS (EI) for C$_{29}$H$_{24}$N$_4$O: 445.2 (MH$^+$).

Example 12

N-(4-methylpyrrolidin-3-yl)-4-[(4-phenylquinazolin-2-yl)amino]benzamide. $^1$H NMR (400 MHz, DMSO-d$_6$): δ 10.24 (s, 1H), 8.18-8.08 (dd, 3H), 7.87-7.79 (m, 7H), 7.64 (d, 3H), 7.40 (t, 1H), 3.92 (m, 1H), 3.09 (q, 2H), 2.68 (q, 1H), 2.37 (q, 1H), 2.07 (m, 1H), 1.01 (d, 3H). MS (EI) for C$_{26}$H$_{25}$N$_5$O: 424.1 (MH$^+$).

Example 13

N-{5-[(dimethylamino)methyl]-2-methylphenyl}-4-[(4-phenylquinazolin-2-yl)amino]benzamide. $^1$H-NMR (400 MHz, DMSO-d$_6$): δ 10.30 (s, 1H), 9.71 (s, 1H), 8.19 (d, 2H), 8.01 (d, 2H), 7.84-7.81 (m, 3H), 7.79-7.76 (m, 2H), 7.63-7.61 (m, 3H), 7.39-7.38 (m, 1H), 7.32 (d, 1H), 7.18 (d, 1H), 7.03 (dd, 1H), 3.38 (s, 2H), 2.24 (s, 3H), 2.13 (m, 6H). MS (EI) for C$_{31}$H$_{29}$N$_5$O: 488.3 (MH$^+$).

Example 14

4-[(4-phenylquinazolin-2-yl)amino]-N-(1,2,3,4-tetrahydroisoquinolin-7-yl)benzamide. $^1$H NMR (400 MHz, DMSO-d$_6$): δ 7.81 (d, 2H), 7.70 (m, 2H), 7.56 (m, 6H), 7.45 (br s, 2H), 7.26 (m, 3H), 6.78 (d, 2H), 3.75 (d, 2H), 2.90 (t, 2H), 2.59 (t, 2H). MS (EI) for C$_{30}$H$_{25}$N$_5$O: 472.2 (MH$^+$).

Example 15

N-(2-methyl-1,2,3,4-tetrahydroisoquinolin-7-yl)-4-[(4-phenylquinazolin-2-yl)amino]benzamide. $^1$H NMR (400 MHz, DMSO-d$_6$): δ 10.24 (s, 1H), 10.00 (s, 1H), 8.18 (d, 2H), 7.96 (d, 2H), 7.90-7.79 (m, 5H), 7.65-7.62 (m, 3H), 7.53 (d, 2H), 7.44-7.40 (m, 1H), 7.08 (d, 1H), 3.47 (s, 2H), 2.78 (t, 2H), 2.60 (t, 2H), 2.34 (s, 3H). MS (EI) for C$_{31}$H$_{27}$N$_5$O: 486.4 (MH$^+$).

Example 16

N-[5-({[2-(dimethylamino)ethyl]amino}sulfonyl)-2-methylphenyl]-4-[(4-phenylquinazolin-2-yl)amino]benzamide. $^1$H NMR (400 MHz, DMSO-d$_6$): δ 10.36 (s, 1H), 9.90 (s, 1H), 8.18 (d, 2H), 8.02 (d, 2H), 7.90-7.79 (m, 6H), 7.65-7.40 (m, 7H), 2.83 (t, 2H), 2.35 (s, 3H), 2.27 (t, 2H), 2.07 (s, 6H). MS (EI) for C$_{32}$H$_{32}$N$_6$O$_3$S: 581.2 (MH$^+$).

Example 17

N-(5-cyclopropyl-1,3,4-thiadiazol-2-yl)-4-[(4-phenylquinazolin-2-yl)amino]benzamide. $^1$H NMR (400 MHz, DMSO-d$_6$): δ 12.70 (s, 1H), 10.40 (s, 2H), 8.15 (m, 4H), 7.85 (m, 5H), 7.60 (m, 3H), 7.40 (m, 1H), 2.38 (m, 1H), 1.15 (m, 2H), 1.00 (m, 2H). MS (EI) for C$_{26}$H$_{20}$N$_6$OS: 465.2 (MH$^+$).

Example 18

N-(2-methyl-1,2,3,4-tetrahydroisoquinolin-5-yl)-4-[(4-phenylquinazolin-2-yl)amino]benzamide. $^1$H-NMR (400 MHz, DMSO-d$_6$): δ 10.32 (s, 1H), 9.62 (s, 1H), 8.18 (d, 2H), 7.98 (d, 2H), 7.92-7.78 (m, 5H), 7.64-7.62 (m, 3H), 7.42 (t, 1H), 7.24 (d, 1H), 7.18 (t, 1H), 6.98 (d, 1H), 3.57 (br s, 2H), 2.80 (app t, 2H), 2.64 (br s, 2H), 2.38 (s, 3H). MS (EI) for C$_{31}$H$_{27}$N$_5$O: 486.2 (MH$^+$).

Example 19

N-(2,6-dimethyl-1,2,3,4-tetrahydroisoquinolin-7-yl)-4-[(4-phenylquinazolin-2-yl)amino]benzamide. $^1$H-NMR (400 MHz, DMSO-d$_6$): δ 10.35 (s, 1H), 9.81 (s, 1H), 8.18 (d, 2H), 7.99 (d, 2H), 7.94-7.88 (m, 5H), 7.64-7.60 (m, 3H), 7.40 (t, 1H), 7.00 (d, 2H), 3.42 (s, 2H), 2.79 (t, 2H), 2.58 (t, 2H), 2.33 (s, 3H), 2.18 (s, 3H). MS (EI) for C$_{32}$H$_{29}$N$_5$O: 500.2 (MH$^+$).

Example 20

N-[2-methyl-5-(4-methylpiperazin-1-yl)phenyl]-4-[(4-phenylquinazolin-2-yl)amino]benzamide. $^1$H NMR (400 MHz, DMSO-d$_6$): δ 10.32 (s, 1H), 9.62 (s, 1H), 8.17 (d, 2H), 7.99 (d, 3H), 7.88-7.78 (m, 6H), 7.64 (m, 4H), 7.41 (t, 1H), 7.10 (d, 1H), 9.96 (d, 1H), 6.77 (m, 1H), 3.90 (t, 4H), 2.47 (t, 4H), 2.23 (s, 6H). MS (EI) for C$_{33}$H$_{32}$N$_6$O: 529.3 (MH$^+$).

Example 21

N-(4-methyl-2,3,4,5-tetrahydro-1,4-benzoxazepin-7-yl)-4-[(4-phenylquinazolin-2-yl)amino]benzamide. $^1$H NMR (400 MHz, DMSO-d$_6$): δ 10.33 (s, 1H), 10.02 (s, 1H), 8.18 (d, 2H), 7.98 (d, 2H), 7.88-7.79 (m, 5H), 7.65-7.63 (m, 3H), 7.55 (m, 1H), 7.42 (m, 1H), 6.95 (d, 1H), 3.96 (m, 2H), 3.65 (s, 2H), 2.89 (m, 2H), 2.30 (s, 3H). MS (EI) for C$_{31}$H$_{27}$N$_5$O$_2$: 502.3 (MH$^+$).

Example 22

N-(3-cyclopropyl-1H-pyrazol-5-yl)-4-[(4-phenylquinazolin-2-yl)amino]benzamide. $^1$H NMR (400 MHz, DMSO-d$_6$): δ 12.15 (s, 1H), 10.50 (s, 1H), 10.30 (s, 1H), 8.15 (d, 2H), 8.05 (d, 2H), 7.90-7.70 (m, 5H), 7.65 (m, 3H), 7.40 (t, 1H), 6.30 (s, 1H), 1.90 (m, 1H), 0.95 (d, 2H), 0.75 (d, 2H). MS (EI) for C$_{27}$H$_{22}$N$_6$O: 447.2 (MH$^+$).

Example 23

N-[2-(2-hydroxyethyl)-1,2,3,4-tetrahydroisoquinolin-5-yl]-4-[(4-phenylquinazolin-2-yl)amino]benzamide. $^1$H NMR (400 MHz, DMSO-d$_6$): δ 10.32 (s, 1H), 9.61 (s, 1H), 8.17 (d, 2H), 7.98 (d, 2H), 7.91-7.76 (m, 5H), 7.67-7.61 (m, 3H), 7.41 (t, 1H), 7.23 (d, 1H), 7.15 (t, 1H), 6.97 (d, 1H), 3.61

(m, 4H), 3.17 (s, 1H), 2.76 (m, 2H), 2.69 (m, 2H), 2.56 (t, 2H). MS (EI) for $C_{32}H_{29}N_5O_2$: 517.0 (MH$^+$).

Example 24

N-(2-{2-[(phenylmethyl)oxy]ethyl}-1,2,3,4-tetrahydroisoquinolin-5-yl)-4-[(4-phenylquinazolin-2-yl)amino]benzamide. $^1$H NMR (400 MHz, DMSO-d$_6$): δ 10.32 (s, 1H), 9.61 (s, 1H), 8.17 (d, 2H), 7.98 (d, 2H), 7.91-7.76 (m, 5H), 7.67-7.61 (m, 3H), 7.74-7.22 (m, 7H), 7.16 (t, 1H), 6.95 (d, 1H), 4.51 (s, 2H), 3.65 (m, 4H), 2.72 (m, 6H). MS (EI) for $C_{39}H_{35}N_5O_2$: 607.0 (MH$^+$).

Example 25

N-[2-methyl-5-(morpholin-4-ylacetyl)phenyl]-4-[(4-phenylquinazolin-2-yl)amino]benzamide. $^1$H NMR (400 MHz, DMSO-d$_6$): δ 10.33 (s, 1H), 9.71 (s, 1H), 8.17 (d, 2H), 7.99 (d, 2H), 7.88-7.78 (m, 5H), 7.63 (m, 3H), 7.43 (t, 1H), 7.34 (s, 1H), 7.21 (d, 1H), 7.14 (d, 1H), 5.03 (m, 1H), 4.70 (m, 1H), 3.57 (m, 4H), 2.48 (m, 4H), 2.22 (s, 3H). MS (EI) for $C_{34}H_{31}N_5O_3$: 559.0 (MH$^+$).

Example 26

N-{2-methyl-5-[(2-methyl-1H-imidazol-1-yl)acetyl]phenyl}-4-[(4-phenylquinazolin-2-yl)amino]benzamide. $^1$H NMR (400 MHz, DMSO-d$_6$): δ 10.32 (s, 1H), 9.75 (s, 1H), 8.02-6.67 (m, 18H), 3.97 (m, 2H), 2.24 (s, 3H), 2.18 (s, 3H). MS (EI) for $C_{34}H_{28}N_6O_2$: 554.0 (MH$^+$).

Example 27

4-[(4-phenylquinazolin-2-yl)amino]-N-(2,3,3-trimethyl-1,2,3,4-tetrahydroisoquinolin-7-yl)benzamide. $^1$H NMR (400 MHz, DMSO-d$_6$): δ 10.32 (s, 1H), 9.95 (s, 1H), 8.02-7.00 (m, 16H), 3.60 (m, 2H), 2.60 (m, 2H), 2.25 (s, 3H), 1.00 (s, 6H). MS (EI) for $C_{33}H_{31}N_5O$: 515.0 (MH$^+$).

Example 28

N-[2,5-bis(hydroxymethyl)phenyl]-4-[(4-phenylquinazolin-2-yl)amino]benzamide. $^1$H NMR (400 MHz, DMSO-d$_6$): δ 10.37 (s, 1H), 10.04 (s, 1H), 8.25-7.07 (m, 16H), 5.66 (t, 1H), 5.25 (t, 1H), 4.62 (d, 1H), 4.51 (d, 1H). MS (EI) for $C_{29}H_{24}N_4O_3$: 477.0 (MH$^+$).

Example 29

Scheme 3

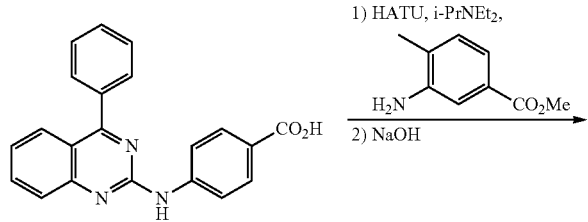

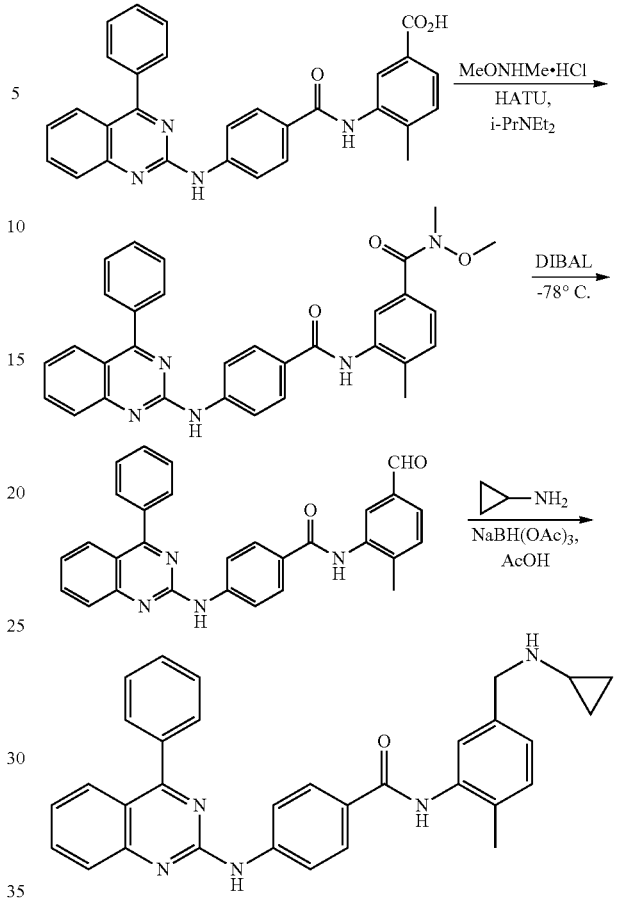

Example 29

4-methyl-3-[({4-[(4-phenylquinazolin-2-yl)amino]phenyl}carbonyl)amino]benzoic acid.

To a stirred solution of 4-(4-phenylquinazolin-2-ylamino)benzoic acid (1.02 g, 2.99 mmol), prepared as described in Example 10, methyl-amino-4-methylbenzooate (496 mg, 3.01 mmol), and Hunig's base (1.57 mL, 9.01 mmol) in dimethylformamide (15 mL) was added HATU (1.14 g, 3.00 mmol). The stirred mixture was heated to 60° C. overnight, then cooled to rt. The reaction was diluted with dichloromethane and washed with 2 N aqueous sodium hydroxide. The organic layer was then dried over sodium sulfate and concentrated on a rotary evaporator. The residue was sonicated with acetonitrile and filtered to give a light yellow solid that was suspended in a mixture of methanol (22 mL) and tetrahydrofuran (11 mL). A 1 N aqueous solution of sodium hydroxide (11 mL) was added and the stirred mixture was heated to 70° C. for 3 h. The reaction mixture was cooled to rt, concentrated on a rotary evaporator and redissolved in water, which was then made acidic with 1 N aqueous hydrochloric acid until the pH of the solution reached 5. The precipitate that formed was collected and dried in vacuo to afford 4-methyl-3-[({4-[(4-phenylquinazolin-2-yl)amino]phenyl}carbonyl)amino]benzoic acid (1.23 g, 86%) as a yellow solid. $^1$H NMR (400 MHz, DMSO-d$_6$): δ 10.34 (s, 1H), 9.82 (s, 1H), 8.18 (d, 2H), 8.00 (d, 2H), 7.95 (s, 1H), 7.90-7.78 (m, 5H), 7.72 (dd, 1H), 7.66-7.64 (m, 3H), 7.42 (ddd, 1H), 7.36 (d, 1H), 2.31 (s, 3H). MS (EI) for $C_{29}H_{22}N_4O_3$: 475.3 (MH$^+$).

N,4-dimethyl-N-(methyloxy)-3-[({4-[(4-phenylquinazolin-2-yl)amino]phenyl}carbonyl)amino]benzamide. To a mixture of 4-methyl-3-[({4-[(4-phenylquinazolin-2-yl)amino]phenyl}carbonyl)-amino]benzoic acid (1.10 g, 2.32 mmol), N,O-dimethylhydroxylamine hydrochloride (226 mg, 2.32 mmol), and Hunig's base (1.62 mL, 9.30 mmol) in dimethylformamide (15 mL) were added HATU (882 mg, 2.32 mmol) and the mixture was stirred at rt for 2 h. The mixture was diluted with dichloromethane and washed with 2 N sodium hydroxide. The separated organic layer was dried over sodium sulfate, concentrated on a rotary evaporator and the residue was purified by short flash column chromatography to give N,4-dimethyl-N-(methyloxy)-3-[({4-[(4-phenylquinazolin-2-yl)amino]phenyl}carbonyl)amino]benzamide (1.16 g, 97%) as a yellow solid. $^1$H NMR (400 MHz, DMSO-$d_6$): δ 10.34 (s, 1H), 9.80 (s, 1H), 8.19 (d, 2H), 8.00 (d, 2H), 7.90-7.79 (m, 5H), 7.67-7.63 (m, 4H), 7.44-7.40 (m, 2H), 7.35 (d, 1H), 3.59 (s, 3H), 3.27 (s, 3H), 2.31 (s, 3H). MS (EI) for $C_{31}H_{27}N_5O_3$: 518.3 (MH$^+$).

N-(5-formyl-2-methylphenyl)-4-[(4-phenylquinazolin-2-yl)amino]benzamide. A stirred solution of N,4-dimethyl-N-(methyloxy)-3-[({4-[(4-phenylquinazolin-2-yl)amino]phenyl}carbonyl)amino]benzamide (1.16 g, 2.24 mmol) in dichloromethane (150 mL) was cooled to −78° C. under nitrogen and a 1 M solution of diisobutylaluminum hydride in dichloromethane (6.7 mL, 6.7 mmol) was added dropwise over 30 min. The cooled solution was stirred for additional 1 h, then excess ethyl acetate was added to quench the reaction. The cooling bath was removed and the mixture was warmed to 0° C. using an ice bath. Methanol (2 mL) and then water (2 mL) was added carefully to the reaction mixture with vigorous stifling. A solution of 1 N hydrochloric acid (20 mL) was then added and the precipitates that formed were collected. The filtrates were separated and the aqueous layer was extracted with dichloromethane. The combined organic extracts were dried over sodium sulfate and concentrated on a rotary evaporator to give yellow solid that was combined with the previously collected precipitate, washed with water and dried under reduced pressure to give N-(5-formyl-2-methylphenyl)-4-[(4-phenylquinazolin-2-yl)amino]benzamide (791 mg, 77%). $^1$H NMR (400 MHz, CD$_3$OD): δ 9.98 (s, 1H), 8.23 (d, 1H), 8.06 (d, 2H), 7.98 (d, 2H), 7.95 (d, 1H), 7.85 (m, 3H), 7.78 (q, 3H), 7.03 (m, 1H), 7.76 (t, 3H), 7.46 (d, 1H), 2.43 (s, 3H). MS (EI) for $C_{29}H_{22}N_4O_2$: 459.0 (MH$^+$).

N-{5-[(cyclopropylamino)methyl]-2-methylphenyl}-4-[(4-phenylquinazolin-2-yl)amino]benzamide. A mixture of N-(5-formyl-2-methylphenyl)-4-(4-phenylquinazolin-2-ylamino)benzamide (250 mg, 0.546 mmol), cyclopropylamine (238 μL, 3.44 mmol), dichloromethane (10 m:), tetrahydrofuran (2 drops) and acetic acid (2 drops) was stirred at rt for 1 h. Sodium triacetoxyborohydride (275 mg, 1.30 mmol) was added and the mixture was stirred overnight. The crude reaction was diluted with dichloromethane, washed with saturated sodium bicarbonate and saturated sodium chloride and dried over sodium sulfate. The solution was concentrated on a rotary evaporator and purified by HPLC to give a yellow solid (143 mg, 52%). $^1$H NMR (400 MHz, DMSO-$d_6$): δ10.32 (s, 1H), 9.69 (s, 1H), 8.17-8.16 (d, 2H), 8.00-7.98 (s, 2H), 7.90-7.86 (m, 3H), 7.85-7.79 (m, 2H), 7.65-7.64 (m, 3H), 7.44-7.40 (t, 1H), 7.31 (s, 1H), 7.20-7.18 (d, 1H), 7.12-7.10 (d, 1H), 3.70 (s, 2H), 2.22 (s, 3H), 2.05 (m, 1H), 0.35-0.32 (m, 2H), 0.27-0.25 (m, 2H). MS (EI) for $C_{32}H_{29}N_5O$: 500.2 (MH$^+$).

Using the procedures described in Scheme 3, the following compounds were prepared.

Example 33

N-[2-methyl-5-(morpholin-4-ylmethyl)phenyl]-4-[(4-phenylquinazolin-2-yl)amino]benzamide. $^1$H NMR (400 MHz, DMSO-$d_6$): δ 10.32 (s, 1H), 9.70 (s, 1H), 8.18 (d, 2H), 8.00 (d, 2H), 7.88-7.79 (m, 5H), 7.65 (m, 3H), 7.44-7.40 (m, 1H), 7.31 (s, 1H), 7.23 (d, 1H), 7.08 (d, 1H), 3.57 (t, 4H), 3.44 (s, 2H), 2.36 (br s, 4H), 2.23 (s, 3H). MS (EI) for $C_{33}H_{31}N_5O_2$: 530.3 (MH$^+$).

Example 34

N-{2-methyl-5-[(4-methylpiperazin-1-yl)methyl]phenyl}-4-[(4-phenylquinazolin-2-yl)amino]benzamide. $^1$H NMR (400 MHz, DMSO-$d_6$): δ 10.32 (s, 1H), 9.70 (s, 1H), 8.18 (d, 2H), 8.00 (d, 2H), 7.90-7.79 (m, 5H), 7.65-7.63 (m, 3H), 7.43 (m, 1H), 7.29 (s, 1H), 7.22 (d, 1H), 7.08 (d, 1H), 3.45 (s, 2H), 2.34 (br s, 8H), 2.22 (s, 3H), 2.14 (s, 3H). MS (EI) for $C_{34}H_{34}N_6O$: 543.3 (MH$^+$).

Example 35

N-[2-methyl-5-(pyrrolidin-1-ylmethyl)phenyl]-4-[(4-phenylquinazolin-2-yl)amino]benzamide. $^1$H NMR (400 MHz, DMSO-$d_6$): δ 10.33 (s, 1H), 9.70 (s, 1H), 8.18 (d, 2H), 8.00 (d, 2H), 7.90-7.79 (m, 5H), 7.65-7.63 (m, 3H), 7.44-7.39 (m, 1H), 7.31 (d, 1H), 7.21 (d, 1H), 7.10 (d, 1H), 3.54 (s, 2H), 2.43 (t, 4H), 2.23 (s, 3H), 1.69 (m, 4H). MS (EI) for $C_{33}H_{31}N_5O$: 514.3 (MH$^+$).

Example 36

N-{3-[(dimethylamino)methyl]-2-methylphenyl}-4-[(4-phenylquinazolin-2-yl)amino]benzamide. $^1$H NMR (400 MHz, DMSO-$d_6$): δ 10.33 (s, 1H), 9.75 (s, 1H), 8.19 (d, 2H), 8.01 (d, 2H), 7.88-7.79 (m, 5H), 7.65-7.63 (m, 3H), 7.43-7.39 (m, 1H), 7.27 (d, 1H), 7.19-7.12 (m, 2H), 3.38 (s, 2H), 2.23 (s, 3H), 2.16 (s, 6H). MS (EI) for $C_{31}H_{29}N_5O$: 488.2 (MH$^+$).

Example 37

N-[2-(dimethylamino)ethyl]-4-methyl-3-[({4-[(4-phenylquinazolin-2-yl)amino]phenyl}carbonyl)amino]benzamide. $^1$H NMR (400 MHz, DMSO-$d_6$): δ 10.34 (s, 1H), 9.89 (s, 1H), 8.41 (t, 1H), 8.20 (d, 2H), 8.03 (d, 2H), 7.88-7.79 (m, 6H), 7.68-7.63 (m, 4H), 7.42 (m, 1H), 7.37 (d, 1H), 3.38 (m, 2H), 2.44 (t, 2H), 2.30 (s, 3H), 2.19 (s, 6H). MS (EI) for $C_{33}H_{32}N_6O_2$: 545.3 (MH$^+$).

Example 38

N-{3-[(dimethylamino)methyl]phenyl}-4-[(4-phenylquinazolin-2-yl)amino]benzamide. $^1$H NMR (400 MHz, DMSO-$d_6$): δ 10.34 (s, 1H), 10.08 (s, 1H), 8.18 (d, 2H), 8.00 (d, 2H), 7.91-7.62 (m, 9H), 7.42 (t, 1H), 7.29 (t, 1H), 7.00 (s, 1H), 3.38 (s, 2H), 2.17 (s, 6H), 2.16 (s, 6H). MS (EI) for $C_{30}H_{27}N_5O$: 475.0 (MH$^+$).

Example 32

N,N,4-trimethyl-3-[({4-[(4-phenylquinazolin-2-yl)amino]phenyl}carbonyl)amino]benzamide. $^1$H NMR (400 MHz, DMSO-$d_6$): δ 10.30 (s, 1H), 9.79 (s, 1H), 8.19 (d, 2H), 8.01 (d, 2H), 7.90-7.78 (m, 5H), 7.64 (m, 3H), 7.46 (d, 1H), 7.42 (m, 1H), 7.34 (d, 1H), 7.21 (m, 1H), 2.98 (s, 6H), 2.30 (s, 3H). MS (EI) for $C_{31}H_{27}N_5O_2$: 502.2 (MH$^+$).

Example 40

N-{5-[(diethylamino)methyl]-2-methylphenyl}-4-[(4-phenylquinazolin-2-yl)amino]benzamide. $^1$H-NMR (400

MHz, DMSO-d$_6$): δ 10.32 (s, 1H), 9.70 (s, 1H), 8.17 (d, 2H), 7.99 (d, 2H), 7.90-7.79 (m, 5H), 7.66-7.64 (m, 3H), 7.44-7.39 (m, 1H), 7.31 (s, 1H), 7.20 (d, 1H), 7.09 (dd, 1H), 3.50 (s, 2H), 2.46 (q, 4H), 2.20 (s, 3H), 0.98 (t, 6H). MS (EI) for C$_{33}$H$_{33}$N$_5$O: 516.4 (MH$^+$).

Example 41

N-[2-methyl-5-(piperidin-1-ylmethyl)phenyl]-4-[(4-phenylquinazolin-2-yl)amino]benzamide. $^1$H-NMR (400 MHz, DMSO-d$_6$): δ 10.32 (s, 1H), 9.70 (s, 1H), 8.17 (d, 2H), 7.99 (d, 2H), 7.90-7.79 (m, 5H), 7.66-7.64 (m, 3H), 7.44-7.40 (m, 1H), 7.28 (s, 1H), 7.20 (d, 1H), 7.07 (dd, 1H), 3.39 (s, 2H), 2.32 (bs, 4H), 2.22 (s, 3H), 1.50-1.47 (m, 4H), 1.39-1.38 (m, 2H). MS (EI) for C$_{34}$H$_{33}$N$_5$O: 528.4 (MH$^+$).

Example 42

N-(5-{[cyclohexyl(methyl)amino]methyl}-2-methylphenyl)-4-[(4-phenylquinazolin-2-yl)amino]benzamide. $^1$H-NMR (400 MHz, DMSO-d$_6$): δ 10.32 (s, 1H), 9.70 (s, 1H), 8.17 (d, 2H), 7.99 (d, 2H), 7.90-7.78 (m, 5H), 7.66-7.63 (m, 3H), 7.44-7.39 (m, 1H), 7.29 (s, 1H), 7.19 (d, 1H), 7.08 (dd, 1H), 3.51 (s, 2H), 2.43-2.37 (m, 1H), 2.22 (s, 3H), 2.10 (s, 3H), 1.80-1.73 (m, 4H), 1.59-1.56 (m, 1H), 1.31-1.14 (m, 4H), 1.12-1.06 (m, 1H). MS (EI) for C$_{36}$H$_{37}$N$_5$O: 556.4 (MH$^+$).

Example 43

4-methyl-N-(3-morpholin-4-ylpropyl)-3-[({4-[(4-phenylquinazolin-2-yl)amino]phenyl}carbonyl)amino]benzamide. $^1$H NMR (400 MHz, DMSO-d$_6$): δ 10.36 (s, 1H), 9.85 (s, 1H), 8.60 (s, 1H), 8.20 (d, 2H), 8.02 (d, 2H), 7.88-7.79 (m, 5H), 7.66 (m, 4H), 7.43 (m, 2H), 3.74 (m, 6H), 3.36 (m, 2H), 2.94 (m, 2H), 2.31 (s, 3H), 2.22 (s, 3H), 1.86 (m, 2H), 1.86 (m, 2H). MS (EI) for C$_{36}$H$_{36}$N$_6$O$_3$: 601.0 (MH$^+$).

Example 44

N-hydroxy-4-methyl-3-[({4-[(4-phenylquinazolin-2-yl)amino]phenyl}carbonyl)amino]benzamide. $^1$H NMR (400 MHz, DMSO-d$_6$): δ 11.22 (br s, 1H), 10.34 (s, 1H), 9.84 (s, 1H), 9.02 (br s, 1H), 8.19 (d, 2H), 8.00 (d, 2H), 7.91-7.78 (m, 5H), 7.66-7.64 (m, 3H), 7.56 (dd, 1H), 7.42 (ddd, 1H), 7.35 (d, 1H), 2.29 (s, 3H). MS (EI) for C$_{29}$H$_{23}$N$_5$O$_3$: 490.3 (MH$^+$).

Example 45

4-methyl-N-(2-morpholin-4-ylethyl)-3-[({4-[(4-phenylquinazolin-2-yl)amino]phenyl}carbonyl)amino]benzamide. $^1$H NMR (400 MHz, DMSO-d$_6$): δ 10.35 (br s, 1H), 9.86 (br s, 1H), 8.55 (s, 1H), 8.20 (d, 2H), 8.02 (d, 2H), 7.91-7.79 (m, 5H), 7.66 (m, 4H), 7.48 (m, 2H), 3.63 (m, 2H), 3.42 (m, 6H), 2.51 (m, 2H), 2.35 (br s, 4H), 1.91 (s, 3H). MS (EI) for C$_{35}$H$_{34}$N$_6$O$_3$: 587.0 (MH$^+$).

Example 46

N-[3-(dimethylamino)propyl]-4-methyl-3-[({4-[(4-phenylquinazolin-2-yl)amino]phenyl}carbonyl)amino]benzamide. $^1$H NMR (400 MHz, DMSO-d$_6$): δ 10.41 (br s, 1H), 9.91 (br s, 1H), 8.68 (s, 1H), 8.26 (d, 2H), 8.23 (d, 2H), 7.96-7.79 (m, 5H), 7.74 (m, 4H), 7.43 (m, 2H), 3.11 (m, 2H), 2.95 (m, 4H), 2.57 (m, 6H), 1.96 (m, 3H), 1.29 (br s, 2H). MS (EI) for C$_{34}$H$_{34}$N$_6$O$_2$: 559.0 (MH$^+$).

Example 47

N-{5-[(2,6-dimethylpiperidin-1-yl)methyl]-2-methylphenyl}-4-[(4-phenylquinazolin-2-yl)amino]benzamide. $^1$H NMR (400 MHz, DMSO-d$_6$): δ 10.32 (s, 1H), 9.75 (s, 1H), 8.20 (d, 2H), 8.00 (d, 2H), 8.00-7.78 (m, 4H), 7.62 (m, 3H), 7.42 (m, 1H), 7.38 (s, 1H), 7.18 (m, 2H), 3.70 (s, 2H), 2.20 (s, 2H), 1.60 (m, 2H), 1.25 (m, 2H), 1.00 (s, 4H). MS (EI) for C$_{36}$H$_{37}$N$_5$O: 556.3 (MH$^+$).

Example 48

N-{2-methyl-5-[(2,2,6,6-tetramethylpiperidin-1-yl)methyl]phenyl}-4-[(4-phenylquinazolin-2-yl)amino]benzamide. $^1$H NMR (400 MHz, DMSO-d$_6$): δ 10.33 (s, 1H), 9.68 (s, 1H), 8.18 (d, 2H), 8.16 (d, 2H), 7.88-7.79 (m, 5H), 7.64 (m, 3H), 7.42 (m, 2H), 7.23 (d, 1H), 7.13 (d, 1H), 3.76 (s, 2H), 2.19 (s, 3H), 1.54-1.47 (m, 6H), 0.98 (s, 12H). MS (EI) for C$_{38}$H$_{41}$N$_5$O: 584.4 (MH$^+$).

Example 49

N-(5-{[4-(cyclopropylmethyl)piperazin-1-yl]carbonyl}-2-methylphenyl)-4-[(4-phenylquinazolin-2-yl)amino]benzamide. $^1$H NMR (400 MHz, CD$_3$OD): δ 8.07 (m, 2H), 7.92 (d, 2H), 7.85 (m, 1H), 7.77-7.70 (m, 4H), 7.53 (m, 3H), 7.42 (s, 1H), 7.34 (d, 1H), 7.31 (m, 1H), 7.20 (m, 1H), 4.53 (s, 2H), 3.67 (br s, 4H), 2.79 (br s, 4H), 2.48 (br s, 2H), 2.30 (s, 3H), 0.89 (m, 1H), 0.55 (d, 2H), 0.16 (d, 2H). MS (EI) for C$_{37}$H$_{36}$N$_6$O$_2$: 597.3 (MH$^+$).

Example 50

N-[2-methyl-5-({4-[(1-methyl-1H-imidazol-2-yl)methyl]piperazin-1-yl}carbonyl)phenyl]-4-[(4-phenylquinazolin-2-yl)amino]benzamide. $^1$H NMR (400 MHz, CD$_3$OD): δ 8.13 (m, 2H), 8.00 (d, 2H), 7.95 (d, 2H), 7.84-7.79 (m, 4H), 7.63-7.60 (m, 4H), 7.46 (s, 1H), 7.46-7.38 (m, 2H), 7.27 (m, 1H), 6.87 (s, 1H), 4.61 (s, 2H), 3.74 (s, 5H), 3.56 (s, 2H), 2.50 (d, 4H), 2.37 (s, 3H). MS (EI) for C$_{38}$H$_{36}$N$_8$O$_2$: 635.3 (MH$^+$).

Example 51

N-(5-{[4-(furan-2-ylmethyl)piperazin-1-yl]carbonyl}-2-methylphenyl)-4-[(4-phenylquinazolin-2-yl)amino]benzamide. $^1$H NMR (400 MHz, CD$_3$OD): δ 8.14 (m, 2H), 8.00 (m, 3H), 7.80 (m, 4H), 7.62 (m, 4H), 7.52 (s, 1H), 7.45 (m, 2H), 7.30 (m, 1H), 6.60 (s, 1H), 6.50 (s, 1H), 4.20 (br s, 2H), 3.80 (br s, 4H), 3.02 (br s, 4H), 2.38 (s, 3H). MS (EI) for C$_{38}$H$_{34}$N$_6$O$_3$: 623.3 (MH$^+$).

Example 52

N-(2-methyl-5-{[4-(phenylmethyl)piperazin-1-yl]carbonyl}phenyl)-4-[(4-phenylquinazolin-2-yl)amino]benzamide. $^1$H NMR (400 MHz, DMSO-d$_6$): δ 10.34 (s, 1H), 9.77 (s, 1H), 8.19 (d, 2H), 8.00 (d, 2H), 7.90-7.79 (m, 5H), 7.64 (m, 3H), 7.40 (m, 2H), 7.28 (m, 5H), 7.26 (m, 1H), 7.17 (m, 1H), 3.51 (m, 6H), 2.40 (br s, 4H), 2.30 (s, 3H). MS (EI) for C$_{40}$H$_{36}$N$_6$O$_2$: 633.3 (MH$^+$).

Example 53

N-[5-(azepan-1-ylmethyl)-2-methylphenyl]-4-[(4-phenylquinazolin-2-yl)amino]benzamide. $^1$H NMR (400 MHz, CDCl$_3$): δ 8.04 (d, 2H), 8.00 (br s, 1H), 7.94 (m, 3H), 7.88 (d 1H), 7.85 (d, 1H), 7.77 (m, 3H), 7.60 (m, 3H), 7.35 (dt, 1H), 7.25 (d, 1H), 3.90 (s, 2H), 2.90 (t, 4H), 2.36 (s, 3H), 2.07 (s, 3H), 1.75 (m, 4H), 1.64 (m, 4H). MS (EI) for $C_{35}H_{35}N_5O$: 542.2 (MH$^+$).

Example 54

N-(2-methyl-5-{[(1,1,3,3-tetramethylbutyl)amino]methyl}phenyl)-4-[(4-phenylquinazolin-2-yl)amino]benzamide. $^1$H NMR (400 MHz, CDCl$_3$): δ 8.03 (d, 2H), 7.92 (m, 4H), 7.88 (d, 2H), 7.76 (m, 4H), 7.66 (m, 3H), 7.35 (t, 1H), 7.16 (q, 2H), 3.79 (s, 2H), 3.15 (br s, 2H), 2.33 (s, 3H), 1.55 (s, 2H), 1.27 (s, 6H), 1.05 (s, 9H). MS (EI) for $C_{37}H_{41}N_5O$: 572.2 (MH$^+$).

Example 55

N-(2-methyl-5-{[(phenylmethyl)amino]methyl}phenyl)-4-[(4-phenylquinazolin-2-yl)amino]benzamide. $^1$H NMR (400 MHz, CDCl$_3$): δ 8.02 (t, 3H), 7.93 (m, 4H), 7.78 (m, 4H), 7.68 (s, 1H), 7.59 (t, 3H), 7.34 (q, 5H), 7.22 (d, 1H), 7.12 (dd, 1H), 3.83 (d, 4H), 2.35 (s, 3H). MS (EI) for $C_{36}H_{31}N_5O$: 550.1 (MH$^+$).

Example 56

N-[5-(3,4-dihydroisoquinolin-2(1H)-ylmethyl)-2-methylphenyl]-4-[(4-phenylquinazolin-2-yl)amino]benzamide. $^1$H NMR (400 MHz, DMSO-d$_6$): δ 10.31 (s, 1H), 9.70 (s, 1H), 8.16 (d, 2H), 7.98 (d, 2H), 7.87-7.78 (m, 5H), 7.65-7.63 (m, 3H), 7.43-7.38 (m, 2H), 7.24 (d, 1H), 7.15 (d, 1H), 7.11-7.10 (m, 3H), 7.00 (d, 1H), 3.63 (s, 2H), 3.55 (s, 2H), 2.84-2.81 (m, 2H), 2.71-2.68 (m, 2H), 2.25 (s, 3H). MS (EI) for $C_{38}H_{33}N_5O$: 576.4 (MH$^+$).

Example 57

N-(2-methyl-5-{[methyl(phenylmethyl)amino]methyl}phenyl)-4-[(4-phenylquinazolin-2-yl)amino]benzamide. $^1$H NMR (400 MHz, DMSO-d$_6$): δ 10.32 (s, 1H), 9.71 (s, 1H), 8.17 (d, 2H), 8.00 (d, 2H), 7.90-7.85 (m, 3H), 7.83-7.79 (m, 2H), 7.66-7.63 (m, 3H), 7.42 (t, 1H), 7.38-7.32 (m, 5H), 7.27-7.23 (m, 2H), 7.14 (d, 1H), 3.51 (s, 2H), 3.48 (s, 2H), 2.23 (s, 3H), 2.04 (s, 3H). MS (EI) for $C_{37}H_{33}N_5O$: 564.2 (MH$^+$).

Example 58

N-(2-methyl-5-{[(1-methylethyl)amino]methyl}phenyl)-4-[(4-phenylquinazolin-2-yl)amino]benzamide. $^1$H NMR (400 MHz, DMSO-d$_6$): δ 10.32 (s, 1H), 9.69 (s, 1H), 8.17 (d, 2H), 7.99 (d, 2H), 7.90-7.75 (m, 5H), 7.67-7.60 (m, 3H), 7.45-7.40 (m, 1H), 7.33 (br s, 1H), 7.10 (d, 1H), 7.12 (d, 1H), 3.69 (s, 2H), 2.73 (m, 1H), 2.22 (s, 3H), 1.01 (d, 6H). MS (EI) for $C_{32}H_{31}N_5O$: 502.0 (MH$^+$).

Example 59

N-(5-{[bis(1-methylethyl)amino]methyl}-2-methylphenyl)-4-[(4-phenylquinazolin-2-yl)amino]benzamide. $^1$H NMR (400 MHz, DMSO-d$_6$): δ 10.32 (s, 1H), 9.67 (s, 1H), 8.16 (d, 2H), 7.99 (d, 2H), 7.90-7.70 (m, 5H), 7.70-7.60 (m, 3H), 7.49-7.40 (m, 1H), 7.32 (br s, 1H), 7.20-7.10 (m, 2H), 3.58 (s, 2H), 2.98 (m, 2H), 2.20 (s, 2H), 1.00 (d, 12H). MS (EI) for $C_{35}H_{37}N_5O$: 544.0 (MH$^+$).

Example 60

N-(5-{[ethyl(methyl)amino]methyl}-2-methylphenyl)-4-[(4-phenylquinazolin-2-yl)amino]benzamide. $^1$H NMR (400 MHz, DMSO-d$_6$): δ 10.30 (s, 1H), 9.70 (s, 1H), 8.16 (d, 2H), 8.00 (d, 2H), 7.88 (m, 2H), 7.85 (s, 1H), 7.80 (m, 2H), 7.64 (m, 3H), 7.42 (t, 1H), 7.30 (s, 1H), 7.20 (d, 2H), 3.40 (s, 2H), 2.40 (q, 2H), 2.22 (s, 3H), 1.02 (t, 3H). MS (EI) for $C_{32}H_{31}N_5O$: 502.2 (MH$^+$).

Example 61

N-(5-{[ethyl(1-methylethyl)amino]methyl}-2-methylphenyl)-4-[(4-phenylquinazolin-2-yl)amino]benzamide. $^1$H NMR (400 MHz, DMSO-d$_6$): δ 10.30 (s, 1H), 9.70 (s, 1H), 8.16 (d, 2H), 8.00 (d, 2H), 7.88 (m, 2H), 7.85 (s, 1H), 7.80 (m, 2H), 7.64 (m, 3H), 7.42 (t, 1H), 7.32 (s, 1H), 7.18 (d, 1H), 7.12 (d, 1H), 3.50 (s, 2H), 2.92 (q, 1H), 2.40 (q, 2H), 2.22 (s, 3H), 1.00 (m, 9H). MS (EI) for $C_{34}H_{35}N_5O$: 530.2 (MH$^+$).

Example 62

N-{5-[1-(dimethylamino)ethyl]-2-methylphenyl}-4-[(4-phenylquinazolin-2-yl)amino]benzamide. $^1$H NMR (400 MHz, DMSO-d$_6$): δ 10.30 (s, 1H), 9.97 (br s, 1H), 9.78 (s, 1H), 8.18 (d, 2H), 8.00 (d, 2H), 7.91-7.79 (m, 5H), 7.66-7.64 (m, 3H), 7.44-7.29 (m, 3H), 2.70-2.55 (m, 4H), 2.29 (s, 6H), 1.58 (s, 3H). MS (EI) for $C_{32}H_{31}N_5O$: 502.0 (MH$^+$).

Example 63

N-[2-methyl-5-(1-morpholin-4-ylethyl)phenyl]-4-[(4-phenylquinazolin-2-yl)amino]benzamide. $^1$H NMR (400 MHz, DMSO-d$_6$): δ 10.30 (s, 1H), 9.71 (s, 1H), 8.17 (d, 2H), 7.99 (d, 2H), 7.90-7.79 (m, 5H), 7.66-7.63 (m, 3H), 7.42 (dt, 1H), 7.29 (br s, 1H), 7.21 (d, 1H), 7.09 (d, 1H), 3.34-3.31 (m, 4H), 2.34-2.31 (m, 8H), 1.28 (s, 3H). MS (EI) for $C_{34}H_{33}N_5O_2$: 544.0 (MH$^+$).

Example 64

N-(2-methyl-5-{[(2-methylpropyl)amino]methyl}phenyl)-4-[(4-phenylquinazolin-2-yl)amino]benzamide. $^1$H NMR (400 MHz, DMSO-d$_6$): δ 10.30 (s, 1H), 9.70 (s, 1H), 8.16 (d, 2H), 7.98 (d, 2H), 7.88 (m, 2H), 7.85 (s, 1H), 7.80 (m, 2H), 7.64 (m, 3H), 7.42 (t, 1H), 7.32 (s, 1H), 7.20 (d, 1H), 7.12 (d, 1H), 3.66 (s, 2H), 2.30 (d, 2H), 2.22 (s, 3H), 1.68 (m, 1H), 0.88 (d, 6H). MS (EI) for $C_{33}H_{33}N_5O$: 516.2 (MH$^+$).

Example 65

N-(2-methyl-5-{[(1-phenylethyl)amino]methyl}phenyl)-4-[(4-phenylquinazolin-2-yl)amino]benzamide. $^1$H NMR (400 MHz, DMSO-d$_6$): δ 10.30 (s, 1H), 9.70 (s, 1H), 8.16 (d, 2H), 8.00 (d, 2H), 7.88 (m, 2H), 7.85 (s, 1H), 7.80 (m, 2H), 7.64 (m, 3H), 7.42 (t, 1H), 7.34 (m, 5H), 7.20 (m, 2H), 7.08 (d, 1H), 3.70 (q, 1H), 3.48 (q, 2H), 2.22 (s, 3H), 1.26 (d, 3H). MS (EI) for $C_{37}H_{33}N_5O$: 564.2 (MH$^+$).

Example 66

N-(5-{[(1,2-dimethylpropyl)amino]methyl}-2-methylphenyl)-4-[(4-phenylquinazolin-2-yl)amino]benzamide. $^1$H NMR (400 MHz, DMSO-d$_6$): δ 10.32 (s, 1H), 9.69 (s, 1H), 8.17 (d, 2H), 7.99 (d, 2H), 7.89-7.78 (m, 5H), 7.64 (m, 3H), 7.40 (t, 1H), 7.19 (s, 1H), 7.13 (dd, 2H), 3.63 (dd, 2H), 2.41 (m, 1H), 2.22 (s, 3H), 1.69 (m, 1H), 0.89 (d, 3H), 0.83 (t, 6H). MS (EI) for $C_{34}H_{35}N_5O$: 530.3 (MH$^+$).

Example 67

N-{5-[(4-ethylpiperazin-1-yl)carbonyl]-2-methylphenyl}-4-[(4-phenylquinazolin-2-yl)amino]benzamide. $^1$H NMR (400 MHz, CD$_3$OD): δ 8.06-7.93 (m, 4H), 7.82 (m, 5H), 7.64-7.49 (m, 5H), 7.36 (d, 1H), 7.27 (m, 1H), 3.52 (br s, 2H), 3.35 (br s, 2H), 3.20 (m, 2H), 3.18 (q, 2H), 3.06 (t, 2H), 2.30 (s, 3H), 1.29 (t, 3H). MS (EI) for C$_{35}$H$_{34}$N$_6$O$_2$: 571.2 (MH$^+$).

Example 68

N-[2-methyl-5-(piperazin-1-ylcarbonyl)phenyl]-4-[(4-phenylquinazolin-2-yl)amino]benzamide. $^1$H NMR (400 MHz, CD$_3$OD): δ 8.07 (m, 3H), 7.98 (m, 3H), 7.89 (m, 3H), 7.69-7.62 (m, 3H), 7.56 (t, 2H), 7.45 (d, 1H), 7.33 (d, 1H), 3.89 (br s, 4H), 3.30 (s, 4H), 2.38 (s, 3H). MS (EI) for C$_{33}$H$_{30}$N$_6$O$_2$: 543.3 (MH$^+$).

Example 69

N-(5-{[4-(2-hydroxyethyl)piperazin-1-yl]carbonyl}-2-methylphenyl)-4-[(4-phenylquinazolin-2-yl)amino]benzamide. $^1$H NMR (400 MHz, DMSO-d$_6$): δ 10.34 (s, 1H), 9.78 (s, 1H), 8.19 (d, 2H), 7.80 (d, 2H), 7.88-7.79 (m, 5H), 7.64 (m, 3H), 7.42 (m, 2H), 7.33 (d, 1H), 4.45 (t, 1H), 3.60 (br s, 2H), 3.51 (q, 2H), 3.40 (br s, 2H), 2.43 (m, 6H), 2.30 (s, 3H). MS (EI) for C$_{35}$H$_{34}$N$_6$O$_3$: 587.4 (MH$^+$).

Example 70

N-(5-{1-[ethyl(3,3,3-trifluoropropyl)amino]ethyl}-2-methylphenyl)-4-[(4-phenylquinazolin-2-yl)amino]benzamide. $^1$H NMR (400 MHz, CD$_3$OD): δ 8.14 (m, 2H), 8.00 (d, 2H), 7.93 (d, 1H), 7.85-7.78 (m, 4H), 7.61 (m, 3H), 7.39-7.35 (m, 2H), 7.27-7.20 (m, 2H), 3.84 (q, 1H), 2.82-2.53 (m, 4H), 2.51 (m, 5H), 1.38 (d, 3H), 1.04 (t, 3H). MS (EI) for C$_{35}$H$_{34}$F$_3$N$_5$O: 598.3 (MH$^+$).

Example 71

N-(5-{1-[bis(3,3,3-trifluoropropyl)amino]ethyl}-2-methylphenyl)-4-[(4-phenylquinazolin-2-yl)amino]benzamide. $^1$H NMR (400 MHz, DMSO-d$_6$): δ 10.32 (s, 1H), 9.69 (s, 1H), 8.17 (d, 2H), 7.99 (d, 2H), 7.90-7.79 (m, 5H), 7.66-7.63 (m, 3H), 7.44-7.39 (m, 1H), 7.36 (s, 1H), 7.23 (d, 1H), 7.15 (d, 1H), 3.89 (q, 1H), 2.76-2.71 (m, 2H), 2.64-2.58 (m, 2H), 2.46-2.38 (m, 4H), 2.23 (s, 3H), 1.30 (d, 3H). MS (EI) for C$_{36}$H$_{33}$F$_6$N$_5$O: 666.3 (MH$^+$).

Example 72

N-(2-methyl-5-{[methyl(1-methylethyl)amino]methyl}phenyl)-4-[(4-phenylquinazolin-2-yl)amino]benzamide. $^1$H NMR (400 MHz, CDCl$_3$): δ 8.10 (d, 2H), 7.94 (m, 5H), 7.76 (m, 3H), 7.65 (d, 2H), 7.54 (m, 3H), 7.34 (br t, 1H), 7.18 (d, 1H), 7.12 (br d, 1H), 3.51 (s, 2H), 2.82 (m, 1H), 2.62 (s, 3H), 2.28 (s, 3H), 1.21 (d, 6H). MS (EI) for C$_{33}$H$_{33}$N$_5$O: 516.4 (MH$^+$).

Example 73

N-[5-(3,4-dihydroquinolin-1(2H)-ylmethyl)-2-methylphenyl]-4-[(4-phenylquinazolin-2-yl)amino]benzamide. $^1$H NMR (400 MHz, CDCl$_3$): δ 8.23-7.70 (m, 13H), 7.58 (m, 3H), 7.35 (t, 1H), 7.18 (d, 1H), 7.30-6.93 (m, 2H), 6.58-6.49 (m, 2H), 4.50 (s, 2H), 3.40 (t, 2H), 2.82 (t, 2H), 2.35 (s, 3H), 2.05 (m, 2H). MS (D) for C$_{38}$H$_{33}$N$_5$O: 576.0 (MH$^+$).

Example 74

N-(2-methyl-5-{[(1-methylpropyl)amino]methyl}phenyl)-4-[(4-phenylquinazolin-2-yl)amino]benzamide. $^1$H NMR (400 MHz, CDCl$_3$): δ 7.92-7.72 (m, 12H), 7.61 (br s, 2H), 7.35 (m, 2H), 7.18 (m, 2H), 4.51 (br s, 1H), 4.18 (m, 1H), 3.82 (s, 2H), 2.58 (d, 2H), 2.38 (s, 3H), 1.81 (m, 1H), 1.22 (m, 1H), 0.92 (d, 5H). MS (EI) for C$_{33}$H$_{33}$N$_5$O: 516.4 (MH$^+$).

Example 75

N-[5-({4-[(4-fluorophenyl)methyl]piperazin-1-yl}carbonyl)-2-methylphenyl]-4-[(4-phenylquinazolin-2-yl)amino]benzamide. $^1$H NMR (400 MHz, DMSO-d$_6$): δ 10.34 (s, 1H), 9.77 (s, 1H), 8.19 (d, 2H), 8.00 (d, 2H), 7.90-7.79 (m, 5H), 7.64 (m, 3H), 7.44-7.33 (m, 5H), 7.17 (q, 3H), 3.61 (br s, 2H), 3.49 (s, 2H), 3.39 (br s, 4H), 2.39 (br s, 4H), 2.29 (s, 3H). MS (EI) for C$_{40}$H$_{35}$FN$_6$O$_2$: 651.3 (MH$^+$).

Example 76

N-(2-methyl-5-{[4-(pyridin-3-ylmethyl)piperazin-1-yl]carbonyl}phenyl)-4-[(4-phenylquinazolin-2-yl)amino]benzamide. $^1$H NMR (400 MHz, CD$_3$OD): δ 8.51 (s, 1H), 8.44 (d, 1H), 8.15 (d, 2H), 8.00-7.93 (q, 3H), 7.86-7.79 (m, 5H), 7.60 (t, 3H), 7.46 (s, 1H), 7.43-7.35 (m, 3H), 7.27 (d, 1H), 3.77 (s, 2H), 3.62 (s, 2H), 3.57 (s, 2H), 2.56 (s, 2H), 2.47 (s, 2H), 2.37 (s, 3H). MS (EI) for C$_{39}$H$_{35}$N$_7$O$_2$: 634.3 (MH$^+$).

Example 77

N-(2-methyl-5-{[4-(pyridin-4-ylmethyl)piperazin-1-yl]carbonyl}phenyl)-4-[(4-phenylquinazolin-2-yl)amino]benzamide. $^1$H NMR (400 MHz, CD$_3$OD): δ 8.85 (d, 2H), 8.08 (m, 5H), 7.98 (m, 3H), 7.89 (m, 3H), 7.69-7.62 (m, 3H), 7.56 (m, 2H), 7.44 (d, 1H), 7.33 (m, 1H), 4.29 (s, 2H), 3.85 (br s, 4H), 3.04 (br s, 4H), 2.38 (s, 3H). MS (EI) for C$_{39}$H$_{35}$N$_7$O$_2$: 634.3 (MH$^+$).

Example 78

1-({4-methyl-3-[({4-[(4-phenylquinazolin-2-yl)amino]phenyl}carbonyl)amino]phenyl}methyl)azetidine-3-carboxylic acid. $^1$H NMR (400 MHz, DMSO-d$_6$): δ 12.50 (br s, 1H), 10.32 (s, 1H), 9.68 (s, 1H), 8.16 (d, 2H), 7.98 (d, 2H), 7.89-7.75 (m, 5H), 7.70-7.60 (m, 3H), 7.45-7.35 (m, 1H), 7.27 (br s, 1H), 7.19 (d, 1H), 7.15 (dd, 1H), 3.52 (s, 2H), 3.40-3.35 (m, 1H), 3.20-3.15 (m, 4H), 2.22 (s, 3H). MS (EI) for C$_{33}$H$_{29}$N$_5$O$_3$: 544.0 (MH$^+$).

Example 79

N-(5-{[(2-hydroxyethyl)amino]methyl}-2-methylphenyl)-4-[(4-phenylquinazolin-2-yl)amino]benzamide. $^1$H NMR (400 MHz, DMSO-d$_6$): δ 10.32 (s, 1H), 9.69 (s, 1H), 8.17 (d, 2H), 7.99 (d, 2H), 7.90-7.75 (m, 5H), 7.70-7.60 (m, 3H), 7.49-7.40 (m, 1H), 7.33 (s, 1H), 7.20 (d, 1H), 7.10 (d, 1H), 4.52 (br t, 1H), 3.71 (s, 2H), 3.48 (m, 2H), 2.59 (t, 2H), 2.22 (s, 3H). MS (D) for C$_{31}$H$_{29}$N$_5$O$_2$: 504.0 (MH$^+$).

Example 80

N-(5-{[(2-hydroxyethyl)(methyl)amino]methyl}-2-methylphenyl)-4-[(4-phenylquinazolin-2-yl)amino]benzamide. $^1$H NMR (400 MHz, DMSO-d$_6$): δ 10.32 (s, 1H), 9.69 (s, 1H), 8.16 (d, 2H), 7.99 (d, 2H), 7.90-7.75 (m, 5H), 7.70-7.60 (m, 3H), 7.49-7.40 (m, 1H), 7.31 (br s, 1H), 7.20 (d, 1H), 7.10 (d, 1H), 4.40 (br t, 1H), 3.55-3.40 (m, 4H), 2.44 (t, 2H), 2.22 (s, 3H), 2.16 (s, 3H). MS (D) for C$_{32}$H$_{31}$N$_5$O$_2$: 518.0 (MH$^+$).

Example 81

4-methyl-N-(8-methyl-8-azabicyclo[3.2.1]oct-3-yl)-3-[({4-[(4-phenylquinazolin-2-yl)amino]phenyl}carbonyl)amino]benzamide. $^1$H NMR (400 MHz, DMSO-d$_6$): δ 10.31 (br s, 1H), 9.83 (br s, 1H), 8.17 (s, 1H), 8.14 (d, 2H), 7.99 (d, 2H), 7.82-7.76 (m, 5H), 7.62 (m, 4H), 7.40 (m, 2H), 4.18 (m, 2H), 2.30 (m, 4H), 2.26 (m, 4H), 1.73 (m, 6H), 1.21 (br s, 2H). MS (D) for $C_{37}H_{36}N_6O_2$: 597.0 (MH$^+$).

Example 82

N-(1,1-dimethyl-2-morpholin-4-ylethyl)-4-methyl-3-[({4-[(4-phenylquinazolin-2-yl)amino]phenyl}carbonyl)amino]benzamide. $^1$H NMR (400 MHz, DMSO-d$_6$): δ 10.30 (br s, 1H), 9.81 (br s, 1H), 8.16 (d, 2H), 7.98 (d, 2H), 7.85-7.78 (m, 5H), 7.62 (m, 4H), 7.57 (s, 1H), 7.32 (m, 2H), 3.22 (br s, 2H), 2.62 (br s, 2H), 2.26 (s, 2H), 1.31 (s, 3H). MS (D) for $C_{37}H_{38}N_6O_3$: 615.0 (MH$^+$).

Example 83

N-(2-hydroxyethyl)-4-methyl-3-[({4-[(4-phenylquinazolin-2-yl)amino]phenyl}carbonyl)amino]benzamide. $^1$H NMR (400 MHz, DMSO-d$_6$): δ 10.34 (br s, 1H), 9.84 (br s, 1H), 8.42 (s, 1H), 8.19 (d, 2H), 8.00 (d, 2H), 7.88-7.79 (m, 5H), 7.68-7.63 (m, 4H), 7.37 (m, 2H), 4.74 (m, 1H), 3.50 (m, 2H), 3.33 (m, 2H), 2.30 (s, 3H). MS (D) for $C_{31}H_{27}N_5O_3$: 518.0 (MH$^+$).

Example 84

N-[5-(2,5-diazabicyclo[2.2.1]hept-2-ylcarbonyl)-2-methylphenyl]-4-[(4-phenylquinazolin-2-yl)amino]benzamide. $^1$H NMR (400 MHz, DMSO-d$_6$): δ 10.34 (br s, 1H), 9.78 (br s, 1H), 8.19 (d, 2H), 8.00 (d, 2H), 7.90-7.79 (m, 5H), 7.65 (m, 4H), 7.54 (s, 1H), 7.40 (m, 2H), 4.64 (s, 1H), 4.31 (s, 2H), 2.31 (m, 2H), 1.91 (s, 2H), 1.75 (m, 1H), 1.59 (m, 1H), 1.23 (br s, 1H). MS (D) for $C_{34}H_{30}N_6O_2$: 555.0 (MH$^+$).

Example 85

N-{5-[(ethylamino)methyl]-2-methylphenyl}-4-[(4-phenylquinazolin-2-yl)amino]benzamide. $^1$H NMR (400 MHz, CDCl$_3$): δ 8.20-7.82 (m, 8H), 7.80-7.71 (m, 4H), 7.58 (m, 3H), 7.34 (d, 1H), 7.18 (d, 1H), 7.12 (d, 1H), 3.80 (s, 2H), 2.90 (br s, 1H), 2.72 (q, 2H), 2.34 (s, 3H), 1.18 (t, 3H). MS (D) for $C_{31}H_{29}N_5O$: 488.2 (MH$^+$).

Example 86

N-{2-methyl-5-[(propylamino)methyl]phenyl}-4-[(4-phenylquinazolin-2-yl)amino]benzamide. $^1$H NMR (400 MHz, CDCl$_3$): δ 8.02-7.89 (m, 8H), 7.80-7.72 (m, 4H), 7.62 (br s, 3H), 7.32 (t, 1H), 7.18 (d, 1H), 7.16 (d, 1H), 3.81 (s, 2H), 2.62 (t, 2H), 2.25 (s, 3H), 1.58 (m, 2H), 0.94 (t, 3H). MS (EI) for $C_{32}H_{31}N_5O$: 502.2 (MH$^+$).

Example 87

N-{2-methyl-5-[(E)-(morpholin-4-ylimino)methyl]phenyl}-4-[(4-phenylquinazolin-2-yl)amino]benzamide. $^1$H NMR (400 MHz, DMSO-d$_6$): δ 10.33 (s, 1H), 9.75 (s, 1H), 8.18-8.16 (d, 2H), 8.01-7.99 (d, 2H), 7.90-7.79 (m, 5H), 7.70 (s, 1H), 7.66-7.63 (m, 4H), 7.44-7.40 (t, 1H), 7.38-7.35 (d, 1H), 7.28-7.25 (d, 1H), 3.78-3.76 (t, 4H), 3.10-3.08 (t, 4H), 2.25 (s, 3H). MS (EI) for $C_{33}H_{30}N_6O_2$: 543.4 (MH$^+$).

Example 88

N-(5-{[(1,3-dimethylbutyl)amino]methyl}-2-methylphenyl)-4-[(4-phenylquinazolin-2-yl)amino]benzamide. $^1$H NMR (400 MHz, DMSO-d$_6$): δ 10.32 (s, 1H), 9.68 (s, 1H), 8.17 (d, 2H), 7.98 (d, 2H), 7.90-7.77 (m, 5H), 7.65 (m, 3H), 7.40 (dt, 1H), 7.32 (s, 1H), 7.15 (dd, 2H), 3.68 (dd, 2H), 2.60 (q, 1H), 2.22 (s, 3H), 1.69 (m, 1H), 1.33 (m, 1H), 1.08 (m 1H), 0.98 (d, 3H), 0.82 (d, 6H). MS (EI) for $C_{35}H_{37}N_5O$: 544.3 (MH$^+$).

Example 89

N-[2-methyl-3-(morpholin-4-ylmethyl)phenyl]-4-[(4-phenylquinazolin-2-yl)amino]benzamide. $^1$H NMR (400 MHz, DMSO-d$_6$): δ 10.32 (s, 1H), 9.75 (s, 1H), 8.17 (d, 2H), 7.99 (d, 2H), 7.90-7.79 (m, 5H), 7.64 (m, 3H), 7.41 (dt, 1H), 7.26 (m, 1H), 7.16 (m, 2H), 3.56 (m, 4H), 3.47 (s, 2H), 2.39 (m, 4H), 2.24 (s, 3H). MS (EI) for $C_{33}H_{31}N_5O_2$: 530.3 (MH$^+$).

Example 90

N-[5-({[2-hydroxy-1-(hydroxymethyl)ethyl]amino}methyl)-2-methylphenyl]-4-[(4-phenylquinazolin-2-yl)amino]benzamide. $^1$H NMR (400 MHz, DMSO-d$_6$): δ 10.32 (s, 1H), 9.70 (s, 1H), 8.16 (d, 2H), 7.99 (d, 2H), 7.90-7.75 (m, 5H), 7.70-7.60 (m, 3H), 7.43 (br t, 1H), 7.34 (br s, 1H), 7.20 (d, 1H), 7.12 (d, 1H), 4.45 (m, 2H), 3.76 (s, 2H), 3.45-3.30 (m, 4H), 2.57 (m, 1H), 2.22 (s, 3H). MS (EI) for $C_{32}H_{31}N_5O_3$: 534.0 (MH$^+$).

Example 91

N-[2-methyl-5-({[2-(methyloxy)ethyl]amino}methyl)phenyl]-4-[(4-phenylquinazolin-2-yl)amino]benzamide. $^1$H NMR (400 MHz, DMSO-d$_6$): δ 10.32 (s, 1H), 9.76 (s, 1H), 8.18 (d, 2H), 7.99 (d, 2H), 7.90-7.75 (m, 5H), 7.65-7.60 (m, 3H), 7.52 (br s, 1H), 7.42 (br t, 1H), 7.20 (d, 1H), 7.10 (d, 1H), 4.02 (s, 2H), 3.55 (t, 2H), 3.29 (s, 3H), 2.97 (br t, 2H), 2.27 (s, 3H). MS (EI) for $C_{32}H_{31}N_5O_2$: 518.0 (MH$^+$).

Example 92

N-(5-{[(2-hydroxy-1,1-dimethylethyl)amino]methyl}-2-methylphenyl)-4-[(4-phenylquinazolin-2-yl)amino]benzamide. $^1$H NMR (400 MHz, DMSO-d$_6$): δ 10.32 (s, 1H), 9.70 (s, 1H), 8.16 (d, 2H), 7.99 (d, 2H), 7.90-7.75 (m, 5H), 7.66-7.60 (m, 3H), 7.43-7.39 (m, 1H), 7.33 (br s, 1H), 7.18 (d, 1H), 7.11 (d, 1H), 4.58 (br t, 1H), 3.61 (s, 2H), 3.24 (d, 2H), 2.21 (s, 3H), 1.00 (s, 6H). MS (D) for $C_{33}H_{33}N_5O_2$: 532.0 (MH$^+$).

Example 93

N-{5-[(4-acetylpiperazin-1-yl)methyl]-2-methylphenyl}-4-[(4-phenylquinazolin-2-yl)amino]benzamide. $^1$H NMR (400 MHz, DMSO-d$_6$): δ 10.32 (s, 1H), 9.70 (s, 1H), 8.17 (d, 2H), 7.99 (d, 2H), 7.84 (m, 5H), 7.65 (m, 3H), 7.42 (m, 1H), 7.32 (s, 1H), 7.23 (d, 1H), 7.09 (m, 1H), 3.47 (s, 2H), 3.42 (m, 4H), 2.38 (m, 2H), 2.31 (m, 2H), 2.23 (s, 3H), 1.97 (s, 3H). MS (D) for $C_{35}H_{34}N_6O_2$: 571.3 (MH$^+$).

Example 94

N-(5-{[4-(2,2-dimethylpropanoyl)piperazin-1-yl]methyl}-2-methylphenyl)-4-[(4-phenylquinazolin-2-yl)amino]

benzamide. ¹H NMR (400 MHz, DMSO-d₆): δ 10.33 (s, 1H), 9.72 (s, 1H), 8.17 (d, 2H), 7.99 (d, 2H), 7.84 (m, 5H), 7.64 (m, 3H), 7.42 (m, 1H), 7.32 (s, 1H), 7.23 (d, 1H), 7.10 (m, 1H), 3.53 (m, 4H), 3.46 (s, 2H), 2.35 (m, 4H), 2.23 (s, 3H), 1.17 (s, 9H). MS (D) for $C_{38}H_{40}N_6O_2$: 613.3 (MH⁺).

Example 95

N-(5-{[bis(2-hydroxyethyl)amino]methyl}-2-methylphenyl)-4-[(4-phenylquinazolin-2-yl)amino]benzamide. ¹H NMR (400 MHz, DMSO-d₆): δ 10.30 (s, 1H), 9.70 (s, 1H), 8.16 (d, 2H), 8.00 (d, 2H), 7.88 (m, 2H), 7.85 (s, 1H), 7.80 (m, 2H), 7.64 (m, 3H), 7.42 (t, 1H), 7.22 (s, 2H), 4.16 (d, 2H), 3.68 (s, 2H), 3.05 (q, 4H), 2.23 (s, 3H), 1.20 (t, 4H). MS (D) for $C_{33}H_{33}N_5O_3$: 548.2 (MH⁺).

Example 96

N-[5-({bis[2-(methyloxy)ethyl]amino}methyl)-2-methylphenyl]-4-[(4-phenylquinazolin-2-yl)amino]benzamide. ¹H NMR (400 MHz, DMSO-d₆): δ 10.30 (s, 1H), 9.70 (s, 1H), 8.16 (d, 2H), 8.00 (d, 2H), 7.88 (m, 2H), 7.85 (s, 1H), 7.80 (m, 2H), 7.64 (m, 3H), 7.42 (t, 1H), 7.30 (s, 1H), 7.20 (d, 1H), 7.10 (d, 1H), 3.62 (s, 2H), 3.42 (t, 4H), 3.20 (s, 6H), 2.64 (t, 4H), 2.22 (s, 3H). MS (D) for $C_{35}H_{37}N_5O_3$: 576.2 (MH⁺).

Example 97

N-(5-{[4-(cyclopentylcarbonyl)piperazin-1-yl]methyl}-2-methylphenyl)-4-[(4-phenylquinazolin-2-yl)amino]benzamide. ¹H NMR (400 MHz, DMSO-d₆): δ 10.32 (s, 1H), 9.70 (s, 1H), 8.17 (d, 2H), 7.99 (d, 2H), 7.86 (m, 3H), 7.80 (m, 2H), 7.64 (m, 3H), 7.42 (m, 1H), 7.32 (s, 1H), 7.23 (d, 1H), 7.10 (m, 1H), 3.47 (m, 6H), 2.94 (m, 1H), 2.34 (m, 4H), 2.24 (s, 3H), 1.78-1.45 (m, 8H). MS (D) for $C_{39}H_{40}H_6O_2$: 625.4 (MH⁺).

Example 98

N-(2-methyl-5-{[4-(phenylcarbonyl)piperazin-1-yl]methyl}phenyl)-4-[(4-phenylquinazolin-2-yl)amino]benzamide. ¹H NMR (400 MHz, DMSO-d₆): δ 10.32 (s, 1H), 9.70 (s, 1H), 8.17 (d, 2H), 7.99 (d, 2H), 7.87 (m, 3H), 7.80 (m, 2H), 7.64 (m, 3H), 7.44 (m, 4H), 7.38 (m, 2H), 7.33 (m, 1H), 7.22 (m, 1H), 7.10 (m, 1H), 3.62 (m, 2H), 3.50 (s, 2H), 3.33 (br s, 2H), 2.40 (m, 4H), 2.23 (s, 3H). MS (EI) for $C_{40}H_{36}N_6O_2$: 633.3 (MH⁺).

Example 99

N-[2-methyl-5-({4-[(methyloxy)acetyl]piperazin-1-yl}methyl)phenyl]-4-[(4-phenylquinazolin-2-yl)amino]benzamide. ¹H NMR (400 MHz, DMSO-d₆): δ 10.32 (s, 1H), 9.70 (s, 1H), 8.17 (d, 2H), 7.99 (d, 2H), 7.87 (m, 3H), 7.80 (m, 2H), 7.64 (m, 3H), 7.42 (m, 1H), 7.32 (s, 1H), 7.23 (d, 1H), 7.09 (m, 1H), 4.06 (s, 2H), 3.47 (s, 2H), 3.44 (m, 2H), 3.37 (m, 2H), 3.27 (d, 3H), 2.35 (m, 4H), 2.24 (s, 3H). MS (EI) for $C_{36}H_{36}N_6O_3$: 601.3 (MH⁺).

Example 100

N-(5-{[ethyl(2,2,2-trifluoroethyl)amino]methyl}-2-methylphenyl)-4-[(4-phenylquinazolin-2-yl)amino]benzamide. ¹H NMR (400 MHz, DMSO-d₆): δ 10.30 (s, 1H), 9.74 (s, 1H), 8.16 (d, 2H), 7.99 (d, 2H), 7.90-7.75 (m, 5H), 7.80-7.60 (m, 3H), 7.42 (br t, 1H), 7.30 (br s, 1H), 7.24 (d, 1H), 7.13 (d, 1H), 3.74 (s, 2H), 3.26 (q, 2H), 2.50 (q, 2H), 2.22 (s, 3H), 0.99 (t, 3H). MS (EI) for $C_{33}H_{30}F_3N_5O$: 570.0 (MH⁺).

Example 101

N-[5-(7-azabicyclo[2.2.1]hept-7-ylmethyl)-2-methylphenyl]-4-[(4-phenylquinazolin-2-yl)amino]benzamide. ¹H NMR (400 MHz, DMSO-d₆): δ 10.32 (s, 1H), 9.69 (s, 1H), 8.16 (d, 2H), 7.99 (d, 2H), 7.80-7.75 (m, 5H), 7.70-7.60 (m, 3H), 7.50-7.35 (m, 1H), 7.33 (br s, 1H), 7.19 (d, 1H), 7.12 (d, 1H), 3.44 (s, 2H), 3.20-3.16 (m, 2H), 2.22 (s, 3H), 1.75-1.62 (m, 4H), 1.28-1.20 (m, 4H). MS (EI) for $C_{35}H_{33}N_5O$: 540.0 (MH⁺).

Example 102

N-(5-{[ethyl(2-hydroxyethyl)amino]methyl}-2-methylphenyl)-4-[(4-phenylquinazolin-2-yl)amino]benzamide. ¹H NMR (400 MHz, DMSO-d₆): δ 10.32 (s, 1H), 9.70 (s, 1H), 8.17 (d, 2H), 7.99 (d, 2H), 7.90-7.70 (m, 5H), 7.65-7.63 (m, 3H), 7.42 (m, 1H), 7.31 (s, 1H), 7.20 (d, 1H), 7.10 (d, 1H), 4.35 (br t, 1H), 3.55 (s, 2H), 3.48 (q, 2H), 2.55-2.45 (m, 4H), 2.22 (s, 3H), 0.98 (t, 3H). MS (EI) for $C_{33}H_{33}N_5O_2$: 532.0 (MH⁺).

Example 103

N-[5-(aminomethyl)-2-methylphenyl]-4-[(4-phenylquinazolin-2-yl)amino]benzamide. ¹H NMR (400 MHz, DMSO-d₆): δ 10.32 (s, 1H), 9.71 (s, 1H), 8.17 (d, 2H), 7.99 (d, 2H), 7.90-7.75 (m, 5H), 7.65-7.60 (m, 3H), 7.43 (m, 1H), 7.37 (s, 1H), 7.20 (d, 1H), 7.10 (d, 1H), 4.20 (br s, 2H), 3.79 (s, 2H), 2.23 (s, 3H). MS (EI) for $C_{29}H_{25}N_5O$: 460.0 (MH⁺).

Example 104

N-{4-[(dimethylamino)methyl]-2-methylphenyl}-4-[(4-phenylquinazolin-2-yl)amino]benzamide. ¹H NMR (400 MHz, DMSO-d₆): δ 10.32 (s, 1H), 9.65 (s, 1H), 8.16 (d, 2H), 7.99 (d, 2H), 7.90-7.75 (m, 5H), 7.65-7.43 (m, 3H), 7.42 (m, 1H), 7.31 (d, 1H), 7.18 (s, 1H), 7.12 (d, 1H), 3.35 (s, 2H), 2.24 (s, 3H), 2.15 (s, 6H). MS (EI) for $C_{31}H_{29}N_5O$: 488.0 (MH⁺).

Example 105

N-(4-{[ethyl(1-methylethyl)amino]methyl}-2-methylphenyl)-4-[(4-phenylquinazolin-2-yl)amino]benzamide. ¹H NMR (400 MHz, DMSO-d₆): δ 10.32 (s, 1H), 9.64 (s, 1H), 8.17 (d, 2H), 7.98 (d, 2H), 7.90-7.78 (m, 5H), 7.64 (m, 3H), 6.92 (m, 1H), 6.78 (d, 1H), 6.70 (m, 2H), 3.48 (s, 2H), 2.93 (m, 1H), 2.42 (q, 2H), 2.24 (s, 3H), 1.00 (d, 6H), 0.97 (t, 3H). MS (EI) for $C_{34}H_{35}N_5O$: 530.3 (MH⁺).

Example 106

N-(2-methyl-4-{[methyl(phenylmethyl)amino]methyl}phenyl)-4-[(4-phenylquinazolin-2-yl)amino]benzamide. ¹H NMR (400 MHz, DMSO-d₆): δ 10.32 (s, 1H), 9.66 (s, 1H), 8.17 (d, 2H), 7.98 (d, 2H), 7.85-7.78 (m, 5H), 7.64 (m, 3H), 7.36-7.32 (m, 6H), 6.24 (m, 3H), 3.51 (s, 2H), 3.48 (s, 2H), 2.25 (s, 3H), 2.09 (s, 3H). MS (EI) for $C_{37}H_{33}N_5O$: 564.3 (MH⁺).

Example 107

N-{4-[(diethylamino)methyl]-2-methylphenyl}-4-[(4-phenylquinazolin-2-yl)amino]benzamide. ¹H NMR (400

MHz, DMSO-$d_6$): δ 10.32 (s, 1H), 9.65 (s, 1H), 8.18-8.16 (d, 2H), 7.99-7.97 (d, 2H), 7.88-7.79 (m, 5H), 7.65-7.63 (m, 3H), 7.44-7.39 (t, 1H), 7.30-7.28 (d, 1H), 7.20 (s, 1H), 7.16-7.14 (d, 1H), 3.50 (s, 2H), 2.46 (q, 4H), 2.24 (s, 3H), 1.00 (t, 6H). MS (EI) for $C_{33}H_{33}N_5O$: 516.4 (MH$^+$).

Example 108

N-[2-methyl-4-(morpholin-4-ylmethyl)phenyl]-4-[(4-phenylquinazolin-2-yl)amino]benzamide. $^1$H NMR (400 MHz, DMSO-$d_6$): δ 10.32 (s, 1H), 9.65 (s, 1H), 8.18-8.16 (d, 2H), 7.99-7.97 (d, 2H), 7.90-7.79 (m, 5H), 7.65-7.64 (m, 3H), 7.44-7.40 (t, 1H), 7.33-7.31 (d, 1H), 7.20 (s, 1H), 7.16-7.14 (d, 1H), 3.60-3.57 (t, 4H), 3.43 (s, 2H), 2.36 (m, 4H), 2.24 (s, 3H). MS (EI) for $C_{33}H_{31}N_5O_2$: 530.4 (MH$^+$).

Example 109

N-(5-{[4-(cyclopropylcarbonyl)piperazin-1-yl]methyl}-2-methylphenyl)-4-[(4-phenylquinazolin-2-yl)amino]benzamide. $^1$H NMR (400 MHz, DMSO-$d_6$): δ 10.33 (s, 1H), 9.71 (s, 1H), 8.17 (d, 2H), 7.99 (d, 2H), 7.86 (m, 3H), 7.81 (m, 2H), 7.64 (m, 3H), 7.42 (m, 1H), 7.33 (s, 1H), 7.23 (d, 1H), 7.10 (m, 1H), 3.67 (br s, 2H), 3.48 (m, 4H), 2.41 (s, 2H), 2.33 (s, 2H), 2.24 (s, 3H), 1.95 (m, 1H), 0.70 (m, 4H). MS (EI) for $C_{37}H_{36}N_6O_2$: 597.3 (MH$^+$).

Example 110

N-{3-[(diethylamino)methyl]-2-methylphenyl}-4-[(4-phenylquinazolin-2-yl)amino]benzamide. $^1$H NMR (400 MHz, DMSO-$d_6$): δ 10.24 (s, 1H), 9.72 (s, 1H), 8.20 (d, 2H), 8.01 (d, 2H), 7.82 (m, 5H), 7.61 (m, 3H), 7.42 (t, 1H), 7.22 (m, 3H), 3.52 (s, 2H), 2.52 (m, 4H), 2.23 (s, 3H), 1.02 (t, 6H). MS (EI) for $C_{33}H_{33}N_5O$: 516.4 (MH$^+$).

Example 111

N-[3-(azepan-1-ylmethyl)-2-methylphenyl]-4-[(4-phenylquinazolin-2-yl)amino]benzamide. $^1$H NMR (400 MHz, DMSO-$d_6$): δ 10.24 (br s, 1H), 9.85 (br s, 1H), 8.24 (d, 2H), 8.02 (d, 2H), 7.88-7.80 (m, 5H), 7.65 (m, 3H), 7.42 (t, 1H), 7.25-7.15 (m, 3H), 3.62 (br s, 1H), 3.38 (s, 3H), 2.43 (br s, 2H), 2.22 (s, 3H), 1.62 (br s, 8H). MS (EI) for $C_{35}H_{35}N_5O$: 542.0 (MH$^+$).

Example 112

4-methyl-3-[({4-[(4-phenylquinazolin-2-yl)amino]phenyl}carbonyl)amino]-N-1H-tetrazol-5-ylbenzamide. $^1$H NMR (400 MHz, DMSO-$d_6$): δ 10.29 (br s, 1H), 9.84 (br s, 1H), 8.08 (d, 2H), 7.97 (d, 2H), 7.87-7.73 (m, 5H), 7.59 (m, 4H), 7.36 (m, 2H), 6.50 (s, 2H), 2.42 (s, 3H). MS (EI) for $C_{30}H_{23}N_9O_2$: 542.0 (MH$^+$).

Example 113

4-methyl-3-[({4-[(4-phenylquinazolin-2-yl)amino]phenyl}carbonyl)amino]benzamide. $^1$H NMR (400 MHz, DMSO-$d_6$): δ 8.22 (d, 2H), 8.03 (d, 2H), 7.93 (d, 2H), 7.86 (m, 2H), 7.82 (m, 2H), 7.71 (d, 1H), 7.64 (m, 3H), 7.46 (d, 2H), 3.90 (br s, 2H), 2.36 (s, 3H). MS (EI) for $C_{29}H_{23}N_5O_2$: 474.1 (MH$^+$).

Example 114

N-{5-[(8aR)-hexahydropyrrolo[1,2-a]pyrazin-2(1H)-ylcarbonyl]-2-methylphenyl}-4-[(4-phenylquinazolin-2-yl)amino]benzamide. $^1$H NMR (400 MHz, DMSO-$d_6$): δ 10.27 (br s, 1H), 9.74 (br s, 1H), 8.55 (s, 1H), 8.11 (d, 2H), 7.92 (d, 2H), 7.82-7.72 (m, 5H), 7.58 (m, 4H), 7.36 (m, 2H), 3.22 (m, 2H), 2.99 (m, 2H), 2.23 (s, 3H), 2.20 (m, 4H), 2.00 (m, 2H), 2.00 (m, 1H), 1.81 (m, 1H), 1.63 (m, 1H). MS (EI) for $C_{36}H_{34}N_6O_2$: 583.0 (MH$^+$).

Example 115

N-{5-[(8aS)-hexahydropyrrolo[1,2-a]pyrazin-2(1H)-ylcarbonyl]-2-methylphenyl}-4-[(4-phenylquinazolin-2-yl)amino]benzamide. $^1$H NMR (400 MHz, DMSO-$d_6$): δ 10.27 (br s, 1H), 9.74 (br s, 1H), 8.54 (s, 1H), 8.10 (d, 2H), 7.94 (d, 2H), 7.78-7.73 (m, 5H), 7.59 (m, 4H), 7.36 (m, 2H), 3.22 (m, 2H), 2.99 (m, 2H), 2.23 (s, 3H), 2.20 (m, 4H), 2.00 (m, 2H), 2.00 (m, 1H), 1.81 (m, 1H), 1.63 (m, 1H). MS (EI) for $C_{36}H_{34}N_6O_2$: 583.0 (MH$^+$).

Example 116

N-(4-{[(2-hydroxyethyl)amino]methyl}-2-methylphenyl)-4-[(4-phenylquinazolin-2-yl)amino]benzamide. $^1$H NMR (400 MHz, DMSO-$d_6$): δ 10.33 (s, 1H), 9.67 (s, 1H), 8.18-8.16 (d, 2H), 8.00-7.98 (d, 2H), 7.90-7.79 (m, 5H), 7.66-7.64 (m, 3H), 7.44-7.40 (t, 1H), 7.30-7.28 (d, 1H), 7.20 (s, 1H), 7.17-7.15 (d, 1H), 4.50 (m, 1H), 3.69-3.67 (d, 2H), 3.47 (m, 2H), 2.60-2.55 (q, 2H), 2.24 (s, 3H), 1.99 (m, 1H). MS (EI) for $C_{31}H_{29}N_5O_2$: 504.4 (MH$^+$).

Example 117

N-(4-{[ethyl(2-hydroxyethyl)amino]methyl}-2-methylphenyl)-4-[(4-phenylquinazolin-2-yl)amino]benzamide. $^1$H NMR (400 MHz, DMSO-$d_6$): δ 10.33 (s, 1H), 9.66 (s, 1H), 8.18-8.16 (d, 2H), 8.00-7.98 (d, 2H), 7.89-7.79 (m, 5H), 7.66-7.64 (m, 3H), 7.44-7.40 (t, 1H), 7.31-7.29 (d, 1H), 7.21 (s, 1H), 7.17-7.15 (d, 1H), 4.39-4.37 (t, 1H), 3.55 (s, 2H), 3.50-3.46 (q, 2H), 3.36 (m, 2H), 2.50 (m, 2H), 2.24 (s, 3H), 1.01-0.98 (t, 3H). MS (EI) for $C_{33}H_{33}N_5O_2$: 532.4 (MH$^+$).

Example 118

N-[2-(hydroxymethyl)-5-(morpholin-4-ylmethyl)phenyl]-4-[(4-phenylquinazolin-2-yl)amino]benzamide. $^1$H NMR (400 MHz, DMSO-$d_6$): δ 10.36 (s, 1H), 10.05 (s, 1H), 8.24-7.07 (m, 16H), 5.67 (s, 1H), 4.61 (s, 2H), 3.58 (m, 4H), 3.46 (s, 2H), 2.38 (m, 4H). MS (EI) for $C_{33}H_{31}N_5O_3$: 546.0 (MH$^+$).

Example 119

N-[3-(morpholin-4-ylmethyl)phenyl]-4-[(4-phenylquinazolin-2-yl)amino]benzamide. $^1$H NMR (400 MHz, DMSO-$d_6$): δ 10.33 (s, 1H), 10.07 (s, 1H), 8.24-6.96 (m, 17H), 3.60 (m, 4H), 3.46 (s, 2H), 2.38 (m, 4H). MS (EI) for $C_{32}H_{29}N_5O_2$: 516.0 (MH$^+$).

Example 120

N-(5-{[cyclopropyl(methyl)amino]methyl}-2-methylphenyl)-4-[(4-phenylquinazolin-2-yl)amino]benzamide. $^1$H NMR (400 MHz, DMSO-$d_6$): δ 10.33 (s, 1H), 9.72 (s, 1H), 8.18 (d, 2H), 8.00 (d, 2H), 7.88-7.79 (m, 5H), 7.65 (s, 2H), 7.43 (m, 1H), 7.24 (s, 1H), 7.21 (d, 1H), 7.05 (m, 1H), 3.52 (s, 2H), 2.22 (s, 3H), 2.16 (s, 3H), 1.73 (m, 1H), 0.47 (m, 2H), 0.36 (m, 2H). MS (EI) for $C_{33}H_{31}N_5O$: 514.3 (MH$^+$).

Example 121

N-[5-(hydroxymethyl)-2-methylphenyl]-4-[(4-phenylquinazolin-2-yl)amino]benzamide. $^1$H NMR (400 MHz, DMSO-$d_6$): δ 10.36 (s, 1H), 9.84 (s, 1H), 8.19 (d, 2H), 8.05 (d, 2H), 7.89-7.76 (m, 5H), 7.61 (s, 3H), 7.40 (t, 1H), 7.31 (s, 1H), 7.22 (m, 1H), 7.13 (m, 1H), 5.11 (m, 1H), 4.47 M, 2H), 2.21 (s, 3H). MS (EI) for $C_{29}H_{24}N_4O_2$: 461.2 (MH$^+$).

Example 122

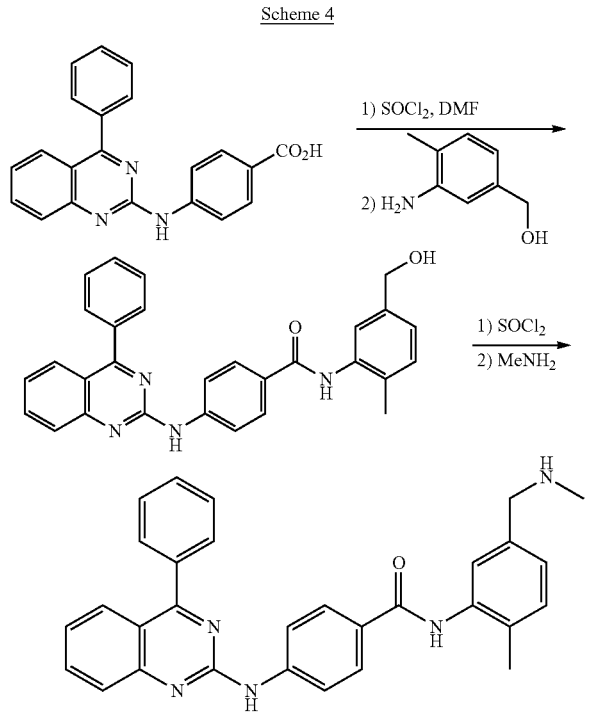

Scheme 4

Example 122

N-{2-methyl-5-[(methylamino)methyl]phenyl}-4-[(4-phenylquinazolin-2-yl)amino]benzamide To a stirred suspension of 4-(4-phenylquinazolin-2-ylamino)benzoic acid (1.19 g, 3.49 mmol), prepared as described in Example 10, in dichloromethane (50 mL) was added a catalytic amount of dimethylformamide (100 µL) and thionyl chloride (1.50 mL, 20.6 mmol), and the resulting mixture was stirred at rt overnight. The solid was filtered, washed with hexanes, and dried under reduced pressure (high vacuum) to give the product (4-(4-phenylquinazolin-2-ylamino)benzoyl chloride) as a yellow solid (1.21 g, 97%). This material was then added portionwise to a solution of commercially available 3-amino-4-methylbenzyl alcohol (600 mg, 4.37 mmol), and triethylamine (1.0 mL, 7.2 mmol) in dichloromethane (50 mL) that had been cooled to 0° C. in an ice bath. The mixture was allowed to warm to rt overnight, then the solid was collected by filtration, washed with saturated sodium bicarbonate and water and dried under reduced pressure to give N-(5-hydroxymethyl-2-methylphenyl)-4-(4-phenylquinazolin-2-ylamino)benzamide as a pure yellow solid (1.33 g, 86%).

To a suspension of N-(5-hydroxymethyl-2-methylphenyl)-4-(4-phenylquinazolin-2-ylamino)benzamide (1.88 g, 4.08 mmol) in dichloromethane (50 mL) that had been cooled to 0° C. in an ice bath was added slowly thionyl chloride (475 µL, 6.54 mmol), and the mixture was stirred at 0° C. for 2 h. Excess thionyl chloride and dichloromethane were removed on a rotary evaporator. The residue was stirred with ether, filtered, washed with ether, and dried to give N-(5-chloromethyl-2-methylphenyl)-4-(4-phenylquinazolin-2-ylamino)benzamide as a yellow solid (2.15 g, 100%). This material was then added to a 1.6 M solution of methylamine in tetrahydrofuran (20 mL, 32 mmol) that had been cooled to 0° C. in an ice bath. The stirred mixture was allowed to warm to rt overnight and then was concentrated on a rotary evaporator. The residue was redissolved in dichloromethane, washed with saturated sodium bicarbonate and dried over sodium sulfate. The solvent was then removed on a rotary evaporator and the residue purified by flash column chromatography to give N-{2-methyl-5-[(methylamino)methyl]-phenyl}-4-[(4-phenylquinazolin-2-yl)amino]benzamide (1.12 g, 57%) as a yellow solid. $^1$H NMR (400 MHz, DMSO-$d_6$): δ 10.33 (s, 1H), 9.71 (s, 1H), 8.17 (d, 2H), 8.00 (d, 2H), 7.89-7.79 (m, 5H), 7.65 (m, 3H), 7.42 (m, 1H), 7.34 (s, 1H), 7.21 (d, 1H), 7.12 (d, 1H), 3.65 (s, 2H), 2.28 (s, 3H), 2.23 (s, 3H). MS (EI) for $C_{30}H_{27}N_5O$: 474.2 (MH$^+$).

Using the procedures described in Scheme 4, the following compounds were prepared.

Example 123

N-(5-{[1,1-dimethylethyl)amino]methyl}-2-methylphenyl)-4-[(4-phenylquinazolin-2-yl)amino]benzamide. $^1$H NMR (400 MHz, DMSO-$d_6$): δ 10.33 (s, 1H), 9.72 (s, 1H), 8.17 (d, 2H), 7.99 (d, 2H), 7.90-7.78 (m, 5H), 7.66-7.62 (m, 3H), 7.44-7.39 (dt, 1H), 7.34 (s, 1H), 7.19 (d, 1H), 7.14-7.11 (dd, 1H), 3.65 (s, 2H), 2.22 (s, 3H), 1.10 (s, 9H). MS (EI) for $C_{33}H_{33}N_5O$: 516.0 (MH$^+$).

Example 124

N-{5-[(cyclopentylamino)methyl]-2-methylphenyl}-4-[(4-phenylquinazolin-2-yl)amino]benzamide. $^1$H NMR (400 MHz, DMSO-$d_6$): δ 10.33 (s, 1H), 9.71 (s, 1H), 8.17 (d, 2H), 7.99 (d, 2H), 7.90-7.78 (m, 5H), 7.66-7.63 (m, 3H), 7.44-7.39 (dt, 1H), 7.33 (s, 1H), 7.20 (d, 1H), 7.14-7.10 (dd, 1H), 3.67 (s, 2H), 3.04-2.98 (m, 1H), 2.22 (s, 3H), 1.76-1.57 (m, 4H), 1.48-1.30 (m, 4H). MS (EI) for $C_{34}H_{33}N_5O$: 528.0 (MH$^+$).

Example 125

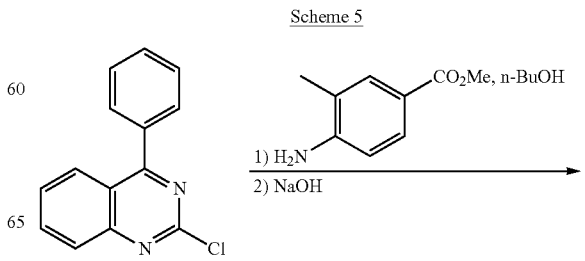

Scheme 5

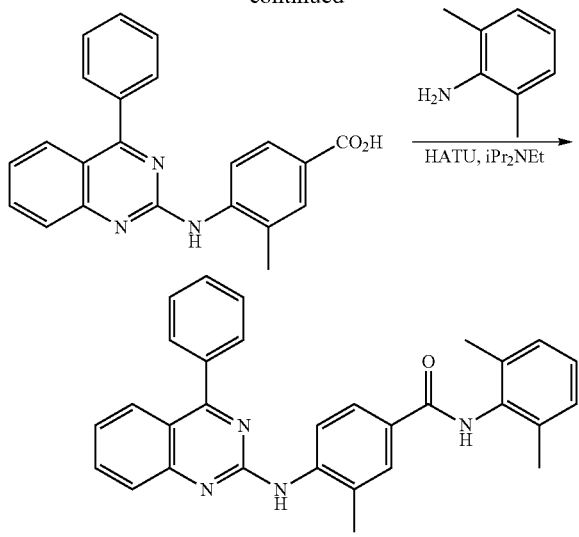

Example 125

N-(2,6-dimethylphenyl)-3-methyl-4-[(4-phenylquinazolin-2-yl)amino]benzamide

A mixture of 2-chloro-4-phenylquinazoline (200 mg, 0.83 mmol) and methyl 4-amino-3-methylbenzoate (137 mg, 0.83 mmol) in n-butanol was heated to 160° C. for 1 h and then cooled to rt. Water (10 mL) was added and the product collected by filtration to give the methyl 3-methyl-4-(4-phenylquinazolin-2-ylamino)benzoate (244 mg, 79%), which was dissolved in a 1:1 mixture of water and methanol (10 mL) containing sodium hydroxide (100 mg, 2.5 mmol). The mixture was heated to 60° C. overnight. Ethyl acetate (100 mL) was added and the phases were separated. The aqueous layer was acidified with 10% aqueous hydrochloric acid and extracted with ethyl acetate. The organic extracts were dried over sodium sulfate, filtered and concentrated on a rotary evaporator to give 3-methyl-4-(4-phenylquinazolin-2-ylamino)benzoic acid (188 mg, 80%).

A stirred solution of 2,6-dimethylaniline (130 μL, 1.06 mmol), 3-methyl-4-(4-phenylquinazolin-2-ylamino)benzoic acid (188 mg, 0.53 mmol), HATU (433 mg, 1.13 mmol) and Hunig's base (350 μL, 2.00 mmol) in dimethylacetamide (10 mL) was heated to 70° C. overnight. The reaction mixture was diluted with ethyl acetate (100 mL) and extracted with a 10% aqueous solution of lithium chloride and a 1 N solution of sodium hydroxide. The combined organic phases were dried over sodium sulfate, filtered and concentrated on a rotary evaporator. The product was purified by preparative reverse phase HPLC ($CH_3CN/H_2O$). Acetonitrile was removed from the isolated pure fractions on a rotary evaporator and the aqueous remainder was lyophilized to give N-(2,6-dimethylphenyl)-3-methyl-4-[(4-phenylquinazolin-2-yl)amino]benzamide as a white solid (114 mg, 47%). $^1$H NMR (400 MHz, DMSO-$d_6$): δ 9.68 (s, 1H), 9.20 (s, 1H), 8.03 (m, 1H), 7.88 (m, 2H), 7.80 (m, 2H), 7.78 (m, 2H), 7.65 (m, 4H), 7.35 (m, 1H), 7.13 (m, 3H), 2.40 (s, 3H), 2.20 (s, 6H). MS (EI) for $C_{30}H_{26}N_4O$: 459.0 (MH$^+$).

Example 126

Following step 1 in Scheme 5, and substituting methyl 4-amino-3-methylbenzoate with 5-amino-2-(2,6-dimethylphenyl)isoindoline-1,3-dione, the following compound was prepared. 2-(2,6-dimethylphenyl)-5-[(4-phenylquinazolin-2-yl)amino]-1H-isoindole-1,3(2H)-dione. $^1$H NMR (400 MHz, DMSO-$d_6$): δ 10.88 (s, 1H), 8.80 (m, 1H), 8.42 (m, 1H), 7.96 (m, 1H), 7.90 (m, 2H), 7.85 (m, 1H), 7.81 (m, 2H), 7.65 (m, 3H), 7.50 (m, 1H), 7.32 (m, 1H), 7.25 (m, 2H), 2.10 (s, 6H). MS (EI) for $C_{30}H_{22}N_4O_2$: 471 (MH$^+$).

Using the procedures in steps 1-3 in Scheme 5, the following compounds in Examples 127-146 were prepared.

N-(2-methylphenyl)-5-[(4-phenylquinazolin-2-yl)amino]pyridine-2-carboxamide. $^1$H NMR (400 MHz, DMSO-$d_6$): δ 10.64 (s, 1H), 10.12 (s, 1H), 9.31 (d, 1H), 8.76 (q, 1H), 8.15 (d, 1H), 7.93 (m, 4H), 7.82 (m, 2H), 7.65 (m, 3H), 7.48 (m, 1H), 7.28 (m, 2H), 7.11 (t, 1H), 2.34 (s, 3H). MS (EI) for $C_{27}H_{21}N_5O$: 432.2 (MH$^+$).

N-{5-[(dimethylamino)methyl]-2-methylphenyl}-5-[(4-phenylquinazolin-2-yl)amino]pyridine-2-carboxamide. $^1$H NMR (400 MHz, DMSO-$d_6$): δ 10.44 (s, 1H), 10.08 (s, 1H), 9.29 (s, 1H), 8.77 (d, 1H), 8.16 (d, 1H), 7.96-7.59 (m, 9H), 7.47 (t, 1H), 7.21 (d, 1H), 7.00 (s, 1H), 3.36 (s, 2H), 2.24 (s, 3H), 2.16 (s, 6H). MS (EI) for $C_{30}H_{28}N_6O$: 490.0 (MH$^+$).

N-(2,6-dimethylphenyl)-3-(methyloxy)-4-[(4-phenylquinazolin-2-yl)amino]benzamide. $^1$H NMR (400 MHz, DMSO-$d_6$): δ 9.72 (s, 1H), 8.84 (m, 1H), 8.43 (s, 1H), 7.88 (m, 3H), 7.80 (m, 3H), 7.70 (m, 1H), 7.65 (m, 3H), 7.44 (m, 1H), 7.14 (s, 2H), 4.02 (s, 3H), 2.22 (s, 6H). MS (EI) for $C_{30}H_{26}N_4O_2$: 475.0 (MH$^+$).

3-bromo-N-(2,6-dimethylphenyl)-4-[(4-phenylquinazolin-2-yl)amino]benzamide. $^1$H NMR (400 MHz, DMSO-$d_6$): δ 9.83 (s, 1H), 8.95 (s, 1H), 8.48 (m, 1H), 8.32 (m, 1H), 8.18 (s, 1H), 8.10 (m, 1H), 7.90 (m, 2H), 7.80 (m, 3H), 7.65 (m, 3H), 7.45 (m, 1H), 7.15 (s, 2H), 2.54 (s, 6H). MS (EI) for $C_{29}H_{23}BrN_4O$: 524.0 (MH$^+$).

2-amino-N-(2,6-dimethylphenyl)-4-[(4-phenylquinazolin-2-yl)amino]benzamide. $^1$H NMR (400 MHz, DMSO-$d_6$): δ 9.98 (s, 1H), 9.30 (s, 1H), 7.85 (m, 3H), 7.78 (m, 3H), 7.70 (s, 1H), 7.64 (m, 3H), 7.39 (m, 1H), 7.13 (m, 1H), 7.10 (s, 3H), 2.20 (s, 6H). MS (EI) for $C_{29}H_{25}N_5O$: 460.0 (MH$^+$).

3-chloro-N-(2,6-dimethylphenyl)-4-[(4-phenylquinazolin-2-yl)amino]benzamide. $^1$H NMR (400 MHz, DMSO-$d_6$): δ 10.40 (s, 1H), 9.75 (s, 1H), 8.30 (m, 1H), 8.10 (m, 1H), 7.90 (m, 3H), 7.80 (m, 3H), 7.65 (m, 4H), 7.45 (m, 1H), 7.15 (s, 2H), 2.28 (s, 6H). MS (EI) for $C_{29}H_{23}ClN_4O$: 479.0 (MH$^+$).

N-(2,6-dimethylphenyl)-3-[(2-morpholin-4-ylethyl)oxy]-4-[(4-phenylquinazolin-2-yl)amino]benzamide. $^1$H NMR (400 MHz, DMSO-$d_6$): δ 9.67 (s, 1H), 8.88 (s, 1H), 8.82 (m, 1H), 7.88 (m, 2H), 7.82 (m, 1H), 7.79 (m, 4H), 7.64 (m, 3H), 7.44 (m, 1H), 7.14 (s, 3H), 4.34 (m, 2H), 3.60 (m, 4H), 2.72 (m, 2H), 2.48 (m, 4H), 2.20 (m, 6H). MS (EI) for $C_{35}H_{35}N_5O_3$: 574.0 (MH$^+$).

N-(2,6-dimethylphenyl)-4-[(4-phenylquinazolin-2-yl)amino]-3-[(2-pyrrolidin-1-ylethyl)oxy]benzamide. $^1$H NMR (400 MHz, DMSO-$d_6$): δ 9.68 (s, 1H), 9.26 (s, 1H), 8.84 (m, 1H), 7.87 (m, 2H), 7.82 (m, 1H), 7.80 (m, 4H), 7.64 (m, 3H), 7.42 (m, 1H), 7.14 (s, 3H), 4.30 (m, 2H), 2.80 (m, 2H), 2.57 (m, 4H), 2.20 (s, 6H), 1.67 (m, 4H). MS (EI) for $C_{35}H_{35}N_5O_2$: 558.0 (MH$^+$).

2-chloro-N-[2-methyl-5-(morpholin-4-ylmethyl)phenyl]-4-[(4-phenylquinazolin-2-yl)amino]benzamide. $^1$H NMR (400 MHz, DMSO-$d_6$): δ 10.40 (s, 1H), 9.83 (s, 1H), 8.34 (s, 1H), 8.05 (m, 1H), 7.86 (m, 3H), 7.80 (m, 3H), 7.64 (m, 4H), 7.44 (m, 2H), 7.30 (m, 1H), 7.10 (m, 1H), 3.58 (br s, 4H), 3.44 (s, 2H), 2.37 (br s, 4H), 2.28 (s, 3H). MS (EI) for $C_{33}H_{30}ClN_5O_2$: 565.0 (MH$^+$).

2-chloro-N-(2,6-dimethylphenyl)-4-[(4-phenylquinazolin-2-yl)amino]benzamide. $^1$H NMR (400 MHz, DMSO-$d_6$): δ 10.40 (s, 1H), 9.73 (s, 1H), 8.32 (m, 1H), 8.10 (m, 1H), 7.87

(m, 3H), 7.70 (m, 3H), 7.64 (m, 3H), 7.44 (m, 1H), 7.13 (s, 3H), 2.28 (s, 6H). MS (EI) for $C_{29}H_{23}ClN_4O_2$: 479.0 (MH+).

N-(2,6-dimethylphenyl)-2-[(2-morpholin-4-ylethyl)oxy]-4-[(4-phenylquinazolin-2-yl)amino]benzamide. $^1$H NMR (400 MHz, DMSO-d$_6$): δ 10.36 (s, 1H), 10.03 (s, 1H), 8.38 (m, 1H), 7.90 (m, 4H), 7.83 (m, 2H), 7.64 (m, 3H), 7.53 (m, 1H), 7.44 (m, 1H), 7.14 (s, 3H), 4.40 (m, 2H), 3.05 (br s, 4H), 2.80 (m, 2H), 2.34 (br s, 4H), 2.20 (s, 6H). MS (EI) for $C_{35}H_{35}N_5O_3$: 574.0 (MH+).

N-(2,6-dimethylphenyl)-4-[(4-phenylquinazolin-2-yl)amino]-2-[(2-pyrrolidin-1-ylethyl)oxy]benzamide. $^1$H NMR (400 MHz, DMSO-d$_6$): δ 10.35 (s, 1H), 10.20 (s, 1H), 8.37 (m, 1H), 8.38 (m, 4H), 7.82 (m, 2H), 7.65 (m, 3H), 7.52 (m, 1H), 7.43 (m, 1H), 7.10 (m, 3H), 4.39 (m, 2H), 2.90 (m, 2H), 2.38 (m, 4H), 2.20 (m, 6H), 1.20 (m, 4H). MS (EI) for $C_{35}H_{35}N_5O_2$: 558.0 (MH+).

N-(2,6-dimethylphenyl)-2-(methyloxy)-4-[(4-phenylquinazolin-2-yl)amino]benzamide. $^1$H NMR (400 MHz, DMSO-d$_6$): δ 10.33 (s, 1H), 9.40 (s, 1H), 8.33 (m, 1H), 7.88 (m, 3H), 7.72 (m, 3H), 7.65 (m, 3H), 7.52 (m, 1H), 7.42 (m, 1H), 7.12 (m, 3H), 4.04 (s, 3H), 2.22 (s, 6H). MS (EI) for $C_{30}H_{26}N_4O_2$: 475.0 (MH+).

N-(2,6-dimethylphenyl)-1-methyl-4-[(4-phenylquinazolin-2-yl)amino]-1H-imidazole-2-carboxamide. $^1$H NMR (400 MHz, DMSO-d$_6$): δ 9.86 (s, 1H), 9.46 (s, 1H), 7.96 (br s, 1H), 7.82 (m, 4H), 7.76 (m, 2H), 7.63 (m, 3H), 7.34 (m, 1H), 7.32 (m, 3H), 4.03 (s, 3H), 2.20 (s, 6H). MS (EI) for $C_{27}H_{24}N_6O$: 449.0 (MH+).

5-chloro-N-(2,6-dimethylphenyl)-4-[(4-phenylquinazolin-2-yl)amino]thiophene-2-carboxamide. $^1$H NMR (400 MHz, DMSO-d$_6$): δ 10.00 (s, 1H), 9.63 (s, 1H), 8.47 (s, 1H), 7.85 (m, 2H), 7.80 (m, 2H), 7.73 (m, 1H), 7.62 (m, 3H), 7.38 (m, 1H), 7.15 (s, 3H), 2.22 (s, 6H). MS (EI) for $C_{27}H_{21}ClN_4OS$: 486.0 (MH+).

N-(2,6-dimethylphenyl)-2-fluoro-4-[(4-phenylquinazolin-2-yl)amino]benzamide. $^1$H NMR (400 MHz, DMSO-d$_6$): δ 10.50 (s, 1H), 9.50 (m, 1H), 8.25 (m, 1H), 7.90 (m, 3H), 7.80 (m, 3H), 7.70 (m, 1H), 7.65 (m, 3H), 7.45 (m, 1H), 7.12 (s, 3H), 2.23 (s, 6H). MS (EI) for $C_{29}H_{23}FN_4O$: 463.0 (MH+).

N-(2,6-dimethylphenyl)-2-(4-methylpiperazin-1-yl)-4-[(4-phenylquinazolin-2-yl)amino]benzamide. $^1$H NMR (400 MHz, DMSO-d$_6$): δ 11.30 (br s, 1H), 10.30 (s, 1H), 8.40 (m, 1H), 7.97 (m, 1H), 7.90 (m, 2H), 7.80 (m, 4H), 7.64 (m, 3H), 7.43 (m, 1H), 7.13 (m, 3H), 3.35 (s, 3H), 3.10 (m, 4H), 2.49 (m, 4H), 2.25 (s, 6H). MS (EI) for $C_{34}H_{34}N_6O$: 543.0 (MH+).

N-(2,6-dimethylphenyl)-2-[(1-methylpiperidin-4-yl)amino]-4-[(4-phenylquinazolin-2-yl)amino]benzamide. $^1$H NMR (400 MHz, DMSO-d$_6$): δ10.05 (s, 1H), 9.38 (s, 1H), 8.20 (m, 1H), 7.85 (m, 7H), 7.75 (m, 1H), 7.64 (m, 2H), 7.40 (m, 1H), 7.10 (m, 3H), 2.88 (br s, 1H), 2.28 (br s, 4H), 2.08 (br s, 4H), 1.98 (s, 6H), 1.50 (br s, 3H). MS (EI) for $C_{35}H_{36}N_6O$: 557.0 (MH+).

2-fluoro-N-[2-methyl-5-(morpholin-4-ylmethyl)phenyl]-4-[(4-phenylquinazolin-2-yl)amino]benzamide. $^1$H NMR (400 MHz, DMSO-d$_6$): δ10.52 (s, 1H), 9.50 (s, 1H), 8.30 (d, 1H), 7.90-7.76 (m, 7H), 7.65-7.60 (m, 3H), 7.54 (s, 1H), 7.45 (m, 1H), 7.22 (d, 1H), 7.06 (d, 1H), 3.57 (m, 4H), 3.43 (s, 2H), 2.36 (m, 4H), 2.26 (s, 3H). MS (EI) for $C_{33}H_{30}FN_5O_2$: 548.0 (MH+).

3-fluoro-N-[2-methyl-5-(morpholin-4-ylmethyl)phenyl]-4-[(4-phenylquinazolin-2-yl)amino]benzamide. $^1$H NMR (400 MHz, DMSO-d$_6$): δ 9.88 (s, 1H), 9.65 (s, 1H), 8.43 (t, 1H), 7.90-7.75 (m, 7H), 7.64-7.63 (m, 3H), 7.42 (m, 1H), 7.29 (s, 1H), 7.23 (d, 1H), 7.11 (d, 1H), 3.57 (m, 4H), 3.44 (s, 2H), 2.36 (m, 4H), 2.22 (s, 3H). MS (EI) for $C_{33}H_{30}FN_5O_2$: 548.0 (MH+).

Example 147

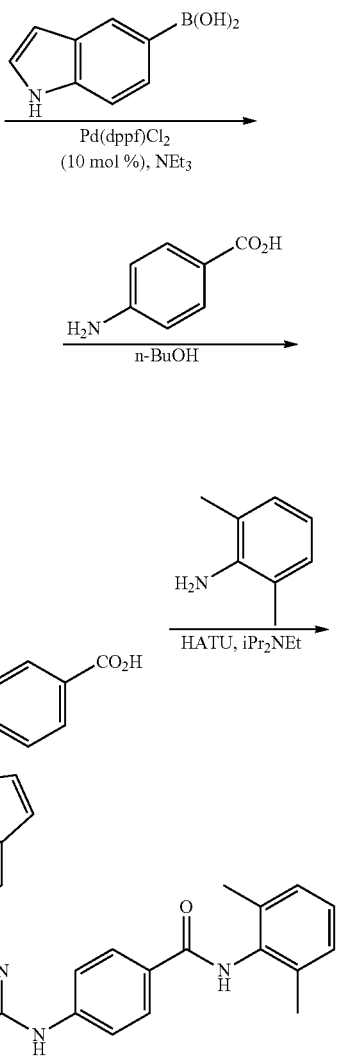

Scheme 6

Example 147

N-(2,6-dimethylphenyl)-4-{[4-(1H-indol-5-yl)quinazolin-2-yl]amino}benzamide

To a round bottomed flask containing 2,4-dichloroquinazaline (800 mg, 4.02 mmol) was added indol-5-boronic acid (647 mg, 4.02 mmol), dichloro-((bis-diphenylphosphino)-ferrocenyl)-palladium (II) (complex with methylene chloride, 235 mg, 0.32 mmol), triethylamine (1.5 mL, 10 mmol), dimethoxyethane (20 mL), and water (0.5 mL). The reaction mixture was heated at 80° C. for 14 h, then cooled to rt and diluted with ethyl acetate. The organic layer was washed with saturated sodium bicarbonate, dried over sodium sulfate, filtered, and concentrated on a rotary evaporator. The material was purified by flash column chromatography to afford 2-chloro-4-(1H-indol-5-yl)quinazoline as a brown solid (740 mg, 66%).

To a tube containing 2-chloro-4-(1H-indol-5-yl)quinazoline (740 mg, 2.65 mmol) was added 4-aminobenzoic acid (363 mg, 2.65 mmol) and n-butanol (10 mL). The mixture was heated at reflux for 1 h while allowing the solvent to boil off, then cooled to rt. Diethyl ether was added and the mixture was filtered to collect 4-(4-(1H-indol-5-yl)quinazolin-2-ylamino)benzoic acid as a yellow solid (869 mg, 86%).

To a round bottomed flask containing 4-(4-(1H-indol-5-yl)quinazolin-2-ylamino)-benzoic acid (428 mg, 1.13 mmol) was added 2,6-dimethylaniline (137 mg, 1.13 mmol), HATU (428 mg, 1.13), Hunig's base (400 µL, 2.3 mmol), and dimethylacetamide (4 mL). The stirred mixture was heated to at 50° C. for 14 h, diluted with water and extracted with ethyl acetate. The combined organic extracts were washed with 5% aqueous lithium chloride and saturated sodium chloride, dried over sodium sulfate, filtered, and concentrated on a rotary evaporator. The crude material was purified by preparative reverse phase HPLC to afford N-(2,6-dimethylphenyl)-4-{[4-(1H-indol-5-yl)quinazolin-2-yl]amino}benzamide as a yellow solid (24 mg, 5%). $^1$H NMR (400 MHz, DMSO-d$_6$): δ 11.45 (s, 1H), 10.23 (s, 1H), 9.60 (s, 1H), 8.19 (d, 2H), 8.02 (m, 4H), 7.83 (m, 2H), 7.62 (m, 2H), 7.51 (m, 1H), 7.41 (m, 1H), 7.13 (s, 3H), 6.63 (m, 1H), 2.20 (s, 6H). MS (EI) C$_{31}$H$_{25}$N$_5$O: 484.2 (MH$^+$).

Examples 148-189

Using the procedures described in Scheme 6, the following compounds were prepared.

N-{5-[(dimethylamino)methyl]-2-methylphenyl}-4-{[4-(4-fluorophenyl)quinazolin-2-yl]amino}benzamide.
$^1$H-NMR (400 MHz, DMSO-d$_6$): δ10.30 (s, 1H), 9.69 (s, 1H), 8.16 (d, 2H), 7.98 (d, 2H), 7.90-7.50 (m, 5H), 7.50-7.41 (m, 3H), 7.31 (m, 1H), 7.21 (d, 1H), 7.07 (dd, 1H), 3.37 (s, 2H), 2.23 (s, 3H), 2.16 (s, 6H). MS (EI) for C$_{31}$H$_{28}$FN$_5$O: 506.0 (MH$^+$).

N-{5-[(dimethylamino)methyl]-2-methylphenyl}-4-{[4-(2-fluorophenyl)quinazolin-2-yl]amino}benzamide.
$^1$H-NMR (400 MHz, DMSO-d$_6$): δ 10.40 (s, 1H), 9.75 (s, 1H), 8.16 (d, 2H), 7.99 (d, 2H), 7.91-7.84 (m, 2H), 7.73-7.67 (m, 2H), 7.57-7.39 (m, 5H), 7.27 (d, 1H), 7.14 (d, 1H), 3.68 (br, 2H), 2.36 (br, 6H), 2.26 (s, 3H). MS (EI) for C$_{31}$H$_{28}$FN$_5$O: 506.0 (MH$^+$).

4-{[4-(3-bromophenyl)quinazolin-2-yl]amino}-N-{5-[(dimethylamino)methyl]-2-methylphenyl}benzamide.
$^1$H-NMR (400 MHz, DMSO-d$_6$): δ 10.34 (s, 1H), 9.70 (s, 1H), 8.18 (d, 2H), 8.02-7.97 (m, 3H), 7.91-7.78 (m, 5H), 7.60 (t, 1H), 7.43 (t, 1H), 7.31 (s, 1H), 7.22 (d, 1H), 7.08 (d, 1H), 3.40 (s, 2H), 2.24 (s, 3H), 2.18 (s, 6H). MS (EI) for C$_{31}$H$_{28}$BrN$_5$O: 566.1 (MH$^+$).

4-{[4-(4-chlorophenyl)quinazolin-2-yl]amino}-N-{5-[(dimethylamino)methyl]-2-methylphenyl}benzamide.
$^1$H-NMR (400 MHz, DMSO-d$_6$): δ 10.36 (s, 1H), 9.73 (s, 1H), 8.17 (d, 2H), 8.00 (d, 2H), 7.90-7.80 (m, 5H), 7.70 (d, 2H), 7.42 (t, 1H), 7.30 (s, 1H), 7.20 (d, 1H), 7.17 (d, 1H), 3.37 (s, 2H), 2.24 (s, 3H), 2.16 (s, 6H). MS (EI) for C$_{31}$H$_{28}$ClN$_5$O: 522.2 (MH$^+$).

4-{[4-(2-chlorophenyl)quinazolin-2-yl]amino}-N-{5-[(dimethylamino)methyl]-2-methylphenyl}benzamide. $^1$H NMR (400 MHz, DMSO-d$_6$): δ 10.44 (s, 1H), 9.72 (s, 1H), 8.17 (d, 2H), 8.01 (d, 2H), 7.88-7.86 (m, 2H), 7.74 (m, 1H), 7.67-7.59 (m, 3H), 7.38 (m, 1H), 7.30 (s, 1H), 7.22 (d, 1H), 7.08 (d, 1H), 3.37 (s, 2H), 2.23 (s, 3H), 2.16 (s, 6H). MS (EI) for C$_{31}$H$_{28}$ClN$_5$O: 522.4 (MH$^+$).

4-{[4-(2,6-difluorophenyl)quinazolin-2-yl]amino}-N-{5-[(dimethylamino)methyl]-2-methylphenyl}benzamide.
$^1$H-NMR (400 MHz, DMSO-d$_6$): δ 10.46 (s, 1H), 9.72 (s, 1H), 8.12 (d, 2H), 7.98 (d, 2H), 7.88 (m, 2H), 7.74 (m, 1H), 7.50 (m, 1H), 7.40 (m, 4H), 7.24 (d, 1H), 7.11 (d, 1H), 3.32 (s, 2H), 2.28 (s, 6H), 2.23 (s, 3H). MS (EI) for C$_{31}$H$_{27}$F$_2$N$_5$O: 524.4 (MH$^+$).

4-{[4-(2,4-difluorophenyl)quinazolin-2-yl]amino}-N-{5-[(dimethylamino)methyl]-2-methylphenyl}benzamide.
$^1$H-NMR (400 MHz, DMSO-d$_6$): δ10.39 (s, 1H), 9.69 (s, 1H), 8.13 (d, 2H), 7.97 (d, 2H), 7.82 (m, 3H), 7.55 (m, 2H), 7.37 (m, 3H), 7.21 (d, 1H), 7.07 (d, 1H), 3.42 (s, 2H), 2.22 (s, 3H), 2.19 (s, 6H). MS (EI) for C$_{31}$H$_{27}$F$_2$N$_5$O: 524.4 (MH$^+$).

4-{[4-(2-bromophenyl)quinazolin-2-yl]amino}-N-{5-[(dimethylamino)methyl]-2-methylphenyl}benzamide.
$^1$H-NMR (400 MHz, CD$_3$OD): δ 8.12 (d, 2H), 7.99 (d, 2H), 7.85-7.78 (m, 3H), 7.60-7.46 (m, 3H), 7.40 (d, 1H), 7.33-7.26 (m, 3H), 7.16 (d, 1H), 3.48 (s, 2H), 2.30 (s, 3H), 2.25 (s, 6H). MS (EI) for C$_{31}$H$_{28}$BrN$_5$O: 566.1 (MH$^+$).

4-{[4-(2'-bromobiphenyl-2-yl)quinazolin-2-yl]amino}-N-{5-[(dimethylamino)methyl]-2-methylphenyl}benzamide. $^1$H-NMR (400 MHz, DMSO-d$_6$): δ 10.25 (s, 1H), 9.70 (s, 1H), 8.08 (d, 2H), 7.97 (d, 2H), 7.74-7.60 (m, 5H), 7.57-7.48 (m, 3H), 7.38 (s, 1H), 7.25 (d, 1H), 7.20 (br, 1H), 7.15-7.07 (m, 3H), 7.02 (m, 1H), 3.60 (s, 2H), 2.30 (s, 6H), 2.24 (s, 3H). MS (EI) for C$_{37}$H$_{32}$BrN$_5$O: 642.2 (MH$^+$).

4-{[4-(3-chlorophenyl)quinazolin-2-yl]amino}-N-{5-[(dimethyl-amino)methyl]-2-methylphenyl}benzamide.
$^1$H-NMR (400 MHz, DMSO-d$_6$): δ 10.36 (s, 1H), 9.70 (s, 1H), 8.18 (d, 2H), 8.00 (d, 2H), 7.92-7.83 (m, 4H), 7.78-7.64 (m, 3H), 7.42 (t, 1H), 7.31 (s, 1H), 7.22 (d, 1H), 7.08 (d, 1H), 3.36 (s, 2H), 2.24 (s, 3H), 2.15 (s, 6H). MS (EI) for C$_{31}$H$_{28}$ClN$_5$O: 522.2 (MH$^+$).

4-{[4-(3,5-dichlorophenyl)quinazolin-2-yl]amino}-N-{5-[(dimethylamino)methyl]-2-methylphenyl}benzamide.
$^1$H-NMR (400 MHz, DMSO-d$_6$): δ 10.35 (s, 1H), 9.68 (s, 1H), 8.14 (d, 2H), 7.97 (d, 2H), 7.85 (m, 6H), 7.43 (m, 1H), 7.28 (s, 1H), 7.19 (d, 1H), 7.05 (d, 1H), 3.33 (s, 2H), 2.20 (s, 6H), 2.12 (s, 3H). MS (EI) for C$_{31}$H$_{27}$Cl$_2$N$_5$O: 556.3 (MH$^+$).

4-{[4-(2,3-dichlorophenyl)quinazolin-2-yl]amino}-N-{5-[(dimethylamino)methyl]-2-methylphenyl}benzamide.
$^1$H-NMR (400 MHz, DMSO-d$_6$): δ 10.46 (s, 1H), 9.72 (s, 1H), 8.15 (d, 2H), 8.00 (d, 2H), 7.92-7.83 (m, 3H), 7.67-7.59 (m, 2H), 7.40 (m, 3H), 7.25 (d, 1H), 7.12 (d, 1H), 3.60 (s, 2H), 2.30 (s, 6H), 2.24 (s, 3H). MS (EI) for C$_{31}$H$_{27}$Cl$_2$N$_5$O: 556.2 (MH$^+$).

N-{5-[(dimethylamino)methyl]-2-methylphenyl}-4-{[4-(1-methyl-1H-pyrrol-2-yl)quinazolin-2-yl]amino}benzamide. $^1$H-NMR (400 MHz, DMSO-d$_6$): δ 10.00 (s, 1H), 9.70 (s, 1H), 8.22 (d, 1H), 8.13 (d, 2H), 8.00 (d, 2H), 7.82 (t, 1H), 7.76 (d, 1H), 7.42 (t, 1H), 7.34 (s, 1H), 7.22 (d, 1H), 7.19 (s, 1H), 7.10 (d, 1H), 6.77 (t, 1H), 6.28 (d, 1H), 3.99 (s, 3H), 3.46 (s, 2H), 2.24 (s, 3H), 2.21 (s, 6H). MS (EI) for C$_{30}$H$_{30}$N$_6$O: 491.4 (MH$^+$).

4-{[4-(2,4-dichlorophenyl)quinazolin-2-yl]amino}-N-{5-[(dimethylamino)methyl]-2-methylphenyl}benzamide.
$^1$H-NMR (400 MHz, DMSO-d$_6$): δ 10.46 (s, 1H), 9.70 (s, 1H), 8.16 (d, 2H), 8.00 (d, 2H), 7.92-7.83 (m, 3H), 7.72-7.68 (m, 2H), 7.42-7.35 (m, 2H), 7.32 (s, 1H), 7.22 (d, 1H), 7.08 (d, 1H), 3.42 (s, 2H), 2.24 (s, 3H), 2.18 (s, 6H). MS (EI) for C$_{31}$H$_{27}$Cl$_2$N$_5$O: 556.0 (MH$^+$).

4-{[4-(3,4-dichlorophenyl)quinazolin-2-yl]amino}-N-{5-[(dimethylamino)methyl]-2-methylphenyl}benzamide.
$^1$H-NMR (400 MHz, DMSO-d$_6$): δ 10.38 (s, 1H), 9.70 (s, 1H), 8.17 (d, 2H), 8.09 (s, 1H), 8.00 (d, 2H), 7.92-7.78 (m, 5H), 7.42 (t, 1H), 7.30 (s, 1H), 7.20 (d, 1H), 7.06 (d, 1H), 3.36

(s, 2H), 2.24 (s, 3H), 2.15 (s, 6H). MS (EI) for $C_{31}H_{27}Cl_2N_5O$: 556.1 (MH$^+$).

4-{[4-(2,5-dichlorophenyl)quinazolin-2-yl]amino}-N-{5-[(dimethylamino)methyl]-2-methylphenyl}benzamide. $^1$H-NMR (400 MHz, DMSO-d$_6$): δ 10.45 (s, 1H), 9.79 (s, 1H), 8.15 (d, 2H), 8.02 (d, 2H), 7.92-7.83 (m, 3H), 7.78-7.70 (m, 2H), 7.42-7.37 (m, 2H), 7.30 (s, 1H), 7.20 (d, 1H), 7.06 (d, 1H), 3.35 (s, 2H), 2.24 (s, 3H), 2.15 (s, 6H). MS (EI) for $C_{31}H_{27}Cl_2N_5O$: 556.3 (MH$^+$).

N-{5-[(dimethylamino)methyl]-2-methylphenyl}-4-{[4-(2-thienyl)quinazolin-2-yl]amino}benzamide. $^1$H-NMR (400 MHz, DMSO-d$_6$): δ 10.13 (s, 1H), 9.69 (s, 1H), 8.38 (d, 1H), 8.12 (d, 2H), 8.03 (m, 1H), 7.96 (m, 3H), 7.87 (m, 1H), 7.77 (m, 1H), 7.47 (m, 1H), 7.35 (m, 1H), 7.28 (s, 1H), 7.20 (d, 1H), 7.05 (d, 1H), 2.52 (s, 2H), 2.21 (s, 3H), 2.14 (s, 6H). MS (D) for $C_{29}H_{27}N_5OS$: 494.2 (MH$^+$).

4-{[4-(3,5-difluorophenyl)quinazolin-2-yl]amino}-N-{5-[(dimethylamino)methyl]-2-methylphenyl}benzamide. $^1$H-NMR (400 MHz, DMSO-d$_6$): δ 10.38 (s, 1H), 9.70 (s, 1H), 8.18 (d, 2H), 8.02 (d, 2H), 7.91-7.82 (m, 3H), 7.60-7.52 (m, 3H), 7.42 (t, 1H), 7.30 (s, 1H), 7.20 (d, 1H), 7.05 (d, 1H), 3.36 (s, 2H), 2.24 (s, 3H), 2.15 (s, 6H). MS (D) for $C_{31}H_{27}F_2N_5O$: 524.2 (MH$^+$).

N-(2,6-dimethylphenyl)-4-[(4-{4-[(trifluoromethyl)oxy]phenyl}quinazolin-2-yl)amino]benzamide. $^1$H-NMR (400 MHz, DMSO-d$_6$): δ 10.35 (s, 1H), 9.72 (s, 1H), 8.18 (d, 2H), 8.04 (d, 2H), 7.95 (d, 2H), 7.91-7.82 (m, 3H), 7.63 (d, 2H), 7.42 (t, 1H), 7.12 (s, 3H), 2.20 (s, 6H). MS (D) for $C_{30}H_{23}F_3N_4O_2$: 529.2 (MH$^+$).

N-(2,6-dimethylphenyl)-4-({4-[4-(methyloxy)phenyl]quinazolin-2-yl}amino)benzamide. $^1$H-NMR (400 MHz, DMSO-d$_6$): δ 10.26 (s, 1H), 9.70 (s, 1H), 8.18 (d, 2H), 8.03 (d, 2H), 7.93 (d, 1H), 7.88-7.76 (m, 4H), 7.40 (t, 1H), 7.20 (d, 2H), 7.12 (s, 3H), 3.89 (s, 3H), 2.20 (s, 6H). MS (D) for $C_{30}H_{26}N_4O_2$: 475.2 (MH$^+$).

N-(2,6-dimethylphenyl)-4-{[4-(1H-pyrazol-4-yl)quinazolin-2-yl]amino}benzamide. $^1$H-NMR (400 MHz, DMSO-d$_6$): δ 10.13 (s, 1H), 9.58 (s, 1H), 8.58 (s, 1H), 8.22 (d, 1H), 8.12 (d, 2H), 7.98 (d, 2H), 7.95 (m, 1H), 7.85 (m, 1H), 7.76 (d, 1H), 7.43 (m, 1H), 7.14 (m, 1H), 7.10 (s, 3H), 2.17 (s, 6H). MS (D) for $C_{26}H_{22}N_6O$: 435.3 (MH$^+$).

N-(2,6-dimethylphenyl)-4-[(4-furan-3-ylquinazolin-2-yl)amino]benzamide. $^1$H NMR (400 MHz, DMSO-d$_6$): δ 10.14 (s, 1H), 9.59 (s, 1H), 8.57 (s, 1H), 8.22 (d, 1H), 8.12 (d, 2H), 7.97 (m, 3H), 7.85 (m, 1H), 7.76 (d, 1H), 7.43 (m, 1H), 7.14 (s, 1H), 7.10 (s, 3H), 2.17 (s, 6H). MS (EI) for $C_{27}H_{22}N_4O_2$: 435.1 (MH$^+$).

N-(2,6-dimethylphenyl)-4-({4-[3-(methyloxy)phenyl]quinazolin-2-yl}amino)benzamide. $^1$H NMR (400 MHz, DMSO-d$_6$): δ 10.32 (s, 1H), 9.71 (s, 1H), 8.18 (d, 2H), 8.03 (d, 2H), 7.90-7.80 (m, 3H), 7.55 (t, 1H), 7.41 (t, 1H), 7.35-7.32 (m, 2H), 7.20 (d, 1H), 7.12 (s, 3H), 3.86 (s, 3H), 2.20 (s, 6H). MS (D) for $C_{30}H_{26}N_4O_2$: 475.2 (MH$^+$).

N-(2,6-dimethylphenyl)-4-({4-[2-(methyloxy)phenyl]quinazolin-2-yl}amino)benzamide. $^1$H NMR (400 MHz, DMSO-d$_6$): δ 10.32 (s, 1H), 9.71 (s, 1H), 8.16 (d, 2H), 8.03 (d, 2H), 7.85-7.78 (m, 2H), 7.59 (t, 1H), 7.42 (d, 2H), 7.32 (t, 1H), 7.28 (d, 1H), 7.16 (t, 1H), 7.12 (s, 3H), 3.72 (s, 3H), 2.20 (s, 6H). MS (EI) for $C_{30}H_{26}N_4O_2$: 475.3 (MH$^+$).

4-({4-[4-(dimethylamino)phenyl]quinazolin-2-yl}amino)-N-(2,6-dimethylphenyl)benzamide. $^1$H NMR (400 MHz, DMSO-d$_6$): δ 10.14 (s, 1H), 9.67 (s, 1H), 8.17 (d, 2H), 8.04-8.00 (m, 3H), 7.84-7.70 (m, 4H), 7.40 (t, 1H), 7.12 (s, 3H), 6.90 (d, 2H), 3.05 (s, 6H), 2.20 (s, 6H). MS (EI) for $C_{31}H_{29}N_5O$: 488.3 (MH$^+$).

3-{2-[(4-{[(2,6-dimethylphenyl)amino]carbonyl}phenyl)amino]quinazolin-4-yl}-N,N-dimethylbenzamide. $^1$H NMR (400 MHz, DMSO-d$_6$): δ 10.33 (s, 1H), 9.62 (s, 1H), 8.18 (d, 2H), 8.02 (d, 2H), 7.90-7.80 (m, 5H), 7.72-7.65 (m, 2H), 7.42 (t, 1H), 7.12 (s, 3H), 3.30 (s, 3H), 3.00 (s, 3H), 2.20 (s, 6H). MS (EI) for $C_{32}H_{29}N_5O_2$: 516.4 (MH$^+$).

4-({4-[4-(aminocarbonyl)phenyl]quinazolin-2-yl}amino)-N-(2,6-dimethylphenyl)benzamide. $^1$H NMR (400 MHz, DMSO-d$_6$): δ 10.36 (s, 1H), 9.65 (s, 1H), 8.22 (s, 1H), 8.17 (d, 2H), 8.13 (d, 2H), 8.02 (d, 2H), 7.91-7.82 (m, 5H), 7.58 (s, 1H), 7.42 (t, 1H), 7.22 (s, 3H), 2.20 (s, 6H). MS (EI) for $C_{30}H_{25}N_5O_2$: 488.3 (MH$^+$).

N-(2,6-dimethylphenyl)-4-({4-[3-(morpholin-4-ylmethyl)phenyl]quinazolin-2-yl}amino)benzamide. $^1$H NMR (400 MHz, DMSO-d$_6$): δ10.30 (s, 1H), 9.68 (s, 1H), 8.18 (d, 2H), 8.02 (d, 2H), 7.90-7.88 (m, 3H), 7.73-7.63 (m, 2H), 7.62-7.54 (m, 2H), 7.40 (t, 1H), 7.12 (s, 3H), 3.60 (m, 6H), 2.42 (t, 4H), 2.20 (s, 6H). MS (EI) for $C_{34}H_{33}N_5O_2$: 544.4 (MH$^+$).

4-{[4-(3,5-dimethylisoxazol-4-yl)quinazolin-2-yl]amino}-N-(2,6-dimethylphenyl)benzamide. $^1$H NMR (400 MHz, DMSO-d$_6$): δ 10.15 (s, 1H), 9.61 (s, 1H), 8.10 (d, 2H), 7.99 (d, 2H), 7.87 (m, 1H), 7.80 (d, 1H), 7.69 (d, 1H), 7.41 (m, 1H), 7.11 (s, 3H), 2.39 (s, 3H), 2.26 (s, 3H), 2.17 (s, 6H). MS (EI) for $C_{28}H_{25}N_5O_2$: 464.3 (MH$^+$).

N-(2,6-dimethylphenyl)-4-[(4-{3-[(4-methylpiperazin-1-yl)methyl]phenyl}quinazolin-2-yl)amino]benzamide. $^1$H NMR (400 MHz, DMSO-d$_6$): δ10.30 (s, 1H), 9.62 (s, 1H), 8.18 (d, 2H), 8.00 (d, 2H), 7.90-7.80 (m, 3H), 7.72-7.65 (m, 2H), 7.60-7.53 (m, 2H), 7.40 (t, 1H), 7.12 (s, 3H), 3.61 (s, 2H), 3.34 (br s, 2H), 2.44 (br s, 6H), 2.20 (s, 9H). MS (EI) for $C_{35}H_{36}N_6O$: 557.3 (MH$^+$).

4-[(4-{3-[(dimethylamino)methyl]phenyl}quinazolin-2-yl)amino]-N-(2,6-dimethylphenyl)benzamide. $^1$H NMR (400 MHz, DMSO-d$_6$): δ 10.32 (s, 1H), 9.61 (s, 1H), 8.18 (d, 2H), 8.00 (d, 2H), 7.90-7.80 (m, 3H), 7.72-7.65 (m, 2H), 7.60-7.52 (m, 2H), 7.41 (t, 1H), 7.12 (s, 3H), 3.53 (s, 2H), 2.21 (s, 6H), 2.19 (s, 6H). MS (EI) for $C_{32}H_{31}N_5O$: 502.4 (MH$^+$).

N-(2,6-dimethylphenyl)-4-({4-[4-(morpholin-4-ylmethyl)phenyl]quinazolin-2-yl}amino)benzamide. $^1$H NMR (400 MHz, DMSO-d$_6$): δ 10.28 (s, 1H), 9.61 (s, 1H), 8.17 (d, 2H), 8.00 (d, 2H), 7.90-7.80 (m, 3H), 7.77 (d, 2H), 7.56 (d, 2H), 7.40 (t, 1H), 7.12 (s, 3H), 3.64-3.59 (m, 6H), 2.42 (t, 4H), 2.20 (s, 6H). MS (EI) for $C_{34}H_{33}N_5O_2$: 544.3 (MH$^+$).

N-(2,6-dimethylphenyl)-4-[(4-{4-[(4-methylpiperazin-1-yl)methyl]phenyl}quinazolin-2-yl)amino]benzamide. $^1$H NMR (400 MHz, DMSO-d$_6$): δ 10.29 (s, 1H), 9.62 (s, 1H), 8.17 (d, 2H), 8.01 (d, 2H), 7.90-7.80 (m, 3H), 7.75 (d, 2H), 7.54 (d, 2H), 7.40 (t, 1H), 7.12 (s, 3H), 3.59 (s, 2H), 2.50-2.30 (m, 8H), 2.20 (s, 6H), 2.16 (s, 3H). MS (EI) for $C_{35}H_{36}N_6O$: 557.5 (MH$^+$).

4-[(4-{4-[(dimethylamino)methyl]phenyl}quinazolin-2-yl)amino]-N-(2,6-dimethylphenyl)benzamide. $^1$H NMR (400 MHz, DMSO-d$_6$): δ 10.30 (s, 1H), 9.62 (s, 1H), 8.17 (d, 2H), 8.02 (d, 2H), 7.90-7.80 (m, 3H), 7.75 (d, 2H), 7.54 (d, 2H), 7.40 (t, 1H), 7.12 (s, 3H), 3.53 (s, 2H), 2.21 (s, 6H), 2.19 (s, 6H). MS (EI) for $C_{32}H_{31}N_5O$: 502.4 (MH$^+$).

N-(2,6-dimethylphenyl)-4-({4-[4-(methylamino)phenyl]quinazolin-2-yl}amino)benzamide. $^1$H NMR (400 MHz, DMSO-d$_6$): δ 10.10 (s, 1H), 9.61 (s, 1H), 8.18 (d, 2H), 8.05-7.98 (m, 3H), 7.83-7.74 (m, 2H), 7.68 (d, 2H), 7.39 (t, 1H), 7.12 (s, 3H), 6.73 (d, 2H), 6.38 (q, 1H), 2.79 (d, 3H), 2.20 (s, 6H). MS (EI) for $C_{30}H_{27}N_5O$: 474.2 (MH$^+$).

N-(2,6-dimethylphenyl)-4-[(4-{4-[(2-methylpropyl)amino]phenyl}quinazolin-2-yl)amino]benzamide. $^1$H NMR (400 MHz, DMSO-d$_6$): δ 10.10 (s, 1H), 9.68 (s, 1H), 8.17 (d, 2H), 8.06-8.00 (m, 3H), 7.82-7.73 (m, 2H), 7.65 (d, 2H), 7.38

(t, 1H), 7.12 (s, 3H), 6.78 (d, 2H), 6.46 (t, 1H), 2.93 (t, 2H), 2.20 (s, 6H), 1.90 (m, 1H), 0.99 (d, 6H). MS (EI) for $C_{33}H_{33}N_5O$: 516.2 (MH+).

N-(2,6-dimethylphenyl)-4-[(4-{4-[(1-methylethyl)amino]phenyl}quinazolin-2-yl)amino]benzamide. $^1$H NMR (400 MHz, DMSO-$d_6$): δ 10.10 (s, 1H), 9.65 (s, 1H), 8.17 (d, 2H), 8.03 (t, 1H), 8.00 (d, 2H), 7.82-7.72 (m, 2H), 7.64 (d, 2H), 7.38 (t, 1H), 7.12 (s, 3H), 6.75 (d, 2H), 6.20 (d, 1H), 3.68 (m, 1H), 2.20 (s, 6H), 1.20 (d, 6H). MS (EI) for $C_{32}H_{31}N_5O$: 502.3 (MH+).

4-{[4-(4-{[3-(dimethylamino)propyl]amino}phenyl)quinazolin-2-yl]amino}-N-(2,6-dimethylphenyl)benzamide. $^1$H NMR (400 MHz, DMSO-$d_6$): δ 10.10 (s, 1H), 9.61 (s, 1H), 8.17 (d, 2H), 8.05-7.98 (m, 3H), 7.82-7.73 (m, 2H), 7.65 (d, 2H), 7.38 (t, 1H), 7.12 (s, 3H), 6.75 (d, 2H), 6.36 (t, 1H), 3.14 (q, 2H), 2.33 (t, 2H), 2.20 (s, 6H), 2.16 (s, 6H), 1.74 (s, 2H). MS (EI) for $C_{34}H_{36}N_6O$: 545.3 (MH+).

N-(2,6-dimethylphenyl)-4-{[4-(1-methyl-1H-pyrazol-4-yl)quinazolin-2-yl]amino}benzamide. $^1$H NMR (400 MHz, DMSO-$d_6$): δ10.08 (s, 1H), 9.60 (s, 1H), 8.62 (s, 1H), 8.30 (d, 1H), 8.20 (s, 1H), 8.14 (d, 2H), 8.00 (d, 2H), 7.85 (m, 1H), 7.75 (d, 1H), 7.44 (t, 1H), 7.13 (s, 3H), 4.01 (s, 3H), 2.20 (s, 6H). MS (EI) for $C_{27}H_{24}N_6O$: 449.3 (MH+).

N-(2,6-dimethylphenyl)-4-{[4-(4-{[3-(ethyloxy)propyl]amino}phenyl)quinazolin-2-yl]amino}benzamide. $^1$H NMR (400 MHz, DMSO-$d_6$): δ10.10 (s, 1H), 9.60 (s, 1H), 8.18 (d, 2H), 8.05-7.98 (m, 3H), 7.82-7.73 (m, 2H), 7.67 (d, 2H), 7.48 (t, 1H), 7.22 (s, 3H), 6.76 (d, 2H), 6.32 (t, 1H), 3.50 (t, 2H), 3.44 (q, 2H), 3.18 (q, 2H), 2.20 (s, 6H), 1.83 (s, 2H), 1.14 (t, 3H). MS (EI) for $C_{34}H_{35}N_5O_2$: 546.4 (MH+).

4-{[4-(4-fluorophenyl)quinazolin-2-yl]amino}-N-[2-methyl-5-(morpholin-4-ylmethyl)phenyl]benzamide. $^1$H NMR (400 MHz, DMSO-$d_6$): δ 10.34 (s, 1H), 9.71 (s, 1H), 8.17 (d, 2H), 8.00 (d, 2H), 7.91-7.83 (m, 6H), 7.50-7.31 (m, 4H), 7.31 (s, 1H), 7.23 (d, 1H), 7.08 (d, 1H), 3.57 (t, 4H), 3.44 (s, 2H), 2.36 (br s, 4H), 2.23 (s, 3H). MS (EI) for $C_{33}H_{30}FN_5O_2$: 548.3 (MH+).

N-[5-(aminomethyl)-2-methylphenyl]-4-{[4-(4-chlorophenyl)-quinazolin-2-yl]amino}benzamide. $^1$H NMR (400 MHz, DMSO-$d_6$): δ 10.36 (s, 1H), 9.72 (s, 1H), 8.16 (m, 2H), 7.98 (m, 2H), 7.88 (m, 1H), 7.84 (m, 4H), 7.72 (m, 2H), 7.42 (m, 1H), 7.32 (br s, 1H), 7.20 (m, 1H), 7.12 (m, 1H), 3.70 (s, 2H), 2.22 (s, 3H). MS (EI) for $C_{29}H_{24}ClN_5O$: 495.0 (MH+).

Example 190

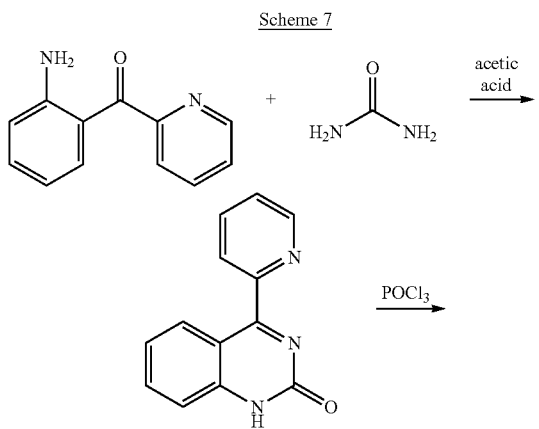

Scheme 7

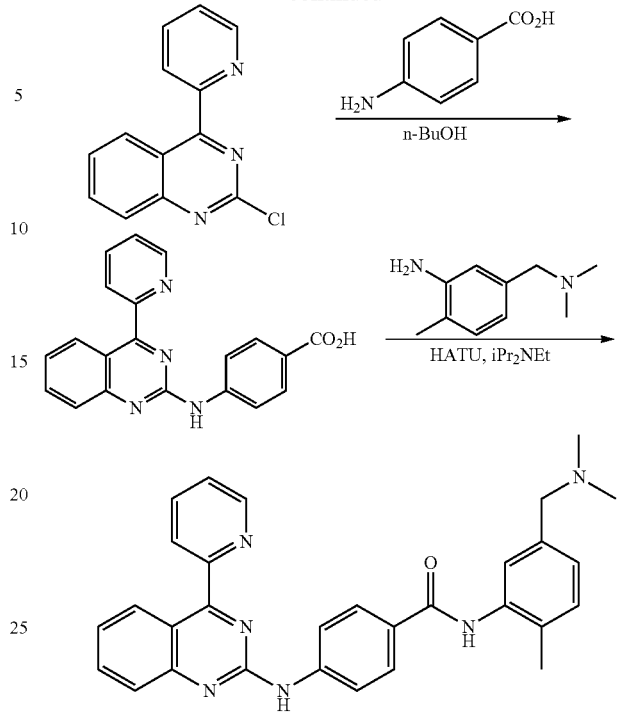

Example 190

N-{5-[(dimethylamino)methyl]-2-methylphenyl}-4-[(4-pyridin-2-ylquinazolin-2-yl)amino]benzamide A solution of 2-aminophenyl-2-pyridyl ketone (0.95 g, 4.8 mmol), urea (500 mg, 8.3 mmol) and acetic acid (10 mL) was stirred at 110° C. for 18 h. The reaction mixture was cooled to rt and filtered. The solid was washed with water and dried under reduced pressure to give 4-(pyridin-2-yl)quinazolin-2 (1H)-one as a yellow solid (0.83 g, 78%), which was dissolved in phosphorous oxychloride (3 mL) and the mixture was stirred at reflux for 30 min. The reaction mixture was cooled to rt and slowly poured over an ice/water mixture. The mixture was filtered and the solid was dried under reduced pressure to give 2-chloro-4-(pyridin-2-yl)quinazoline as an off-white solid (56 mg, 6%).

To a solution of 2-chloro-4-(pyridin-2-yl)quinazoline (60 mg, 0.25 mmol) in butanol was added 4-aminobenzoic acid (36 mg, 0.26 mmol) and the stirred mixture was heated to reflux for 20 min, after which time the reaction mixture was cooled and the solvent removed on a rotary evaporator. The residue was redissolved in dimethylformamide (20 mL) and 5-((dimethyl-amino)methyl)-2-methylaniline (50 mg, 0.30 mmol), HATU (170 mg, 0.45 mmol) and Hunig's base (150 μL, 0.87 mmol) were added to the solution. The stirred mixture was heated to 70° C. for 18 h, then diluted with ethyl acetate and the solution was extracted with 10% aqueous lithium chloride and 1 N hydrochloric acid. The combined acidic washes were made basic with saturated sodium bicarbonate and extracted with ethyl acetate. The combined organic extracts were then dried over sodium sulfate, filtered and concentrated on a rotary evaporator. The product was purified by preparative reverse phase HPLC to give N-{5-[(dimethylamino)methyl]-2-methylphenyl}-4-[(4-pyridin-2-ylquinazolin-2-yl)amino]benzamide as a yellow solid (39 mg, 16% yield). $^1$H-NMR (400 MHz, DMSO-$d_6$): δ11.30 (s, 1H), 10.30 (s, 1H), 9.68 (s, 1H), 8.84-8.83 (m, 1H), 8.49-8.47 (d, 1H), 8.16-8.09 (m, 3H), 8.16-8.09 (m, 2H), 7.99-7.97 (m, 2H), 7.43-7.39 (m, 1H), 7.37 (s, 1H), 7.21 (d, 2H), 7.07 (d, 1H), 3.43 (br s, 2H), 2.22 (s, 6H), 2.20 (s, 3H). MS (EI) for $C_{30}H_{28}N_6O$: 489.3 (MH$^+$).

Example 191

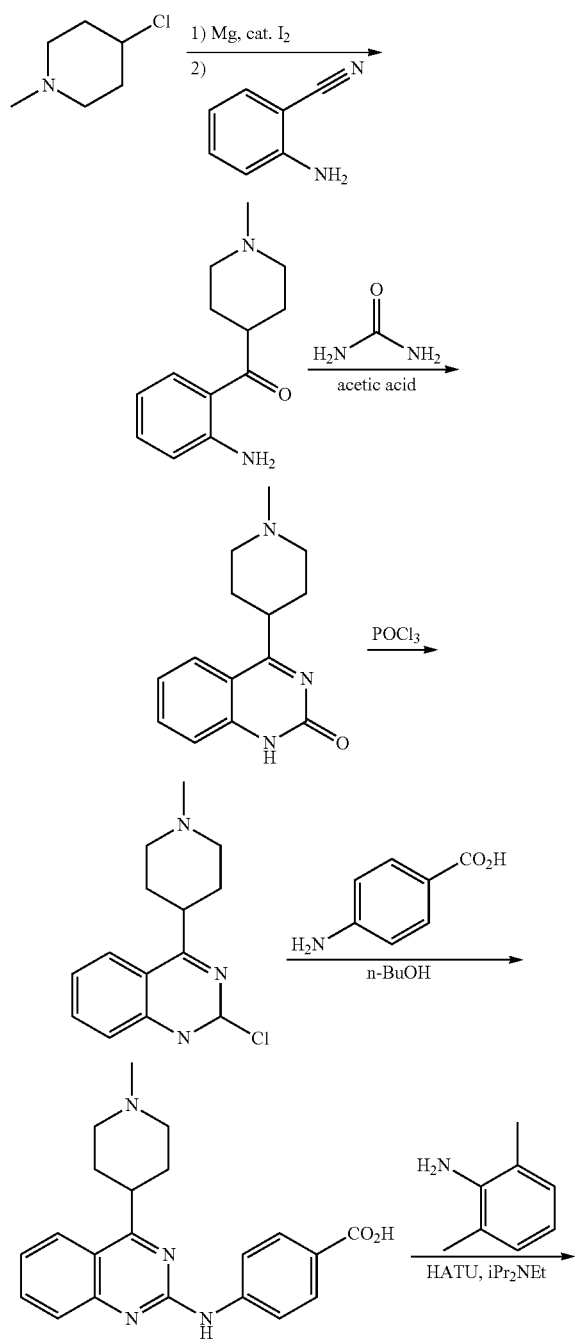

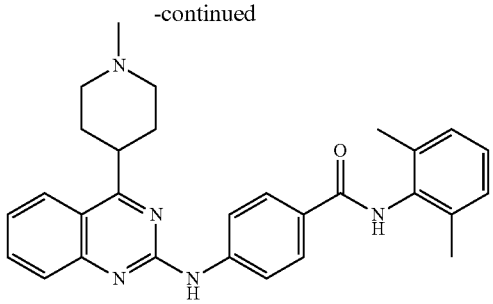

Example 191

N-(2,6-dimethylphenyl)-4-{[4-(1-methylpiperidin-4-yl)quinazolin-2-yl]amino}benzamide To a suspension of magnesium (1.8 g, 74 mmol) in dry THF (50 mL) in a flame-dried round bottomed flask under nitrogen was added 4-chloro-1-methylpiperidine (9.0 g, 68 mmol). A crystal of iodine and a catalytic amount of cyclohexylmagnesium chloride was added and the mixture was heated to reflux for 2 h. A gray precipitate formed, which was removed via vacuum filtration under a nitrogen atmosphere. To the filtrate was added a solution of 2-aminobenzonitrile (1.6 g, 14 mmol) in dry THF (15 mL). The stirred mixture was heated to 45° C. for 2 h. Ice was added and the reaction was quenched with 1 M sulfuric acid. The mixture was extracted with ethyl acetate and the acidic aqueous layer was then neutralized with 1 N sodium hydroxide, concentrated on a rotary evaporator and extracted with ethyl acetate. The combined organics were dried over sodium sulfate, filtered and concentrated to afford (2-aminophenyl)(1-methylpiperidin-4-yl)methanone as a yellow oil (1.0 g, 7%).

A stirred mixture of (2-aminophenyl)(1-methylpiperidin-4-yl)methanone (1.10 g, 4.58 mmol), urea (550 mg, 9.17 mmol) and acetic acid (15 mL) was heated to overnight. The mixture was cooled to rt, neutralized with 1 N sodium hydroxide and concentrated to ~10 mL on a rotary evaporator. The aqueous residue was extracted with ethyl acetate and the combined organics were dried over sodium sulfate, filtered and concentrated on a rotary evaporator to afford 4-(1-methylpiperidin-4-yl)quinazolin-2(1H)-one as a yellow solid (1.10 g, 97%).

A stirred mixture of 4-(1-methylpiperidin-4-yl)quinazolin-2(1H)-one (500 mg, 2.29 mmol) and phosphorous oxychloride (5 mL, 56 mmol) was heated to reflux for 3 h. The reaction was then concentrated on a rotary evaporator and treated with ice water. The aqueous mixture was then extracted with ethyl acetate, and the combined organic extracts were dried over sodium sulfate, filtered and concentrated on a rotary evaporator. The residue was treated with 4-aminobenzoic acid (534 mg, 3.90 mmol), triethylamine (660 μL, 4.58 mmol) and n-butanol (5 mL) and the mixture was heated to 140° C. for 25 min. The mixture was cooled and the solvent removed on a rotary evaporator. This material was then treated with HATU (1.63 g, 4.29 mmol) and Hunig's base (1.1 mL, 6.3 mmol) in dimethylformamide (10 mL) and the mixture stirred until it became homogenous. To this mixture was added 2,6-dimethylaniline (620 mg, 5.12 mmol) and the reaction was heated to 50° C. overnight. The mixture was cooled to rt, diluted with water and extracted with ethyl acetate. The combined organic extracts were washed with 1 N sodium bicarbonate and a 5% aqueous solution of lithium chloride, then was extracted with 1 N hydrochloric acid. The combined acidic washes were neutralized with 1 N sodium hydroxide and extracted with dichloromethane. These combined organic extracts were dried over sodium sulfate, filtered and concentrated on a rotary evaporator. Purification of this material via preparative reverse phase HPLC gave N-(2,6-dimethylphenyl)-4-{[4-(1-methylpiperidin-4-yl)quinazolin-2-yl]amino}benzamide as a white solid (19.7 mg, 2%). $^1$H NMR (400 MHz, CDCl$_3$): δ 8.02-7.95 (m, 5H), 7.85-7.72 (m, 3H), 7.44-7.32 (m, 2H), 7.18-7.08 (m, 3H), 4.20-3.65 (br s, 3H), 3.55-3.45 (m, 1H), 3.20 (d, 2H), 2.44 (s, 3H), 2.39-2.18 (m, 10H), 2.07 (s, 2H), 1.99 (d, 2H). MS (EI) for $C_{29}H_{31}N_5O$: 466.0 (MH$^+$).

Examples 192-224

Using the procedures described in Scheme 8, the following compounds were prepared.

4-[(6-chloro-4-phenylquinazolin-2-yl)amino]-N-(2-methylphenyl)benzamide. $^1$H NMR (400 MHz, DMSO-d$_6$): δ 10.45 (s, 1H), 9.73 (s, 1H), 8.16 (d, 2H), 8.00 (d, 2H), 7.90-7.79 (m, 5H), 7.63 (m, 5H), 7.38-7.16 (m, 5H), 2.25 (s, 3H). MS (EI) for $C_{28}H_{21}ClN_4O$: 465.2 (MH$^+$).

N-(2,6-dimethylphenyl)-4-[(6-methyl-4-phenylquinazolin-2-yl)amino]benzamide. $^1$H NMR (400 MHz, DMSO-d$_6$): δ 10.23 (s, 1H), 9.60 (s, 1H), 8.16 (d, 2H), 8.01 (d, 2H), 7.79-7.75 (m, 4H), 7.64 (m, 4H), 7.13 (s, 3H), 2.41 (s, 3H), 2.20 (s, 6H). MS (EI) for $C_{30}H_{26}N_4O$: 459.2 (MH$^+$).

4-{[6,7-bis(methyloxy)-4-phenylquinazolin-2-yl]amino}-N-(2,6-dimethylphenyl)benzamide. $^1$H NMR (400 MHz, DMSO-d$_6$): δ 10.05 (s, 1H), 9.57 (s, 1H), 8.14 (d, 2H), 7.97 (d, 2H), 7.83 (m, 3H), 7.63 (m, 3H), 7.24 (s, 1H), 7.15 (s, 1H), 7.13 (s, 3H), 4.01 (s, 3H), 3.76 (s, 3H), 2.19 (s, 6H). MS (EI) for $C_{31}H_{28}N_4O_3$: 505.2 (MH$^+$).

4-[(6-chloro-4-phenylquinazolin-2-yl)amino]-N-methyl-N-phenylbenzamide. $^1$H NMR (400 MHz, DMSO-d$_6$): δ 10.23 (s, 1H), 7.86 (m, 3H), 7.80 (m, 1H), 7.74 (m, 3H), 7.62 (m, 3H), 7.29 (t, 2H), 7.23 (d, 2H), 7.18 (d, 3H), 3.38 (s, 3H). MS (EI) for $C_{28}H_{21}ClN_4O$: 465.0 (MH$^+$).

4-[(6-chloro-4-phenylquinazolin-2-yl)(methyl)amino]-N-(2,6-dimethylphenyl)benzamide. $^1$H NMR (400 MHz, DMSO-d$_6$): δ 9.76 (s, 1H), 8.03 (d, 2H), 7.82 (dd, 1H), 7.75 (d, 1H), 7.72 (m, 3H), 7.66 (s, 1H), 7.64 (s, 1H), 7.61 (m, 3H), 7.13 (s, 3H), 3.69 (s, 3H), 2.19 (s, 6H). MS (EI) for $C_{30}H_{25}ClN_4O$: 493.1 (MH$^+$).

4-[(6-chloro-4-phenylquinazolin-2-yl)amino]-N-cyclopropylbenzamide. $^1$H-NMR (400 MHz, DMSO-d$_6$): δ 10.40 (s, 1H), 8.30 (d, 1H), 8.06 (d, 2H), 7.90-7.75 (m, 7H), 7.66-7.64 (m, 3H), 2.84 (q, 1H), 0.71-0.67 (m, 2H), 0.57-0.055 (m, 2H). MS (EI) for $C_{24}H_{19}ClN_4O$: 415 (MH$^+$).

4-[(6-chloro-4-phenylquinazolin-2-yl)amino]-N-[2-(pyrrolidin-1-ylmethyl)phenyl]benzamide. $^1$H NMR (400 MHz, DMSO-d$_6$): δ 11.80 (s, 1H), 10.47 (s, 1H), 8.36 (d, 1H), 8.19 (d, 2H), 7.92-7.78 (m, 8H), 7.65 (m, 3H), 7.32 (t, 1H), 7.25 (d, 2H), 7.02 (t, 1H), 3.84 (s, 2H), 2.58 (s, 4H), 1.85 (s, 4H). MS (EI) for $C_{32}H_{28}ClN_5O$: 534.2 (MH$^+$).

4-[(6-chloro-4-phenylquinazolin-2-yl)amino]-N-[2-(morpholin-4-ylmethyl)phenyl]benzamide. $^1$H NMR (400 MHz, DMSO-d$_6$): δ 11.24 (s, 1H), 10.49 (s, 1H), 8.33 (d, 1H), 8.20 (d, 2H), 7.97-7.78 (m, 7H), 7.66 (m, 3H), 7.33 (s, 1H), 7.26 (d, 1H), 7.05 (t, 1H), 3.73 (s, 2H), 3.66 (t, 4H), 2.48 (br s, 4H). MS (EI) for $C_{32}H_{28}ClN_5O_2$: 550.2 (MH$^+$).

4-[(6-chloro-4-phenylquinazolin-2-yl)amino]-N-(2-morpholin-4-ylphenyl)benzamide. $^1$H NMR (400 MHz, DMSO-d$_6$): δ 10.51 (s, 1H), 9.54 (s, 1H), 8.21 (m, 3H), 7.98 (d, 2H), 7.90 (s, 2H), 7.82-7.77 (m, 3H), 7.66 (m, 3H), 7.32 (d, 1H), 7.18 (m, 2H), 3.82 (t, 4H), 2.88 (t, 4H). MS (EI) for $C_{31}H_{26}ClN_5O_2$: 534.3 (MH$^+$).

4-[(6-chloro-4-phenylquinazolin-2-yl)amino]-N-(2-fluorophenyl)benzamide. $^1$H NMR (400 MHz, DMSO-d$_6$): δ 10.47 (s, 1H), 9.95 (s, 1H), 8.17 (d, 2H), 8.01 (s, 2H), 7.92 (m, 1H), 7.86-7.77 (m, 3H), 7.67-7.60 (m, 4H), 7.32-7.20 (m, 3H). MS (EI) for $C_{27}H_{18}ClFN_4O$: 469.1 (MH$^+$).

N-{1-[(2,6-dichlorophenyl)acetyl]piperidin-4-yl}-4-phenylquinazolin-2-amine. $^1$H NMR (400 MHz, DMSO-d$_6$): δ 7.70 (m, 5H), 7.60 (m, 5H), 7.45 (d, 1H), 7.18 (m, 1H), 4.25 (m, 2H), 4.15 (t, 1H), 4.02 (d, 2H), 3.45 (m, 1H), 2.90 (t, 1H), 2.05 (d, 1H), 2.00 (d, 1H), 1.65 (m, 1H), 1.45 (m, 1H). MS (EI) for $C_{27}H_{24}Cl_2N_4O$: 491.1 (MH$^+$).

N-(2,6-dimethylphenyl)-4-{[6-(4-methylpiperazin-1-yl)-4-phenylquinazolin-2-yl]amino}benzamide. $^1$H NMR (400 MHz, DMSO-d$_6$): δ 10.15 (s, 1H), 9.65 (br s, 1H), 9.58 (s, 1H), 8.13 (d, 2H), 8.00 (d, 2H), 7.84-7.78 (m, 4H), 7.65-7.62 (m, 3H), 7.15-7.13 (m, 4H), 3.81 (d, 2H), 3.25 (d, 2H), 3.18 (m, 2H), 2.94 (m, 2H), 2.86 (s, 3H), 2.19 (s, 3H). MS (EI) for $C_{34}H_{34}N_6O.C_2H_3O_2$: 541.4 (MH$^+$).

4-[(6-chloro-4-phenylquinazolin-2-yl)amino]-N-{3-[(dimethylamino)methyl]phenyl}benzamide. $^1$H NMR (400 MHz, DMSO-d$_6$): δ 10.46 (s, 2), 10.16 (s, 1H), 8.17 (d, 2H), 8.00 (d, 2H), 7.92-7.80 (m, 6H), 7.72-7.65 (m, 4H), 7.37 (t, 1H), 7.11 (d, 1H), 3.79 (s, 2H), 2.44 (s, 6H). MS (EI) for $C_{30}H_{26}ClN_5O$: 508.2 (MH$^+$).

4-[(6-chloro-4-phenylquinazolin-2-yl)amino]-N-(4-methylpyrrolidin-3-yl)benzamide. $^1$H NMR (400 MHz, DMSO-d$_6$): δ 10.36 (s, 1H), 8.20 (d, 1H), 8.08 (d, 2H) 7.87-7.75 (m, 7H), 7.65 (m, 3H), 3.91 (m, 1H), 3.09 (m, 2H), 2.66 (m, 1H), 2.38 (q, 1H), 2.09 (m, 1H), 1.03 (d, 3H). MS (EI) for $C_{26}H_{24}ClN_5O$: 458.2 (MH$^+$).

N-(2-aminophenyl)-4-[(6-chloro-4-phenylquinazolin-2-yl)amino]benzamide. $^1$H NMR (400 MHz, DMSO-d$_6$): δ 10.40 (s, 1H), 9.99 (s, 1H), 8.18-8.16 (d, 2H), 8.07-7.99 (m, 3H), 7.91-7.99 (m, 4H), 7.67-7.66 (m, 3H), 7.36 (d, 1H), 7.19-7.10 (m, 2H), 7.03-7.01 (m, 1H). MS (EI) for $C_{27}H_{20}ClN_5O$: 466 (MH$^+$).

N-(2,6-dimethylphenyl)-4-{[7-(methyloxy)-4-phenylquinazolin-2-yl]amino}benzamide. $^1$H-NMR (400 MHz, DMSO-d$_6$): δ 10.20 (s, 1H), 9.60 (s, 1H), 8.17 (d, 2H), 8.00 (d, 2H), 7.78-7.70 (m, 3H), 7.64-7.58 (m, 3H), 7.20 (d, 1H), 7.12 (s, 3H), 7.02 (dd, 1H), 3.97 (s, 3H), 2.20 (s, 6H). MS (EI) for $C_{30}H_{26}N_4O_2$: 475.2 (MH$^+$)

N-(2,6-dimethylphenyl)-4-[(7-hydroxy-4-phenylquinazolin-2-yl)amino]benzamide. $^1$H-NMR (400 MHz, DMSO-d$_6$): δ 10.10 (s, 1H), 9.59 (s, 1H), 8.12 (d, 2H), 7.98 (d, 2H), 7.76-7.68 (m, 3H), 7.62-7.58 (m, 3H), 7.12 (s, 3H), 7.02 (d, 1H), 6.92 (d, 1H), 2.19 (s, 6H). MS (EI) for $C_{29}H_{24}N_4O_2$: 461.4 (MH$^+$).

N-(2,6-dimethylphenyl)-4-({7-[(3-morpholin-4-ylpropyl)oxy]-4-phenylquinazolin-2-yl}amino)benzamide. $^1$H-NMR (400 MHz, DMSO-d$_6$): δ 10.18 (s, 1H), 9.60 (s, 1H), 8.16 (d, 2H), 8.00 (d, 2H), 7.78-7.70 (m, 3H), 7.64-7.59 (m, 3H), 7.18 (d, 1H), 7.12 (s, 3H), 7.00 (d, 1H), 4.23 (t, 2H), 3.59 (t, 4H), 2.45 (t, 2H), 2.38 (t, 4H), 2.20 (s, 6H), 1.96 (m, 2H). MS (EI) for $C_{36}H_{37}N_5O_3$: 588.3 (MH$^+$).

4-[(6-chloro-4-phenylquinazolin-2-yl)amino]-N-(2-ethylphenyl)benzamide. $^1$H-NMR (400 MHz, DMSO-d$_6$): δ 10.40 (s, 1H), 9.73 (s, 1H), 8.14 (d, 2H), 7.99 (d, 2H), 7.91-7.77 (m, 5H), 7.68-7.76 (m, 3H), 7.33-7.29 (m, 2H), 7.25-7.21 (m, 2H), 2.64 (q, 2H), 1.41 (t, 3H). MS (EI) for $C_{29}H_{23}ClN_4O$: 479.0 (MH$^+$).

N-(2-chlorophenyl)-4-[(6-chloro-4-phenylquinazolin-2-yl)amino]benzamide. $^1$H-NMR (400 MHz, DMSO-d$_6$): δ 10.50 (s, 1H), 9.87 (s, 1H), 8.16 (d, 2H), 8.00 (d, 2H), 7.92-7.86 (m, 2H), 7.82-7.77 (m, 3H), 7.67-7.63 (m, 4H), 7.56 (dd, 1H), 7.42-7.38 (m, 1H), 7.31-7.27 (m, 1H). MS (EI) for $C_{27}H_{18}Cl_2N_4O$: 487.1 (MH$^+$).

4-[(6-chloro-4-phenylquinazolin-2-yl)amino]-N-{5-[(dimethylamino)methyl]-2-methylphenyl}benzamide. $^1$H NMR (400 MHz, DMSO-d$_6$): δ 10.44 (s, 1H), 9.71 (s, 1H), 8.15 (d, 2H), 8.00 (d, 2H), 7.91-7.63 (m, 8H), 7.31 (s, 1H), 7.21 (d, 2H), 7.07 (d, 1H), 3.36 (s, 2H), 2.24 (s, 3H), 2.15 (s, 6H). MS (EI) for C$_{31}$H$_{28}$ClN$_5$O: 523.0 (MH$^+$).

N-{5-[(dimethylamino)methyl]-2-methylphenyl}-4-{[4-(1-methylethyl)quinazolin-2-yl]amino}benzamide. $^1$H-NMR (400 MHz, DMSO-d$_6$): δ 9.98 (s, 1H), 9.68 (s, 1H), 8.18 (d, 1H), 8.13 (d, 2H), 7.96 (d, 2H), 7.80 (m, 1H), 7.70 (d, 1H), 7.38 (m, 2H), 7.24 (m, 1H), 7.11 (d, 1H), 3.95 (m, 1H), 3.32 (s, 2H), 2.30 (s, 6H), 2.23 (s, 3H), 1.37 (d, 6H). MS (EI) for C$_{28}$H$_{31}$N$_5$O: 454.4 (MH$^+$).

N-(2,6-dimethylphenyl)-4-{[4-(1-methylethyl)quinazolin-2-yl]amino}benzamide. $^1$H-NMR (400 MHz, DMSO-d$_6$): δ 9.96 (s, 1H), 9.58 (s, 1H), 8.17 (d, 1H), 8.12 (d, 2H), 7.97 (d, 2H), 7.80 (m, 1H), 7.71 (m, 1H), 7.40 (m, 1H), 7.11 (s, 3H), 3.93 (m, 1H), 2.16 (s, 6H), 1.36 (d, 6H). MS (EI) for C$_{26}$H$_{26}$N$_4$O: 411.4 (MH$^+$).

4-[(4-cyclopropylquinazolin-2-yl)amino]-N-(2,6-dimethylphenyl)benzamide. $^1$H-NMR (400 MHz, CD$_3$OD): δ 8.27 (d, 1H), 8.06-7.96 (m, 4H), 7.79-7.68 (m, 2H), 7.42-7.37 (m, 1H), 7.13 (s, 3H), 2.90-2.82 (m, 1H), 2.27 (s, 6H), 1.41-1.36 (m, 2H), 1.26-1.20 (m, 2H). MS (EI) for C$_{26}$H$_{24}$N$_4$O: 409.0 (MH$^+$).

N-(2,6-dimethylphenyl)-4-[(4-methylquinazolin-2-yl)amino]benzamide. $^1$H NMR (400 MHz, CDCl$_3$): δ 8.03-7.91 (m, 5H), 7.83-7.73 (m, 2H), 7.52 (s, 1H), 7.42-7.31 (m, 2H), 7.18-7.10 (m, 3H), 2.96 (s, 3H), 3.30 (s, 6H). MS (EI) for C$_{24}$H$_{22}$N$_4$O: 383.0 (MH$^+$).

N-[2-methyl-5-(morpholin-4-ylmethyl)phenyl]-4-[(4-methylquinazolin-2-yl)amino]benzamide. $^1$H NMR (400 MHz, CDCl$_3$): δ 8.47 (s, 1H), 8.14 (s, 1H), 8.09-7.88 (m, 5H), 7.86-7.77 (m, 2H), 7.62-7.53 (m, 1H), 7.48-7.37 (m, 1H), 7.33 (d, 1H), 7.27 (s, 1H), 4.27 (br s, 2H), 4.14 (s, 2H), 3.94 (br s, 2H), 3.31 (br s, 2H), 2.91 (m, 5H), 2.39 (s, 3H). MS (EI) for C$_{28}$H$_{29}$N$_5$O$_2$: 468.4 (MH$^+$).

4-[(6-chloro-4-phenylquinazolin-2-yl)amino]-N-[2-methyl-5-(morpholin-4-ylmethyl)phenyl]benzamide. $^1$H NMR (400 MHz, DMSO-d$_6$): δ 10.45 (s, 1H), 9.72 (s, 1H), 8.16-8.14 (d, 2H), 8.00-7.98 (d, 2H), 7.92-7.89 (m, 2H), 7.88-7.77 (m, 3H), 7.68-7.65 (m, 3H), 7.31 (s, 1H), 7.23-7.21 (d, 1H), 7.10-7.08 (d, 1H), 3.58-3.56 (t, 4H), 3.44 (s, 2H), 2.36 (m, 4H), 2.22 (s, 3H). MS (EI) for C$_{33}$H$_{30}$ClN$_5$O$_2$: 564.0 (MH$^+$).

4-[(4-ethylquinazolin-2-yl)amino]-N-[2-methyl-5-(morpholin-4-ylmethyl)phenyl]benzamide. $^1$H-NMR (400 MHz, CD$_3$OD): δ 8.13-8.06 (m, 3H), 7.97 (d, 2H), 7.79-7.71 (m, 2H), 7.42-7.35 (m, 1H), 7.34 (s, 1H), 7.27 (d, 1H), 7.18 (d, 1H), 3.69 (t, 4H), 3.55 (s, 2H), 3.30-3.23 (m, 2H), 2.51 (br s, 4H), 2.30 (s, 3H), 1.48-1.42 (dt, 3H). MS (EI) for C$_{29}$H$_{31}$N$_5$O$_2$: 482.0 (MH$^+$).

4-[(4-cyclopropylquinazolin-2-yl)amino]-N-[2-methyl-5-(morpholin-4-ylmethyl)phenyl]benzamide. $^1$H-NMR (400 MHz, CD$_3$OD): δ 8.30 (d, 1H), 8.10-7.93 (m, 4H), 7.80-7.70 (m, 2H), 7.44-7.38 (m, 1H), 7.34 (s, 1H), 7.27 (d, 1H), 7.19 (d, 1H), 3.69 (t, 4H), 3.54 (s, 2H), 2.92-2.85 (m, 1H), 2.50 (br s, 4H), 2.30 (s, 3H), 1.42-1.37 (m, 2H), 1.27-1.21 (m, 2H). MS (EI) for C$_{30}$H$_{31}$N$_5$O$_2$: 494.0 (MH$^+$).

4-{[4-(1-methylethyl)quinazolin-2-yl]amino}-N-[2-methyl-5-(morpholin-4-ylmethyl)phenyl]benzamide. $^1$H NMR (400 MHz, CDCl$_3$): δ 8.06-7.89 (m, 6H), 7.83-7.65 (m, 3H), 7.51 (s, 1H), 7.41-7.34 (t, 1H), 7.19 (d, 1H), 7.10 (d, 1H), 3.92-3.81 (m, 1H), 3.77-3.66 (m, 4H), 3.53 (s, 3H), 2.59-2.42 (m, 4H), 2.35 (s, 3H), 1.47-1.39 (m, 6H). MS (EI) for C$_{30}$H$_{33}$N$_5$O$_2$: 496.0 (MH$^+$).

4-{[4-(1-methylethyl)quinazolin-2-yl]amino}-N-(2-methyl-5-{[methyl(phenylmethyl)amino]methyl}phenyl)benzamide. $^1$H NMR (400 MHz, CDCl$_3$): δ 8.06-7.88 (m, 6H), 7.83-7.73 (m, 2H), 7.66 (s, 1H), 7.45 (s, 1H), 7.42-7.29 (m, 5H), 7.25-7.13 (m, 2H), 3.92-3.81 (m, 1H), 3.66-3.45 (m 4H), 2.35 (s, 3H), 2.20 (s, 3H), 1.48-1.41 (m, 4H). MS (EI) for C$_{34}$H$_{35}$N$_5$O: 530.0 (MH$^+$).

N-(2-methyl-5-{[methyl(phenylmethyl)amino]methyl}phenyl)-4-[(4-methylquinazolin-2-yl)amino]benzamide. $^1$H NMR (400 MHz, DMSO-d$_6$): δ 10.16 (s, 1H), 9.70 (s, 1H), 8.17-8.14 (d, 2H), 8.13-8.10 (d, 1H), 8.00-7.97 (d, 2H), 7.85-7.81 (t, 1H), 7.74-7.72 (d, 1H), 7.45-41 (t, 1H), 7.38-7.31 (m, 3H), 7.29-7.22 (m, 2H), 7.15-7.13 (d, 1H), 3.50 (s, 2H), 3.48 (s, 2H), 2.86 (s, 3H), 2.23 (s, 3H), 2.09 (s, 3H). MS (EI) for C$_{32}$H$_{31}$N$_5$O: 502.0 (MH$^+$).

4-[(4-ethylquinazolin-2-yl)amino]-N-(2-methyl-5-{[methyl(phenylmethyl)amino]methyl}phenyl)benzamide. $^1$H NMR (400 MHz, DMSO-d$_6$): δ 10.10 (s, 1H), 9.70 (s, 1H), 8.20-8.10 (m, 3H), 8.00-7.95 (d, 2H), 7.85-7.70 (m, 2H), 7.46-7.10 (m, 9H), 3.49 (d, 4H), 3.30-3.21 (q, 2H), 2.23 (s, 3H), 2.08 (s, 3H), 1.38 (t, 3H). MS (EI) for C$_{33}$H$_{33}$N$_5$O: 516.3 (MH$^+$).

Example 225

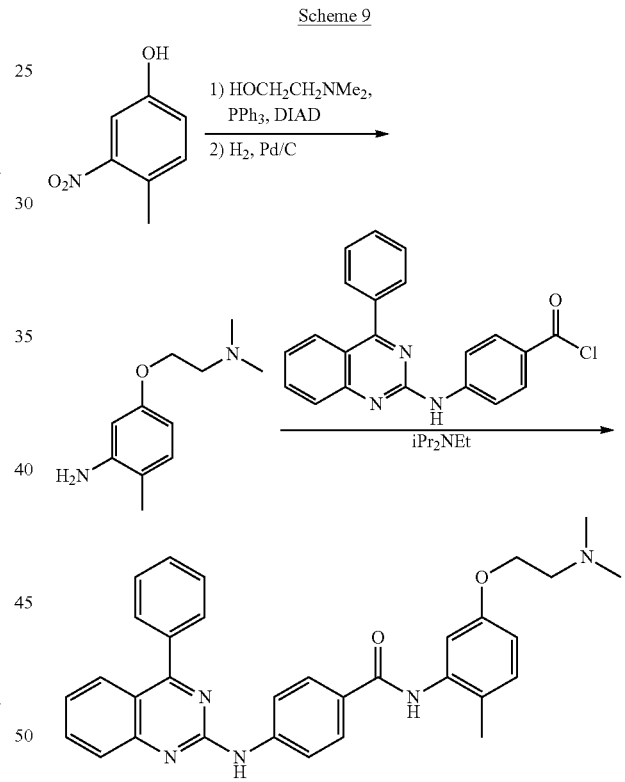

Example 225

N-(5-{[2-(dimethylamino)ethyl]oxy}-2-methylphenyl)-4-[(4-phenylquinazolin-2-yl)amino]benzamide To a solution of 4-methyl-3-nitrophenol (250 mg, 1.6 mmol) in dichloromethane (50 mL) was added triphenylphosphine (542 mg, 2.45 mmol), N,N-dimethylethanolamine (246 μL, 2.45 mmol) and diisopropylazo dicarboxylate (475 μL, 2.45 mmol), and the reaction was stirred at rt under nitrogen for 1 h. The solution was concentrated on a rotary evaporator and purified by flash column chromatography to give a yellow solid (286 mg, 80%). This material was dissolved in ethanol (50 mL) and placed in a hydrogenation vessel with 5% palladium on carbon (100 mg) and a drop of concentrated hydrochloric acid. The reaction was shaken on a Parr apparatus under a hydrogen atmosphere (~45 ppm) for 1 h, then filtered through Celite and washed with methanol. The solvent was removed on a rotary evaporator to give 5-(2-(dimethylamino)ethoxy)-2-methylaniline (262 mg, 100%), which was used without further purification. This material was dissolved in tetrahydrofuran (100 mL), and Hunig's base (300 µL, 1.7 mmol) and 4-(4-phenylquinazolin-2-ylamino) benzoyl chloride (530 mg, 1.48 mmol, vide supra) were added. The mixture was stirred at rt overnight, then concentrated on a rotary evaporator and purified by preparative reverse phase HPLC to give N-(5-{[2-(dimethylamino)ethyl]oxy}-2-methylphenyl)-4-[(4-phenylquinazolin-2-yl)amino]benzamide as a yellow solid (76 mg, 11%). $^1$H NMR (400 MHz, DMSO-$d_6$): δ 10.32 (s, 1H), 9.63 (s, 1H), 8.18 (d, 2H), 7.79 (d, 2H), 7.90-7.79 (m, 5H), 7.66-7.63 (m, 3H), 7.43-7.40 (m, 1H), 7.18 (d, 1H), 7.06 (d, 1H), 6.79 (m, 1H), 4.10 (t, 2H), 2.86 (br s, 2H), 2.39 (s, 6H), 2.19 (s, 3H). MS (EI) for $C_{32}H_{31}N_5O_2$: 518.4 (MH$^+$).

Using the procedures described in Scheme 9, the following compounds were prepared.

Example 226

N-{2-methyl-5-[(3-morpholin-4-ylpropyl)oxy]phenyl}-4-[(4-phenylquinazolin-2-yl)amino]benzamide. $^1$H NMR (400 MHz, DMSO-$d_6$): δ 10.32 (s, 1H), 9.62 (s, 1H), 8.18 (d, 2H), 7.99 (d, 2H), 7.90-7.78 (m, 5H), 7.65 (m, 3H), 7.42 (m, 1H), 7.17 (d, 1H), 7.03 (s, 1H), 6.75 (m, 1H), 4.00 (t, 2H), 3.58 (br s, 4H), 2.49 (br s, 4H), 1.89 (br s, 2H). MS (EI) for $C_{35}H_{35}N_5O_3$: 574.3 (MH$^+$).

Example 227

N-(3-{[2-(dimethylamino)ethyl]oxy}-2-methylphenyl)-4-[(4-phenylquinazolin-2-yl)amino]benzamide. $^1$H NMR (400 MHz, DMSO-$d_6$): δ 10.32 (s, 1H), 9.76 (s, 1H), 8.18 (d, 2H), 8.00 (d, 2H), 7.90-7.79 (m, 5H), 7.64 (m, 3H), 7.43-7.39 (m, 1H), 7.16 (t, 1H), 6.96 (d, 1H), 6.90 (d, 1H), 4.08 (t, 2H), 2.69 (t, 2H), 2.26 (s, 6H), 2.07 (s, 3H). MS (EI) for $C_{32}H_{31}N_5O_2$: 518.4 (MH$^+$).

Example 228

N-{2-methyl-5-[(2-morpholin-4-ylethyl)oxy]phenyl}-4-[(4-phenylquinazolin-2-yl)amino]benzamide. $^1$H NMR (400 MHz, DMSO-$d_6$): δ 10.31 (s, 1H), 9.62 (s, 1H), 8.16 (d, 2H), 7.97 (d, 2H), 7.88-7.76 (m, 5H), 7.63-7.61 (m, 3H), 7.40 (m, 1H), 7.15 (d, 1H), 7.02 (br s, 1H), 6.76 (d, 1H), 4.05 (br s, 2H), 3.57 (br s, 4H), 2.67 (br s, 2H), 2.46 (br s, 2H), 2.16 (s, 3H). MS (EI) for $C_{34}H_{33}N_5O_3$: 560.3 (MH$^+$).

Example 229

Scheme 10

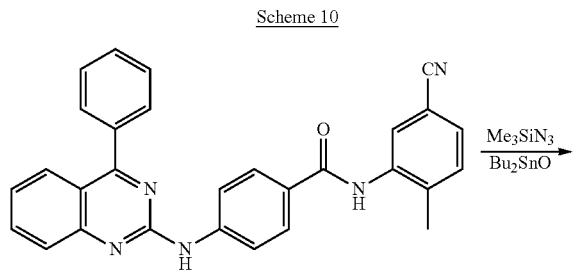

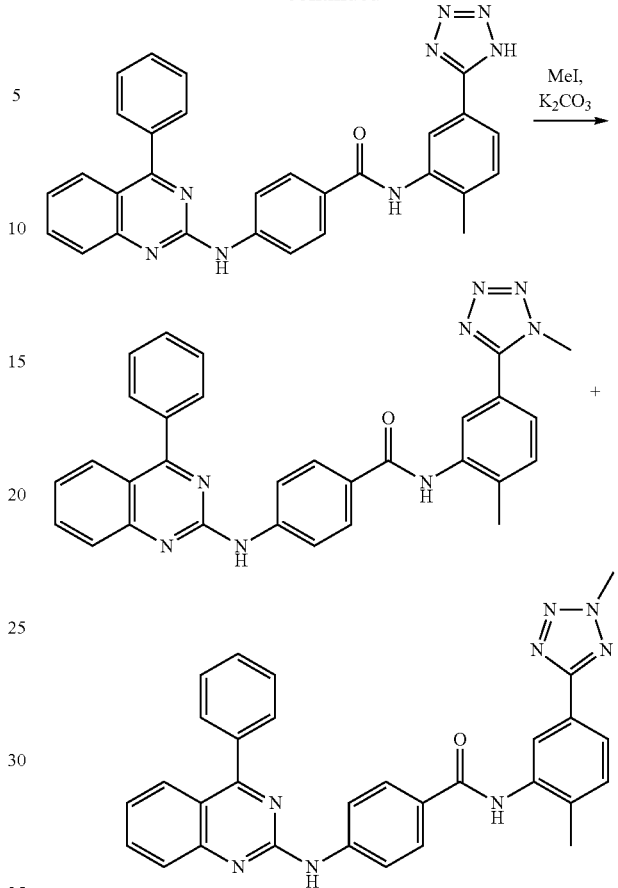

Example 229

N-[2-methyl-5-(1H-tetrazol-5-yl)phenyl]-4-[(4-phenylquinazolin-2-yl)amino]benzamide A mixture of N-(5-cyano-2-methylphenyl)-4-[(4-phenylquinazolin-2-yl)amino]benzamide (273 mg, 0.600 mmol), prepared as described in Example 10, trimethylsilylazide (160 µL, 1.2 mmol), and dibutyltin oxide (36 mg, 0.060 mmol) in dimethoxyethane (6 mL) was reacted in the microwave reactor (120° C., 100 psi, 2). The reaction was then concentrated on a rotary evaporator and the residue was purified by preparative reverse phase HPLC to give N-[2-methyl-5-(1H-tetrazol-5-yl)phenyl]-4-[(4-phenylquinazolin-2-yl)amino]benzamide (242 mg, 81%) as a yellow solid. $^1$H NMR (400 MHz, DMSO-$d_6$): δ 10.36 (s, 1H), 9.91 (s, 1H), 8.20 (d, 2H), 8.13 (d, 1H), 8.03 (d, 2H), 7.91-7.79 (m, 5H), 7.67-7.63 (m, 3H), 7.53 (d, 1H), 7.42 (ddd, 1H), 2.36 (s, 3H). MS (EI) for $C_{29}H_{22}N_8O$: 499.3 (MH$^+$).

N-[2-methyl-5-(2-methyl-2H-tetrazol-5-yl)phenyl]-4-[(4-phenylquinazolin-2-yl)amino]benzamide. To a stirred solution of N-[2-methyl-5-(1H-tetrazol-5-yl)phenyl]-4-[(4-phenylquinazolin-2-yl)amino]benzamide (100 mg, 0.20 mmol) in dimethylformamide (2 mL) was added potassium carbonate (83 mg, 0.60 mmol) and methyl iodide (100 µL, 1.6 mmol) and the mixture was allowed to stir at rt overnight. The mixture was purified by preparative reverse phase HPLC to give N-[2-methyl-5-(2-methyl-2H-tetrazol-5-yl)phenyl]-4-[(4-phenylquinazolin-2-yl)amino]benzamide (51 mg, 50%). $^1$H NMR (400 MHz, DMSO-$d_6$): δ10.34 (s, 1H), 9.84 (s, 1H), 8.20 (d, 2H), 8.16 (d, 1H), 8.02 (d, 2H), 7.91-7.78 (m, 5H), 7.66-7.64 (m, 3H), 7.47 (d, 1H), 7.42 (ddd, 1H), 4.43 (s, 3H), 2.35 (s, 3H). MS (EI) for $C_{30}H_{24}N_8O$: 513.3 (MH$^+$).

Example 231

N-[2-methyl-5-(1-methyl-1H-tetrazol-5-yl)phenyl]-4-[(4-phenylquinazolin-2-yl)amino]benzamide. From the same reaction above, the HPLC purification also provided N-[2-methyl-5-(1-methyl-1H-tetrazol-5-yl)phenyl]-4-[(4-phenylquinazolin-2-yl)amino]benzamide (7.1 mg, 7%). $^1$H NMR (400 MHz, DMSO-d$_6$): δ 10.35 (s, 1H), 9.93 (s, 1H), 8.20 (d, 2H), 8.02 (d, 2H), 7.93 (d, 1H), 7.90-7.79 (m, 5H), 7.67-7.64 (m, 3H), 7.54 (d, 1H), 7.42 (ddd, 1H), 4.20 (s, 3H), 2.38 (s, 3H). MS (EI) for $C_{30}H_{24}N_8O$: 513.2 (MH$^+$).

Example 232

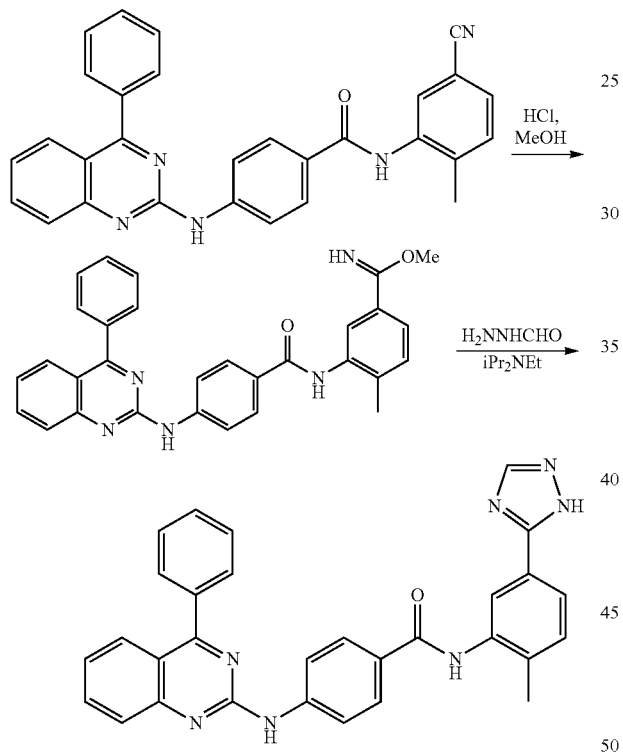

Example 232

Methyl 4-methyl-3-[({4-[(4-phenylquinazolin-2-yl)amino]phenyl}-carbonyl)amino]benzenecarboximidoate Anhydrous hydrochloric acid gas was bubbled into a suspension of N-(5-cyano-2-methylphenyl)-4-[(4-phenylquinazolin-2-yl)amino]benzamide (273 mg, 0.60 mmol), prepared as described in Example 10, in absolute ethanol (5 mL) for 10 min and the flask was affixed with a drying tube and allowed to stand in the refrigerator overnight. The reaction was concentrated on a rotary evaporator to give methyl 4-methyl-3-[({4-[(4-phenylquinazolin-2-yl)amino]phenyl}carbonyl)amino]benzenecarboximidoate as a yellow solid (311 mg, 100%). $^1$H NMR (400 MHz, DMSO-d$_6$): δ 11.90 (br s, 1H), 11.20 (br s, 1H), 10.40 (s, 1H), 9.95 (s, 1H), 8.20 (t, 2H), 8.03 (t, 2H), 7.87 (m, 3H), 7.82 (m, 3H), 7.65 (t, 3H), 7.43 (dt, 1H), 7.38 (d, 1H), 4.30 (s, 3H), 2.42 (s, 3H). MS (EI) for $C_{30}H_{25}N_5O_2$: 488.1 (MH$^+$).

N-[2-methyl-5-(1H-1,2,4-triazol-5-yl)phenyl]-4-[(4-phenylquinazolin-2-yl)amino]benzamide. A mixture of methyl 4-methyl-3-[({4-[(4-phenylquinazolin-2-yl)amino]phenyl}carbonyl)amino]benzenecarboximidoate (50 mg, 0.10 mmol), formylhydrazine (30 mg, 0.5 mmol) and Hunig's base (17 µL, 0.20 mmol) in ethanol (2 mL) was heated to 150° C. in a sealed tube overnight. The reaction was cooled to rt and concentrated on a rotary evaporator. The residue was purified by preparative reverse phase HPLC to give N-[2-methyl-5-(1H-1,2,4-triazol-5-yl)phenyl]-4-[(4-phenylquinazolin-2-yl)amino]benzamide (10.9 mg, 22%) as a yellow solid. $^1$H NMR (400 MHz, DMSO-d$_6$): δ 10.34 (s, 1H), 9.84-9.82 (m, 2H), 8.62 (s, 1H), 8.19 (d, 2H), 8.06-7.99 (m, 3H), 7.90-7.78 (m, 5H), 7.66-7.63 (m, 3H), 7.42 (ddd, 1H), 7.36 (d, 1H), 2.36 (s, 3H). MS (EI) for $C_{30}H_{23}N_7O$: 498.2 (MH$^+$).

Example 234

Using the procedures described in Scheme 11, the following compound was prepared. N-{5-[diethylamino)(imino)methyl]-2-methylphenyl}-4-[(4-phenylquinazolin-2-yl)amino]benzamide. $^1$H NMR (400 MHz, CD$_3$OD): δ 8.08 (s, 1H), 8.04 (s, 1H), 8.01 (m, 2H), 7.88 (m, 2H), 7.84 (m, 2H), 7.64 (m, 4H), 7.65 (d, 1H), 7.46 (dt, 1H), 7.38 (m, 1H), 3.68 (q, 2H), 3.45 (q, 2H), 2.44 (s, 3H), 1.38 (t, 3H), 1.23 (t, 3H). MS (EI) for $C_{33}H_{32}N_6O$: 529.2 (MH$^+$).

Example 235

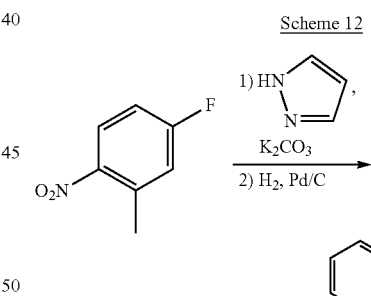

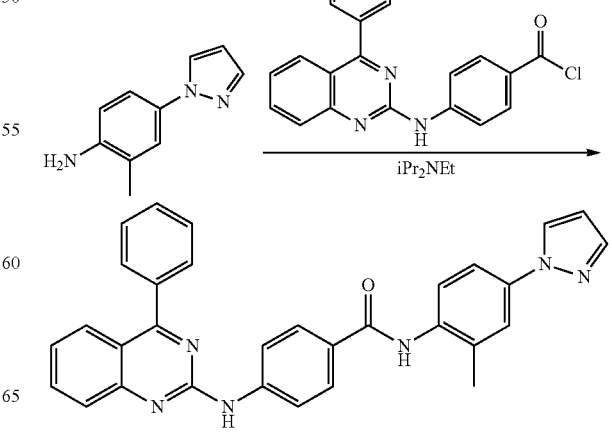

Example 235

N-[2-methyl-4-(1H-pyrazol-1-yl)phenyl]-4-[(4-phenylquinazolin-2-yl)amino]benzamide To a solution of 5-fluoro-2-nitrotoluene (1.27 g, 8.20 mmol) and pyrazole (1.3 g, 19.3 mmol) in dimethylformamide (32 mL) was added potassium carbonate (1.3 g, 9.7 mmol), and the mixture was heated to 100° C. overnight. The reaction was cooled, diluted with water and extracted with ethyl acetate. The combined organic extracts were washed with 10% aqueous lithium chloride, water and saturated sodium chloride, then dried over sodium sulfate and concentrated on a rotary evaporator to give 1-(3-methyl-4-nitrophenyl)-1H-pyrazole (1.78 g, 100%). This material was dissolved in ethanol (50 mL) and, after addition of 5% palladium on carbon (100 mg), the reaction was stirred under a balloon of hydrogen overnight. The mixture was filtered through Celite and washed with ethanol. The solvent was removed on a rotary evaporator to give 2-methyl-4-(1H-pyrazol-1-yl) aniline. A portion of this material (52 mg, 0.30 mmol) was added to a solution of 4-(4-phenylquinazolin-2-ylamino)benzoyl chloride (110 mg, 0.30 mmol) and Hunig's base (157 µL, 0.90 mmol) in tetrahydrofuran (2 mL) and the reaction was allowed to stir at rt overnight. The mixture was concentrated on a rotary evaporator and purified by flash column chromatography to give N-[2-methyl-4-(1H-pyrazol-1-yl)phenyl]-4-[(4-phenylquinazolin-2-yl)amino]benzamide (90 mg, 60%) as a yellow solid. $^1$H NMR (400 MHz, DMSO-d$_6$): δ 10.30 (s, 1H), 9.80 (s, 1H), 8.50 (d, 1H), 8.20 (d, 2H), 8.02 (d, 2H), 7.86 (m, 3H), 7.80 (m, 3H), 7.75 (d, 1H), 7.70 (dd, 1H), 7.64 (t, 3H), 7.50 (d, 1H), 7.42 (m, 1H), 6.58 (t, 1H), 2.30 (s, 3H). MS (EI) for C$_{31}$H$_{24}$N$_6$O: 497.4 (MH$^+$).

Example 236

Using the procedures described in Scheme 12, N-[4-(1H-imidazol-1-yl)-2-methylphenyl]-4-[(4-phenylquinazolin-2-yl)amino]benzamide was prepared. $^1$H NMR (400 MHz, DMSO-d$_6$): δ 10.30 (s, 1H), 9.80 (s, 1H), 8.42 (s, 1H), 8.20 (d, 2H), 8.02 (d, 2H), 7.88 (m, 2H), 7.86 (m, 1H), 7.82 (m, 3H), 7.64 (m, 3H), 7.62 (s, 1H), 7.52 (s, 2H), 7.42 (t, 1H), 7.20 (s, 1H), 2.34 (s, 3H). MS (EI) for C$_{31}$H$_{24}$N$_6$O: 497.2 (MH$^+$).

Example 237

Scheme 13

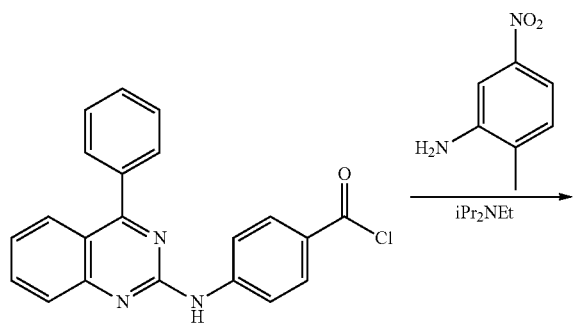

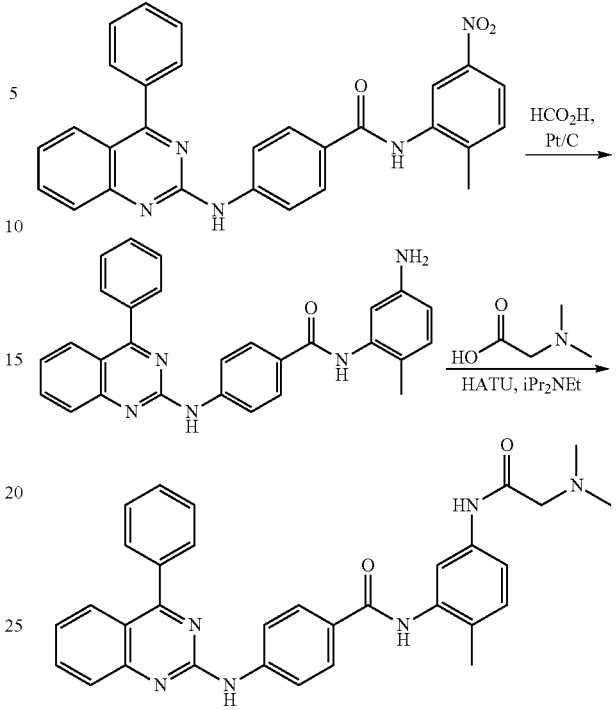

Example 237

N-(2-methyl-5-nitrophenyl)-4-[(4-phenylquinazolin-2-yl)amino]benzamide

To a solution of 4-(4-phenylquinazolin-2-ylamino)benzoyl chloride (1.56 g, 4.35 mmol) and Hunig's base (1.3 mL, 7.5 mmol) in tetrahydrofuran (50 mL) and dichloromethane (10 mL) was added 2-methyl-5-nitroaniline (726 mg, 4.78 mmol), and the reaction was allowed to stir at rt overnight. The mixture was concentrated on a rotary evaporator and purified by flash column chromatography to give N-(2-methyl-5-nitrophenyl)-4-[(4-phenylquinazolin-2-yl)amino] benzamide (522 mg, 58%) as a yellow solid. $^1$H NMR (400 MHz, DMSO-d$_6$): δ 10.46 (s, 1H), 10.03 (s, 1H), 8.49 (d, 1H), 8.27 (d, 2H), 8.10 (d, 3H), 7.80 (m, 5H), 7.73 (m, 3H), 7.66 (d, 1H), 7.50 (dt, 1H), 2.50 (s, 3H). MS (EI) for C$_{28}$H$_{21}$N$_5$O$_3$: 476.0 (MH$^+$).

N-(5-amino-2-methylphenyl)-4-[(4-phenylquinazolin-2-yl)amino]benzamide. A stirred mixture of N-(2-methyl-5-nitrophenyl)-4-[(4-phenylquinazolin-2-yl)amino]benzamide (500 mg, 1.05 mmol), formic acid (140 µL, 3.71 mmol), potassium formate (312 mg, 3.71 mmol) and 5% platinum on carbon (150 mg, catalytic) in tetrahydrofuran (10 mL) and ethanol (10 mL) was heated to reflux for 1 h. The mixture was filtered while hot through Celite and washed with hot ethanol. Water was added until the mixture became cloudy, then the volatile solvents were removed on a rotary evaporator. The solid was collected by filtration to give N-(5-amino-2-methylphenyl)-4-[(4-phenylquinazolin-2-yl)amino]benzamide (397 mg, 85%). $^1$H NMR (400 MHz, DMSO-d$_6$): δ 10.20 (s, 1H), 9.46 (s, 1H), 8.15 (d, 2H), 7.97 (d, 2H), 7.84 (m, 5H), 7.65 (m, 3H), 7.42 (m, 1H), 6.89 (d, 1H), 6.65 (d, 1H), 6.39 (dd, 1H), 2.08 (s, 3H). MS (EI) for C$_{28}$H$_{23}$N$_5$O: 446.1 (MH$^+$).

N-{5-[(N,N-dimethylglycyl)amino]-2-methylphenyl}-4-[(4-phenylquinazolin-2-yl)amino]benzamide. To a stirred mixture of N-(5-amino-2-methylphenyl)-4-[(4-phenylquinazolin-2-yl)amino]benzamide (200 mg, 0.45 mmol), N,N-dimethylglycine (70 mg, 0.68 mmol) and Hunig's base (365 µL, 2.1 mmol) in dimethylformamide (1 mL) was added HATU (310 mg, 0.82 mmol). The stirred mixture was heated to 80° C. for 1 h, the cooled to rt and purified by preparative reverse phase HPLC to give N-{5-[(N,N-dimethylglycyl)amino]-2-methylphenyl}-4-[(4-phenylquinazolin-2-yl)amino]benzamide (83 mg, 35%) as a yellow solid. $^1$H NMR (400 MHz, DMSO-d$_6$): δ 10.32 (s, 1H), 9.71 (s, 1H), 8.18 (d, 2H), 7.99 (d, 2H), 7.85 (m, 6H), 7.65 (m, 3H), 7.45 (dq, 2H), 7.18 (d, 1H), 3.06 (s, 2H), 2.28 (s, 6H), 2.0 (s, 3H). MS (EI) for C$_{32}$H$_{30}$N$_6$O$_2$: 531.1 (MH$^+$).

Using the procedures described in Scheme 13, the following compounds were prepared.

Example 240

N-{2-methyl-5-[(morpholin-4-ylacetyl)amino]phenyl}-4-[(4-phenylquinazolin-2-yl)amino]benzamide. $^1$H NMR (400 MHz, DMSO-d$_6$): δ 10.30 (s, 1H), 9.70 (s, 2H), 8.18 (d, 2H), 7.98 (d, 2H), 7.84 (m, 5H), 7.70 (d, 1H), 7.64 (m, 3H), 7.43 (m, 2H), 7.20 (d, 1H), 3.64 (t, 4H), 3.02 (s, 2H), 2.41 (m, 4H), 2.20 (s, 3H). MS (EI) for C$_{34}$H$_{32}$N$_6$O$_3$: 573.2 (MH$^+$).

Example 241

N-{2-methyl-5-[(2-methylalanyl)amino]phenyl}-4-[(4-phenylquinazolin-2-yl)amino]benzamide. $^1$H NMR (400 MHz, DMSO-d$_6$): δ 10.38 (br t, 1H), 9.86 (br s, 1H), 8.21 (d, 2H), 8.02 (d, 2H), 7.90-7.62 (m, 9H), 7.42 (m, 2H), 7.20 (d, 1H), 3.42 (br s, 2H), 2.20 (s, 3H), 1.32 (s, 6H). MS (EI) for C$_{32}$H$_{30}$N$_6$O$_2$: 531.0 (MH$^+$).

Example 242

N-{5-[(N,N-diethylglycyl)amino]-2-methylphenyl}-4-[(4-phenylquinazolin-2-yl)amino]benzamide. $^1$H NMR (400 MHz, DMSO-d$_6$): δ 10.33 (s, 1H), 9.73 (s, 1H), 9.63 (s, 1H), 8.18 (d, 2H), 8.00 (d, 2H), 7.88 (m, 2H), 7.86 (m, 1H), 7.80 (m, 2H), 7.72 (s, 1H), 7.64 (s, 3H), 7.42 (q, 2H), 7.20 (d, 1H), 3.14 (s, 2H), 2.60 (q, 4H), 2.20 (s, 3H), 1.02 (t, 6H). MS (EI) for C$_{34}$H$_{34}$N$_6$O$_2$: 559.28 (MH$^+$).

Example 243

Scheme 14

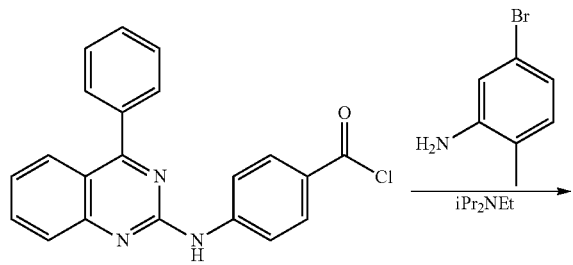

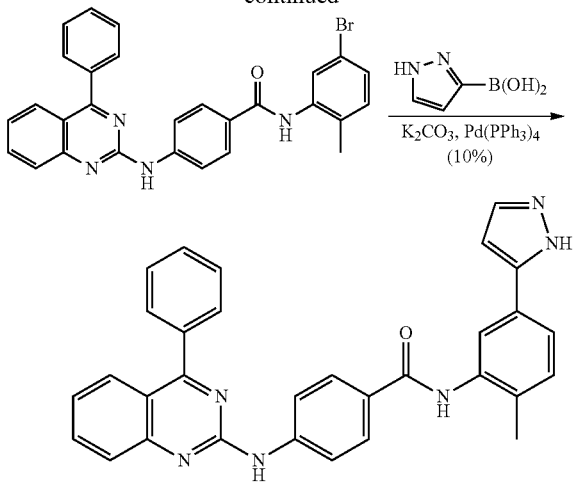

Example 243

N-(5-bromo-2-methylphenyl)-4-[(4-phenylquinazolin-2-yl)amino]benzamide

To a solution of 4-(4-phenylquinazolin-2-ylamino)benzoyl chloride (1.0 g, 2.8 mmol) and Hunig's base (600 µL, 3.4 mmol) in tetrahydrofuran (25 mL) was added 5-bromo-2-methylaniline (600 mg, 3.2 mmol), and the reaction was allowed to stir at rt overnight. The mixture was concentrated on a rotary evaporator and purified by flash column chromatography to give N-(5-bromo-2-methylphenyl)-4-[(4-phenylquinazolin-2-yl)amino]benzamide (1.0 g, 70%) as a yellow solid. $^1$H NMR (400 MHz, DMSO-d$_6$): δ 10.34 (s, 1H), 9.77 (s, 1H), 8.18 (d, 2), 7.98 (d, 2H), 7.82 (m, 6H), 7.65 (m, 4H), 7.41 (dt, 1H), 7.35 (dd, 1H), 7.25 (d, 1H), 2.24 (s, 3H). MS (EI) for C$_{28}$H$_{21}$BrN$_4$O: 511.2 (MH$^+$).

N-[2-methyl-5-(1H-pyrazol-5-yl)phenyl]-4-[(4-phenylquinazolin-2-yl)amino]benzamide. A mixture of N-(5-bromo-2-methylphenyl)-4-[(4-phenylquinazolin-2-yl)amino]benzamide (116 mg, 0.228 mmol), pyrazole-2-boronic acid (218 mg, 1.9 mmol), potassium carbonate (1.4 mmol) and tetrakis(triphenylphosphine)palladium (27 mg, 0.023 mmol) in dioxane (2 mL) was heated to 110° C. overnight. The reaction was cooled, concentrated on a rotary evaporator and purified by preparative reverse phase HPLC to give N-[2-methyl-5-(1H-pyrazol-5-yl)phenyl]-4-[(4-phenylquinazolin-2-yl)amino]benzamide (78 mg, 69%) as a yellow solid. $^1$H NMR (400 MHz, DMSO-d$_6$): δ 10.33 (s, 1H), 9.79 (s, 1H), 8.18 (d, 2H), 8.02 (d, 2H), 7.86 (m, 3H), 7.80 (m, 3H), 7.70 (s, 1H), 7.64 (m, 3H), 7.60 (dd, 1H), 7.42 (dt, 1H), 7.31 (d, 1H), 6.69 (d, 1H), 2.50 (s, 3H). MS (EI) for C$_{31}$H$_{24}$N$_6$O: 497.1 (MH$^+$).

Example 245

Using the procedures described in Scheme 14, the following compound was prepared. N-[2-methyl-5-(1H-pyrazol-4-yl)phenyl]-4-[(4-phenylquinazolin-2-yl)amino]benzamide. $^1$H NMR (400 MHz, DMSO-d$_6$): δ 8.22 (d, 2H), 8.12 (d, 1H), 8.03 (d, 2H), 7.90 (d, 1H), 7.86 (t, 2H), 7.82 (m, 3H), 7.64 (t, 3H), 7.62 (d, 1H), 7.42 (m, 3H), 7.27 (d, 1H), 2.26 (s, 3H), 2.27 (s, 3H). MS (EI) for C$_{31}$H$_{24}$N$_6$O: 497.0 (MH$^+$).

Example 246

Scheme 15

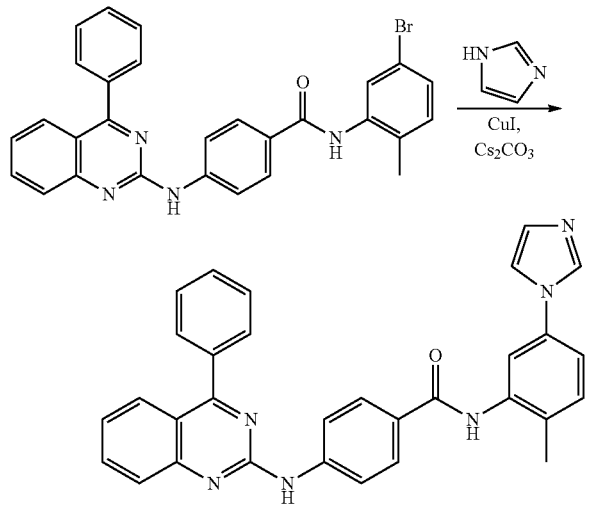

Example 246

N-[5-(1H-imidazol-1-yl)-2-methylphenyl]-4-[(4-phenylquinazolin-2-yl)amino]benzamide A mixture of N-(5-bromo-2-methylphenyl)-4-[(4-phenylquinazolin-2-yl)amino]benzamide (198 mg, 0.39 mmol), prepared as described in Example 14, copper (I) iodide (90 mg, 0.47 mmol), 1S,2S—$N^1,N^2$-dimethylcyclohexane-1,2-diamine (25 mg, 0.17 mmol), cesium carbonate (270 mg, 0.83 mmol) and imidazole (40 mg, 0.59 mmol) in dimethylformamide (400 μL) were combined in a sealed tube under an atmosphere of nitrogen and heated to 110° C. overnight. Upon cooling to rt, the reaction mixture was partitioned between saturated sodium bicarbonate and ethyl acetate. Insoluble material was filtered and the two layers of filtrate were separated. The aqueous phase was further extracted with ethyl acetate, and the combined organic layers were washed with saturated sodium chloride, dried over sodium sulfate and concentrated on a rotary evaporator. The resulting residue was purified by preparative reverse phase HPLC to give N-[5-(1H-imidazol-1-yl)-2-methylphenyl]-4-[(4-phenylquinazolin-2-yl)amino]benzamide (31 mg, 16%). $^1$H NMR (400 MHz, DMSO-$d_6$): δ 10.37 (s, 1H), 9.88 (s, 1H), 8.26 (s, 1H), 8.20 (d, 2H), 8.02 (d, 2H), 7.90-7.70 (m, 8H), 7.65 (m, 2H), 7.45 (m, 3H), 7.12 (s, 1H), 2.30 (s, 3H). MS (EI) for $C_{31}H_{24}N_6O$: 497.2 (MH$^+$).

Example 247

Scheme 16

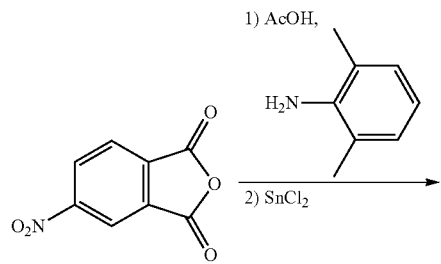

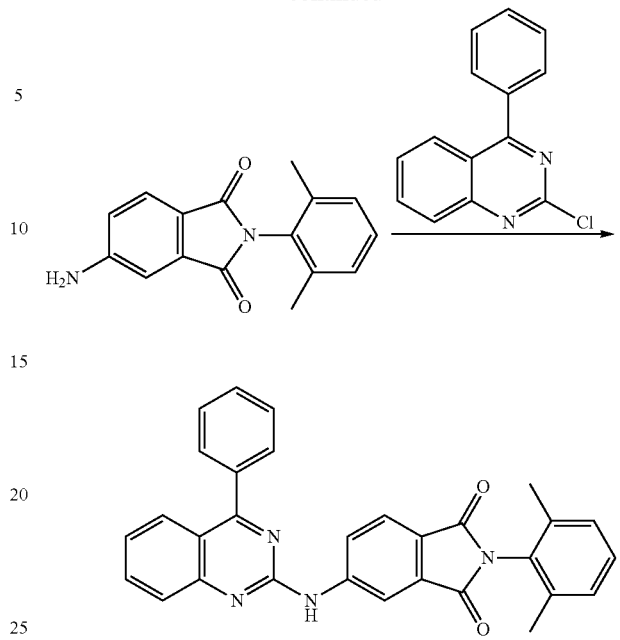

Example 247

2-(2,6-dimethylphenyl)-5-[(4-phenylquinazolin-2-yl)amino]-1H-isoindole-1,3(2H)-dione A mixture of 5-nitrophthalic anhydride (1.0 g, 5.2 mmol) and 2,6-dimethylaniline (0.65 mL, 5.3 mmol) in acetic acid (50 mL) was heated at 100° C. overnight (14 h). The reaction mixture was cooled, diluted with ethyl acetate and washed with saturated sodium bicarbonate. The organic phase was dried over anhydrous sodium sulfate, filtered and concentrated. The product was dissolved in ethanol (50 mL), tin (II) chloride (1.4 g, 6.2 mmol) was added and the mixture was heated to reflux for 5 h. The reaction mixture was cooled and made basic by adding aqueous 2 N sodium hydroxide. Ethyl acetate was added and the layers were separated. The organic layer was washed with water and saturated sodium chloride, dried over anhydrous sodium sulfate, filtered and concentrated on a rotary evaporator to give 5-amino-2-(2,6-dimethylphenyl)isoindoline-1,3-dione (0.93 g, 67%), which was used without further purification.

A mixture of 2-chloroquinazoline (0.62 g, 2.6 mmol) and 5-amino-2-(2,6-dimethylphenyl)isoindoline-1,3-dione (0.69 g, 2.6 mmol) in n-butanol (10 mL) was heated at 120° C. until all of the butanol had evaporated. Additional butanol (10 mL) was added and the process repeated twice. After the reaction mixture was cooled, water was added (20 mL). A precipitate which formed was collected by suction filtration. N,N-Dimethylacetamide (5 mL) was added to dissolve the solid which was purified by preparative reverse-phase HPLC to give 2-(2,6-dimethylphenyl)-5-[(4-phenylquinazolin-2-yl)amino]-1H-isoindole-1,3(2H)-dione (0.26 g, 21%). $^1$H NMR (400 MHz, DMSO-$d_6$): δ10.88 (s, 1H), 8.80 (m, 1H), 8.42 (m, 1H), 7.96 (m, 1H), 7.90 (m, 2H), 7.85 (m, 1H), 7.81 (m, 2H), 7.65 (m, 3H), 7.50 (m, 1H), 7.32 (m, 1H), 7.25 (m, 2H), 2.10 (s, 6H). MS (EI) for $C_{30}H_{22}N_4O_2$: 471.0 (MH$^+$).

Example 248

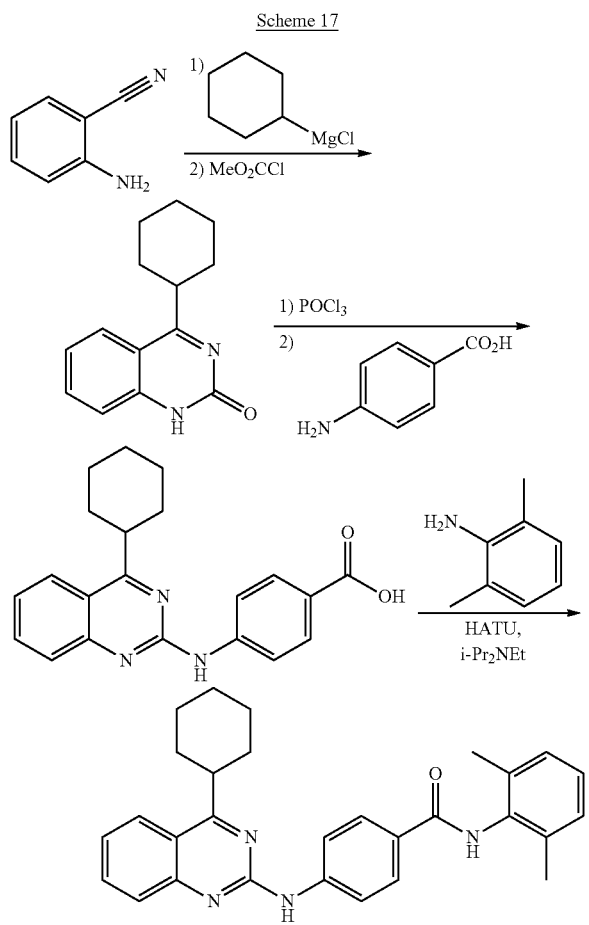

4-[(4-cyclohexylquinazolin-2-yl)amino]-N-(2,6-dimethylphenyl)benzamide

To a dried round-bottomed flask containing cyclohexylmagnesium chloride (26 mL, 51 mmol) in anhydrous ether (10 mL) was added dropwise a solution of 2-aminobenzonitrile (2.0 g, 17 mmol) in anhydrous ether. The mixture was stirred at rt for 2 h, then cooled to 0° C., and a solution of methyl chloroformate (2.6 mL, 34 mmol) in dry ether (10 mL) was added. The reaction mixture was returned to rt and stirred for 2 d. The reaction was quenched with 1 N hydrochloric acid and stirred for 30 min. The precipitate that formed was collected by vacuum filtration, washed with ethyl acetate and dried to give 4-cyclohexylquinazolin-2(1H)-one (545 mg, 14%) as a tan solid.

A mixture of 4-cyclohexylquinazolin-2(1H)-one (500 mg, 2.2 mmol) and phosphorous oxychloride (10 mL, 111 mmol) was heated to reflux for 1 h. The volatiles were removed under reduced pressure, and then the residue was treated with ice water and extracted with ethyl acetate. The combined organic extracts were washed with saturated sodium chloride and dried over sodium sulfate. The solvent was removed on a rotary evaporator, and to this residue was added 4-aminobenzoic acid (300 mg, 2.2 mmol), triethylamine (435 μL, 3.0 mmol) and n-butanol (5 mL). This mixture was heated to 140° C. for 25 min. The mixture was cooled to rt and triturated with ether. The residual solid was collected via vacuum filtration, washed with ether and dried to afford 4-(4-cyclohexylquinazolin-2-ylamino)benzoic acid (370 mg, 48%) as an off white solid.

To a stirred mixture of 4-(4-cyclohexylquinazolin-2-ylamino)benzoic acid (300 mg, 0.86 mmol), HATU (327 mg, 0.86 mmol) and Hunig's base (555 μL, 4.3 mmol) in dimethylformamide (1 mL) was added 2,6-dimethylaniline (620 mg, 5.12 mmol) and the reaction was heated to 50° C. overnight. The mixture was cooled to rt, diluted with water and extracted with ethyl acetate. The combined organic extracts were washed with 1 N sodium bicarbonate and a 5% aqueous solution of lithium chloride, then was extracted with 1 N hydrochloric acid. The combined acidic washes were neutralized with 1 N sodium hydroxide and extracted with dichloromethane. These combined organic extracts were dried over sodium sulfate, filtered and concentrated on a rotary evaporator. The residue obtained was purified by recrystallization from methanol to give 4-[(4-cyclohexylquinazolin-2-yl)amino]-N-(2,6-dimethylphenyl)benzamide as a white solid (99.8 mg, 27%). $^1$H NMR (400 MHz, CDCl$_3$): δ 8.06-7.94 (m, 5H), 7.82-7.71 (m, 2H), 7.58-7.49 (br s, 1H), 7.39-7.33 (m, 2H), 7.16-7.12 (m, 3H), 3.53-3.44 (m, 1H), 2.65-2.59 (s, 5H), 2.31 (s, 6H), 2.04-1.91 (m, 4H), 1.89-1.70 (m, 3H), 1.60-1.31 (m, 3H). MS (EI) for $C_{29}H_{30}N_4O$: 451.0 (MH$^+$).

Example 249

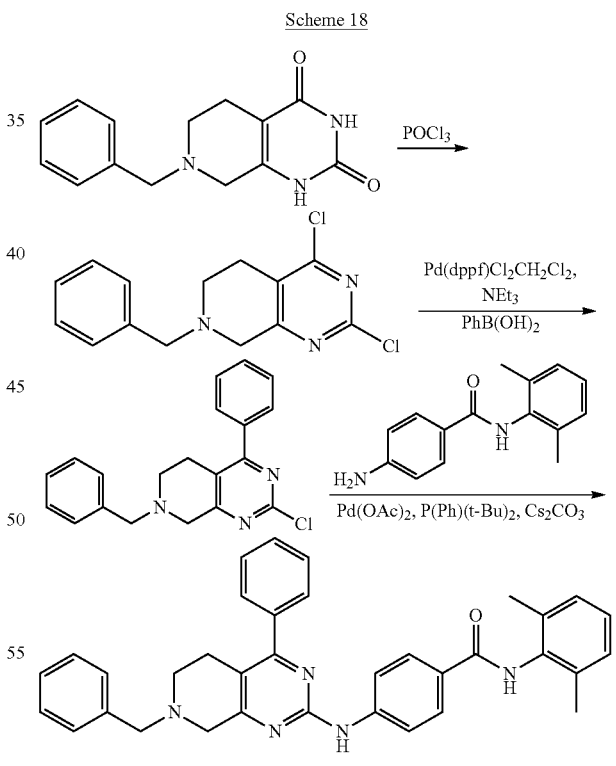

N-(2,6-dimethylphenyl)-4-{[4-phenyl-7-(phenylmethyl)-5,6,7,8-tetrahydropyrido[3,4-d]pyrimidin-2-yl]amino}benzamide A solution of commercially available 7-benzyl-5,6,7,8-tetrahydropyrido[3,4-d]pyrimidine-2,4(1H,3H)-dione (2.18 g, 8.5 mmol), and phosphorus oxychloride (25 mL, 0.27 mol)

was stirred at 110° C. for 18 h. The reaction mixture was cooled to rt and concentrated on a rotary evaporator. The residue was treated with concentrated ammonium hydroxide until basic, extracted with ethyl acetate and the combined organic layers were washed with saturated sodium chloride, dried over sodium sulfate and concentrated on a rotary evaporator to give 7-benzyl-2,4-dichloro-5,6,7,8-tetrahydropyrido[3,4-d]pyrimidine as a grey solid that was used without further purification.

To a round bottomed flask containing 7-benzyl-2,4-dichloro-5,6,7,8-tetrahydropyrido[3,4-d]pyrimidine (578 mg, 1.96 mmol) was added phenylboronic acid (260 mg, 2.13 mmol), dichloro-((bis-diphenylphosphino)ferrocenyl)-palladium (II) (complex with methylene chloride, 160 mg, 0.32 mmol), triethylamine (600 µL, 4.3 mmol), dimethoxyethane (20 mL), and water (0.5 mL). The reaction mixture was heated to 80° C. for 14 h, then cooled to rt and diluted with ethyl acetate. The organic layer was washed with saturated sodium bicarbonate, dried over sodium sulfate, filtered, and concentrated on a rotary evaporator. The material was purified by flash column chromatography to afford 7-benzyl-2-chloro-4-phenyl-5,6,7,8-tetrahydropyrido[3,4-d]pyrimidine (210 mg, 32%).

To a round bottomed flask containing 7-benzyl-2-chloro-4-phenyl-5,6,7,8-tetrahydropyrido[3,4-d]pyrimidine (73 mg, 0.22 mmol) was added commercially available 4-amino-N-(2,6-dimethylphenyl)benzamide (56 mg, 0.23 mmol), diacetoxypalladium (II), (12 mg, 0.05 mmol) di-tert-butyl(phenyl)phosphine (39 mg, 0.13 mmol), cesium carbonate (125 mg, 0.38 mmol), and toluene (5 mL). The reaction mixture was heated to 100° C. for 14 h, then cooled to rt and diluted with ethyl acetate. The organic layer was washed with saturated sodium bicarbonate, dried over sodium sulfate, filtered, and concentrated on a rotary evaporator. The material was purified by flash column chromatography to afford N-(2,6-dimethylphenyl)-4-{[4-phenyl-7-(phenylmethyl)-5,6,7,8-tetrahydropyrido[3,4-d]pyrimidin-2-yl]amino}benzamide (60 mg, 50%) as an off white solid. $^1$H NMR (400 MHz, DMSO-d$_6$): δ 9.95 (s, 1H), 9.53 (s, 1H), 7.93 (m, 4H), 7.61 (m, 2H), 7.50 (m, 3H), 7.29 (m, 5H), 7.11 (m, 3H), 3.64 (m, 2H), 3.56 (m, 2H), 2.90 (m, 2H), 2.81 (m, 2H), 2.17 (s, 6H). MS (EI) for $C_{35}H_{33}N_5O$: 540.3 (MH$^+$).

Example 250

N-(2,6-dimethylphenyl)-4-[(4-phenyl-5,6,7,8-tetrahydropyrido[3,4-d]pyrimidin-2-yl)amino]benzamide A mixture of N-(2,6-dimethylphenyl)-4-{[4-phenyl-7-(phenylmethyl)-5,6,7,8-tetrahydropyrido[3,4-d]pyrimidin-2-yl]amino}benzamide (60 mg, 0.11 mmol), prepared as described in Example 249, 1,4-cyclohexadiene (11 µL, 0.11 mmol) and 10% palladium on carbon (8 mg) in ethanol (2 mL) were heated to 80° C. overnight. Upon cooling to rt, the reaction mixture was filtered through celite and concentrated on a rotary evaporator. The resulting residue was purified by preparative reverse phase HPLC to give N-(2,6-dimethylphenyl)-4-[(4-phenyl-5,6,7,8-tetrahydropyrido[3,4-d]pyrimidin-2-yl)amino]benzamide (31 mg, 62%) as a white solid. $^1$H NMR (400 MHz, DMSO-d$_6$): δ 9.87 (s, 1H), 9.52 (s, 1H), 7.96 (m, 4H), 7.62 (m, 2H), 7.52 (m, 3H), 7.11 (m, 3H), 3.75 (m, 2H), 3.05 (m, 2H), 2.79 (m, 2H), 2.17 (s, 6H). MS (EI) for $C_{28}H_{27}N_5O$: 450.2 (MH$^+$).

Using the procedures described in Examples 249 and 250, the following compounds were made.

Example 251

N-(2,6-dimethylphenyl)-4-{[4-phenyl-6-(phenylmethyl)-5,6,7,8-tetrahydropyrido[4,3-d]pyrimidin-2-yl]amino}benzamide. $^1$H NMR (400 MHz, DMSO-d$_6$): δ 11.16 (s, 1H), 10.05 (m, 1H), 9.54 (s, 1H), 7.93 (m, 4H), 7.69-7.29 (m, 9H), 7.11 (m, 3H), 4.57-4.26 (m, 2H), 3.76-3.56 (m, 2H), 2.92-2.62 (m, 4H), 2.17 (s, 6H). MS (EI) for $C_{35}H_{33}N_5O$: 540.3 (MH$^+$).

Example 252

N-(2,6-dimethylphenyl)-4-[(4-phenyl-5,6,7,8-tetrahydropyrido[4,3-d]pyrimidin-2-yl)amino]benzamide. $^1$H NMR (400 MHz, DMSO-d$_6$): δ 9.89 (s, 1H), 9.53 (s, 1H), 7.92 (m, 4H), 7.67 (m, 2H), 7.52 (m, 3H), 7.11 (m, 3H), 3.87 (m, 2H), 2.89 (m, 2H), 2.63 (m, 2H), 2.17 (s, 6H). MS (EI) for $C_{28}H_{27}N_5O$: 450.1 (MH$^+$).

Scheme 19

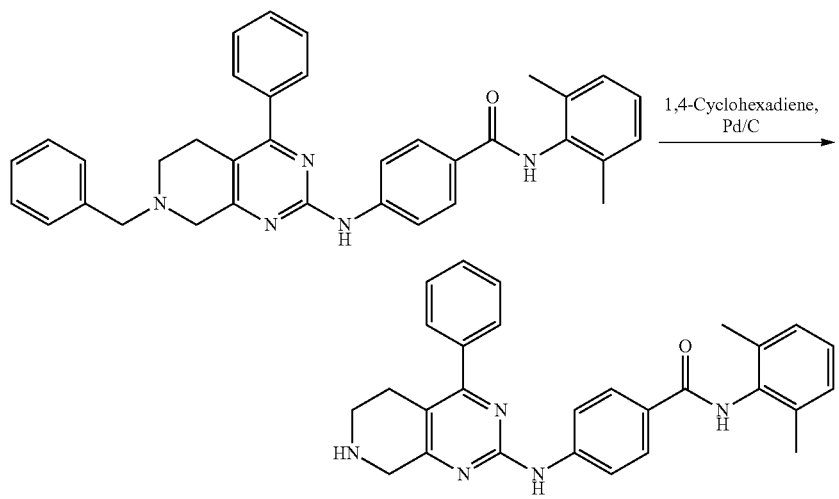

Example 253

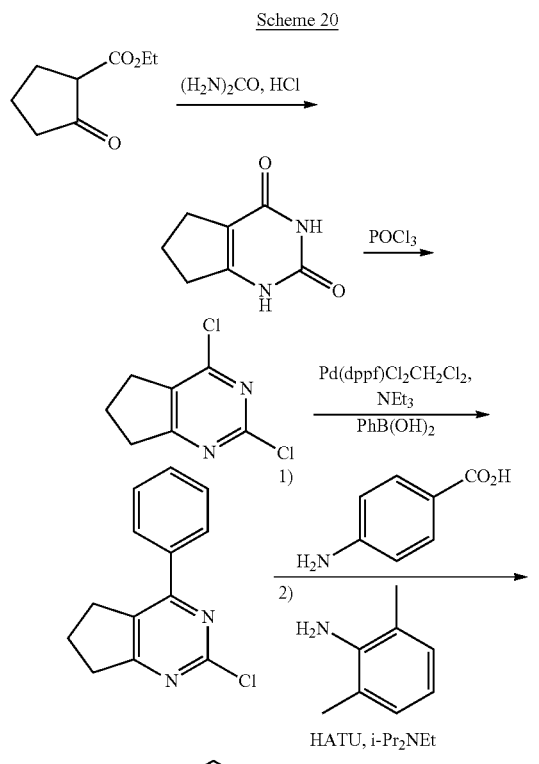

N-(2,6-dimethylphenyl)-4-[(4-phenyl-6,7-dihydro-5H-cyclopenta[d]pyrimidin-2-yl)amino]benzamide A solution of ethyl 2-oxocyclopentanecarboxylate (15.6 g, 0.10 mol), urea (9.0 g 0.15 mol) and hydrochloric acid (37%, aqueous, 5 mL) in EtOH (100 mL) was heated to 80° C. for 24 h. The mixture was cooled to rt and the precipitate was collected by filtration and dried to afford 6,7-dihydro-1H-cyclopenta[d]pyrimidine-2,4(3H,5H)-dione (11.1 g, 73%) as a white solid.

A stirred mixture of 6,7-dihydro-1H-cyclopenta[d]pyrimidine-2,4(3H,5H)-dione (10.0 g, 0.66 mol) and phosphorus oxychloride (300 mL) was heated to 105° C. for 30 min. The reaction mixture was cooled to rt and slowly poured over an ice/water mixture. The solid that formed was collected by filtration, washed with water (50 mL) and dried under reduced pressure to give 2,4-dichloro-6,7-dihydro-5H-cyclopenta[d]pyrimidine (8.5 g, 74%) as an off-white solid.

To a round bottomed flask containing 2,4-dichloro-6,7-dihydro-5H-cyclopenta[d]pyrimidine (1.85 g, 10.5 mmol) was added phenylboronic acid (1.43 g, 11.8 mmol), dichloro-((bis-diphenylphosphino)ferrocenyl)-palladium (II) (complex with methylene chloride), (800 mg, 0.98 mmol), triethylamine (4.1 mL, 29 mmol), dimethylformamide (30 mL), and water (2 mL). The reaction mixture was heated to 80° C. for 14 h, then cooled to rt and diluted with ethyl acetate. The organic layer was washed with saturated sodium bicarbonate, dried over sodium sulfate, filtered, and concentrated on a rotary evaporator. The material was purified by flash column chromatography to afford 2-chloro-4-phenyl-6,7-dihydro-5H-cyclopenta[d]pyrimidine (1.25 g, 52%) as an off-white solid.

To a stirred mixture of 2-chloro-4-phenyl-6,7-dihydro-5H-cyclopenta[d]pyrimidine (1.3 g, 5.4 mmol) in 2-propanol (30 mL) was added 4-aminobenzoic acid (0.82 g, 6.0 mmol) and the mixture was heated to reflux for 4 h. The mixture was cooled to rt and the precipitate was collected by filtration, washed with 2-propanol and dried to give the intermediate benzoic acid as a yellow solid (1.5 g, 84%). A portion of this intermediate (1.3 g, 3.9 mmol) was treated with 2,6-dimethylaniline (498 mg, 4.12 mmol), triethylamine (2.1 mL, 15 mmol) and HATU (1.91 g, 5.00 mmol) in dimethylformamide (10 mL). The stirred mixture was heated to 80° C. overnight, then cooled to rt. The reaction was diluted with ethyl acetate and extracted with water. The organic layer was washed with saturated sodium bicarbonate and concentrated on a rotary evaporator. The resulting residue was purified by preparative reverse phase HPLC to give N-(2,6-dimethylphenyl)-4-[(4-phenyl-6,7-dihydro-5H-cyclopenta[d]pyrimidin-2-yl)amino]benzamide (1.18 g, 69%) as a light yellow solid. $^1$H NMR (400 MHz, CD$_3$OD): δ 7.98 (m, 6H), 7.56 (m, 3H), 7.17 (m, 3H), 3.18 (m, 2H), 2.98 (m, 2H), 2.25 (s, 6H), 2.17 (m, 2H). MS (EI) for C$_{28}$H$_{26}$N$_4$O: 435.2 (MH$^+$).

Example 254

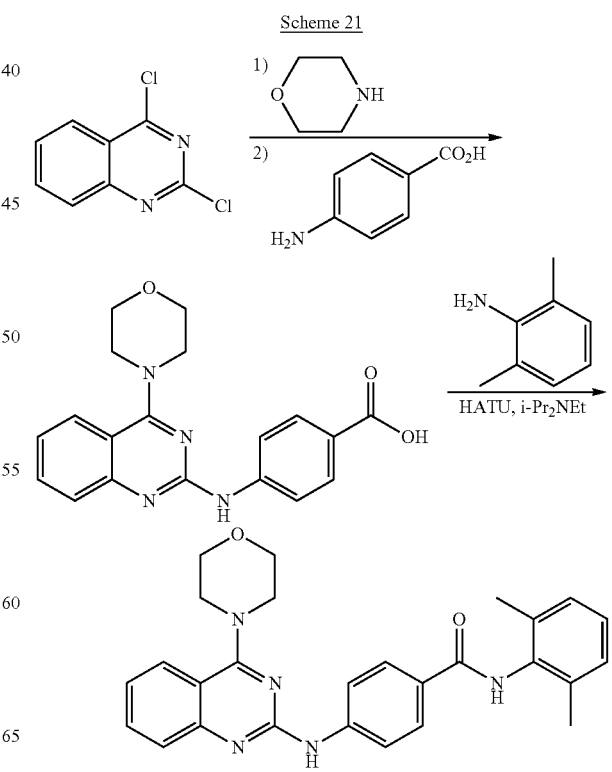

N-(2,6-dimethylphenyl)-4-[(4-morpholin-4-ylquinazolin-2-yl)amino]benzamide

A mixture of 2,4-dichloroquinazoline (200 mg, 1.00 mmol) and morpholine (131 mg, 1.50 mmol) in dimethylformamide (1 mL) was stirred at rt for 5 min. The reaction mixture was diluted with ethyl acetate, washed with saturated sodium bicarbonate and 5% aqueous lithium chloride and dried over sodium sulfate. The solvent was removed on a rotary evaporator to give a white solid. A mixture of this material and 4-aminobenzoic acid (119 mg, 0.868 mmol) in n-butanol (2.5 mL) was heated to 135° C. until the butanol was boiled off. The solid residue was collected and washed with water to give 4-(4-morpholinoquinazolin-2-ylamino) benzoic acid (303 mg, 100%) an off-white solid that was used without further purification. This material was combined with 2,6-dimethylaniline (210 mg, 1.73 mmol), Hunig's base (300 μL, 1.72 mmol) and HATU (329 mg, 0.865 mmol) in DMF (5 mL), and the mixture was heated to 65° C. overnight. The reaction was cooled to rt, diluted with ethyl acetate and extracted with water. The organic layer was washed with saturated sodium bicarbonate and concentrated on a rotary evaporator. The resulting residue was purified by preparative reverse phase HPLC to give N-(2,6-dimethylphenyl)-4-[(4-morpholin-4-ylquinazolin-2-yl)amino]benzamide (120 mg, 26%) as a white solid. $^1$H NMR (400 MHz, DMSO-d$_6$): δ 10.50 (bs, 1H), 9.70 (bs, 1H), 8.05-8.01 (m, 3H), 7.83-7.79 (m, 3H), 7.63 (d, 1H), 7.40 (t, 1H), 7.13 (s, 3H), 3.97 (bs, 4H), 3.84-3.82 (m, 4H), 2.19 (s, 6H). MS (EI) for $C_{27}H_{27}N_5O_2$: 454.0 (MH$^+$).

Example 255

Using procedures described in Example 254, N-[2-methyl-5-(morpholin-4-ylmethyl)phenyl]-4-[(4-morpholin-4-ylquinazolin-2-yl)amino]benzamide was prepared. $^1$H NMR (400 MHz, CD$_3$OD): δ 7.94 (s, 4H), 7.86 (d, 1H), 7.66-7.58 (m, 2H), 7.35 (s, 1H), 7.27-7.23 (m, 2H), 7.19-7.17 (m, 1H), 3.88-3.86 (m, 4H), 3.77-3.75 (m, 4H), 3.70-3.68 (m, 4H), 3.58 (s, 2H), 2.55 (bs, 4H), 2.29 (s, 3H), 1.97 (s, 2H). MS (EI) for $C_{31}H_{34}N_6O_3$: 539.0 (MH$^+$).

Example 255

Scheme 22

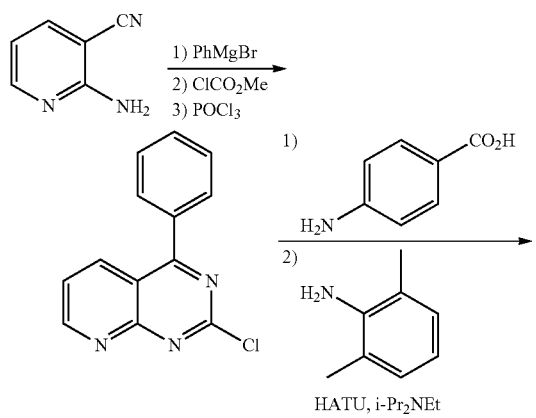

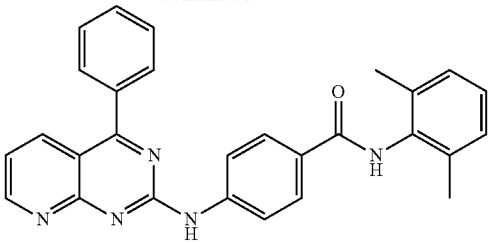

N-(2,6-dimethylphenyl)-4-[(4-phenylpyrido[2,3-d]pyrimidin-2-yl)amino]benzamide To a stirred solution of phenylmagnesium bromide (8.46 mL, 3.0 M in ether, 25.4 mmol) in anhydrous tetrahydrofuran (10 mL) at rt was added slowly a solution of 2-aminonicotinonitrile (1.01 g, 8.46 mmol) in anhydrous tetrahydrofuran (10 mL). The mixture was stirred at rt for 2 h, then cooled to 0° C. in an ice water bath. To this mixture was added slowly a solution of methyl chloroformate (1.31 mL, 16.9 mmol) in anhydrous tetrahydrofuran (10 mL) such that the internal temperature never rose above 0° C. Upon completion of the addition, the mixture was allowed to warm to rt overnight, then quenched with 3N hydrochloric acid. The mixture was neutralized with 2 N aqueous sodium hydroxide and extracted with ethyl acetate. The combined organic extracts were washed with saturated sodium chloride, dried over sodium sulfate and concentrated on a rotary evaporator to give the intermediate (215 mg, 11%) as a yellow solid that was used without further purification. This material was combined with phosphorus oxychloride (5 mL) and the mixture was heated to 110° C. for 1 h. The volatiles were removed on a rotary evaporator to afford 2-chloro-4-phenylpyrido[2,3-d]pyrimidine (233 mg, 100%) as a yellow solid.

A mixture of 2-chloro-4-phenylpyrido[2,3-d]pyrimidine (233 mg, 0.965 mmol), 4-aminobenzoic acid (133 mg, 0.965 mmol), Hunig's base (300 μL, 1.72 mmol) and n-butanol (5 mL) was heated to 138° C. for 30 min. The solvent was removed on a rotary evaporator to give the intermediate acid as a black oil that was treated with 2,6-dimethylaniline (88 mg, 0.73 mmol), Hunig's base (100 μL, 0.57 mmol) and HATU (137 mg, 0.36 mmol) in DMF (1 mL) The mixture was heated to 60° C. overnight. The reaction was cooled to rt and purified by preparative reverse phase HPLC to give N-(2,6-dimethylphenyl)-4-[(4-phenylpyrido[2,3-d]pyrimidin-2-yl)amino]benzamide (29.6 mg, 18%) as a yellow solid. $^1$H NMR (400 MHz, CD$_3$OD): δ 8.96 (d, 1H), 8.61-8.58 (m, 1H), 8.20 (d, 2H), 8.05 (d, 2H), 7.86-7.84 (m, 2H), 7.67-7.61 (m, 3H), 7.51 (dd, 1H), 7.13 (s, 3H), 2.27 (s, 6H). MS (EI) for $C_{28}H_{23}N_5O$: 446.0 (MH$^+$).

Example 256

Using the procedures described in Example 255, N-[2-methyl-5-(morpholin-4-ylmethyl)phenyl]-4-[(4-phenylpyrido[2,3-d]pyrimidin-2-yl)amino]benzamide was prepared. $^1$H NMR (400 MHz, DMSO-d$_6$): δ 10.60 (s, 1H), 9.77 (s, 1H), 7.60 (dd, 1H), 8.26 (dd, 1H), 8.21 (d, 2H), 8.02 (d, 2H), 7.83-7.81 (m, 2H), 7.68-7.64 (m, 3H), 7.44 (dd, 1H), 7.30 (s, 1H), 7.24-7.22 (m, 1H), 7.11-7.10 (m, 1H), 3.58 (bs, 4H), 3.44 (s, 2H), 3.26 (bs, 4H), 2.23 (s, 3H). MS (EI) for $C_{32}H_{30}N_6O_2$: 531.0 (MH$^+$).

BIOLOGICAL EXAMPLES

Biological Example 1

Light II Assay

The SHh-Smo assay is a cell-based reporter assay in the SHh Light II cell line (NIH-3T3), available through the American Tissue Culture Center (ATCC). This cell line harbors a Gli-luciferase (firefly) reporter which displays 6-14-fold induction upon stimulation with the N-terminal fragment of recombinant hedgehog protein or the small molecule agonist HhAg1.5 (Frank-Kamenetsky, et. al. *J Bio,* 2002, 1, 10.). In addition, this cell line contains a constitutively expressed renilla luciferase reporter (via CMV promoter) which can be used as a readout to detect any non-specific compound effects, including cytotoxicity.

Test compounds were serially diluted in DMSO and 1.5 μL aliquots were transferred to 384-well non-binding plates. Compounds were diluted with 85 μL of assay media (DMEM+0.5% FBS, 5 mM Hepes, 1% NEAA, 1% PenStrep, 0.8% Geneticin). Cell plates were prepared by adding 50 μL of assay media (240 cells/μL) to white TC coated 384-well plates (final cell concentration is 12,000 cells/well). Cell plates were incubated overnight at 37° C.

Media was removed from the cell plates and 30 μL of compound in assay media+rSHh (1.5 μg/well) was added to the cell plates. Plates were incubated at 37° C. for 24 hours. Following overnight incubation, media was aspirated from the cell plates and 20 μL of luciferase media (Bright-glo, Promega) was added to the cell. Cells were incubated for 5 minutes and measured on an Envision™ plate reader (Perkn Elmer) using the luciferase detection protocol. IC50 values were calculated as a percentage inhibition of luciferase signal from rSHh stimulated cells compared to unstimulated cells.

Compounds of the invention were tested in this assay and demonstrated the ability to modulate Hedgehog pathway activity. The compounds described in Table 1 were all tested in this assay and have activity of less than about 2 μM. The following embodiments are directed to the compounds themselves as well as their use in a method of treating. For example, in one embodiment of the invention, the Hedgehog pathway modulator is selected from the compounds in Table 1 having cellular activity in the Light II assay of about 2000 nM or less. In another embodiment, the Hedgehog pathway modulator is selected from the compounds in Table 1 having cellular activity in the Light II assay of about 250 nM or less. In another embodiment, the Hedgehog pathway modulator is selected from the compounds in Table 1 having cellular activity in the Light II assay of about 100 nM or less. In another embodiment, the Hedgehog pathway modulator is selected from the compounds in Table 1 having cellular activity in the Light II assay of about 30 nM or less. In another embodiment, the Hedgehog pathway modulator is selected from the compounds in Table 1 having cellular activity in the Light II assay of about 20 nM or less. In another embodiment, the Hedgehog pathway modulator is selected from the compounds in Table 1 having cellular activity in the Light II assay of about 10 nM or less. In another embodiment, the Hedgehog pathway modulator is selected from the compounds in Table 1 having cellular activity in the Light II assay of about 5 nM or less.

Representative Biological Data

| Compound Name | Activity in Light II Assay (nM) |
|---|---|
| 3-fluoro-N-[2-methyl-5-(morpholin-4-ylmethyl)phenyl]-4-[(4-phenylquinazolin-2-yl)amino]benzamide | 6.2 |
| N-[2-(dimethylamino)ethyl]-4-methyl-3-[({4-[(4-phenylquinazolin-2-yl)amino]phenyl}carbonyl)amino]benzamide | 16.4 |
| N-(2-methyl-5-{[methyl(phenylmethyl)amino]methyl}phenyl)-4-[(4-methylquinazolin-2-yl)amino]benzamide | 3.4 |
| N-{3-[(dimethylamino)methyl]phenyl}-4-[(4-phenylquinazolin-2-yl)amino]benzamide | 6.1 |
| N-(2,6-dimethylphenyl)-4-{[4-phenyl-6-(phenylmethyl)-5,6,7,8-tetrahydropyrido[4,3-d]pyrimidin-2-yl]amino}benzamide | 155.9 |
| N-(2-methyl-1,2,3,4-tetrahydroisoquinolin-7-yl)-4-[(4-phenylquinazolin-2-yl)amino]benzamide | 5.8 |
| N-[2-methyl-5-(1H-pyrazol-5-yl)phenyl]-4-[(4-phenylquinazolin-2-yl)amino]benzamide | 6.3 |
| 5-chloro-N-(2,6-dimethylphenyl)-4-[(4-phenylquinazolin-2-yl)amino]thiophene-2-carboxamide | 166.3 |
| N-{2-methyl-5-[(2-morpholin-4-ylethyl)oxy]phenyl}-4-[(4-phenylquinazolin-2-yl)amino]benzamide | 6.2 |
| N-(2,6-dimethylphenyl)-4-[(4-phenylpyrido[2,3-d]pyrimidin-2-yl)amino]benzamide | 3.6 |
| N-(2,6-dimethylphenyl)-4-[(4-phenyl-6,7-dihydro-5H-cyclopenta[d]pyrimidin-2-yl)amino]benzamide | 25.8 |
| 4-phenyl-N-[1-(phenylcarbonyl)piperidin-4-yl]quinazolin-2-amine | 68.4 |
| N-{5-[(4-ethylpiperazin-1-yl)carbonyl]-2-methylphenyl}-4-[(4-phenylquinazolin-2-yl)amino]benzamide | 23.9 |
| 4-[(4-cyclopropylquinazolin-2-yl)amino]-N-(2,6-dimethylphenyl)benzamide | 2.8 |
| N-{5-[(dimethylamino)methyl]-2-methylphenyl}-4-{[4-(2-thienyl)quinazolin-2-yl]amino}benzamide | 21.0 |
| 4-{[4-(1-methylethyl)quinazolin-2-yl]amino}-N-[2-methyl-5-(morpholin-4-ylmethyl)phenyl]benzamide | 17.8 |

Biological Example 2

Daoy-Gli1 Assay

Daoy is a human medulloblastoma line that responds to sonic hedgehog by induction of numerous genes including the pathway components Gli1 and PTCH1. This assay measures the Hh-specific induction of an endogenous target gene in a human tumor cell line. Activating mutations in the GPCR-like receptor Smoothened (Smo) are found in around 40% of sporadic BCC (6, 12-14) and 25% of primitive neuroectodermal tumours (12, 14). Forced expression of the mutant Smo receptors in the Daoy medulloblastoma cell line (W353L and S533N) results in elevated pathway activity that is not further induced by the addition of rSHh-N. These engineered cell lines, Daoy_Smo_W535L and Daoy_Smo_S533N, were used to assess the ability of compounds to inhibit the function of a pathologically relevant mutant receptor.

Daoy cells were plated at $3\times10^4$ cells/well in 96-well plates in MEM/10% FCS, and the following day cells were serum-starved in MEM/0.05% FCS for 24 hrs. Cells were subsequently treated for 24 hrs with 50 μg/mL rSHh-N in MEM/0.05% FCS/0.3% DMSO plus or minus compounds. KAAD-cyclopamine was the control antagonist. The starting dose was 1000 nM for the Compounds of the Invention. Compound treatments were done in triplicate as six-point doses with four-fold serial dilutions. Following compound treatment, mRNA isolation, cDNA synthesis, and TaqMan® reactions were done with the following kits: mRNA Catcher™ (Invitrogen) and TaqMan® (Applied Biosystems). TaqMan® reactions were done in quadruplicate using duplexed probes for Gli1 (target) and β2-macroglobulin (control). Gli1 induction by rSHh is generally ten-fold to twenty-fold using this protocol.

Compounds of the invention were tested in this assay and demonstrated the ability to modulate Hedgehog pathway activity. The following embodiments are directed to the compounds themselves as well as their use in a method of treating. For example, in one embodiment of the invention, the Hedgehog pathway modulator is selected from the compounds in Table 1 having cellular activity in the Daoy-Gli1 assay of about 2800 nM or less. In another embodiment, the Hedgehog pathway modulator is selected from the compounds in Table 1 having cellular activity in the Daoy-Gli1 assay of about 1000 nM or less. In another embodiment, the Hedgehog pathway modulator is selected from the compounds in Table 1 having cellular activity in the Daoy-Gli1 assay of about 450 nM or less. In another embodiment, the Hedgehog pathway modulator is selected from the compounds in Table 1 having cellular activity in the Daoy-Gli1 assay of about 200 nM or less. In another embodiment, the Hedgehog pathway modulator is selected from the compounds in Table 1 having cellular activity in the Daoy-Gli1 assay of about 50 nM or less. In another embodiment, the Hedgehog pathway modulator is selected from the compounds in Table 1 having cellular activity in the Daoy-Gli1 assay of about 20 nM or less. In another embodiment, the Hedgehog pathway modulator is selected from the compounds in Table 1 having cellular activity in the Daoy-Gli1 assay of about 10 nM or less. In another embodiment, the Hedgehog pathway modulator is selected from the compounds in Table 1 having cellular activity in the Daoy-Gli1 assay of about 6 nM or less. In another embodiment, the Hedgehog pathway modulator is selected from the compounds in Table 1 having cellular activity in the Daoy-Gli1 assay of about 4 nM or less.

Biological Example 3

Hedgehog Cell-Based Readout: Real Time PCR (Taqman®) Assay in KYSE-180 Cells

KYSE-180 is a human esophageal cancer line shown to be responsive to SHh stimulation as measured by the induction of numerous Hh-responsive genes, including the pathway Gli1 and PTCH1. This assay measures the Hh-specific induction of an endogenous target gene in a human tumor cell line.

KYSE-180 cells were plated at $1.4 \times 10^5$ cells in RPMI/10% FCS in 96-well plates. The following day cells were serum-starved in MEM/0.05% FCS for 24 hrs. Cells were subsequently treated for 24 hrs in MEM/0.05% FCS/0.3% DMSO plus or minus compounds. Compound treatments were done in triplicate as six-point dose responses with four-fold serial dilutions. Following compound treatment, mRNA isolation, cDNA synthesis, and TaqMan® reactions were done with the following kits: mRNA Catcher™ (Invitrogen) and TaqMan® (Applied Biosystems). TaqMan® reactions were done in quadruplicate using duplexed probes for Gli1 (target) and 132-macroglobulin (control). Gli1 induction by rSHh is generally five-fold to ten-fold for KYSE-180 cells using this protocol.

Biological Example 4

Hedgehog Cell-Based Readouts: Gli1, G12 and Gli3 Protein Accumulation

Both Gli1 and Gli2 has been shown to function primarily as a transcriptional activator and elevated Hh signaling results in the accumulation of the active Gli1 and Gli2 proteins. On the other hand, Gli3 has both transcriptional activator and repressor functions. In the absence of Hh signaling, the larger Gli3 activator (Gli3A, 190 kDa) is processed to the smaller repressor form (Gli3R, 85 kDa), while stimulation of the pathway results in the accumulation of Gli3A at the expense of the Gli3R. Assessing the levels of these proximal readouts in Hh-responsive cell lines in vitro and in vivo (from tumor xenografts) provides a direct readout for pathway activation.

Biological Example 5

Hedgehog Cell-Based Readouts: Gli1, Gl2 and Gli3 Protein AccumulationImmunoprecipitation (IP)-Western Protocol Three µg of capture antibody (anti-Gli1 (AF3324, R&D Systems, anti-Gli2 (sc-28674, Santa Cruz Biotechnology) or anti-Gli3 (sc-20688, Santa Cruz Biotechnology) were independently incubated with 2000 µg of total protein from cleared lysates (from tumors or cell-based studies) were used overnight at 4° C. in the presence of 20 µL of protein G-coated Sepharose beads (Amersham). The beads were washed four times with lysis buffer (50 mM Tris-HCl, pH 8.0, 150 mM NaCl, 1% Triton X-100, 0.1% SDS, 0.5% sodium deoxycholate, 1 mM EDTA, 50 mM NaF, 1 mM sodium pyrophosphate, 1 mM sodium orthovanadate, 2 mM phenylmethylsulfonyl fluoride, 10 µg/ml aprotinin, 5 µg/mL leupeptin and 5 µg/mL pepstatin A). Capture beads were mixed with 20 µL LDS sample buffer and reducing reagent and heated at 75° C. for 10 minutes. Samples were loaded onto Criterion 4-12% Bis-Tris gels (Biorad), and proteins were transferred to nitrocellulose membranes. Gli proteins were detected by blotting with primary antibodies (anti-Gli1 (sc-20687, Santa Cruz Biotechnology, anti-Gli2 (sc-28674, Santa Cruz Biotechnology) or anti-Gli3 (sc-20688, Santa Cruz Biotechnology)) at 1:200 dilution in 5% non-fat milk/TBST overnight at 4° C. Blots were washed three times in TBST and blotted with HRP-conjugated anti-rabbit antibody in 5% non-fat milk/TBST) for 60 min using the ReliaBLOT kit (WB120, Bethyl Labs). Membranes were probed with for 5 min at room temperature with SuperSignal West Pico kit (Pierce) and exposed to film. Quantification was done using ImageQuant TL.

Biological Examples 6-9

Pharmacodynamic Xenograft Tumor Models

Daoy Human Medulloblastoma Cell Line

The human Daoy medulloblastoma cell line was engineered to over-express the N-terminal domain of sonic hedgeghog (SHh-N). A single clone (clone4) of this line with elevated levels of SHh (verified by Taqman® analysis) was chosen based on high levels of in vitro expression of Gli1 and Ptch1 mRNA. Furthermore, analysis of this clone grown as a xenograft in female athymic mice revealed elevated levels of both human and mouse Hh responsive genes (Gli1 and Ptch1) when compared to tumors comprised of the parental Daoy cell line as assessed in real-time PCR (Taqman®) assays with species specific primers. Therefore, this cell line was utilized to assess the ability of hedgehog pathway inhibitors to modulate the activity of the pathway in vivo.

Intradermal (ID) tumors were generated by implanting $5 \times 10^6$ cells (in HBSS)+50% Matrigel (in HBSS) into the hind flank of nude mice. Compounds were administered to tumor-bearing mice by oral gavage (po). Tumors were collected at different time points followed by RNA isolation, cDNA synthesis, and TaqMan® reactions with the kits: mRNA Catcher™ (Invitrogen) and TaqMan® (Applied Biosystems), respectively. TaqMan® reactions were done in quadruplicate using duplexed probes for Gli1 (target) and GAPDH (control). Additionally, whole blood was collected and plasma prepared for bioanalytical analysis of compounds. Bioanalytical analysis of crude tumor lysates was also done.

Panc-1 Human Pancreatic Cancer Cell Line

Panc-1 human pancreatic ductal carcinoma cells were found to express the SHh ligand. The mouse Hh responsive genes (Gli1 and Ptch1) were found to be upregulated in the mouse stromal compartment in Panc-1 tumors grown in female nude mice hosts and administration of Hh pathway inhibitors reduced the expression level mouse Gli1 and Ptchl. In contrast, no significant inhibition of the human Hh responsive genes following Hh inhibitor administration in mice harboring Panc-1 tumors was observed. Therefore, Panc-1 xenografts tumors represent clinically-relevant model of pancreatic tumors that secrete SHh and regulate the activity of the Hh pathway in the stromal compartment that supports tumor growth. The majority of human pancreatic adenocarcinomas and its precursor lesion abnormally express SHh. In addition, the forced expression of SHh in a prostate xenograft tumor model has been shown to enhance tumor growth. For implantation in vivo, $3\times10^6$ cells in 100 μL cold Hanks balanced salt solution were injected into the right hind flank of female nude mice.

HT-29 Human Colon Cancer Cell Line

HT29 cells represent differentiated human colon adenocarcinoma. This cell line was reported in the literature to respond to exogenous SHh stimulation. Analysis revealed overexpression of SHh and IHh ligands. The mouse Hh responsive genes (Gli1 and Ptch1) are upregulated in the mouse stromal compartment in Panc-1 tumors grown in female nude mice hosts and administration of Hh pathway inhibitors reduced the expression level mouse Gli1 and Ptchl. In contrast, no significant inhibition was observed of the human Hh responsive genes following Hh inhibitor administration in mice harboring HT-29 tumors. Therefore, HT-29 xenograft tumors represent clinically-relevant model of colon tumors that secrete SHh and regulate the activity of the Hh pathway in the stromal compartment that supports tumor growth. It has been reported in the literature that dysregulation of SHh pathway is very often found in human colorectal cancers. In addition, the forced expression of SHh in a prostate xenograft tumor model has been shown to enhance tumor growth. Therefore, HT-29 xenograft tumors are a relevant model to investigate the effect of SHh pathway inhibitors in human colorectal adenocarcinoma. For implantation in vivo, $2\times10^6$ cells in 100 μL cold Hanks balanced salt solution were injected into the right hind flank of female nude mice.

U-87MG Human Glioblastoma Cell Line

U-87MG cell line was previous described in the literature to be sensitive to Smo inhibitor cylopamine treatment, both in vitro and in vivo studies. In addition, this cell line was reported to express a number of stemness genes, indicating presence of tumor stem cells, which may be responsible for tumor self-renewal and regrowth after following chemotherapy. Significance of stem cells for clinical course of glioblastomas appears to be well established, and targeting this cell population with Hh inhibitors may provide therapeutic advantage. Thus, U-87MG globlastoma xenografts can provide a valuable and relevant animal models for testing the effect of Hh pathway inhibitors on stem cell-driven regrowth and chemoresistance of CNS tumors. For implantation in vivo, $2\times10^6$ cells in 100 μl cold Hanks balanced salt solution were injected into the right hind flank of female nude mice.

Biological Example 10

Pharmacodynamic Study Protocol

Subcutaneous xenograft tumors were generated in nude mice as described above. Compounds were administered to tumor-bearing mice by oral gavage (po) in formulations that were specific to each chemical scaffold, which varied from solutions to homogenous suspensions. Tumors were collected at different time points followed by RNA isolation, cDNA synthesis, and TaqMan® reactions with the kits: mRNA Catcher™ (Invitrogen) and TaqMan® (Applied Biosystems), respectively. TaqMan® reactions were done in quadruplicate using species-specific probes for mouse and human Gli1, Ptch1 and GAPDH (control). Whole blood and crude tumor lysates were collected and prepared for bioanalytical analysis to determine the concentrations of the test compounds.

Biological Example 11-12

Efficacy Study Protocols

Single Agent Treatment

The standard experimental design for these studies involved oral administration of Smo inhibitors at dose range expected to modulate the Hh signaling pathway based on PD studies. The dosing regimen is initiated when the established solid tumors reached ~100 mg. Exploration of alternative dose regimens was also performed by administration of the compounds in a cyclical fashion (q2d or q3d). Throughout the dosing period of 14 days, tumor size was measured twice weekly and body weight was measured daily. Tolerability was monitored in these studies by daily measurement of body weight. Blood plasma samples were collected for clinical chemistry and hematology analysis and to determine plasma profile of compound concentration.

Combined and/or Sequential Treatment with Standard Chemotherapeutics

Cancer stem cells are defined as discrete cell populations that express specific cell-surface markers and display highly enhanced survival, self-renewal, and tumorigenicity properties. These cancer stem cells, in some experimental contexts described in the literature, have shown to confer resistance to currently used chemotherapy. In the literature, the hedgehog pathway has been shown to be essential for stem cell renewal in tumors of the breast, central nervous system, and in multiple myeloma. Further, upregulation of Hh signaling has been described in the literature following chemotherapy in an esophageal cancer model. Pancreatic cancer and gliomas are among the most chemoresistant human malignancies and stemness gene expression profile ("stemness signature") was described in clinical samples as well as in xenograft models of both tumor types in the literature. These tumors models are used to address if inhibitors of Hh pathway can potentiate efficacy of standard chemotherapeutic agents when administered in combined treatment or defer tumor regrowth when used sequentially after the administration of a chemotherapy. Antimetabolite treatments, such as gemcitabine, are used in combination in Panc-1 pancreatic cancer and temozolomide, an alkylating agent, are used in U-87MG glioblastoma tumor xenograft models.

In concurrent combination treatment, Hh pathway inhibitors are administered in combination with the standard chemotherapy agents (gemcitabine or temozolomide). Single agent treatments are conducted to evaluate potential additive or synergistic effects when the compounds are administered in combination. The dosing regimen is initiated when the established solid tumors reached ~100 mg. Throughout the dosing period of 14 days, tumor size was measured twice weekly and body weight was measured daily. Tolerability was monitored in these studies by daily measurement of body weight. Blood plasma samples were collected for clinical chemistry and hematology analysis and to determine plasma profile of compound concentration.

In sequential regimens, single agent standard chemotherapeutics (gemcitabine or temozolomide) are administered for a period of 14 days to inhibit tumor growth and/or induce tumor regression. Subsequent to the standard chemotherapeutics treatment, Hh inhibitors are dosed to determine their effect on tumor regrowth. Treatment with Hh inhibitors can be initiated immediately after completion standard chemotherapy or after certain "off-treatment" period, depending on the study design. The dosing regimen is initiated when the established solid tumors reached ~100 mg. Throughout the dosing period of 14 days, tumor size was measured twice weekly and body weight was measured daily. Tolerability was monitored in these studies by daily measurement of body weight. Blood plasma samples were collected for clinical chemistry and hematology analysis and to determine plasma profile of compound concentration.

Immunohistochemistry

At the termination of efficacy studies, tumors were excised and examined histologically for induction of apoptosis (TUNEL), microvessel density (CD31 staining), proliferating cells (Ki67 staining) and necrosis (hematoxylin/eosin staining). Additionally, tumor sections were stained for expression of SHh pathway (Gli1, SHh, Smo) and biomarkers of cancer stem cells (eg. Nestin, CD131, ALDH). Tolerability was monitored in these studies by daily measurement of body weight. Blood plasma samples were collected for clinical chemistry and hematology analysis and to determine plasma profile of compound concentration.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed:
1. A Compound of Formula I

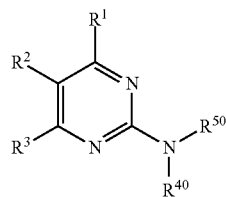

I or a single isomer thereof and optionally as a pharmaceutically acceptable salt thereof, where $R^1$ is alkyl, cycloalkyl, phenyl, or heteroaryl where the cycloalkyl, phenyl, and heteroaryl are optionally substituted with 1, 2, or 3 $R^6$;

$R^2$ and $R^3$ together with the pyrimidinyl to which they are attached form a quinazolinyl optionally substituted at the 5-, 6-, 7-, and 8-positions with one or two groups independently selected from alkyl, alkoxy, halo, hydroxy, heterocycloalkylalkyloxy, heterocycloalkyl, and heterocycloalkyl substituted with alkyl; or each $R^6$, when $R^6$ is present, is independently selected from alkyl, alkoxy, amino, alkylamino, dialkylamino, halo, haloalkyl, haloalkoxy, halophenyl, aminocarbonyl, alkylaminocarbonyl, dialkylaminocarbonyl, hydroxyalkyl, alkoxycarbonyl, aminoalkyl, alkylaminoalkyl, dialkylaminoalkyl, aminoalkylamino, alkylaminoalkylamino, dialkylaminoalkylamino, alkyloxyalkylamino, heterocycloalkyl, and heterocycloalkylalkyl; where the heterocycloalkyl, either alone or as part of heterocycloalkylalkyl, is optionally substituted with alkyl or alkoxycarbonyl;

$R^{40}$ is hydrogen or alkyl;
$R^{50}$ is selected from

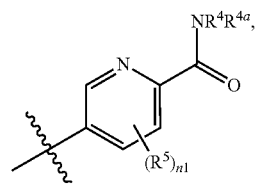

n1 is 0, 1, or 2;
each $R^5$, when $R^5$ is present, is independently alkyl, hydroxy, alkoxy, amino, alkylamino, dialkylamino, halo, nitro, heterocycloalkyl, heterocycloalkylamino, or heterocycloalkylalkyloxy;
  where each heterocycloalkyl, either alone or as part of another group in $R^5$, is independently optionally substituted with alkyl or alkoxycarbonyl;
$R^{4a}$ is hydrogen or alkyl;
$R^4$ is heteroaryl substituted with one $R^8$ and additionally substituted with 1 or 2 $R^{8a}$, wherein heteroaryl is selected from 1,2,3,4-tetrahydroisoquinolinyl or 2,3,4,5-tetrahydro-1,4-benzoxazepinyl; or $R^4$ is phenyl substituted with one $R^{29}$ and additionally substituted with 1 or 2 $R^{9a}$;
each $R^8$ is independently alkyl, cycloalkyl, phenylalkyloxyalkyl, or $R^{9b}$;
each $R^{8a}$ is independently hydrogen, halo, or $R^8$;
each $R^{9a}$ is independently hydrogen, $R^{9b}$, or $R^{9a}$;
$R^{29}$ is alkyl substituted with —$NR^{15}R^{15a}$; or alkyl substituted with optionally substituted heterocycloalkyl;
each $R^{9b}$, when $R^{9b}$ is present, is independently amino, alkylamino, dialkylamino, optionally substituted heterocycloalkyl, optionally substituted heterocycloalkylalkyloxy, aminoalkyloxy, alkylaminoalkyloxy, dialkylaminoalkyloxy, optionally substituted heteroaryl, cyano, —$C(O)R^{14}$, —$CR^{14a}(NR^{14b})$, —$C(=NR^{24})R^{24a}$, —$S(O)_2NR^{13}R^{13a}$,
—$NR^{23}C(O)R^{23a}$—$C(O)NR^{12}R^{12a}$, or alkyl substituted with one or two $R^{11}$;
each $R^{9c}$, when $R^{9c}$ is present, is independently alkyl, haloalkyl, hydroxyalkyl, halo, hydroxy, alkoxy, cyano, nitro, or phenylcarbonyl;

each $R^{11}$ is independently selected from hydroxy, $-NR^{15}R^{15a}$, optionally substituted heteroaryl, optionally substituted heterocycloalkyl, and optionally substituted cycloalkyl;

$R^{12}$ is hydrogen or alkyl and $R^{12a}$ is hydrogen, hydroxy, alkoxy, alkyl, aminoalkyl, alkylaminoalkyl, dialkylaminoalkyl, hydroxyalkyl, optionally substituted heterocycloalkyl, optionally substituted heterocycloalkylalkyl, or optionally substituted heteroaryl; or $R^{12}$ and $R^{12a}$ together with the nitrogen to which they are attached form a heterocycloalkyl optionally substituted with 1, 2, or 3 groups independently selected from alkyl, hydroxyalkyl, haloalkyl, alkylcarbonyl, alkoxycarbonyl, optionally substituted cycloalkyl, optionally substituted cycloalkylalkyl, optionally substituted heteroaryl, optionally substituted heteroarylalkyl, optionally substituted phenyl, and optionally substituted phenylalkyl;

$R^{13}$ is hydrogen or alkyl;

$R^{13a}$ is alkyl, aminoalkyl, alkylaminoalkyl, or dialkylaminoalkyl;

each $R^{14}$ is independently hydrogen, alkyl, hydroxy, alkoxy, optionally substituted heteroarylalkyl, or optionally substituted heterocycloalkylalkyl;

each $R^{14a}$ is hydrogen or alkyl;

$R^{14b}$ is alkoxy, amino, alkylamino, dialkylamino, or optionally substituted heterocycloalkyl;

$R^{15}$ is hydrogen, alkyl, alkoxyalkyl, hydroxyalkyl, or haloalkyl;

$R^{15a}$ is hydrogen, alkyl, alkoxyalkyl, haloalkyl, hydroxyalkyl, carboxyalkyl, aminocarbonylalkyl, alkylaminocarbonylalkyl, dialkylaminocarbonylalkyl, optionally substituted cycloalkyl, or optionally substituted phenylalkyl;

$R^{23}$ is hydrogen or alkyl;

$R^{23a}$ is hydrogen, alkyl, aminoalkyl, alkylaminoalkyl, dialkylaminoalkyl, or optionally substituted heterocycloalkylalkyl;

$R^{24}$ is hydrogen or alkyl, hydroxy, or alkoxy; and $R^{24a}$ is hydroxy, alkoxy, amino, alkylamino, or dialkylamino.

2. The Compound of claim 1 where $R^{40}$ is hydrogen and $R^2$ and $R^3$ together with the pyrimidinyl to which they are attached form a quinazolinyl optionally substituted at the 5-, 6-, 7-, and 8-positions with one or two groups independently selected from alkyl, alkoxy, halo, and hydroxy; or a single isomer thereof and optionally as a pharmaceutically acceptable salt-thereof.

3. The Compound of claim 2 where $R^2$ and $R^3$ together with the pyrimidinyl to which they are attached form a quinazolinyl that is not substituted at the 5-, 6-, 7-, or 8-position; or a single isomer thereof and optionally as a pharmaceutically acceptable salt thereof.

4. The Compound of claim 3 where $R^1$ is alkyl; or a single isomer thereof and optionally as a pharmaceutically acceptable salt thereof.

5. The Compound of claim 3 where $R^1$ is heteroaryl optionally substituted with 1, 2, or 3 $R^6$; or a single isomer thereof and optionally as a pharmaceutically acceptable salt thereof.

6. The Compound of claim 3 where $R^1$ is cycloalkyl optionally substituted with 1, 2, or 3 $R^6$; or a single isomer thereof and optionally as a pharmaceutically acceptable salt thereof.

7. The Compound of claim 3 where $R^1$ is phenyl substituted with one or two $R^6$ where each $R^6$ is independently amino, alkylamino, dialkylamino, aminocarbonyl, alkylaminocarbonyl, dialkylaminocarbonyl, heterocycloalkylalkyl (optionally substituted with alkyl or alkoxycarbonyl), aminoalkylamino, alkylaminoalkylamino, or dialkylaminoalkylamino; or a single isomer thereof and optionally as a pharmaceutically acceptable salt thereof.

8. The Compound of claim 3 where $R^1$ is unsubstituted phenyl; or a single isomer thereof and optionally as a pharmaceutically acceptable salt thereof.

9. The Compound of claim 1 according to Formula Ib

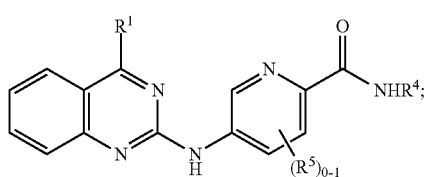

or a single isomer thereof and optionally as a pharmaceutically acceptable salt thereof.

10. The Compound of claim 9 where $R^4$ is heteroaryl substituted with one $R^8$, wherein heteroaryl is selected from 1,2,3,4-tetrahydroisoquinolinyl or 2,3,4,5-tetrahydro-1,4-benzoxazepinyl; or a single isomer thereof and optionally as a pharmaceutically acceptable salt thereof.

11. The Compound of claim 9 where $R^4$ is phenyl substituted with $R^{29}$ and additionally substituted with 1 or 2 $R^{9a}$; or a single isomer thereof and optionally as a pharmaceutically acceptable salt thereof.

12. The Compound of claim 3 where $R^1$ is alkyl, cycloalkyl, or heteroaryl, where the cycloalkyl and heteroaryl are optionally substituted with 1, 2, or 3 $R^6$; $R^{50}$ is

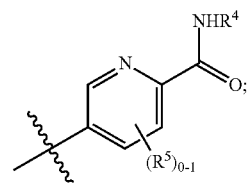

$R^4$ is phenyl substituted with one $R^{29}$ and additionally substituted with 1 or 2 $R^{9a}$ and each $R^{9a}$ is independently hydrogen or $R^{9c}$; or a single isomer thereof and optionally as a pharmaceutically acceptable salt thereof.

13. A method of preparing a compound of claim 1 which method comprises reacting an intermediate of formula 8, or a salt, hydrate, solvate, or combination thereof:

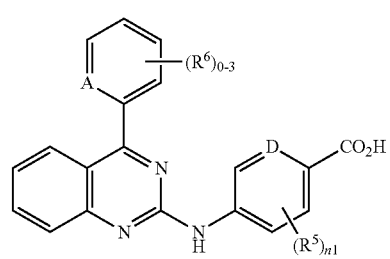

where A is CH or N, and D is N; with an intermediate of formula 9:

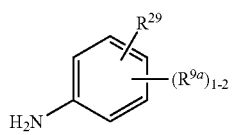

to yield a Compound of Formula XI:

XI

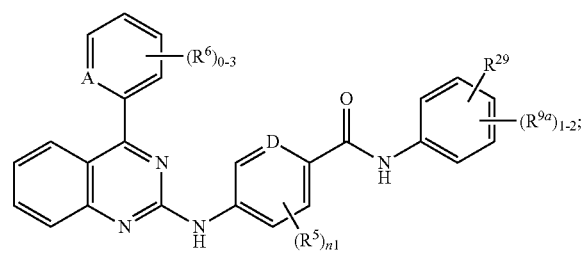

and optionally separating individual isomers; and optionally modifying any of the $R^6$, $R^{29}$, and $R^{9a}$ groups; and optionally forming a pharmaceutically acceptable salt thereof; or reacting an intermediate of formula II, or a salt, hydrate, solvate, or combination thereof:

11

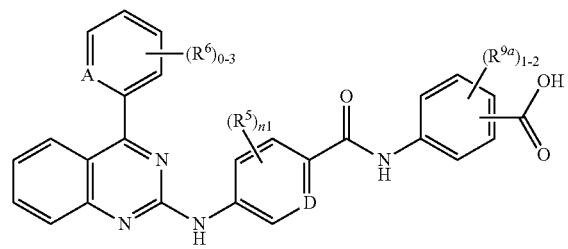

where A is CH or N, and D is N; with an intermediate of formula $NHR^{12}R^{12a}$ to yield a Compound of formula 8f 8f

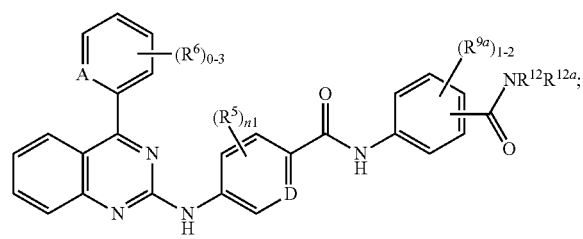

and optionally separating individual isomers; and optionally modifying any of the $R^6$, $R^{9a}$, and $R^{12a}$ groups; and optionally forming a pharmaceutically acceptable salt thereof; or reacting an intermediate of formula 13, or a salt, hydrate, solvate, or combination thereof:

13

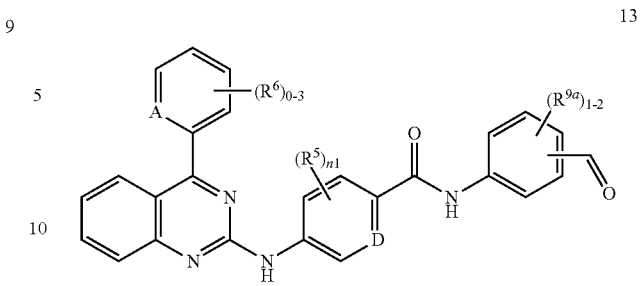

where A is CH or N, and D is N; with an intermediate of formula $NHR^{15}R^{15a}$ to yield a Compound of Formula XII:

XII

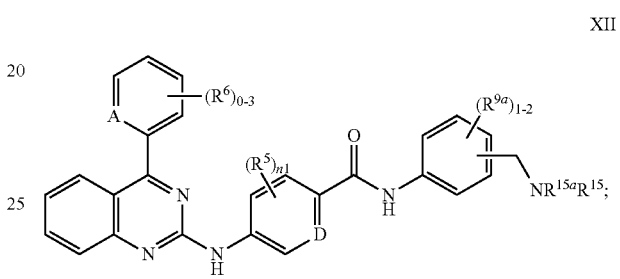

and optionally separating individual isomers; and optionally modifying any of the $R^6$, $R^{9a}$, and $R^{15a}$ groups; and optionally forming a pharmaceutically acceptable salt thereof; or reacting an intermediate of formula 15a, or a salt, hydrate, solvate, or combination thereof:

15a

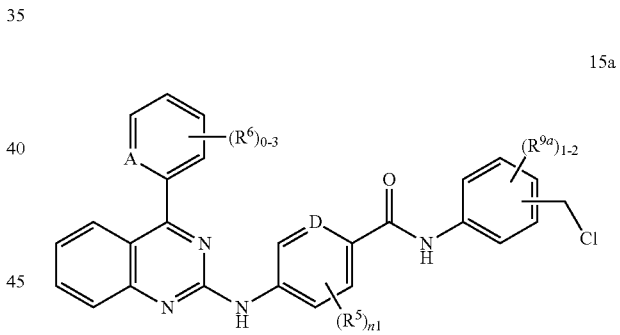

where A is CH or N, and D is N; with an intermediate of formula $NH_2R^{15}$ to yield a Compound of Formula XIII:

XIII

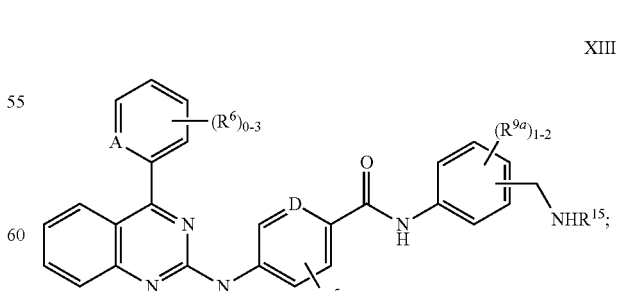

and optionally separating individual isomers; and optionally modifying any of the $R^6$, $R^{9a}$, and $R^{15}$ groups; and optionally forming a pharmaceutically acceptable salt thereof; or reacting an intermediate of formula 23, or a salt, hydrate, solvate, or combination thereof:

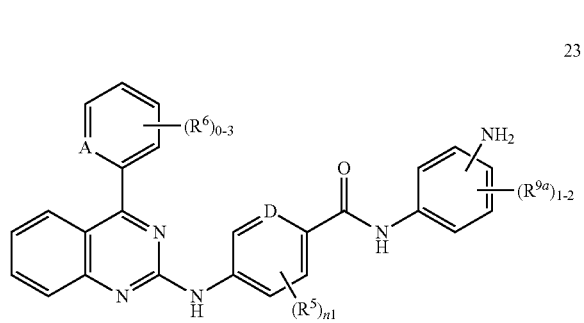

23 where A is CH or N, and D is N; with an intermediate of formula $R^{23a}C(O)OH$ or $R^{23a}C(O)Cl$ to yield a Compound of Formula XIV

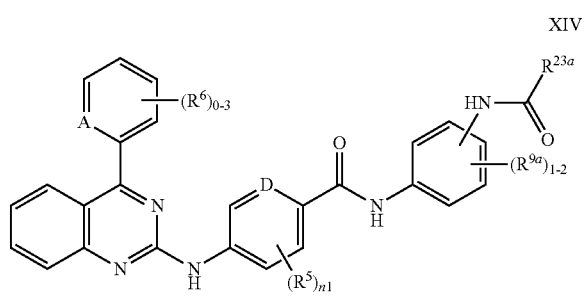

XIV and optionally separating individual isomers; and optionally modifying any of the $R^6$, $R^{9a}$, and $R^{23a}$ groups; and optionally forming a pharmaceutically acceptable salt thereof; or
reacting an intermediate of formula 26, or a salt, hydrate, solvate, or combination thereof:

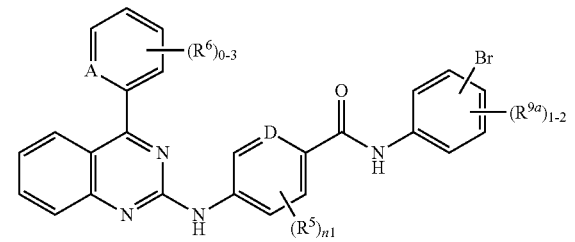

26 where A is CH or N, and D is N; with an intermediate of formula $R''B(OH)_2$ where $R''$ is optionally substituted heteroaryl to yield a Compound of Formula XV:

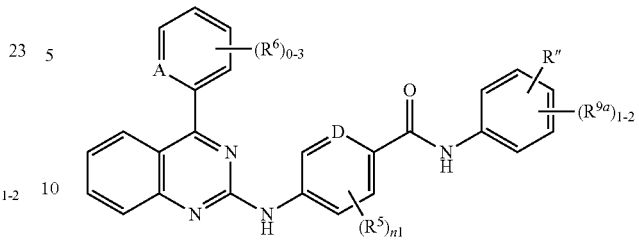

XV and optionally separating individual isomers; and optionally modifying any of the $R^6$, $R^{9a}$, and $R''$ groups; and optionally forming a pharmaceutically acceptable salt thereof;
reacting an intermediate of formula 31, or a salt, hydrate, solvate, or combination thereof:

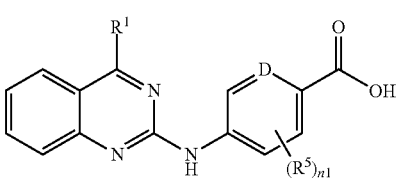

31 where $R^1$ is cycloalkyl, and D is N; with an intermediate of formula 9 as defined above to yield a Compound of the Invention of Formula XVI

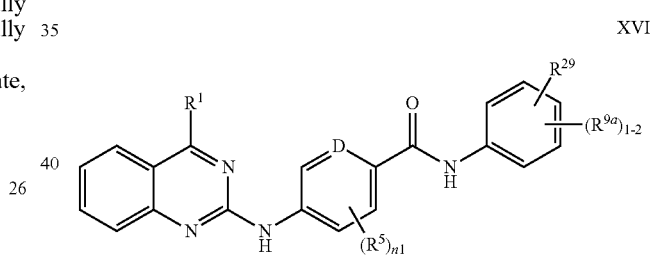

XVI where $R^{29}$ and $R^{9a}$ are as defined in the Summary of the Invention for a Compound of Formula I; and optionally separating individual isomers; and optionally modifying any of the $R^1$, $R^{9a}$, and $R^{29}$ groups; and optionally forming a pharmaceutically acceptable salt thereof.

14. A pharmaceutical composition comprising a compound according to claim 1 or a single isomer thereof, optionally as a pharmaceutically acceptable salt thereof, and a pharmaceutically acceptable carrier, excipient, or diluent.

* * * * *